US011674950B2

(12) United States Patent
Lane et al.

(10) Patent No.: US 11,674,950 B2
(45) Date of Patent: Jun. 13, 2023

(54) METHODS DETERMINING AND TREATING CELLULAR RESISTANCE TO ADP-RTBOSYLATING TOXIN

(71) Applicants: Dana-Farber Cancer Institute, Inc., Boston, MA (US); The Brigham and Women's Hospital, Inc., Boston, MA (US)

(72) Inventors: Andrew Lane, Needham, MA (US); Jon Aster, Lexington, MA (US)

(73) Assignees: Dana-Farber Cancer Institute, Inc., Boston, MA (US); The Brigham and Women's Hospital, Inc., Boston, MA (US)

( * ) Notice: Subject to any disclaimer, the term of this patent is extended or adjusted under 35 U.S.C. 154(b) by 354 days.

(21) Appl. No.: 16/756,545

(22) PCT Filed: Oct. 30, 2018

(86) PCT No.: PCT/US2018/058222
§ 371 (c)(1),
(2) Date: Apr. 16, 2020

(87) PCT Pub. No.: WO2019/089603
PCT Pub. Date: May 9, 2019

(65) Prior Publication Data
US 2021/0325368 A1 Oct. 21, 2021

Related U.S. Application Data

(60) Provisional application No. 62/579,583, filed on Oct. 31, 2017.

(51) Int. Cl.
*A61K 45/06* (2006.01)
*G01N 33/50* (2006.01)
*G01N 33/574* (2006.01)

(52) U.S. Cl.
CPC .......... *G01N 33/5011* (2013.01); *A61K 45/06* (2013.01); *G01N 33/57426* (2013.01)

(58) Field of Classification Search
CPC ................................................ G01N 33/5011
USPC ...................................................... 435/7.23
See application file for complete search history.

(56) References Cited

U.S. PATENT DOCUMENTS 6,147,060 A * 11/2000 Zasloff .................... A61P 35/00
514/110

FOREIGN PATENT DOCUMENTS

| WO | WO-2007/143858 A1 | 12/2007 |
|---|---|---|
| WO | WO-2016/146833 A1 | 9/2016 |
| WO | WO-2016/207324 A1 | 12/2016 |
| WO | WO-2017/013585 A1 | 1/2017 |
| WO | WO-2019/089603 A1 | 5/2019 |

OTHER PUBLICATIONS

Wei et al (JBC, 2013, 288(17): 12305-12312).*
Hu et al (Leuk Res, 2013, 37(11): 1-14).*
Folkman, J. ("Angiogenesis in cancer, vascular, rheumatoid, and other diseases" Nature Medicine, vol. 1, pp. 27-31, 1995).*
Benton et al (British Journal of Haematology, 2014, 167: 356-365).*
Morita et al (Oncology, 2006, 71: 437-445).*
Konopleva et al, Blood, 2012, 120(21): Abstract 3625).*
Frankel et al (Blood, 2013, 122(21): p. 2682).*
Frolova et al (BJH, 2014, 166: 862-874).*
Fabris et al (Genes, Chromosomes & Cancer, 2008, 47: 781-793).*
Vermeer et al (Cancer Res, 2008, 68(8): 2689-2698).*
Bruening et al (Cancer Research, 1999, 59: 4973-4983).*
International Search Report and Written Opinion for International Application No. PCT/US2018/058222 dated Feb. 7, 2019.
Mayer et al., "Influence of DPH1 and DPH5 Protein Variants on the Synthesis of Diphthamide, the Target of ADP-Ribosylating Toxins," Toxins, 9(3):1-11 (2017).
Stahl et al., "Loss of diphthamide pre-activates NF-kB and death receptor pathways and renders MCF7 cells hypersensitive to tumor necrosis factor," Proc Natl Acad Sci USA, 112(34):10732-10737 (2015).
Wei et al., "Immunotoxin resistance via reversible methylation of the DPH4 promoter is a unique survival strategy," Proc Natl Acad Sci USA, 109(18):6898-6903 (2012).
Weldon et al., "A guide to taming a toxin-recombinant immunotoxins constructed from Pseudomonas exotoxin A for the treatment of cancer," FEBS J, 278(23):4683-4700 (2011).

* cited by examiner

*Primary Examiner* — Sean E Aeder
(74) *Attorney, Agent, or Firm* — Foley Hoag LLP

(57) ABSTRACT

The present invention is based in part on the identification of DPH1 and other members of the diphthamide synthesis pathway as biomarkers of resistance to an ADP-ribosylating toxin in a cell, and methods for identification, assessment, and treatment of a condition that is resistant to an ADP-ribosylating toxin.

35 Claims, 29 Drawing Sheets

Specification includes a Sequence Listing.

RED – SL-401-APC; GREEN – CFSE (intracellular); BLUE – DAPI (nucleus)

ADP Ribosylation IHC assay in THP1 cells

Stain: primary: ADP-biotin
secondary: streptavidin-HRP

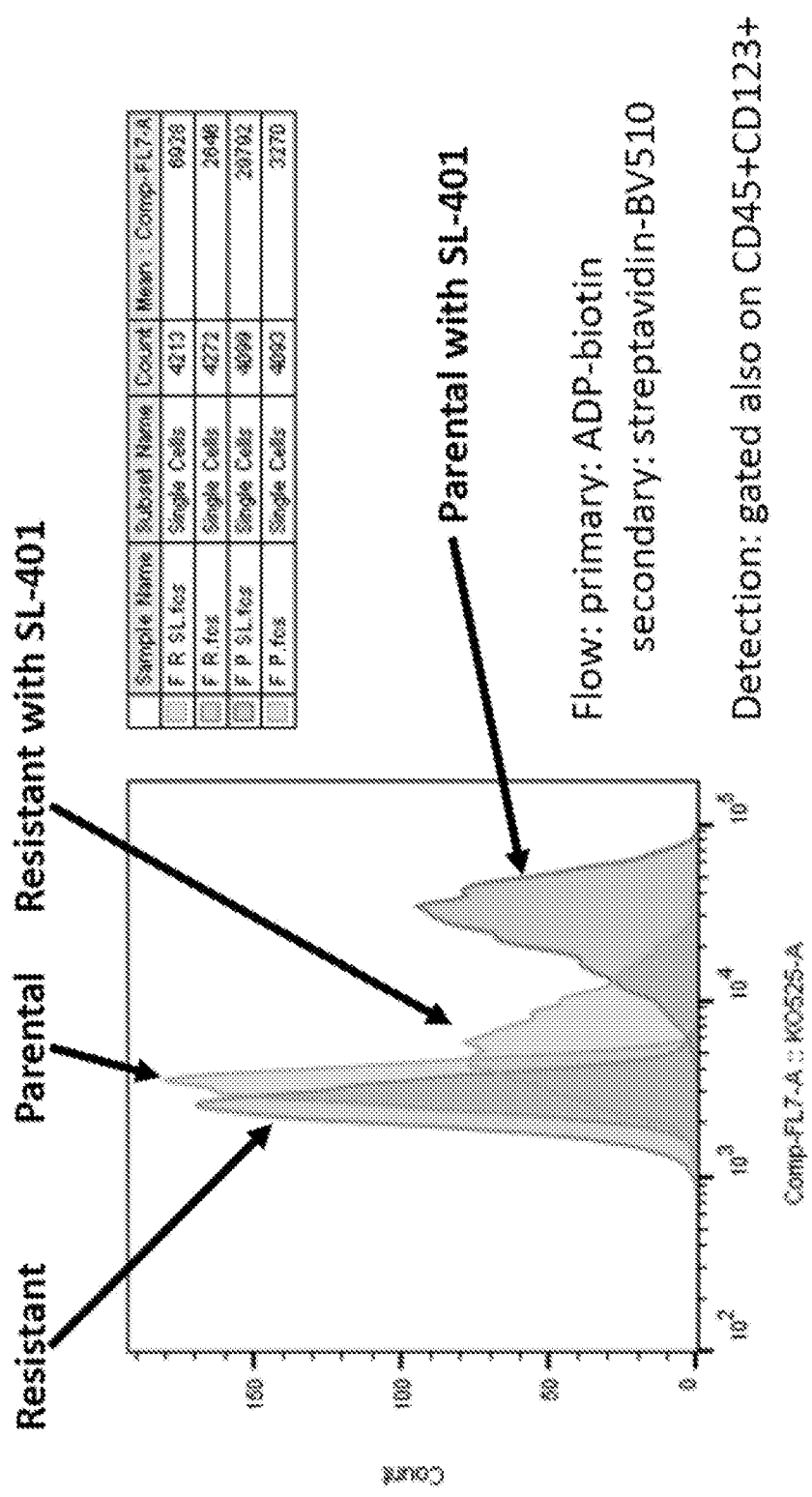

US 11,674,950 B2

METHODS DETERMINING AND TREATING CELLULAR RESISTANCE TO ADP-RTBOSYLATING TOXIN

CROSS-REFERENCE TO RELATED APPLICATIONS

This application is the U.S. national phase of International Patent Application No. PCT/US2018/058222, filed on 30 Oct. 2018, which claims the benefit of priority to U.S. Provisional Application Ser. No. 62/579,583, filed on 31 Oct. 2017; the entire contents of each of said applications are incorporated herein in their entirety by this reference.

STATEMENT OF RIGHTS

This invention was made with government support under grant number R01 CA225191-01 awarded by the National Institutes of Health. The government has certain rights in the invention.

BACKGROUND OF THE INVENTION

CD123, or the interleukin 3 (IL3) receptor alpha chain, is expressed on the cell surface of many hematologic malignancies, particularly those in the myeloid lineage, including acute myeloid leukemia (AML), myelodysplastic syndrome (MDS), chronic myelomonocytic leukemia (CMML), and myeloproliferative neoplasms (MPNs). Blastic plasmacytoid dendritic cell neoplasm (BPDCN) is an aggressive hematologic cancer with prominent skin in addition to blood and bone marrow involvement, thought to result from malignant transformation of plasmacytoid dendritic cells or their precursors. BPDCN is defined pathologically by particularly high levels of CD123 cell-surface expression and may be pathologically related to AML. Finally, the putative "leukemia stem cell" (LSC) or "leukemia initiating cell" (LIC) subpopulation proposed to represent the self-renewing subset of cells that can regenerate the entire malignant population in AML is enriched for CD123 expression. For these reasons, therapeutic targeting of cells that express CD123 is an attractive strategy in hematologic malignancies.

Tagraxofusp (SL-401, DT-IL3) is a new targeted biologic agent consisting of recombinant IL3 fused to a truncated diphtheria toxin. Tagraxofusp delivers the cytotoxic activity of DT to cells that express CD123. After internalization, the catalytic domain of DT catalyzes ADP ribosylation of eukaryotic elongation factor 2 (eEF2), blocking protein synthesis and killing the target cell. Tagraxofusp is currently being evaluated in clinical trials in several hematologic malignancies, and early data indicates the drug is particularly active in patients with BPDCN. However, the determinants of response and mechanisms of resistance to tagraxofusp are largely unknown.

Tagraxofusp as a single agent is effective at inducing remission in many patients, particularly in those with BPDCN. However, some patients are initially refractory to treatment and others relapse after initial response, and some CD123-expressing malignancies are less initially responsive. Some cancers that express the IL3 receptor (CD123) can initially respond to standard anti-cancer therapies, but even these cancers generally become resistant to such therapies. The determinants of the resistance are largely unknown. Accordingly, there is a great need to identify the mechanisms of de novo and acquired resistance to ADP-ribosylating toxins in order to develop improved diagnostic, prognostic, and therapeutic strategies.

SUMMARY OF THE INVENTION

The present invention is based, at least in part, on the discovery of a biomarker (i.e. DPH1) which predicts the resistance to therapy with an ADP-ribosylating toxin (e.g., a bacterial toxin either alone or conjugated to a targeting moiety, such as an IL3-conjugated toxin like SL-401) in cancers (e.g., CD123+ cancers), and that the resistance is reversible with a hypomethylating agent (e.g., azacitidine). Accordingly, the present invention relates, in part, to methods for stratifying patients who are predicted to be resistant to toxin based upon a determination and analysis of at least one member of the diphthamide synthesis pathway according to amount (e.g., copy number or level of expression) and/or activity, relative to a control. Such analyses can be used to perform a number of diagnostic and prognostic assays described herein either alone or in combination with useful therapeutic regimens (e.g., based on predictions of clinical response, subject survival or relapse, timing of adjuvant or neoadjuvant treatment, etc.). In addition, methods of treating cancers (e.g., CD123+ cancer), such as those that are resistant to an ADP-ribosylating toxin, are described herein.

In one aspect, a method of identifying the likelihood of a cell in a subject to be resistant to an ADP-ribosylating toxin is provided. The method comprises a) obtaining or providing a sample comprising the cells from a subject; b) measuring the copy number, amount, and/or activity of at least one member of the diphthamide synthesis pathway in the cells of the subject sample; and c) comparing said copy number, amount, and/or activity of at least one member of the diphthamide synthesis pathway in a control, wherein a significantly decreased copy number, amount, and/or activity of at least one member of the diphthamide synthesis pathway in the cells of the subject sample relative to the control identifies the cell as being more likely to be resistant to the ADP-ribosylating toxin, and wherein a significantly increased copy number, amount, and/or activity of at least one member of the diphthamide synthesis pathway in the subject sample relative to the control sample identifies the cell as being less likely to be resistant to the ADP-ribosylating toxin.

Numerous embodiments are further provided that can be applied to any aspect of the present invention and/or combined with any other embodiment described herein. For example, in one embodiment, the method further comprises recommending, prescribing, or administering the ADP-ribosylating toxin if the cell is determined to be less likely to be resistant to the ADP-ribosylating toxin. In another embodiment, the method further comprises recommending, prescribing, or administering a therapy other than the ADP-ribosylating toxin as a single agent if the cell is determined to be likely to be resistant to the ADP-ribosylating toxin. In still another embodiment, the cell is a cancer cell. In yet another embodiment, the therapy other than the ADP-ribosylating toxin is the anti-cancer therapy selected from the group consisting of a hypomethylating agent, targeted therapy, chemotherapy, radiation therapy, and/or hormonal therapy, optionally wherein the anti-cancer therapy comprises the ADP-ribosylating toxin. In another embodiment, the anti-cancer therapy is administered to the subject in combination with the ADP-ribosylating toxin, optionally wherein the anti-cancer therapy is administered before, after, or concurrently with the ADP-ribosylating toxin. In still another embodiment, the targeted therapy is an immunotherapy. In yet another embodiment, the immunotherapy is cell-based. In another embodiment, the immunotherapy comprises a cancer vaccine and/or virus. In still another embodiment, immunotherapy inhibits an immune checkpoint. In yet another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM4-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In another embodiment, the immune checkpoint is PD1, PD-L1, or CTLA-4. In still another embodiment, the anti-cancer therapy is a cytotoxic chemotherapy. In yet another embodiment, the cytotoxic chemotherapy is selected from the group consisting of cytarabine, doxorubicin, vincristine, azacitidine, venetoclax (ABT-199), navitoclax and Obatoclax. In another embodiment, the control is determined from a cancerous or non-cancerous sample from either the subject or a member of the same species to which the subject belongs. In still another embodiment, the control is a sample that comprises cells or does not comprise cells. In yet another embodiment, the control sample comprises cells that are resistant to the ADP-ribosylating or are not resistant to the ADP-ribosylating toxin.

In another aspect, a method of assessing the efficacy of an agent for treating a condition that is resistant to an ADP-ribosylating toxin in a subject is provided. The method comprises a) detecting in a subject sample comprising affected cells at a first point in time the copy number, amount, and/or activity of at least one member of the diphthamide synthesis pathway; b) repeating step a) during at least one subsequent point in time after administration of the agent; and c) comparing the copy number, amount, and/or activity of at least one member of the diphthamide synthesis pathway from steps a) and b), wherein a significantly increased copy number, amount, and/or activity of at least one member of the diphthamide synthesis pathway, in the affected cells of the subsequent sample as compared to the copy number, amount, and/or activity in the affected cells of the sample at the first point in time, indicates that the agent treats the condition that is resistant to the ADP-ribosylating toxin in the subject.

As described above, numerous embodiments are further provided that can be applied to any aspect of the present invention and/or combined with any other embodiment described herein. For example, in one embodiment, between the first point in time and the subsequent point in time, the subject has undergone treatment, completed treatment, and/or is in remission for the condition. In another embodiment, the first and/or at least one subsequent sample is selected from the group consisting of ex vivo and in vivo samples. In still another embodiment, the first and/or at least one subsequent sample is obtained from an animal model of the condition. In yet another embodiment, the first and/or at least one subsequent sample is a portion of a single sample or pooled samples obtained from the subject. In another embodiment, the condition is a cancer. In still another embodiment, the sample comprises cells, serum, peritumoral tissue, and/or intratumoral tissue obtained from the subject. In yet another embodiment, the method further comprises determining responsiveness to the agent by measuring at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

In still another aspect, a cell-based assay for screening for agents that have a cytotoxic or cytostatic effect on cells that are resistant to an ADP-ribosylating toxin is provided. The method comprises contacting the cell with a test agent, and determining the ability of the test agent to increase the copy number, amount, and/or activity of at least one member of the diphthamide synthesis pathway.

As described above, numerous embodiments are further provided that can be applied to any aspect of the present invention and/or combined with any other embodiment described herein. For example, in one embodiment, the step of contacting occurs in vivo, ex vivo, or in vitro. In another embodiment, the cells that are resistant to the ADP-ribosylating toxin are contacted with the test agent in combination with the ADP-ribosylating toxin, optionally wherein the test agent is administered before, after, or concurrently with the ADP-ribosylating toxin. In still another embodiment, the cell-based assay further comprises determining a reduction in the viability or proliferation of the cells. In yet another embodiment, the agent is administered in a pharmaceutically acceptable formulation. In another embodiment, the subject sample is selected from the group consisting of whole blood, serum, plasma, urine, cells, cell lines, and biopsies. In still another embodiment, the at least one member of the diphthamide synthesis pathway is selected from the group consisting of DPH1, DPH2, DPH3, DPH4, DPH5, DPH6, and DPH7. In yet another embodiment, the reagent is selected from the group consisting of an antibody, an antibody derivative, and an antibody fragment which specifically binds to the at least one member of the diphthamide synthesis pathway. In another embodiment, the amount of the at least one member of the diphthamide synthesis pathway is assessed by detecting the presence in the sample of a transcribed polynucleotide or portion thereof. In still another embodiment, the transcribed polynucleotide is an mRNA or a cDNA. In yet another embodiment, the step of detecting further comprises amplifying the transcribed polynucleotide. In another embodiment, the transcribed polynucleotide is detected by identifying a nucleic acid that anneals with the at least one member of the diphthamide synthesis pathway nucleic acid, or a portion thereof, under stringent hybridization conditions.

In yet another aspect, a method of treating a subject afflicted with a condition that is resistant to an ADP-ribosylating toxin is provided. The method comprises administering to the subject a therapeutically effective amount of the ADP-ribosylating toxin in combination with a therapeutically effective amount of an agent that increases the copy number, amount, and/or activity of at least one member of the diphthamide synthesis pathway, thereby treating the subject afflicted with the condition that is resistant to the ADP-ribosylating toxin.

As described above, numerous embodiments are further provided that can be applied to any aspect of the present invention and/or combined with any other embodiment described herein. For example, in one embodiment, the agent is administered before, after, or concurrently with the ADP-ribosylating toxin. In another embodiment, the agent comprises a hypomethylating agent (HMA), optionally wherein the HMA dose is a sub-cytotoxic dose. In still another embodiment, the HMA is selected from the group consisting of azacitidine, decitabine, guadecitabine (SGI-110), zebularine, and MG98. In yet another embodiment, the agent comprises at least one member of the diphthamide synthesis pathway polypeptide molecule, or biologically active fragment thereof. In another embodiment, the at least one member of the diphthamide synthesis pathway polypeptide molecule is at least 80% identical over its full length to a polypeptide selected from Table 1, or a biologically active fragment thereof. In still another embodiment, the agent comprises a nucleic acid encoding at least one member of the diphthamide synthesis pathway polypeptide molecule, or biologically active fragment thereof. In yet another embodiment, the nucleic acid encoding the at least one member of the diphthamide synthesis pathway polypeptide molecule is at least 80% identical over its full length to a nucleic acid sequence selected from Table 1, or a portion thereof that encodes the biologically active fragment. In another embodiment, the nucleic acid is an mRNA or cDNA of at least one member of the diphthamide synthesis pathway. In still another embodiment, the at least one member of the diphthamide synthesis pathway is selected from the group consisting of DPH1, DPH2, DPH3, DPH4, DPH5, DPH6, and DPH7. In yet another embodiment, the condition is a cancer. In another embodiment, the agent reduces the number of proliferating cells in the cancer and/or reduces the volume or size of a tumor of the cancer. In another embodiment, the agent is administered in a pharmaceutically acceptable formulation.

In another embodiment, the method further comprises administering to the subject anti-cancer therapy other than ADP-ribosylating toxin as a single agent, optionally wherein the anti-cancer therapy is administered before, after, or concurrently with the agent and/or the ADP-ribosylating toxin. In still another embodiment, the anti-cancer therapy is selected from the group consisting of targeted therapy, chemotherapy, radiation therapy, and/or hormonal therapy. In yet another embodiment, the immunotherapy is cell-based. In another embodiment, the immunotherapy comprises a cancer vaccine and/or virus. In still another embodiment, the immunotherapy inhibits an immune checkpoint. In yet another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In another embodiment, the immune checkpoint is PD1, PD-L1, or CTLA-4.

As described above, numerous embodiments are further provided that can be applied to any aspect of the present invention and/or combined with any other embodiment described herein. For example, in one embodiment, the cancer is a CD123+ cancer. In another embodiment, the CD123+ cancer is selected from the group consisting of acute myeloid leukemia (AML), blastic plasmacytoid dendritic cell neoplasm (BPDCN), myelodysplastic syndromes (MDS), Myeloproliferative neoplasms (MPN), acute lymphoblastic leukemia (ALL), chronic myeloid leukemia (CML), chronic myelomonocytic leukemia (CMML), hairy cell leukemia, non-Hodgkin lymphoma (NHL), and Hodgkin lymphoma. In still another embodiment, the ADP-ribosylating toxin is an IL3-conjugated toxin. In yet another embodiment, the ADP-ribosylating toxin ribosylates eEF2. In another embodiment, the IL3-conjugated toxin is selected from the group consisting of IL3-conjugated diphtheria toxin (DT), IL3-conjugated Pseudomonas exotoxin (PE), and IL3-conjugated Cholix toxin (CT). In still another embodiment, the IL3-conjugated DT comprises a truncated DT or a full-length DT, optionally wherein the IL3-conjugated DT is SL-401. In yet another embodiment, the IL3 polypeptide is a full-length IL3. In another embodiment, the subject is an animal model of cancer (e.g., CD123+ cancer). In still another embodiment, the animal model is a mouse model. In yet another embodiment, the subject is a mammal. In another embodiment, the mammal is a mouse or a human. In still another embodiment, the mammal is a human. In another embodiment, the copy number, amount, and/or activity of at least one member of the diphthamide synthesis pathway is determined by detecting the ADP ribosylation by the toxin. In still another embodiment, the ADP ribosylation is detected by western blot, immunohistochemistry, microscopy, and/or flow cytometry. In yet another embodiment, the ADP ribosylation of eEF2 is detected. In another embodiment, the ADP-ribosylating toxin uses NAD+ as the source of ADP ribose. In still another embodiment, the NAD+ is conjugated with a label (e.g., biotin). In yet another embodiment, the ADP ribosylation is detected using streptavin-conjugated enzyme, dye, or fluorescent marker. In another embodiment, the detection of the ADP ribosylation further comprises staining the cells with additional markers. In still another embodiment, the ADP-ribosylating toxin conjugates to an antibody or a cytokine. In yet another embodiment, the ADP-ribosylating toxin inhibits the function of eEF2.

BRIEF DESCRIPTION OF FIGURES

FIG. 1A shows CD123 MFI and relative blast percentage in bone marrow plotted from another illustrative patient before, during, and after tagraxofusp treatment, which shows maintenance of CD123 at a stable level despite significant changes in the relative percentage of BPDCN blasts. FIG. 1B shows an illustrative example bone marrow aspirate flow cytometry from a patient with BPDCN before, during, and after tagraxofusp which shows the malignant CD4+CD123+ BPDCN blasts (green) and the CD4-CD123+ non-blast cells (purple). FIG. 1C shows mean fluorescence intensity (MFI) of CD123 staining as measured by flow cytometry in bone marrow aspirates plotted before, during, and after tagraxofusp treatment and annotated as malignant blasts of AML or BPDCN, or as putative non-blast CD123-positive cells. FIG. 1D shows the CD123 (IL3RA) dependency score (x-axis) plotted against IL3RA RNA expression level for cell lines in Project Achilles. AML cell lines are labeled orange and others are green. Negative dependency scores signify that a cell line has a relative growth disadvantage when CD123/IL3RA is depleted in a genome-wide pooled shRNA assay.

FIG. 4 shows confocal microscopy results 60 minutes after exposure of parental or tagraxofusp-resistant CAL1 cells to APC-tagged tagraxofusp (red), co-stained with CFSE (intracellular proteins, green) and Hoechst 33342 (DNA, blue).

FIG. 5 shows the results of MTT assays for viability of CAL1 and SHI1 parental and tagraxofusp-resistant subcultures after exposure to full-length diphtheria toxin (DT).

FIG. 6 shows that BH3 profiling of SHI1 and CAL1 parental and tagraxofusp-resistant (R1-2) subcultures revealed an increase in overall mitochondrial apoptotic priming in resistant cells after stimulation with a BIM BH3 peptide. In addition, more selective peptide treatment showed that resistant cells were more dependent upon BCL2 and/or BCL-XL (based on increased sensitivity to BAD and HRK peptides).

FIG. 14A and FIG. 14B shows the results of cytotoxicity assays of parental and tagraxofusp-resistant AML (THP1) and BPDCN (CAL1) cells after 2 weeks of pulsatile treatment with non-cytotoxic doses of azacitidine or vehicle, or with weekly exposure to 1 µg/ml tagraxofusp. FIG. 14C shows the results of quantitative RT-PCR for DPH1 expression in biological triplicates of the indicated cells.

FIG. 16A shows a volcano plot of differentially expressed genes between CAL1 (BPDCN) and SHI1 (AML) parental cells compared to three independent tagraxofusp-resistant subclones of each (n=6 parental and 6 resistant subclones). The log 2 fold change in expression in resistant compared to parental is plotted on the x-axis, and the –log P value on the y-axis. FIG. 16B shows the results of Western blotting for DPH1 and actin in parental and tagraxofusp-resistant CAL1 cells. FIG. 16C shows the log 2 fold change in gene expression associated with tagraxofusp resistance (as from FIG. 16A), which is plotted gene-by-gene versus the CRISPRi score for CTx-DTA resistance from Gilbert et al. (2014) *Cell* 159:647-661. Negative values represent lower expression in resistant cells, and positive values represent genes that conferred CTX-DTA resistance when their expression was inhibited. FIG. 16D shows the results of an in vitro ADP-ribosylation assay in the presence of tagraxofusp (top row) and Western blotting for eEF2, DPH1, and actin (bottom rows) for parental THP1 and tagraxofusp-resistant cells expressing a doxycycline-inducible full-length DPH1 cDNA, an N-terminal truncated enzymatically-inactive DPH1, or empty vector. FIG. 16E shows results of a viability assay after treatment with serial dilutions of tagraxofusp in parental and tagraxofusp-resistant cells expressing doxycycline inducible DPH1 or variants as in FIG. 16D. FIG. 16F shows the results of an in vitro ADP-ribosylation assay with or without tagraxofusp (top row) and Western blotting for eEF2, DPH1, and actin (bottom rows) for parental THP1 and tagraxofusp-resistant (R1-3) subclones.

FIG. 17A shows peripheral blood human CD45+CD123+ cells as a percent of the peripheral blood mononuclear cells in NSG mice engrafted with one of three BPDCN PDXs, treated at day 0 with 5 days of tagraxofusp at 100 µg/kg/d or vehicle. A subset of animals in each group were retreated with another five-day cycle at the time of progression (>2% in peripheral blood), and in PDX 3 a subset received a third cycle at the time of progression. FIG. 17B shows Kaplan-Meier progression-free survival (PFS) and overall survival (OS) curves for combined recipients of all three PDXs that received either one cycle of tagraxofusp (n=18) or vehicle (n=19). Curves are compared by log-rank test. FIG. 17C shows the representative peripheral blood flow cytometry showing no downregulation of CD123 expression on the surface of BPDCN PDXs at the time of progression after two cycles of tagraxofusp or vehicle. FIG. 17D shows the sections from mouse spleens harvested on day 7 after treatment with tagraxofusp or vehicle and stained with hematoxalin & eosin or the indicated antibodies in immunohistochemistry. FIG. 17E shows the peripheral blood disease burden measured by CD45+CD123+ flow cytometry and spleen size reduction in animals treated with tagraxofusp as compared to vehicle. FIG. 17F shows the disease burden measured by peripheral blood human CD45+CD123+ flow cytometry in animals engrafted with BPDCN PDX cells after two cycles of treatment (at days 0 and 30) with vehicle, azacitidine, tagraxofusp, or the combination of azacitidine and tagraxofusp. FIG. 17G shows the Kaplan-Meier overall survival (OS) curves from the time of treatment start for animals after treatments described in panel G (n=10 mice per arm). All curves are statistically significant compared to each other. Relevant P values include Log-rank P values: Vehicle vs AZA: P<0.0001; AZA vs SL-401: P<0.0001; SL-401 vs SL-401+AZA: P=0.009. FIG. 17H shows the log 2 fold change in blast gene expression by RNA-sequencing after tagraxofusp compared to prior to treatment (for AMLs from patients) or at progression after tagraxofusp compared to vehicle (for BPDCN PDXs) plotted against CTx-DTA resistance CRISPRi score (Gilbert et al. (2014) Cell 159:647-661) highlighting changes in the diphthamide synthesis pathway genes DPH1-7.

FIG. 20 shows single cell flow cytometric ADP-ribosylation assay for SL-401 dependent ADP ribosylation activity in leukemia cells. THP1 human AML cells are shown that are parental SL-401 sensitive or SL-401 resistant. The single cell flow based ADP-riboslyation assay was performed without and with present, as indicated, showing an SL-401-dependent ADP ribosylation activity that is diminished in the SL-401 resistant cells.

Figure 1A:
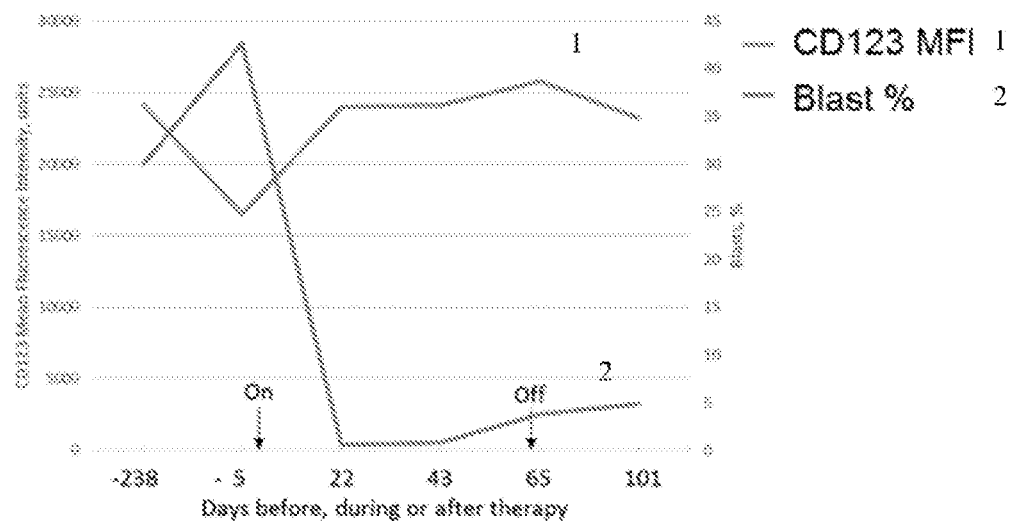
FIG. 1A-FIG. 1D show that CD123 is maintained on the surface of leukemia blasts during, after, and at relapse following treatment with SL-401.

For any figure showing a bar histogram, curve, or other data associated with a legend, the bars, curve, or other data presented from left to right for each indication correspond directly and in order to the boxes from top to bottom, or from left to right, of the legend.

DETAILED DESCRIPTION OF THE INVENTION

The present invention is based, at least in part, on the discovery that members of the diphthamide synthesis pathway and the output of the diphtamid synthesis pathway (e.g., DPH1 and/or ADP ribosylation of proteins like eEF2) are biomarkers that predict the resistence of cancers (e.g., CD123+ cancers, such as AML, MDS, BPDCN, and the like) to treatment with an ADP-ribosylating toxin (e.g., SL-401), and the resistance is reversible with a hypomethylating agent (e.g., azacitidine, decitabine, and the like). DNA methylation-mediated silencing of DPH1, the first enzyme in the diphthamide synthesis pathway, was found in AML and BPDCN cells resistant to tagraxofusp. For example, CD123+ AML and BPDCN cells that are resistant to SL-401 were determined to have downregulation of DPH1 and DPH1 loss was sufficient to mediate SL-401 resistance in such CD123+ cancers. Hypomethylating agents like azacitidine were determined herein to reverse SL-401 resistance in association with an increased level of DPH1. Using patient-derived xenografts in vivo it was found that the combination of tagraxofusp and azacitidine were more effective than either agent alone. Accordingly, the present invention relates, in part, to methods for identifying cells that are sensitive or resistant to an ADP ribosylating toxin (such as in vitro assays of cells lines, subject cells, and the like), and stratifying patients who are predicted to be resistant to ADP-ribosylating toxin, based upon a determination and analysis of members of the diphthamide synthesis pathway according to amount (e.g., copy number or level of expression) and/or activity, relative to a control. Such analyses can be used to perform a number of diagnostic and prognostic assays described herein either alone or in combination with useful therapeutic regimens (e.g., based on predictions of clinical response, subject survival or relapse, timing of adjuvant or neoadjuvant treatment, etc.). The present invention also relates, in part, to methods for treating a subject afflicted with a condition (e.g., cancer, such as a CD123+ cancer) that is resistant to an ADP-ribosylating toxin (e.g., IL3-conjugated toxin), such as by administering to the subject a therapeutically effective amount of the ADP-ribosylating toxin in combination with a therapeutically effective amount of an agent that increases the copy number, amount, and/or activity of at least one member of the diphthamide synthesis pathway.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors. The activity of the biomarker may be measured using methods or assays described herein. For example, the activity of the diphthamide synthesis pathway can be measured by detecting ADP ribosylation by a toxin of interest or its conjugates.

In one embodiment, NAD+ may be provided as the source for ADP ribosylation by the toxin or its conjugates. In another embodiment, NAD+ may be conjugated with a tag or a detectable label such as one or more of many well-known labels described herein like radiolabels, fluorescent labels, immunodetecable labels, and the like. In still another embodiment, NAD+ may be conjugated with biotin in a way that ADP ribsylated proteins using such NAD+ as the source are labeled with biotin.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CHi domains; (ii) a F(ab')$_2$ fragment, a bivalent fragment comprising two Fab fragments linked by a disulfide bridge at the hinge region; (iii) a Fd fragment consisting of the VH and CHi domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention that has been determined to be predictive of resistance to an ADP-ribosylating toxin (e.g., IL3-conjugated toxin) in a cell (e.g., a CD123+ cancer cell). Biomarkers can include, without limitation, nucleic acids (e.g., genomic nucleic acids and/or transcribed nucleic acids) and proteins, including those shown in Table 1, the Examples, and the Figures. Many biomarkers listed in Table 1 are also useful as therapeutic targets. In one embodiment, such targets are DPH1 or other members in the diphthamide synthesis pathway such as those described herein and/or shown in Table 1.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. As used herein, the term "cancer" includes premalignant as well as malignant cancers. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

Cancers that have grown into these structures or that have spread to distant lymph nodes or to other organs are considered unresectable, so treatments other than surgery are usually the best option.

In certain embodiments, the cancer is acute myeloblastic leukemia (AML). The AML can be adult AML, pediatric AML, or both. Acute myeloid leukemia (AML), also known as acute myelogenous leukemia, acute myeloblastic leukemia, acute granulocytic leukemia or acute nonlymphocytic leukemia, is a fast-growing form of cancer of the blood and bone marrow characterized by fatigue, shortness of breath, easy bruising and bleeding, and increased risk of infection. AML is the most common type of acute leukemia. It occurs when the bone marrow begins to make blasts, cells that have not yet completely matured. These blasts normally develop into white blood cells. However, in AML, these cells do not develop and are unable to ward off infections. In AML, the bone marrow may also make abnormal red blood cells and platelets. The number of these abnormal cells increases rapidly, and the abnormal (leukemia) cells begin to crowd out the normal white blood cells, red blood cells and platelets that the body needs. AML involves higher percentages of dedifferentiated and undifferentiated cells, including more blasts (myeloblasts, monoblasts, and megakaryoblasts) than other leukemias. AML subtypes are classified based on the cell type from which the leukemia develops. The eight common AML subtypes include myeloblastic (M0) on special analysis, myeloblastic (M1) without maturation, myeloblastic (M2) with maturation, promyeloctic (M3), myelomonocytic (M4), monocytic (M5), erythroleukemia (M6), and megakaryocytic. Generally, the standard of care of treating AML is initial treatment with chemotherapy aimed at inducing a remission, although additional chemotherapy or a hematopoietic stem cell transplant may follow.

The early signs of AML are often vague and nonspecific, and may be similar to those of influenza or other common illnesses. Some generalized symptoms include fever, fatigue, weight loss or loss of appetite, shortness of breath, anemia, easy bruising or bleeding, petechiae (flat, pin-head sized spots under the skin caused by bleeding), bone and joint pain, and persistent or frequent infections. Enlargement of the spleen may occur in AML, but it is typically mild and asymptomatic. Lymph node swelling is rare in AML, in contrast to acute lymphoblastic leukemia. The skin is involved about 10% of the time in the form of leukemia cutis. Rarely, Sweet's syndrome, a paraneoplastic inflammation of the skin, can occur with AML. Some people with AML may experience swelling of the gums because of infiltration of leukemic cells into the gum tissue. Rarely, the first sign of leukemia may be the development of a solid leukemic mass or tumor outside of the bone marrow, called a chloroma. The first clue to a diagnosis of AML is typically an abnormal result on a complete blood count. While an excess of abnormal white blood cells (leukocytosis) is a common finding, and leukemic blasts are sometimes seen, AML can also present with isolated decreases in platelets, red blood cells, or even with a low white blood cell count (leukopenia). While a presumptive diagnosis of AML can be made by examination of the peripheral blood smear when there are circulating leukemic blasts, a definitive diagnosis usually requires an adequate bone marrow aspiration and biopsy. Marrow or blood is examined under light microscopy, as well as flow cytometry, to diagnose the presence of leukemia, to differentiate AML from other types of leukemia (e.g. acute lymphoblastic leukemia—ALL), and to classify the subtype of disease. A sample of marrow or blood is typically also tested for chromosomal abnormalities by routine cytogenetics or fluorescent in situ hybridization. Genetic studies may also be performed to look for specific mutations in genes, such as FLT3, nucleophosmin, and KIT, which may influence the outcome of the disease. Cytochemical stains on blood and bone marrow smears are helpful in the distinction of AML from ALL, and in sub-classification of AML. The combination of a myeloperoxidase or Sudan black stain and a nonspecific esterase stain will provide the desired information in most cases. The myeloperoxidase or Sudan black reactions are most useful in establishing the identity of AML and distinguishing it from ALL. The nonspecific esterase stain is used to identify a monocytic component in AMLs and to distinguish a poorly differentiated monoblastic leukemia from ALL.

The two most commonly used classification schemata for AML are the older French-American-British (FAB) system and the newer World Health Organization (WHO) system. According to the widely used WHO criteria, the diagnosis of AML is established by demonstrating involvement of more than 20% of the blood and/or bone marrow by leukemic myeloblasts, except in the three best prognosis forms of AML with recurrent genetic abnormalities (t(8;21), inv(16), and t(15;17)) in which the presence of the genetic abnormality is diagnostic irrespective of blast percent. The French-American-British (FAB) classification involves a blast percentage of at least 30% in bone marrow (BM) or peripheral blood (PB) for the diagnosis of AML. AML must be carefully differentiated from "preleukemic" conditions such as myelodysplastic or myeloproliferative syndromes, which are treated differently. Fluorescent in situ hybridization performed on blood or bone marrow is often used for diagnosis since it can identify the chromosomal translocation [t(15;17)(q22;q12);] (PML/RARA fusion protein oncogene) that characterizes APL, which is different from AML.

In certain embodiments, the cancer is blastic plasmacytoid dendritic cell neoplasm (BPDCN). BPDCN is a rare and aggressive hematologic malignancy of the bone marrow and blood that can affect other organs such as the lymph nodes, spleen, central nervous system, and skin. It is categorized by the World Health Organization (4th edition, 2008) under acute myeloid leukemia (AML). In fact, skin lesions are present in most patients with BPDCN. These skin lesions are often a deep purple color, and patients often develop multiple lesions. More men than women are diagnosed with BPDCN (~3:1 ratio), and it is most common in patients age 60 years and older.

The diagnosis of BPDCN has evolved over time as clinical and pathologic technologies have improved. In addition to morphology, the appearance of skin and bone marrow cells under the microscope, immunohistochemistry and flow cytometry are now routinely used to determine whether the cells are positive for the classic triad of BPDCN: CD4, CD56, and CD123. A fourth marker, T-cell leukemia/lymphoma 1 (TCL1), has also been shown to be helpful in pinning down a diagnosis. Cytogenetics can also be used to aid in making a diagnosis. Chromosomal karyotype, flow cytometry, and molecular features may help to differentiate this condition from other, similar diagnoses, such as AML, ALL, and cutaneous T-cell lymphoma.

There is still no current consensus on the best first therapeutic treatment for patients with BPDCN. Most patients respond to intensive chemotherapy, but relapses are almost inevitable with median overall survival (OS) in the largest patient series ranging from 8 to 12 months except for patients who could benefit from allogenic hematopoietic stem cell transplantation (allo-HSCT). There is an urgent need for novel, targeted therapies to improve the treatment of BPDCN. CD123 appears to be overexpressed in essentially 100% of cases and is readily accessible for tumor targeting with the newer approaches. One example of a targeted therapy that is currently in clinical trials is diphtheria toxin DT388-IL3 (SL-401).

In certain embodiments, the cancer is myelodysplastic syndrome (MDS). There are approximately 20,000 new cases of myelodysplastic syndrome (MDS) each year in the U.S. Patients with myelodysplastic syndromes typically have low blood cell counts in at least one or more of red blood cells, white blood cells, and platelets. Upon examination, the bone marrow usually is found to be dysplastic or hyperplastic, meaning there are too many poorly functioning blood stem cells in the marrow. A small percentage of MDS patients have hypoplastic bone marrow, meaning there are too few blood stem cells in the marrow, which make the disease look similar to aplastic anemia. Nearly half of people with MDS have no symptoms at time of diagnosis. When signs and symptoms do occur they can include anemia, weakness, fatigue, headache, bruising, increased bleeding, rash, fevers, mouth sores and lingering illness. MDS occurs at an increasing frequency in older people, but it can occur in children too. In less than a third of patients, MDS progresses over time to become acute leukemia. The average age of diagnosis is 70 years old. Treatments for MDS may vary considerably, depending on the type of MDS, the history of the patient, and the age and ability to tolerate certain treatment regimens. Treatment options include supportive care, chemotherapy-related agents, and stem cell transplantation (which is typically used only in patients under 50). However, the remission rate for existing treatments in relatively low, and new therapies are needed.

Interleukin-3 (IL3) is a cytokine that supports the proliferation and differentiation of multi-potential and committed myeloid and lymphoid progenitors (Nitsche et al. (2003) *Stem Cells* 21: 236-244). Human interleukin-3 mediates its effects by binding to human IL3 receptor, which is a hetrodimeric structure and consists of an IL3 binding α-subunit (IL3Rα, CD123) and a common beta subunit (IL3Rβc or CD131). The α subunit is essential for ligand binding and confers specificity on the receptor. The β subunit is also shared by the granulocyte macrophage-colony stimulating factor (GM-CSF) and IL5 receptors, and is required for high affinity ligand binding and signal transduction. Binding of IL3 induces the heterodimerization of the α- and β-receptor subunits. The IL3 receptor is over-expressed, relative to certain normal hematopoietic cells, on multiple hematological cancers including AML, B cell acute lymphocytic leukemia (B-ALL), hairy cell leukemia, Hodgkin's disease, and certain aggressive non-Hodgkin's lymphomas (Munoz. et al. (2001) *Haematologica* 86:1261-1269; Riccioni. et al. (2005) *Leuk Lymphoma* 46:303-311; Testa. et al. (2004) *Leukemia* 18:219-226), as well as on the cancer stem cells of AML, myelodsyplastic syndrome (MDS), T cell ALL (T-ALL), and chronic myeloid leukemia (CML) (Jordan et al. (2000) *Leukemia* 14:1777-1784; Florian et al. (2006) *Leuk. Lymphoma* 47:207-222; Lhermitte et al. (2006) *Leukemia* 20:1908-1910; and Hogge et al. (2004) *Clin. Caner Res.* 12:1284-1291).

The term "CD123" refers to interleukin 3 receptor subunit alpha, an interleukin 3 specific subunit of the heterodimeric IL3 receptor. Interleukin-3 receptor alpha chain (IL3Rα or CD123) is strongly expressed on progenitor hematologic cancer cells, but is virtually undetectable on normal bone marrow cells. Over-expression of CD123 on AML blasts, CD34+ leukemic progenitors and LSCs relative to normal hematopoietic cells has been widely reported. The alpha subunit of the human IL3 receptor (IL3Rα or CD123) is strongly expressed in 45%-95% of AML, 40%-100% of B-cell lineage acute lymphocytic leukemia (B-ALL), and 85% of hairy cell leukemia (HCL) (Graf et al. (2004) *Eur. J. Haematol.* 72:89-106; Jordan et al. (2000) *Leukemia* 14:1777-1784; Munoz et al. (2001) *Haematologica* 86:1261-1269; Testa et al. (2002) *Blood* 100:2980-2988). The expression of IL3Rα is elevated in the primitive LSC population (CD34+/CD38−) in AML, chronic myelogenous leukemia (CML), and some other myeloid malignancies, but is not detectable in normal hematopoietic cells and progenitors (Florian et al. (2006) *Leuk. Lymphoma* 47:207-222; Jordan et al. (2000) *Leukemia* 14:1777-1784; Hogge et al. (2004) *Clin. Cancer Res.* 12:1284-1291. Overexpression of CD123 on AML cells confers a range of growth advantages over normal hematopoietic cells, with a large proportion of AML blasts reported to proliferate in culture in response to IL3. Moreover, high-level CD123 expression on AML cells has been correlated with the level of IL3-stimulated STAT-5 activation; the proportion of cycling cells; more primitive cell surface phenotypes; and resistance to apoptosis. Clinically, high CD 123 expression in AML is associated with lower survival duration, a lower complete remission rate and higher blast counts at diagnosis.

The term "CD123+ cancer" as used herein includes but is not limited to, a proliferative disease associated with expression of CD123 or condition associated with cells which express CD123 including, e.g., a cancer or malignancy or a precancerous condition such as a myelodysplasia, a myelodysplastic syndrome or a preleukemia, or an atypical or non-classical cancer. In one embodiment, a cancer associated with expression of CD123 is a hematological cancer. The hematological cancer includes but is not limited to AML, myelodysplastic syndrome, ALL, hairy cell leukemia, Prolymphocytic leukemia, Chronic myeloid leukemia, Hodgkin lymphoma, Blastic plasmacytoid dendritic cell neoplasm, and the like.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-off point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide immunotherapy that generally increases immune responses against the cancer. Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

As used herein, the term "hypomethylating agent" or "HMA" refers to an agent that reduces or reverses DNA methylation, either at a specific site (e g, a specific CpG island) or generally throughout a genome. In some embodiments, the DNA hypomethylating agent is a DNA methyltransferase inhibitor (DNMTi). The DNMTi may be a small molecule, a biologic, an antisense RNA, a small interfering RNA (siRNA), and combinations thereof. For example, the DNMTi may be a small molecule such as a nucleoside analog. As used herein, a "nucleoside analog" means a molecule that resembles a naturally occurring nucleoside, but which has a chemical or physical modification on the base and/or the sugar moiety, such as a different or additional side group. Such analogs are discussed in, e.g., Scheit, *Nucleotide Analogs* (John Wiley & Son, 1980) and Uhlman et al. (1990) *Chemical Reviews* 90:543-584. Non-limiting examples of DNMTi nucleoside analogs include azacitidine (5-azacytidine), decitabine (5-aza-2'-deoxycytidine), FdCyd (5-fluoro-2'-deoxycitidine), DHAC(5,6-dihydro-5-azacytidine), zebularine (1-(β-D-Ribofuranosyl)-1,2-dihydropyrimidin-2-one), fazarabine (1-β-D-arabinofuranosyl-5-azacytosine), 5-aza-2'-deoxycytidine-p-deoxyguanosine, fluorocyclopentenylcytosine, NPEOC-DAC(2-(p-nitrophenyl) ethoxycarbonyl-5-aza-2'-deoxycytidine), CP-4200, MG98, T-dCyd(4'-thio-2'-deoxycytidine), RX-3117 (fluorocyclopentenylcytosine) (Rexahn Pharmaceuticals Inc., Rockville, Md.), guadecitabine/SGI-110 (5-aza-2'-deoxycytidine-p-deoxyguanosine) (Astex Pharmaceuticals, Dublin, Calif.), 5-aza-T-dCyd (5-aza-4'-thio-2'-deoxycytidine), DNA methyltransferase inhibitors (IkerChem, San Sebastian, Spain), EGX-30P (EpiGenX Pharmaceuticals, Santa Barbara, Calif.), MeTase inhibitor (MethylGene, Montreal, Canada), prodrugs thereof, pharmaceutically acceptable salts thereof, and combinations thereof.

The DNMTi may also be a non-nucleoside analog. Non-limiting examples of DNTMi non-nucleoside analogs include hydralizine, disulfiram, procaine, procainamide, epigallocatechin gallate, psammaplins, RG108 ((S)-2-(1,3-dioxo-1,3-dihydro-isoindol-2-yl)-3-(1H-indol-3-yl)-propionic acid), antineoplaston AS2-1 (Burzynski Research Institute, Houston, Tex.), mithramycin A, nanaomycin A, SGI-1027, halomon, prodrugs thereof, pharmaceutically acceptable salts thereof, and combinations thereof. Furthermore, the DNMTi may be a biologic. Non-limiting examples of DNMTi biologies include CC-014 (CellCentric, Cambridge, UK), CC-034 (CellCentric), and combinations thereof.

Additionally, the DNMTi may be an antisense RNA. Non-limiting examples of DNTMi antisense RNA include MG-98 (MethylGene, Montreal, Canada).

Additional examples of DNMTi are described in PCT/US2012/060663 and EP 3207932, which are incorporated herein by references.

The term "diphthamide synthesis pathway" or "diphthamide biosynthesis pathway" refers to a posttranslational modification pathway that leads to diphthamide modification of proteins, such as the eEF2 protein. For example, eukaryotic translation elongation factor 2 (eEF2) is a highly conserved protein and essential for protein biosynthesis. The diphthamide modification at His715 of human eEF2 (or at the corresponding position in other species) is conserved in all eukaryotes and in archaeal counterparts. It is generated by proteins that are encoded by seven genes. Proteins encoded by diphthamide biosynthesis protein 1 (DPH1), DPH2, DPH3, and DPH4 (DNAJC24) attach a 3-amino-3-carboxypropyl (ACP) group to eEF2. This intermediate is converted by the methyl-transferase DPH5 to diphthine, which is subsequently amidated to diphthamide by DPH6 and DPH7. Diphthamide-modified eEF2 is the target of ADP ribosylating toxins, including *pseudomonas* exotoxin A (PE) and diphtheria toxin (DT). These bacterial proteins enter cells and catalyze ADP ribosylation of diphthamide using nicotinamide adenine dinucleotide (NAD) as substrate. This inactivates eEF2, arrests protein synthesis, and kills the cell. "Diphthamide synthesis pathway nucleic acids and proteins" refer to nucleic acids and proteins, respectively of the diphthamide synthesis pathway enzymes, which are provided in the examples and include, for example, diphthamide biosynthesis 1 (DPH1), diphthamide biosynthesis 2 (DPH2), diphthamide biosynthesis 3 (DPH3), diphthamide biosynthesis 4 (DPH4), diphthamide biosynthesis 5 (DPH5), diphthamide biosynthesis 6 (DPH6), and diphthamide biosynthesis 7 (DPH7). One or more of these enzymes are useful as biomarkers diagnostic, prognostic, and/or predictive of response to ADP-ribosylating toxin (e.g., IL3-conjugated toxin) as described herein.

As used herein, the term "DPH1" refers to diphthamide biosynthesis 1, an enzyme involved in the biosynthesis of diphthamide, a modified histidine found only in elongation factor-2 (eEF2). Diphthamide biosynthesis consists of three steps. In the first step, four enzymes (Dph1-Dph4) are necessary to transfer a 3-amino-3-carboxypropyl (ACP) group to H715. Next, the methyltransferase Dph5 is required to generate diphthine, which is then converted to diphthamide by Dph6 and Dph7 catalyzed amidation (Liu et al. (2004) *Mol Cell Biol* 24(21):9487-97). Diphthamide residues in eEF2 are targeted for ADP-ribosylation by diphtheria toxin and *Pseudomonas* exotoxin. Within cells, the toxins catalyze ADP-ribosylation of the diphthamide of eEF2 using NAD as ADP-ribosyl donor. The consequence of ADP-ribosylation of eEF2 is an arrest of protein translation and cell death. Defects in DPH1 have been associated with both ovarian cancer and autosomal recessive intellectual disability with short stature, craniofacial, and ectodermal anomalies. When overexpressed, DPH1 suppresses colony formation ability and growth rate of ovarian cancer cells. DPH1 also acts as a tumor suppressor in lung and breast cancers. In addition, DPH1 plays a role in embryonic growth, organogenesis and postnatal survival. Diseases associated with DPH1 include developmental delay with short stature, dysmorphic features, sparse hair syndrome, and craniofacial dysplasia-short stature-ectodermal anomalies-intellectual disability syndrome. DPH1-related pathways include metabolism of proteins, gamma carboxylation, hypusine formation and arylsulfatase activation.

The term "DPH2" refers to Diphthamide Biosynthesis Protein 2, one of two human genes similar to the yeast gene dph2. The yeast gene was identified by its ability to complement a diphthamide mutant strain, and thus functions in diphthamide biosynthesis. Diphthamide is a post-translationally modified histidine residue present in elongation factor 2 (EF2) that is the target of diphtheria toxin ADP-ribosylation. DPH2 is required for the first step in the synthesis of diphthamide, a post-translational modification of histidine which occurs in translation elongation factor 2 (EEF2).

The term "DPH3" refers to Diphthamide Biosynthesis Protein 3, a CSL zinc finger-containing protein that is required for dipthamide biosynthesis. The encoded protein is necessary for the initial step in the modification of a histidine residue in elongation factor-2 to diphthamide. This modified residue is a target for ADP ribosylation by the bacterial toxins diphtheria toxin and Pseudomonas exotoxin A. DPH3 is essential for the first step in the synthesis of diphthamide, a post-translational modification of histidine which occurs in elongation factor 2 (EEF2) and which can be ADP-ribosylated by diphtheria toxin and by Pseudomonas exotoxin A (Eta). Down-regulation of DPH3 increases extracellular release of proteoglycans, indicating a possible role in the secretion process. DPH3 stimulates binding of GNEFR to SEC5.

The term "DPH4" refers to Diphthamide Biosynthesis Protein 4, one of several enzymes involved in synthesis of diphthamide in EEF2. DPH4 stimulates the ATPase activity of several Hsp70-type chaperones. This ability is enhanced by iron-binding. The iron-bound form is redox-active and can function as electron carrier. DPH4 plays a role in the diphthamide biosynthesis, a post-translational modification of histidine which occurs in translation elongation factor 2 (EEF2) which can be ADP-ribosylated by diphtheria toxin and by Pseudomonas exotoxin A (Eta).

The term "DPH5" refers to Diphthamide Biosynthesis Protein 5, a component of the diphthamide synthesis pathway. Diphthamide is a post-translationally modified histidine residue found only on translation elongation factor 2. It is conserved from archaebacteria to humans, and is targeted by diphtheria toxin and Pseudomonas exotoxin A to halt cellular protein synthesis. The yeast and Chinese hamster homologs of this protein catalyze the trimethylation of the histidine residue on elongation factor 2, resulting in a diphthine moiety that is subsequently amidated to yield diphthamide. DPH5 is a S-adenosyl-L-methionine-dependent methyltransferase that catalyzes four methylations of the modified target histidine residue in translation elongation factor 2 (EF-2), to form an intermediate called diphthine methyl ester. The four successive methylation reactions represent the second step of diphthamide biosynthesis.

The term "DPH6" refers to Diphthamide Biosynthesis Protein 6, an amidase that catalyzes the last step of diphthamide biosynthesis using ammonium and ATP. DPH6 is one of the serveral enzymes in the Diphthamide biosynthesis pathway which converts an L-histidine residue in the translation elongation factor (EEF2) to diphthamide.

The term "DPH7" refers to Diphthamide Biosynthesis Protein 7. DPH7 contains a WD-40 domain, and is involved in diphthamide biosynthesis. A similar protein in yeast functions as a methylesterase, converting methylated diphthine to diphthine, which can then undergo amidation to produce diphthamide. DPH7 catalyzes the demethylation of diphthine methyl ester to form diphthine, an intermediate diphthamide biosynthesis, a post-translational modification of histidine which occurs in translation elongation factor 2 (EEF2) which can be ADP-ribosylated by diphtheria toxin and by Pseudomonas exotoxin A (Eta).

The term "expression signature" or "signature" refers to a group of two or more coordinately expressed biomarkers. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "IL3" refers to proteins having amino acid sequences which are substantially similar to the native Interleukin-3 amino acid sequences and which are biologically active in that they are capable of binding to IL3 receptors, transducing a biological signal initiated by binding to IL3 receptors, or cross-reacting with anti-IL3 antibodies raised against IL3. In some embodiments, an IL3 polypeptide is at least 50%, at least 65%, at least 70%, at least 75%, at least 80%, at least 85%, at least 90%, or at least 95% identical to a native IL3 amino acid sequence (e.g., a native human IL3 amino acid sequence). The IL3 polypeptide may be from any species. The nucleotide and/or amino acid sequences of IL3 polypeptides can be found in the literature or public databases, or the nucleotide and/or amino acid sequences can be determined using cloning and sequencing techniques known to one of skill in the art. In some embodiments, the IL3 is a mammalian IL3. In a preferred embodiment, an IL3 polypeptide is human IL3, an analog, derivative, or a fragment thereof. The amino acid sequence of human IL3 can be found in the GenBank database (e.g., Accession No. AAC08706). The term "IL3" also includes analogs or variants of IL3 molecules which exhibit at least some biological activity in common with native IL3. Exemplary analogs or variants of IL3 are disclosed in EP Publ. No. 282,185 and PCT/AU1992/000535.

The term "IL3-conjugated toxin" of the present invention comprises the full-length, mature (lacking the signal peptide) interleukin-3 protein (IL3), or a portion, analog or derivative thereof that binds to the interleukin-3 receptor (e.g., CD123) or a subunit thereof expressed on a cell surface, conjugated through a recombinant technology or through chemical (covalent) bond to a toxin that inhibits eEF2 (e.g., ribosylates eEF2), or a portion, analog or derivative thereof, which toxin preferably lacks the native cell binding domain. Fragments, analogs, and derivatives of IL3 can be used in the "IL3-conjugated toxin" provided that when fused to toxin portion of the conjugate, such fragments, analogs and derivatives maintain the ability to bind a subunit of the IL3 receptor or the native IL3 receptor expressed on the surface of a cell. Preferably, the binding kinetics of the fragments, analogs or derivatives remain the same or vary only by not more than 25%. An exemplary conjugate comprising a modified IL3 with amino acid substitution K116W in human IL3. Another exemplary conjugate comprises human IL3 missing amino acids 125-133. Both of these conjugates with mutant IL3 sequences exhibit enhanced binding to the IL3 receptor and exhibit greater cytotoxicity against leukemia cells. (For non-limiting examples of conjugates, see Liu et al. (2004) *Exp. Hematol.* 32:277-281; Hogge et al. (2006) *Clin. Cancer Res.* 12:1284-1291; Testa et al. (2005) *Blood* 106:2527-2529; and Klein et al. (2001) *Biochem. Biophys. Res. Comm.* 288:1244-1249).

One such "IL3-conjugated toxin" is the DT388 IL3 conjugate (SL-401). DT388IL3 (SL-401) was constructed by fusing the gene encoding the catalytic and translocation domains of DT (amino acids 1-388) via a Met-His linker with human IL3 (Frankel et al. (2000) *Leukemia* 14: 576-585). DT388IL3 has been shown to be potently and selectively cytotoxic to IL3R (e.g., CD123) positive AML cell lines and primary leukemia cells derived from patients (Frankel et al. (2000) *Protein Eng.* 13: 575-581; Alexander et al. (2001) *Leuk. Res.* 25: 875-881; Alexander et al. (2000) *Bioconj. Chem.* 11:564-568; Feuring-Buske et al. (2002) *Cancer Res.* 62: 1730-1736). Additional studies found that high affinity variants of the DT388IL3 compound, named DT388-IL3[K116W] (based on the mutation of a lysine at amino acid 116 to tryptophan) and DT388IL3[Δ125-133] (based on a deletion of amino acids 125-133 in the IL3 domain), had increased potency against leukemia cells (Hogge et al. (2006) *Clin. Cancer Res.* 12: 1284-1291; Testa et al. (2005) *Blood* 106: 2527-2529). DT388IL3 also demonstrated in vivo anti-tumor efficacy in certain mouse models of human leukemia (Black et al. (2003) *Leukemia* 17: 155-159; Feuring-Buske et al. (2002) *Cancer Res.* 62: 1730-1736; and Hogge et al. (2004) *LeukRes.* 28: 1221-1226). Safety was shown at therapeutically active doses in rodents and monkeys (Black et al. (2003) *Leukemia* 17: 155-159; Cohen et al. (2004) *LeukLymph* 45: 1647-1656; Cohen et al. (2005) *Cancer Immunol. Immunother.* 54: 799-806). Clinical batches of DT388IL3 were prepared and an IND obtained (BB IND #11314) (Urieto et al. (2004) *Protein Exp. Purif* 33: 123-133). Additional examples are described in US Publ. No. 2008/0138313, which is incorporated herein by reference.

An exemplary amino acid sequence for SL-401 is provided below:

MGADDVVDSSKSFVMENFSSYHGTKPGYVDSIQKGIQKPKSGTQGNYD

DDWKGFYSTDNKYDAAGYSVDNENPLSGKAGGVVKVTYPGLTKVLALKV

DNAETIKKELGLSLTEPLMEQVGTEEFIKRFGDGASRVVLSLPFAEGSS

SVEYINNWEQAKALSVELEINFETRGKRGQDAMYEYMAQACAGNRVRRS

VGSSLSCINLDWDVIRDKTKTKIESLKEHGPIKNK1VISESPNKTVSEE

KAKQYLEEFHQTALEHPELSELKTVTGTNPVFAGANYAAWAVNVAQVID

SETADNLEKTTAALSILPGIGSVMGIADGAVHHNTEEIVAQSIALSSLM

VAQAIPLVGELVDIGFAAYNFVESIINLFQVVHNSYNRPAYSPGHKTRP

*HM*APMTQTTSLKTSWVNCSNMIDEIITHLKQPPLPLLDFNNLNGEDQDI

LMENNLRRPNLEAFNRAVKSLQNASAIESILKNLLPCLPLATAAPTRHP

IHIKDGDWNEFRRKLTFYLKTLENAQAQQTTLSLAW
(Bold: Diphtheria toxin fragment 1-388; Italics: His-Met linker; Normal: human IL-3)

As used herein, the terms "toxin" refers to any cytotoxic or otherwise anticellular agent that has such a killing or suppressive property. The term "toxin" includes, but is not limited to abrin, anthrax toxin, bryodin, botulinum toxin, cholix toxin ("CT"), cholera exotoxin ("CET"), diphtheria toxin ("DT"), *Escherichia coli* labile toxin, gelonin, modeccin, momordin, mistletoe lectin, *Pseudomonas* exotoxin (or "PE"), pertussis toxin, pokeweed antiviral protein, ricin, shiga toxin, saporin, trichosanthin, viscumin, volkensin, or modified toxins thereof. Additional examples are described in U.S. Patent Publ. No. 2011/0288238, which is incorporated herein by reference. A subset of these toxins kill target cells by inhibiting protein biosynthesis. For example, bacterial toxins such as diphtheria toxin or *Pseudomonas* exotoxin inhibit protein synthesis by inactivating elongation factor 2 (eEF2). Plant toxins such as ricin, abrin, and bacterial toxin shiga toxin, inhibit protein synthesis by directly inactivating the ribosomes (Olsnes, S. & Phil, A. *Molecular action of toxins and viruses*, eds. Cohen, P. & vanHeyningen, S., Elsevier Biomedical Press, Amsterdam, 51-105, 1982).

The term "ADP-ribosylating toxin" refers to toxin that is capable of adding one or more ADP-ribose moieties to a protein. In some embodiments, the protein that is ADP-ribosylated is eEF2.

In some embodiments, the toxin is an ADP-ribosyltransferase. *Pseudomonas* exotoxin ("PE"), diphtheria toxin ("DT"), and cholix toxin ("CT") irreversibly ribosylate elongation factor 2 ("eEF-2") in eukaryotic cells, causing the death of affected cells by inhibiting their ability to synthesize proteins. Since eEF-2 is essential for protein synthesis in eukaryotic cells, inactivation of the eEF-2 in a eukaryotic cell causes death of the cell. The sequences and structure of PE, DT, and CT are well known in the art. ADP-ribosylating cytotoxins and variants thereof that find use are described, for example, in application PCT/US2009/046292, U.S. Patent Publ. No. 2009/0142341, U.S. Patent Publ. No. 2012/0276190, and U.S. Patent Publ. No. 2011/0144004, the disclosures of all of which are hereby incorporated herein by reference in their entirety for all purposes.

Diphtheria toxin can be produced by *Corynebacterium diphtheriae* as a 535 amino acid polypeptide with a molecular weight of approximately 58 kD (Greenfield et al. (1983) *Proc. Natl. Acad. Sci.* 80:6853-6857; Pastan et al. Annu. (1992) *Rev. Biochem.* 61:331-354; Collier et al. (1971) *J. Biol. Chem.* 246:1496-1503). It is secreted as a single-chain polypeptide consisting of 2 functional domains. The N-terminal domain (A-chain) contains the cytotoxic moiety whereas the C-terminal domain (B-chain) is responsible for binding to the cells and facilitates toxin endocytosis. Conversely, the mechanism of cytotoxicity for diphtheria toxin is based on ADP-ribosylation of EF-2 thereby blocking protein synthesis and producing cell death. The 2 functional domains in diphtheria toxin are linked by an arginine-rich peptide sequence as well as a disulphide bond. Once the diphtheria toxin is internalized into the cell, the arginine-rich peptide linker is cleaved by trypsin-like enzymes and the disulphide bond (Cys 186-201) is reduced. The cytotoxic domain is subsequently translocated into the cytosol substantially as described above for ricin and elicits ribosomal inhibition and cytotoxicity. Mutated forms of DT suitable for use in immunotoxins are known in the art. See, e.g., U.S. Pat. Nos. 5,208,021 and 5,352,447. Fragments, analogs and derivatives of diphtheria toxin can be useful in the present application.

In one embodiment, *Pseudomonas* exotoxin is a 66 kD single-chain toxin protein secreted by *Pseudomonas aeruginosa* with a similar mechanism of cytotoxicity to that of diphtheria toxin (Pastan et al. (1992) *Annu. Rev. Biochem.* 61:331-354; Ogata et al. (1992) *J. Biol. Chem.* 267:25396-25401; Vagil et al. (1977) *Infect. Immunol.* 16:353-361). *Pseudomonas* exotoxin consists of 3 conjoint functional domains. The first domain Ia (amino acids 1-252) is responsible for cell binding and toxin endocytosis, a second domain II (amino acids 253-364) is responsible for toxin translocation from the endocytic vesicle to the cytosol, and a third domain III (amino acids 400-613) is responsible for protein synthesis inhibition and cytotoxicity. After *Pseudomonas* exotoxin enters the cell, the liberation of the cytotoxic domain is effected by both proteolytic cleavage of a polypeptide sequence in the second domain (near Arg 279) and the reduction of the disulphide bond (Cys 265-287) in the endocytic vesicles. In essence, the overall pathway to cytotoxicity is analogous to diphtheria toxin with the exception that the toxin translocation domain in *Pseudomonas* exotoxin is structurally distinct.

The term *Pseudomonas* exotoxin ("PE") as used herein includes reference to forms of PE which have been modified but which retain cytotoxic function. Thus, the PE molecule can be truncated to provide a fragment of PE which is cytotoxic but which does not bind cells, as in the fragments known as PE38 and PE40, or can have mutations which reduce non-specific binding, as in the version called "PE4E", in which four residues are mutated to glutamic acid. Further, a portion of the PE sequence can be altered to increase toxicity, as in the form called "PE38 KDEL", in which the C-terminal sequence of native PE is altered, or the form of PE discussed herein, in which the arginine corresponding to position 490 of the native PE sequence is replaced by alanine, glycine, valine, leucine, or isoleucine.

The genes for diptheria toxin and *Pseudomonas* exotoxin have been cloned and sequenced, and the 3-dimensional structures of the toxin proteins have been elucidated and described (Columblatti, M. et al. (1986) *J. Biol. Chem.* 261:3030-3035; Allured et al. (1986) *Proc. Natl. Acad. Sci.* 83:1320-1324; Gray et al. (1984) *Proc. Natl. Acad. Sci.* 81:2645-2649; Greenfield et al. (1983) *Proc. Natl. Acad. Sci.* 80:6853-6857; Collier et al. (1982) *J. Biol. Chem.* 257:5283-5285).

As used herein, the term "Cholix toxin" or "CT" refers to a toxin expressed by some strains of *Vibrio cholerae* that do not cause cholera disease. According to the article reporting the discovery of the Cholix toxin (Jorgensen et al. (2008) *J Biol Chem.* 283(16):10671-10678), mature cholix toxin is a 70.7 kD, 634 residue protein, FIG. 9C of PCT/US2009/046292. The Jorgensen authors deposited in the NCBI Entrez Protein database a 642-residue sequence which consists of what they termed the full length cholix toxin A chain plus, at the N-terminus an additional 8 residues, consisting of a 6 histidine tag flanked by methionine residues, presumably introduced to facilitate expression and separation of the protein. The 642-residue sequence is available on-line in the Entrez Protein database under accession number 2Q5T_A and can be converted to the 634 amino acid sequence by simply deleting the first 8 amino acids of the deposited sequence. Mature CT has four domains: Domain Ia (amino acid residues 1-269), Domain II (amino acid residues 270-386), Domain Ib (amino acid residues 387-415), and Domain III (amino acid residues 417-634).

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a biological function, such as the function of a protein, is inhibited if it is decreased as compared to a reference state, such as a control like a wild-type state. For example, activity of a mutant eEF2 or an eEF2 that is contacted with an eEF2 inhibitor is inhibited or deficient if the activity is decreased due to the mutation and/or contact with the inhibitor, in comparison to the wild-type eEF2 and/or the eEF2 not contacted with the inhibitor. Such inhibition or deficiency can be induced, such as by application of agent at a particular time and/or place, or can be constitutive, such as by a heritable mutation. Such inhibition or deficiency can also be partial or complete (e.g., essentially no measurable activity in comparison to a reference state, such as a control like a wild-type state). Essentially complete inhibition or deficiency is referred to as blocked.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as a PD-1 pathway inhibitor therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or underactivity, emergence, expression, growth, remission, recurrence or resistance of tumors before, during or after therapy, for determining the likelihood of response of a cancer to an ADP-ribosylating toxin. Such predictive use of the biomarker may be confirmed by, e.g., (1) increased or decreased copy number (e.g., by FISH, FISH plus SKY, single-molecule sequencing, e.g., as described in the art at least at Augustin et al. (2001) *J. Biotechnol.*, 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular ADP-ribosylating toxin treatment or non-ADP-ribosylating toxin treatment or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia. In one embodiment, a metaplasia is a pre-malignant lesion.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., CD123+ cancers), development of one or more clinical factors, or recovery from the disease.

The term "response to anti-cancer therapy" relates to any response of the hyperproliferative disorder (e.g., cancer) to an anti-cancer agent, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., an ADP-ribosylating toxin, such as SL-401, in combination with a hypomethylating agent) is able to produce a significant decrease in tumor volume at a level of statistical significance (e.g., $p<0.05$) when compared to tumor volume of untreated tumor in the circumstance where the primary cancer therapy (e.g., an ADP-ribosylating toxin such as SL-401) alone is unable to produce a statistically significant decrease in tumor volume compared to tumor volume of untreated tumor. This generally applies to tumor volume measurements made at a time when the untreated tumor is growing log rhythmically. In some mebodiments, the combination allows for a dose defined as a "sub-cytotoxic dose" of one or more of the agents of the combination. A "sub-cytotoxic dose" is a dose that does not necessarily induce cell death (CD) but still has a negative effect on cell growth. For example, a sub-cytotoxic dose of a hypomethylating agent is a dose that does not induce cell deathper se but epigenetically modifies methylation such that DPH1 expression is increased. Such sub-cytotoxic doses of hypomethylating agents such as azacitidine and decitabine are well-known in the art (see, for example, the package inserts of the FDA-approved compounds).

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G et al. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., chemotherapeutic, and/or radiation therapy). In some embodiments, normal cells are not affected to an extent that causes the normal cells to be unduly injured by the ADP-ribosylating toxin or non-ADP-ribosylating toxin treatment. An increased sensitivity or a reduced sensitivity to a therapeutic treatment is measured according to a known method in the art for the particular treatment and methods described herein below, including, but not limited to, cell proliferative assays (Tanigawa, N et al. (9821) *Cancer Res* 42: 2159-2164), cell death assays (Weisenthal, L et al. (1984) *Cancer Res* 94: 161-173; Weisenthal, L et al. (1985) *Cancer Treat Rep* 69: 615-632; Weisenthal, L et al. Harwood Academic Publishers, 1993: 415-432; Weisenthal, L (1994) *Contrib Gynecol Obstet* 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anti-cancer agents (e.g., combination of ADP-ribosylating toxin with an agent that increases copy number, amount, and/or activity of at least one member of the diphthamide synthesis pathway) can be greater than the sum of the separate effects of the anticancer agents alone. In some embodiments, a cancer that is resistant to the ADP-ribosylating toxin is significantly or synergistically more responsive when treated with combination of ADP-ribosylating toxin with an agent that increases copy number, amount, and/or activity of at least one member of the diphthamide synthesis pathway, such as a SL-401 and azacitidine in combination.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a condition (e.g., cancer, such as CD123+ cancer). The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

In one embodiment, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 1) are well known in the art and readily available on publicly available databases, such as the National Center for Biotechnology Information (NCBI). For example, exemplary nucleic acid and amino acid sequences derived from publicly available sequence databases are provided below. It is to be noted that the terms described above can further be used to refer to any combination of features described herein regarding the biomarkers. For example, any combination of sequence composition, percentage identify, sequence length, domain structure, functional activity, etc. can be used to describe a biomarker of the present invention.

Human DPH1 nucleic acid (NM_001383, NM_001346574, NM_001346575, NM_001346576) and amino acid (NP_001374, NP_001333503, NP_001333504, NP_001333505) sequences are publicly available on the GenBank database maintained by the U.S. National Center for Biotechnology Information. Nucleic acid and polypeptide sequences of DPH1 orthologs in species other than humans are also well known and include, for example, mouse DPH1 (NM_144491, NP_652762), chimpanzee DPH1 (XM_511255, XP_511255), monkey DPH1 (XM_015118202, XP_014973688), frog DPH1 (XM_012956575, XP_012812029), cattle DPH1 (NM_001076899, NP_001070367), rat DPH1 (NM_001105809, NP_001099279), and chicken DPH1 (NM_001030716, NP_001025887). Representative sequences of DPH1 orthologs are presented below in Table 1.

DPH1 agents, including antibodies, nucleic acids, and the like are well-known in the art. Anti-DPH1 antibodies suitable for detecting DPH1 protein are well-known in the art and include, for example, antibodies AP51311PU-N and TA340016 (Origene), antibodies NBP1-56693 and NBP1-57711 (Novus Biologicals, Littleton, Colo.), antibody Cat #30-785 (ProSci, Poway, Calif.), etc. In addition, reagents are well-known for detecting DPH1. Moreover, multiple siRNA, shRNA, CRISPR constructs for reducing DPH1 expression can be found in the commercial product lists of the above-referenced companies, such as siRNA products #sc-62727 and sc-62728 and CRISPR product #sc-410763 from Santa Cruz Biotechnology, RNAi products SR301256 and TR313385, and CRISPR products KN221955 and KN304770 (Origene), and multiple CRISPR products from GenScript (Piscataway, N.J.). It is to be noted that the term can further be used to refer to any combination of features described herein regarding DPH1 molecules. For example, any combination of sequence composition, percentage identify, sequence length, domain structure, functional activity, etc. can be used to describe an DPH1 molecule of the present invention.

Human DPH2 nucleic acid (NM_001384.4, NM_001039589.1, NM_001319165.1, NM_001319166.1, NM_001319167.1, NM_001319168.1, NM_001319169.1, NM_001319170.1, NM_001319171.1) and amino acid (NP_001375.2, NP_001034678.1, NP_001306094.1, NP_001306097.1, NP_001306095.1. NP_001306096.1 and NP_001306099.1, NP_001306098.1, and NP_001306100.1) sequences are publicly available on the GenBank database maintained by the U.S. National Center for Biotechnology Information. Nucleic acid and polypeptide sequences of DPH2 orthologs in species other than humans are also well known and include, for example, mouse DPH2 (NM_026344.3, NP_080620.1), dog DPH2 (XM_003432004.4 and XP_003432052.1, XM_532611.6 and XP_532611.2, and XM_022428050.1 and XP_022283758.1), frog DPH2 (XKM 0029315824 and NP_0029316>281), cattle DPH2 (XN_0249897751 and XP_024845543.1), rat DPH2 (NM_001015007.1 and NP_001015007.1), and chicken DPH2 (NM_001006538.1 and NP_001006538.1). Representative sequences of DPH2 orthologs are presented below in Table 1.

Anti-DPH2 antibodies suitable for detecting DPH2 protein are well-known in the art and include, for example, antibody TA340018 (Origene), antibodies NBP2-03732 and NBP2-46475 (Novus Biologicals, Littleton, Colo.), antibody Cat #PA5-14207 (ThermoFisher Scientific), antibody Cat #30-786 (ProSci, Poway, Calif.), etc. In addition, reagents are well-known for detecting DPH2. Moreover, multiple siRNA, shRNA, CRISPR constructs for reducing DPH2 expression can be found in the commercial product lists of the above-referenced companies, such as siRNA products #sc-78577 and sc-143158 and CRISPR product #sc-409607 from Santa Cruz Biotechnology, RNAi products SR415760 and TL316520, and CRISPR product KN304771 (Origene), and multiple CRISPR products from GenScript (Piscataway, N.J.). It is to be noted that the term can further be used to refer to any combination of features described herein regarding DPH2 molecules. For example, any combination of sequence composition, percentage identify, sequence length, domain structure, functional activity, etc. can be used to describe a DPH2 molecule encompassed by the present invention.

Human DPH3 nucleic acid (NM_206831.2 and NM_001047434.2) and amino acid (NP_996662.1 and NP_001040899.1) sequences are publicly available on the GenBank database maintained by the U.S. National Center for Biotechnology Information. Nucleic acid and polypeptide sequences of DPH3 orthologs in species other than humans are also well known and include, for example, mouse DPH3 (NM_172254.4 and NP_758458.1, NM_001047433.2 and NP_001271275.1, NM_001284346.1 and NP_001040898.1), chimpanzee DPH3 (XM_6312.4 and XP_516312.2, XM_003309649.4 and XP_003309697.1), monkey DPH3 (XM_015140840.1 and XP_014996326.1), dog DPH3 (XM_848056.5 and XP_8531491), frog DPH3 (NM_001016157.2 and NP_001016157.1), cattle DPH3 (NM_001113299.2 and NP_001106770.1, NM_001303541.1 and NP_001290470.1), rat DPH3 (NM_001134850.1 and NP_001128322.1), and chicken DPH3 (NM_001302106.1 and NP_001289035.1). Representative sequences of DPH3 orthologs are presented below in Table 1.

Anti-DPH3 antibodies suitable for detecting DPH3 protein are well-known in the art and include, for example, antibody NBP1-84276 (Novus Biologicals, Littleton, Colo.), antibody Cat #PA5-14207 (ThermoFisher Scientific), etc. In addition, reagents are well-known for detecting DPH3. Moreover, multiple siRNA, shRNA, CRISPR constructs for reducing DPH3 expression can be found in the commercial product lists of the above-referenced companies, such as siRNA products #sc-63235 and sc-106708 and CRISPR product #sc-416814 from Santa Cruz Biotechnology, RNAi products SR317235 and TR318290, and CRISPR products KN204203 and KN304772 (Origene), and multiple CRISPR products from GenScript (Piscataway, N.J.). It is to be noted that the term can further be used to refer to any combination of features described herein regarding DPH3 molecules. For example, any combination of sequence composition, percentage identify, sequence length, domain structure, functional activity, etc. can be used to describe a DPH3 molecule encompassed by the present invention.

Human DPH4 nucleic acid (NM_181706.4) and amino acid (NP_859057.4) sequences are publicly available on the GenBank database maintained by the U.S. National Center for Biotechnology Information. Nucleic acid and polypeptide sequences of DPH4 orthologs in species other than humans are also well known and include, for example, mouse DPH4 (NM_026992.3 and NP_081268.1), chimpanzee DPH4 (XM_001141859.4 and XP_001141859.1), monkey DPH4 (NM_001261745.1 and NP_001248674.1), frog DPH4 (NM_001044478.2 and NP_001037943.2), cattle DPH4 (NM_001078102.1 and NP_001071570.1), rat DPH4 (NM_001191853.1 and NP_001178782.1), and chicken DPH4 (NM_001190896.1 and NP_001177825.1). Representative sequences of DPH4 orthologs are presented below in Table 1.

Anti-DPH4 antibodies suitable for detecting DPH4 protein are well-known in the art and include, for example, antibody AP51294PU-N (Origene), antibodies NBP1-87969 and NBP1-87968 (Novus Biologicals, Littleton, Colo.), antibody ab75210 (AbCam, Cambridge, Mass.), antibody Cat #PA5-14207 (ThermoFisher Scientific), antibody Cat #58-326 (ProSci, Poway, Calif.), etc. In addition, reagents are well-known for detecting DPH4. Moreover, multiple siRNA, shRNA, CRISPR constructs for reducing DPH4 expression can be found in the commercial product lists of the above-referenced companies, such as siRNA products #sc-63237 and sc-63238 and CRISPR product #sc-417461 from Santa Cruz Biotechnology, RNAi products SR314706 and TR300354, and CRISPR products KN304691 and KN209088 (Origene), and multiple CRISPR products from GenScript (Piscataway, N.J.). It is to be noted that the term can further be used to refer to any combination of features described herein regarding DPH4 molecules. For example, any combination of sequence composition, percentage identify, sequence length, domain structure, functional activity, etc. can be used to describe a DPH4 molecule encompassed by the present invention.

Human DPH5 nucleic acid (NM_001077394.1, NM_001077395.1, NM_015958.2) and amino acid (NP_057042.2, NP_001070863.1) sequences are publicly available on the GenBank database maintained by the U.S. National Center for Biotechnology Information. Nucleic acid and polypeptide sequences of DPH5 orthologs in species other than humans are also well known and include, for example, mouse DPH5 (NM_027193.2 and NP_0814692), chimpanzee DPH5 (XM_009426488.2 and XP_009424763.1, XM_009426474.2 and XP_009424749.1, XM_009426449.2 and XP_009424724.1, XM_513597.5 and XP_513597.1, XM_001137561.4 and XP_001137561.1, XM_009426482.3 and XP_009424757.1, XM_009426468.3 and XP_009424743.1, XM_009426443.3 and XP_009424718.1, XM_009426433.3 and XP_009424708.1, XM_009426459.3 and XP_009424734.1, XM_009426453.3 and XP_009424728.1, XM_009426409.3 and XP_009424684.1, XM_024347392.1 and XP_0242031601, XM_016923353.1 and XP_016778842.1), dog DPH5 (XM_005621859.3 and XP_005621916.1, XM_014114802.2 and XP_013970277.1), monkey DPH5 (NM_001257957.1 and NP_001244886.1), frog DPH5 (NM_001005058.1 and NP_00100058.1), cattle DPH5 (NM_001076821.1 and NP_001070289.1), rat DPH5 (NM_001017449.1 and NP_001017449.1), and chicken DPH5 (XM_422306.5 and XP_422306.1, XM_025153094.1 and XP_025008862.1). Representative sequences of DPH5 orthologs are presented below in Table 1.

Anti-DPH5 antibodies suitable for detecting DPH5 protein are well-known in the art and include, for example, antibodies NBP2-13934 and H00051611-B01P (Novus Biologicals, Littleton, Colo.), ab69347 (AbCam, Cambridge, Mass.), antibody Cat #PA5-14207 (ThermoFisher Scientific), etc. In addition, reagents are well-known for detecting DPH5. Moreover, multiple siRNA, shRNA, CRISPR constructs for reducing DPH5 expression can be found in the commercial product lists of the above-referenced companies, such as siRNA products #sc-88546 and sc-103315 and CRISPR product #sc-412225 from Santa Cruz Biotechnology, RNAi products SR309874 and TL306987V, and CRISPR products KN304773 and KN208759 (Origene), and multiple CRISPR products from GenScript (Piscataway, N.J.). It is to be noted that the term can further be used to refer to any combination of features described herein regarding DPH5 molecules. For example, any combination of sequence composition, percentage identify, sequence length, domain structure, functional activity, etc. can be used to describe a DPH5 molecule encompassed by the present invention.

Human DPH6 nucleic acid (NM_080650.3, NM_001141972.1) and amino acid (NP_542381.1, NP_001135444.1) sequences are publicly available on the GenBank database maintained by the U.S. National Center for Biotechnology Information. Nucleic acid and polypeptide sequences of DPH6 orthologs in species other than humans are also well known and include, for example, mouse DPH6 (NM_001356438.1 and NP_001343367.1, NM_025675.5 and NP_079951.1, NM_001356439.1 and NP_001343368.1), chimpanzee DPH6 (NM_001280404.1 and NP_001267333.1), monkey DPH6 (NM_001266595.1 and NP_001253524.1), dog DPH6 (XM_022412512.1 and XP_022268220.1), frog DPH6 (XM_018096829.1 and XP_017952318.1, XM_002932836.4 and XP_002932882.1, XM_004917268.3 and XP_004917325.1), cattle DPH6 (NM_001077016.1 and NP_001070484.1), rat DPH6 (NM_001014181.1 and NP_001014203.1), and chicken DPH6 (XM_025150733.1 and XP_025006501.1, XM_025150729.1 and XP_025006497.1, XM_025150731.1 and XP_025006499.1, XM_025150732.1 and XP_025006500.1, XM_025150730.1 and XP_025006498.1, XM_025150734.1 and XP_025006502.1, XM_015287348.2 and XP_015142834.2, XM_025150735.1 and XP_025006503.1, XM_015287349.2 and XP_015142835.2, XM_015287351.2 and XP_015142837.2, XM_015287350.2 and XP_015142836.1). Representative sequences of DPH6 orthologs are presented below in Table 1.

Anti-DPH6 antibodies suitable for detecting DPH6 protein are well-known in the art and include, for example, antibodies NBP1-91691 and NBP2-56252 (Novus Biologicals, Littleton, Colo.), antibody Cat #PA5-14207 (ThermoFisher Scientific), etc. In addition, reagents are well-known for detecting DPH6. Moreover, multiple siRNA, shRNA, CRISPR constructs for reducing DPH6 expression can be found in the commercial product lists of the above-referenced companies, such as CRISPR product #sc-413817 from Santa Cruz Biotechnology, RNAi products SR313945 and TL306486V, and CRISPR products KN304774 and KN209471 (Origene), and multiple CRISPR products from GenScript (Piscataway, N.J.). It is to be noted that the term can further be used to refer to any combination of features described herein regarding DPH6 molecules. For example, any combination of sequence composition, percentage identify, sequence length, domain structure, functional activity, etc. can be used to describe a DPH6 molecule encompassed by the present invention.

Human DPH7 nucleic acid (NM_138778 tNM_001346370.1, NM_001346371.1, NM_001346372.1, NM_001346373.1, NM_001346374.1, NM_001346375.1, NM_001346376.1, NM_001346377.1, NM_001346378.1, NM_001346379.1, NM_001346380.1, NM_001346381.1, NM_001346382.1, NM_001346383.1, NM_001346384.1, NM_001346385.1, NM_001346386.1, NM_001346387.1, NM_001346388.1, NM_001346389.1, NM_001346390.1, NM_001346391.1, NM_001346392.1, NM_001346393.1, NM_001346394.1, NM_001346395.1, NM_001346396.1) and amino acid (NP_620133.1, NP_001333299.1, NP_001333300.1, NP_001333301.1, NP_001333302.1, NP_001333303.1, NP_001333304.1, NP_001333305.1, NP_001333306.1, NP_001333307.1, NP_001333308.1, NP_001333309.1, NP_001333310.1, NP_001333311.1, NP_001333312.1, NP_001333313.1, NP_001333314.1, NP_001333315.1, NP_001333316.1, NP_001333317.1, NP_001333318.1, NP_001333319.1, NP_001333320.1, NP_001333321.1, NP_001333322.1, NP_001333323.1. NP_001333324.1, and NP_001333325.1) sequences are publicly available on the GenBank database maintained by the U.S. National Center for Biotechnology Information. Nucleic acid and polypeptide sequences of DPH7 orthologs in species other than humans are also well known and include, for example, mouse DPH7 (NM_026044.4 and NP_080320.1, NM_001355554.1 and NP_001342483.1, NM_001355556.1 and NP_001342485.1, NM_001355557.1 and NP_001342486.1, NM_0013555581 and NP_001342487.1, NM_001355559.1 and NP_001342488.1, NM_001355560.1 and NP_001342489.1, NM_001355561.1 and NP_001342490.1), chimpanzee DPH7 (XM_016962287.2 and XP_016817776.2, XM_024346022.1 and XP_024201790.1, XM_024346021.1 and XP_024201789.1, XM_024346020.1 and XP_024201788.1, XM_016962286.2 and XP_016817775.2), monkey DPH7 (XM_015116226.1 and XP_014971712.1), dog DPH7 (XM_022423514.1 and XP_022279222.1), frog DPH7 (XM_018090266.1 and XP_017945755.1), and chicken DPH7 (XM_415537.5 and XP_415537.4, XM_015279665.2 and XP_015135151.1, XM_015279667.2 and XP_015135153.1, XM_015279666.2 and XP_015135152.1). Representative sequences of DPH7 orthologs are presented below in Table 1.

Anti-DPH7 antibodies suitable for detecting DPH7 protein are well-known in the art and include, for example, antibodies AP54555PU-N and TA333533 (Origene), antibodies NBP1-86714 and NBP2-20902 (Novus Biologicals, Littleton, Colo.), antibody Cat #56-454 (ProSci, Poway, Calif.), etc. In addition, reagents are well-known for detecting DPH7. Moreover, multiple siRNA, shRNA, CRISPR constructs for reducing DPH7 expression can be found in the commercial product lists of the above-referenced companies, such as CRISPR product #sc-413952 from Santa Cruz Biotechnology, RNAi products SR314216 and TL300469V, and CRISPR products KN205735 and KN304775 (Origene), and multiple CRISPR products from GenScript (Piscataway, N.J.). It is to be noted that the term can further be used to refer to any combination of features described herein regarding DPH7 molecules. For example, any combination of sequence composition, percentage identify, sequence length, domain structure, functional activity, etc. can be used to describe a DPH7 molecule encompassed by the present invention.

TABLE 1

```
SEQ ID NO: 1 Homo sapiens diphthamide biosynthesis 1 (DPH1) cDNA,
transcript variant 1 (NM_001383)
     1    atgcgcaggc aggtgatggc ggcgctggtc gtatccgggg cagcggagca gggcggccga 61    gacggccctg gcagaggtcg ggcccctcgg ggccgcgtgg ccaatcagat cccccctgag 121    atcctgaaga accctcagct gcaggcagca atccgggtcc tgccttccaa ctacaacttt 181    gagatcccca agaccatctg gaggatccaa caagcccagg ccaagaaggt ggccttgcaa 241    atgccggaag gctcctcct ctttgcctgt accattgtgg atatcttgga aaggttcacg 301    gaggccgaag tgatggtgat gggtgacgtg acctacgggg cttgctgtgt ggatgacttc 361    acagcgaggg ccctgggagc tgacttcttg gtgcactacg gccacagttg cctgattccc 421    atggacacct cggcccaaga cttccgggtg ctgtacgtct tgtggacat ccggatagac 481    actacacacc tcctggactc tctccgcctc accttccc cagccactgc ccttgccctg 541    gtcagcacca ttcagtttgt gtcgaccttg caggcagccg cccaggagct gaaagccgag 601    tatcgtgtga gtgtcccaca gtgcaagccc ctgtccctg gagagatcct gggctgcaca 661    tcccccgac tgtccaaaga ggtggaggcc gttgtgtatc ttggagatgg ccgcttccat 721    ctggagtctg tcatgattgc caacccccaat gtccccgctt accggtatga cccatatagc 781    aaagtcctat ccagagaaca ctatgaccac cagcgcatgc aggctgctcg ccaagaagcc 841    atagccactg cccgctcagc taagtcctgg ggccttattc tgggcacttt gggccgccag
```

TABLE 1-continued

| | |
|---|---|
| 901 | ggcagtccta agatcctgga gcacctggaa tctcgactcc gagccttggg cctttccttt |
| 961 | gtgaggctgc tgctctctga gatcttcccc agcaagctta gcctacttcc tgaggtggat |
| 1021 | gtgtgggtgc aggtggcatg tccacgtctc tccattgact ggggcacagc cttccccaag |
| 1081 | ccgctgctga cacccctatga ggcggccgtg gctctgaggg acatttcctg gcagcagccc |
| 1141 | tacccgatgg acttctacgc tggcagctcc ttggggccct ggacggtgaa ccacgccag |
| 1201 | gaccgccgtc ccacgccccc gggccggccc gcgcggggga aggtgcagga ggggtccgcg |
| 1261 | cgtccccctt cggccgtggc ttgcgaggac tgcagctgca gggacgagaa ggtggcgccg |
| 1321 | ctggctcctt ga |

SEQ ID NO: 2 Homo sapiens diphthamide biosynthesis 1 (DPH1) cDNA, transcript variant 2 (NM_001346574)

| | |
|---|---|
| 1 | atgcgcaggc aggtgatggc ggcgctggtc gtatccgggg cagcggagca gggcggccga |
| 61 | gacggccctg cagaggtcg ggcccctcgg ggccgcgtgg ccaatcagat ccccccctgag |
| 121 | atcctgaaga accctcagct gcaggcagca atccgggtcc tgccttccaa ctacaacttt |
| 181 | gagatcccca agaccatctg gaggatccaa caagcccagg ccaagaaggt ggccttgcaa |
| 241 | atgccggaag gcctcctcct ctttgcctgt accattgtgg atatcttgga aaggttcacg |
| 301 | gaggccgaag tgatggtgat gggtgacgtg acctacgggg cttgctgtgt ggatgacttc |
| 361 | acagcgaggg ccctgggagc tgacttcttg gtgcactacg ccacagttg cctgattccc |
| 421 | atggacacct cggcccaaga cttccgggtg ctgtacgtct tgtggacat ccggatagac |
| 481 | actacacacc tcctggactc tctccgcctc acctttcccc cagccactgc ccttgccctg |
| 541 | gtcagcacca ttcagtttgt gtcgaccttg caggcagccg cccaggagct gaaagccgag |
| 601 | tatcgtgtga gtgtcccaca gtgcaagccc ctgtccctg gagagatcct gggctgcaca |
| 661 | tccccccgac tgtccaaaga ggtggaggcc gttgtgtatc ttggagatgg ccgcttccat |
| 721 | ctggagtctg tcatgattgc caaccccaat gtccccgctt accggtatga cccatatagc |
| 781 | aaagtcctat ccagagaaca ctatgaccac cagcgcatgc aggctgctcg ccaagaagcc |
| 841 | atagccactg cccgctcaca cctggaatct cgactccgag ccttgggcct ttcctttgtg |
| 901 | aggctgctgc tctctgagat cttccccagc aagcttagcc tacttcctga ggtggatgtg |
| 961 | tgggtgcagg tggcatgtcc acgtctctcc attgactggg gcacagcctt ccccaagccg |
| 1021 | ctgctgacac cctatgaggc ggccgtggct ctgagggaca tttcctggca gcagcccac |
| 1081 | ccgatggact ctacgctgg cagctccttg ggccctgga cggtgaacca cggccaggac |
| 1141 | cgccgtcccc acgccccggg ccggccgcg cggggggagg tgcaggaggg gtccgcgcgt |
| 1201 | ccccttcgg ccgtggcttg cgaggactgc agctgcaggg acgagaaggt ggcgccgctg |
| 1261 | gctccttga | |

SEQ ID NO: 3 Homo sapiens diphthamide biosynthesis 1 (DPH1) cDNA, transcript variant 3 (NM_001346575)

| | |
|---|---|
| 1 | atgcgcaggc aggtgatggc ggcgctggtc gtatccgggg cagcggagca gggcggccga |
| 61 | gacggccctg cagaggtcg ggcccctcgg ggccgcgtgg ccaatcagat ccccccctgag |
| 121 | atcctgaaga accctcagct gcaggcagca atccgggtcc tgccttccaa ctacaacttt |
| 181 | gagatcccca agaccatctg gaggatccaa caagcccagg ccaagaaggt ggccttgcaa |
| 241 | atgccggaag gcctcctcct ctttgcctgt accattgtgg atatcttgga aaggttcacg |
| 301 | gaggccgaag tgatggtgat gggtgacgtg acctacgggg cttgctgtgt ggatgacttc |
| 361 | acagcgaggg ccctgggagc tgacttcttg gtgcactacg ccacagttg cctgattccc |
| 421 | atggacacct cggcccaaga cttccgggtg ctgtacgtct tgtggacat ccggatagac |

TABLE 1-continued

```
 481    actacacacc tcctggactc tctccgcctc acctttcccc cagccactgc ccttgccctg
 541    gcagccgccc aggagctgaa agccgagtat cgtgtgagtg tcccacagtg caagcccctg
 601    tcccctggag agatcctggg ctgcacatcc cccgactgt ccaaagaggt ggaggccgtt
 661    gtgtatcttg gagatggccg cttccatctg gagtctgtca tgattgccaa ccccaatgtc
 721    cccgcttacc ggtatgaccc atatagcaaa gtcctatcca gagaacacta tgaccaccag
 781    cgcatgcagg ctgctcgcca agaagccata gccactgccc gctcacacct ggaatctcga
 841    ctccgagcct tgggcctttc ctttgtgagg ctgctgctct ctgagatctt ccccagcaag
 901    cttagcctac ttcctgaggt ggatgtgtgg gtgcaggtgg catgtccacg tctctccatt
 961    gactggggca cagccttccc caagccgctg ctgacaccct atgaggcggc cgtggctctg
1021    agggacattt cctggcagca gccctacccg atggacttct acgctggcag ctccttgggg
1081    ccctggacgg tgaaccacgg ccaggaccgc cgtccccacg ccccgggccg gcccgcgcgg
1141    gggaaggtgc aggaggggtc cgcgcgtccc ccttcggccg tggcttgcga ggactgcagc
1201    tgcagggacg agaaggtggc gccgctggct ccttga
```

SEQ ID NO: 4 *Homo sapiens* diphthamide biosynthesis 1 (DPH1) cDNA, transcript variant 4 (NM_001346576)
```
   1    atggacacct cggcccaaga cttccgggtg ctgtacgtct tgtggacat ccggatagac
  61    actacacacc tcctggactc tctccgcctc acctttcccc cagccactgc ccttgccctg
 121    gtcagcacca ttcagtttgt gtcgaccttg caggcagccg cccaggagct gaaagccgag
 181    tatcgtgtga gtgtcccaca gtgcaagccc ctgtccctg gagagatcct gggctgcaca
 241    tccccccgac tgtccaaaga ggtggaggcc gttgtgtatc ttggagatgg ccgcttccat
 301    ctggagtctg tcatgattgc caaccccaat gtccccgctt accggtatga cccatatagc
 361    aaagtcctat ccagagaaca ctatgaccac cagcgcatgc aggctgctcg ccaagaagcc
 421    atagccactg cccgctcagc taagtcctgg ggccttattc tgggcacttt gggccgccag
 481    ggcagtccta agatcctgga gcacctggaa tctcgactcc gagccttggg ccttttccttt
 541    gtgaggctgc tgctctctga gatcttcccc agcaagctta gcctacttcc tgaggtggat
 601    gtgtgggtgc aggtggcatg tccacgtctc tccattgact ggggcacagc cttccccaag
 661    ccgctgctga caccctatga ggcggccgtg gctctgaggg acatttcctg gcagcagccc
 721    tacccgatgg acttctacgc tggcagctcc ttggggcccct ggacggtgaa ccacggccag
 781    gaccgccgtc ccacgcccc gggccggccc gcgcggggga aggtgcagga ggggtccgcg
 841    cgtccccctt cggccgtggc ttgcgaggac tgcagctgca gggacgagaa ggtggcgccg
 901    ctggctcctt ga
```

SEQ ID NO: 5 *Homo sapiens* diphthamide biosynthesis 1 (DPH1) amino acid sequence, isoform 1 (NP_001374)
```
   1    MRRQVMAALV VSGAAEQGGR DGPGRGRAPR GRVANQIPPE ILKNPQLQAA IRVLPSNYNF
  61    EIPKTIWRIQ QAQAKKVALQ MPEGLLLFAC TIVDILERFT EAEVMVMGDV TYGACCVDDF
 121    TARALGADFL VHYGHSCLIP MDTSAQDFRV LYVFVDIRID TTHLLDSLRL TFPPATALAL
 181    VSTIQFVSTL QAAAQELKAE YRVSVPQCKP LSPGEILGCT SPRLSKEVEA VVYLGDGRFH
 241    LESVMIANPN VPAYRYDPYS KVLSREHYDH QRMQAARQEA IATARSAKSW GLILGTLGRQ
 301    GSPKILEHLE SRLRALGLSF VRLLLSEIFP SKLSLLPEVD VWVQVACPRL SIDWGTAFPK
 361    PLLTPYEAAV ALRDISWQQP YPMDFYAGSS LGPWTVNHGQ DRRPHAPGRP ARGKVQEGSA
 421    RPPSAVACED CSCRDEKVAP LAP
```

TABLE 1-continued

SEQ ID NO: 6 Homo sapiens diphthamide biosynthesis 1 (DPH1) amino acid
sequence, isoform 2 (NP_001333503)

```
  1  MRRQVMAALV VSGAAEQGGR DGPGRGRAPR GRVANQIPPE ILKNPQLQAA IRVLPSNYNF
 61  EIPKTIWRIQ QAQAKKVALQ MPEGLLLFAC TIVDILERFT EAEVMVMGDV TYGACCVDDF
121  TARALGADFL VHYGHSCLIP MDTSAQDFRV LYVFVDIRID TTHLLDSLRL TFPPATALAL
181  VSTIQFVSTL QAAAQELKAE YRVSVPQCKP LSPGEILGCT SPRLSKEVEA VVYLGDGRFH
241  LESVMIANPN VPAYRYDPYS KVLSREHYDH QRMQAARQEA IATARSHLES RLRALGLSFV
301  RLLLSEIFPS KLSLLPEVDV WVQVACPRLS IDWGTAFPKP LLTPYEAAVA LRDISWQQPY
361  PMDFYAGSSL GPWTVNHGQD RRPHAPGRPA RGKVQEGSAR PPSAVACEDC SCRDEKVAPL
421  AP
```

SEQ ID NO: 7 Homo sapiens diphthamide biosynthesis 1 (DPH1) amino acid
sequence, isoform 3 (NP_001333504)

```
  1  MRRQVMAALV VSGAAEQGGR DGPGRGRAPR GRVANQIPPE ILKNPQLQAA IRVLPSNYNF
 61  EIPKTIWRIQ QAQAKKVALQ MPEGLLLFAC TIVDILERFT EAEVMVMGDV TYGACCVDDF
121  TARALGADFL VHYGHSCLIP MDTSAQDFRV LYVFVDIRID TTHLLDSLRL TFPPATALAL
181  AAAQELKAEY RVSVPQCKPL SPGEILGCTS PRLSKEVEAV VYLGDGRFHL ESVMIANPNV
241  PAYRYDPYSK VLSREHYDHQ RMQAARQEAI ATARSHLESR LRALGLSFVR LLLSEIFPSK
301  LSLLPEVDVW VQVACPRLSI DWGTAFPKPL LTPYEAAVAL RDISWQQPYP MDFYAGSSLG
361  PWTVNHGQDR RPHAPGRPAR GKVQEGSARP PSAVACEDCS CRDEKVAPLA P
```

SEQ ID NO: 8 Homo sapiens diphthamide biosynthesis 1 (DPH1) amino acid
sequence, isoform 4 (NP_001333505)

```
  1  MDTSAQDFRV LYVFVDIRID TTHLLDSLRL TFPPATALAL VSTIQFVSTL QAAAQELKAE
 61  YRVSVPQCKP LSPGEILGCT SPRLSKEVEA VVYLGDGRFH LESVMIANPN VPAYRYDPYS
121  KVLSREHYDH QRMQAARQEA IATARSAKSW GLILGTLGRQ GSPKILEHLE SRLRALGLSF
181  VRLLLSEIFP SKLSLLPEVD VWVQVACPRL SIDWGTAFPK PLLTPYEAAV ALRDISWQQP
241  YPMDFYAGSS LGPWTVNHGQ DRRPHAPGRP ARGKVQEGSA RPPSAVACED CSCRDEKVAP
301  LAP
```

SEQ ID NO: 9 Mus musculus diphthamide biosynthesis 1 (DPH1) cDNA,
(NM_144491)

```
  1  atggcggcgc tggttgtgtc cgagactgcg gagccaggaa gccgagtcgg ccctggcaga
 61  ggtcgcatct ctcgggggcg actggccaat cagatccccc ctgaggtcct gaacaacccc
121  cagttacagg ctgctgtcca agttctgcct tctaactaca actttgagat ccccaaaacc
181  atctggagaa tccagcaggc ccaggccaag aaggtggcct acaaatgcc agaaggcctc
241  ctcctctttg cctgcactat tgtggatatc ttggaaaggt tcacagaggc tgaggtgatg
301  gtgatgggtg atgtcaccta tggggcttgc tgtgtggatg acttcactgc aagggccttg
361  ggagttgact tcctggtgca ctatggtcac agctgtctag tccccatgga cacctccgtt
421  caagacttcc gagtcttgta tgtcttcgtg gatatccgga tagacactgc ccaccttctg
481  gactcggtcc gcctcacctt taccccaggc agctcactcg ctctggtcag caccattcag
541  tttgtgtcaa ccttacaggc agctgcacag gagctgaaag ctgattatca catcagtgtc
601  ccacagtgca agcccctgtc ccctggggag atcctaggct gcacatcccc tcggctatcc
661  aaggaagtgg aagctgttgt gtatcttgga gatggccgct tcatctgga gtctgtcatg
721  attgccaacc ctaatatacc tgcttaccgg tatgacccat atggcaaagt cctatccaga
781  gaatactatg accatcgcg catgcaggcc actcgccagg aagccattgc tgctgcacgc
841  tcagccaaat cctggggcct tattctggga accttgggcc gccagggcag tcccaagatc
```

TABLE 1-continued

```
 901   ctggagcact tggaatctca gctcagaaac ttgggacttc ctttcgtgag gctgttgctc
 961   tctgagatct tccccagcaa gctcagtcta cttcctgagg tggatgtgtg ggtgcaggtg
1021   gcatgtccac gcctctccat tgactggggt tcagcctttc ccaagccact gctgacaccg
1081   tacgaggcag ctgtggccct gaaggacatt tcttggcagc aaccctaccc catggacttc
1141   tactctggca gctccttagg gccatggaca gtgaactacg gtcgggaccg agcacctcgg
1201   ggtctctgcc agcctgcatc tgacaaggtg cagcaagggt ccagaggcgg ctctccagcc
1261   ccagcctgtg agagttgcaa ctgcgcagac cagaaggcta cttcgccggc tccctga
```

SEQ ID NO: 10 Mus musculus diphthamide biosynthesis 1 (DPH1) amino acid sequence, (NP_652762)
```
  1    MAALVVSETA EPGSRVGPGR GRISRGRLAN QIPPEVLNNP QLQAAVQVLP SNYNFEIPKT
 61    IWRIQQAQAK KVALQMPEGL LLFACTIVDI LERFTEAEVM VMGDVTYGAC CVDDFTARAL
121    GVDFLVHYGH SCLVPMDTSV QDFRVLYVFV DIRIDTAHLL DSVRLTFTPG SSLALVSTIQ
181    FVSTLQAAAQ ELKADYHISV PQCKPLSPGE ILGCTSPRLS KEVEAVVYLG DGRFHLESVM
241    IANPNIPAYR YDPYGKVLSR EYYDHQRMQA TRQEAIAAAR SAKSWGLILG TLGRQGSPKI
301    LEHLESQLRN LGLPFVRLLL SEIFPSKLSL LPEVDVWVQV ACPRLSIDWG SAFPKPLLTP
361    YEAAVALKDI SWQQPYPMDF YSGSSLGPWT VNYGRDRAPR GLCQPASDKV QQGSRGGSPA
421    PACESCNCAD QKATSPAP
```

SEQ ID NO: 11 Pan troglodytes (chimpanzee) diphthamide biosynthesis 1 (DPH1) cDNA (XM_511255)
```
  1    atgcgcaggc aggtgatggc ggcgctggtt gtatccgggg cagcggagca gggcggccga
 61    aacggccctg gcagaggtcg ggcccctcgg ggccgcgtgg ccaatcagat ccccccctgag
121    atcctgaaga accctcagct gcaggcagca atgcgggtcc tgccttccaa ctacaacttt
181    gagatcccca agaccatctg gaggatccaa caagcccagg ccaagaaggt ggccttgcag
241    atgccggaag gcctcctcct ctttgcctgt accattgtgg atatcttgga aaggttcacg
301    gaggccgaag tgatggtgat gggtgacgtg acctacgggg cttgctgtgt ggatgacttc
361    acagcgaggg ccctgggagc tgacttcttg gtgcactacg gccacagttg cctgattccc
421    atggacacct cggcccaaga cttccgggtg ctgtacgtct tgtgggacat ccggatagac
481    actacgcacc tcctggactc tctccgcctc acctttcccc cagccactgc ccttgccctg
541    gtcagcacca ttcagtttgt gtcgaccttg caggcagccg cccaggagct gaaagccgag
601    tatcgtgtga gtgtcccaca gtgcaagccc ctgtcccctg gagagatcct gggctgcaca
661    tccccccgac tgtccaaaga ggtgaggcc gttgtgtatc ttggagatgg ccgcttccat
721    ctggagtctg tcatgattgc caaccccaat gtccccgctt accggtatga cccatatagc
781    aaagtcctat ccagagaaca ctatgaccac cagcgcatgc aggctgctcg ccaagaagcc
841    atagccactg cccgctcagc taagtcctgg ggcttattc tgggcacttt gggccgccag
901    ggcagtccta agatcctgga gcacctggaa tctcaactcc gagccttggg ccttttcctt
961    gtgaggctgc tgctctctga gatcttcccc agcaagctta gcctacttcc cgaggtggat
1021   gtgtgggtgc aggtggcatg tccacgtctc tccattgact ggggcacagc cttccccaag
1081   ccgctgctga caccctatga ggcggccgtg gctctgaggg acatttcctg gcagcagccc
1141   tacccgatgg acttctacgc tggcagctct tggggccct ggacggtgaa ccacgccag
1201   gaccgccgtc cccacgcccc gggccggccc gcgcggggga aggtgcagga ggggtccgcg
1261   cgtcccccctt cagccgtggc ttgcgaggat tgcagctgca gggacgagaa ggtggcgccg
1321   ctggctccctt ga
```

TABLE 1-continued

SEQ ID NO: 12 *Pan troglodytes* (chimpanzee) diphthamide biosynthesis 1 (DPH1) amino acid sequence (XP_511255)

```
  1   MRRQVMAALV VSGAAEQGGR NGPGRGRAPR GRVANQIPPE ILKNPQLQAA MRVLPSNYNF
 61   EIPKTIWRIQ QAQAKKVALQ MPEGLLLFAC TIVDILERFT EAEVMVMGDV TYGACCVDDF
121   TARALGADFL VHYGHSCLIP MDTSAQDFRV LYVFVDIRID TTHLLDSLRL TFPPATALAL
181   VSTIQFVSTL QAAAQELKAE YRVSVPQCKP LSPGEILGCT SPRLSKEVEA VVYLGDGRFH
241   LESVMIANPN VPAYRYDPYS KVLSREHYDH QRMQAARQEA IATARSAKSW GLILGTLGRQ
301   GSPKILEHLE SQLRALGLSF VRLLLSEIFP SKLSLLPEVD VWVQVACPRL SIDWGTAFPK
361   PLLTPYEAAV ALRDISWQQP YPMDFYAGSS LGPWTVNHGQ DRRPHAPGRP ARGKVQEGSA
421   RPPSAVACED CSCRDEKVAP LAP
```

SEQ ID NO: 13 *Macaca mulatta* (Rhesus monkey) diphthamide biosynthesis 1 (DPH1) cDNA (XM_015118202)

```
   1   atggcggcgc tggttgtgtc ccgggcagcg gagcagggcg gccgaaacgg ccctggcaga
  61   gttcgggccc ctcggggccg cgtggccaat cagatccccc ctgagatcct gaagaactcc
 121   cagctgcagg cagcaatcca ggtcctgcct ccaactaca actttgagat ccccaagacc
 181   atctggagga tccaacaagc ccaggccaag aaggtggcct tgcaaatgcc ggaaggcctc
 241   ctcctctttg cctgtaccat cgtggatatc ttggaaaggt tcacggaggc tgaagtgatg
 301   gtgatgggtg acgtgaccta tggggcttgc tgtgtggatg acttcacggc gagggccctg
 361   ggagctgact tcttggtgca ctatggccac agttgcctgg ttcccatgga cacctcggcc
 421   caagacttcc gggtgctgta cgtctttgtg gacatccgga tagacactgc ccacctcctg
 481   gactctctcc gcctcacctt tcccccagcc accgcccttg ccctggtcag caccattcag
 541   tttgtgtcga ccttgcaggc agccgcccag gagctgaaag ctgagtaccg tgtgagtgtc
 601   ccacagtgca agcccctgtc cctggagag attctgggct gcacatcccc ccgactgccc
 661   gaagaggtgg aggccgttgt gtatcttgga gatggccgct tccatctgga gtctgtcatg
 721   attgccaacc ccaatgtccc cgcttaccgg tatgacccgt acagcaaagt cctgtccaga
 781   gagcactatg accaccagcg catgcgggct gctcgccagg aagccatagc caccgcccgc
 841   tccgctaagt cctggggcct tattctgggc actctgggcc gccagggcag tcctaagatc
 901   ctggagcacc tggaatctcg actccgagcc ttgggccttt ccttcgtgag gctgctgctc
 961   tctgagatct tccccagcaa gcttggccta cttccgagg tggatgtgtg ggtgcaggtg
1021   gcatgtccac gtctctccat tgactgggc acagccttcc caagcctct gctgacaccc
1081   tatgaggcgg ccgtggctct gagggacatt tcctggcagc agccctaccc gatggacttc
1141   tacgctggca gctccttggg gccctggacg gtgaaccacg gcctggaccg gcgtccccag
1201   accccgggcc gacccacgcg ggggaaggtg caggaggggt ccacgcatcc ccctcagcc
1261   gtggcttgcg aggactgcag ctgcagagac aagaaggtgg cgccgcttgc tccttga
```

SEQ ID NO: 14 *Macaca mulatta* (Rhesus monkey) diphthamide biosynthesis 1 (DPH1) amino acid sequence (XP_014973688)

```
  1   MAALVVSRAA EQGGRNGPGR VRAPRGRVAN QIPPEILKNS QLQAAIQVLP SNYNFEIPKT
 61   IWRIQQAQAK KVALQMPEGL LLFACTIVDI LERFTEAEVM VMGDVTYGAC CVDDFTARAL
121   GADFLVHYGH SCLVPMDTSA QDFRVLYVFV DIRIDTAHLL DSLRLTFPPA TALALVSTIQ
181   FVSTLQAAAQ ELKAEYRVSV PQCKPLSPGE ILGCTSPRLP EEVEAVVYLG DGRFHLESVM
241   IANPNVPAYR YDPYSKVLSR EHYDHQRMRA ARQEAIATAR SAKSWGLILG TLGRQGSPKI
```

TABLE 1-continued

```
301    LEHLESRLRA LGLSFVRLLL SEIFPSKLGL LPEVDVWVQV ACPRLSIDWG TAFPKPLLTP

361    YEAAVALRDI SWQQPYPMDF YAGSSLGPWT VNHGLDRRPQ TPGRPTRGKV QEGSTHPPSA

421    VACEDCSCRD KKVAPLAP
```

SEQ ID NO: 15 Bos taurus (cattle) diphthamide biosynthesis 1 (DPH1) cDNA (NM_001076899)
```
   1    atggcggcgc tggtggcggc cgaggccgca gagtcttgca gccgaaacgg cccgggcaga 61    ggtcgagccc ctcggggccg cttggccaat cagatcccgg ctgagatcct gaacaatccc 121    cagctgcagg cggccatcca agtcctgcct tccaactata actttgaggt tcccaagacc 181    atctggagga tccaacaggc ccaggccaag aaggtggcct acaaatgcc cgaaggcctc 241    ctcctcttcg cctgtaccat tgtggatatc ttggaaaggt tcacggaggc cgaagtgatg 301    gtgatgggag acgtgaccta cggggcttgc tgtgtggacg acttcactgc aagagccttg 361    ggagctgact tcctggtcca ctatggccac agctgcctgg ttcccatgga cacctcggcc 421    caagacttcc gggtgctgta tgtctttgtg gacatccgga tagacactgc ccacctcctg 481    gactctatcc gcctcacctt ccccccagcc agtgcccttg cgctggtcag caccattcag 541    ttcgtgtcaa ccttgcaggc agctgcccaa gagctgaaag ctgagtatcg tgtgagtgtc 601    ccacagtgca agcccctgtc tcctggggag attctgggct gcacgtctcc ctgcctaccc 661    aaggaggtgg aggctgtggt gtatcttgga gatggccgct tccacctgga gtctgtcatg 721    atcgccaacc ctaacatctc cgcttaccga tacgacccct acagcaaggt cctgtccaga 781    gagcactatg accaccagcg catgcaggcc aaccgccagg aagccatagc cactgcccgg 841    tcagctaaat cctggggtct catcctgggc actttgggcc gccaaggcag tcccaagatc 901    ctggagcacc tggaatctcg gctccaagcc ttgggacttc ccttcgtgag gctgctgctc 961    tctgagatct cccccagcaa gctcagcctc cttcccgagg tggatgtgtg ggtgcaggtg 1021    gcatgtccac gcctgtccat cgactgggt acagccttcc ccaagccgct gctcacaccc 1081    tatgaggcgg cggtggcctt gagggacatt tcctggcagc agccctaccc tatggacttc 1141    tacgccagca gctccttggg gccgtgacg gtgaaccacg gcgggatcg gctgctccag 1201    gtcccaggcc ggctggccct ggggaaggtt caggggggc ccgcgcgccc ctctccagcc 1261    gcggcttgcg aggcttgcag ctgcagagac gaggaggtgt cgccgatcgc tctctga
```

SEQ ID NO: 16 Bos taurus (cattle) diphthamide biosynthesis 1 (DPH1) amino acid sequence (NP_001070367)
```
   1    MAALVAAEAA ESCSRNGPGR GRAPRGRLAN QIPAEILNNP QLQAAIQVLP SNYNFEVPKT

61    IWRIQQAQAK VALQMPEGL LLFACTIVDI LERFTEAEVM VMGDVTYGAC VDDFTARAL

121    GADFLVHYGH SCLVPMDTSA QDFRVLYVFV DIRIDTAHLL DSIRLTFPPA SALALVSTIQ

181    FVSTLQAAAQ ELKAEYRVSV PQCKPLSPGE ILGCTSPCLP KEVEAVVYLG DGRFHLESVM

241    IANPNISAYR YDPYSKVLSR EHYDHQRMQA NRQEAIATAR SAKSWGLILG TLGRQGSPKI

301    LEHLESRLQA LGLPFVRLLL SEIFPSKLSL LPEVDVWVQV ACPRLSIDWG TAFPKPLLTP

361    YEAAVALRDI SWQQPYPMDF YASSSLGPWT VNHGRDRLLQ VPGRLALGKV QGGPARPSPA

421    AACEACSCRD EEVSPIAL
```

SEQ ID NO: 17 Rattus norvegicus (rat) diphthamide biosynthesis 1 (DPH1) cDNA (NM_001105809)
```
   1    atggcggcgc tggttgtgcc gagacttcc gagccaggaa gccgagtcgg ccctggcaga 61    ggtcgcatct ctcggggccg actggccaat cagatccccc ctgagatcct gaacagtccc 121    cagctacagg ccgctgtcca tgccctgcct tctaactaca actttgagat ccccaagacc 181    atctggagga tccagcaagc ccaggccaag aaggtggcct acaaatgcc agaaggcctc
```

TABLE 1-continued

```
 241   ctgctctttg cctgcaccat tgtggatatc ttggaaaggt tcacaaaggc tgaggtgatg
 301   gtgatgggcg atgtgaccta cggagcatgc tgtgtggacg acttcactgc aagggccttg
 361   ggagttgact tcctggtgca ctatggccac agctgcctag tccccatgga cacctcagtc
 421   caagacttcc gtgtgctgta tgtctttgtg gatatccgga tagacactgc ccaccttctg
 481   gactcggtcc gcctcacctt caccccaggc agctcgcttg ctctggtcag caccattcag
 541   tttgtgtcaa ctttacaggc agctgcccag gagctgaaag ctgattatca catcagtgtc
 601   ccacagtgca agcccttgtc ccctggggag atcctaggct gcacgtcccc tcgactaccc
 661   aaggaagtgg aagctgttgt gtatcttgga gatggccgct tccatctgga gtctgtcatg
 721   atcgccaacc ctaatatacc tagttaccgg tacgacccat atagcaaagt cctatccaga
 781   gaatactatg accatcagcg catgcaggcc actcgtcagg aagccatcgc tgctgcacgc
 841   tcagccaagt tctggggcct tattctggga actttgggcc gccagggaag tcccaaggtc
 901   ctggagcact ggaatctca gctcagaaac ttgggacttc ctttcctgag gctgcttctc
 961   tctgagatct tccccagcaa gctcagtcta cttccttcgg tggacgtgtg ggtgcaggtg
1021   gcatgtccac gcctctccat tgactgggc tcagccttc caagccact gctgacaccc
1081   tacgaggcag ctgtggccct gaaagagatt tcttggcagc aaccctaccc tatggacttc
1141   tacgctggca gctccttagg gccatggaca gtgaaccatg gtcgggaccg agcacccagg
1201   ggtctctgcc agcctgcatc cgacaaggtg cagcaggggt ccagaggcca ctctccagtc
1261   ccggcctgtg agggctgcag ctgcgcagac cagaaagcta caccgccagc tccctga
```

SEQ ID NO: 18 *Rattus norvegicus* (rat) diphthamide biosynthesis 1 (DPH1) amino acid sequence (NP_001099279)

```
  1   MAALVVPETS EPGSRVGPGR GRISRGRLAN QIPPEILNSP QLQAAVHALP SNYNFEIPKT
 61   IWRIQQAQAK KVALQMPEGL LLFACTIVDI LERFTKAEVM VMGDVTYGAC CVDDFTARAL
121   GVDFLVHYGH SCLVPMDTSV QDFRVLYVFV DIRIDTAHLL DSVRLTFTPG SSLALVSTIQ
181   FVSTLQAAAQ ELKADYHISV PQCKPLSPGE ILGCTSPRLP KEVEAVVYLG DGRFHLESVM
241   IANPNIPSYR YDPYSKVLSR EYYDHQRMQA TRQEAIAAAR SAKFWGLILG TLGRQGSPKV
301   LEHLESQLRN LGLPFLRLLL SEIFPSKLSL LPSVDVWVQV ACPRLSIDWG SAFPKPLLTP
361   YEAAVALKEI SWQQPYPMDF YAGSSLGPWT VNHGRDRAPR GLCQPASDKV QQGSRGHSPV
421   PACEGCSCAD QKATPPAP
```

SEQ ID NO: 19 *Gallus gallus* (chicken) diphthamide biosynthesis 1 (DPH1) cDNA (NM_001030716)

```
  1   atggccgcac cgcagcgttc cggcagcgcg gctcttctgc cctccgccaa cggcgcaggc
 61   cgagccccac gtcgcactgc ccgccaggtc cccgaggagc tgctgaacaa tgtggagctg
121   cggagggcga tggggctct gccctccaac tacaacttcg agatcccaa aaccatctgg
181   cggatccagc aggcgggagc caaaaaggtg gccctgcaga tgccggaggg gctgctcatg
241   tttgcctgca ccatcgcaga tatcattgag cggttcacgg acgccaaggc ggtggtgatg
301   ggcgatgtga cctacggcgc gtgctgcgtg gacgactaca gcgcgggc tctgggtgct
361   gacttcttgg tgcactatgg acacagctgc ctgatcccca tcgatgcac gcgtgggctg
421   aagatgctct acgtcttcgt ggacatcaag attgacacat cccatttcct cgacaccatc
481   cgcttcaact tcgccgtggg ctcttccctg ccctggtca gcaccatcca gttcgtggca
541   gcagtgcagg cggcctcaca gggagctgcag tcacagtaca aggtgtgcgt gccccagtgc
601   aagccgctgt ccctggtga tatactgggc tgcacatcgc ccggctcgc acgggacacc
661   gatgccattg tctatttggg ggatggccgt ttccacctgg agtccatcat gatcgccaac
```

TABLE 1-continued

```
 721  ccggggatac cgcctacag gtatgatccc tacagcaagg tcttctcgca ggagcattat
 781  gcccatgacc gcatgcgtga agcccggcag gctgccatcc gctccgccgc ccgcgcccgg
 841  tgctgggggc tgctgctggg caccctgggg cgacagggat ccccgccat cctacagcac
 901  ctggagtcac ggctgcgtgc cctgggccgg ccctttgtgc gggtgctgct gtctgagatc
 961  ttccccagca agctgcagct cttttgacagc gtggatgcgt gggtgcagat cgcctgtccc
1021  cggctctcca tcgactgggg ggaggcattc agcaaaccac tgctgacacc ctatgaggca
1081  gcggtggctc ttggggacat cgagtggcaa cagccgtacc ccatggactt ctatgccagt
1141  caatccctgg gccgtggac ggccaaccac acagcgcggc cgcccagga aagccaccc
1201  gcaaccccca gcctgaagaa tggcactgag gggtcccgca gtgcccaccc gcctgaggac
1261  acggccacct cctga
```

SEQ ID NO: 20 *Gallus gallus* (chicken) diphthamide biosynthesis 1 (DPH1) amino acid sequence (NP_001025887)

```
  1  MAAPQRSGSA ALLPSANGAG RAPRRTARQV PEELLNNVEL REAMGALPSN YNFEIPKTIW
 61  RIQQAGAKKV ALQMPEGLLM FACTIADIIE RFTDAKAVVM GDVTYGACCV DDYTARALGA
121  DFLVHYGHSC LIPIDATRGL KMLYVFVDIK IDTSHFLDTI RFNFAVGSSL ALVSTIQFVA
181  AVQAASQELQ SQYKVCVPQC KPLSPGEILG CTSPRLARDT DAIVYLGDGR FHLESIMIAN
241  PGIPAYRYDP YSKVFSQEHY AHDRMREARQ AAIRSAARAR CWGLLLGTLG RQGSPAILQH
301  LESRLRALGR PFVRVLLSEI FPSKLQLFDS VDAWVQIACP RLSIDWGEAF SKPLLTPYEA
361  AVALGDIEWQ QPYPMDFYAS QSLGPWTANH TARPAQEKPP ATPSLKNGTE GSRSAHPPED
421  TATS
```

SEQ ID NO: 21 *Gallus gallus* (chicken) diphthamide biosynthesis 1 (DPH1) cDNA, transcript variant X1 (XM_015295752)

```
   1  atgttcgacg gggcggcggt gaataacgga gcgctgcccc cttcccacc ccccgccgg
  61  ctgtggggga gaacgctgct gagtgcccgc tggtgggaag ggggccgagc cccacgtcgc
 121  actgcccgcc aggtcccga ggagctgctg aacaatgtgg agctgcggga ggcgatgggg
 181  gctctgccct ccaactacaa cttcgagatc cccaaaacca tctgcggat ccagcaggcg
 241  ggagccaaaa aggtggccct gcagatgccg gaggggctgc tcatgttgc ctgcaccatc
 301  gcagatatca ttgagcggtt cacggacgcc aaggcggtgg tgatgggcga tgtgacctac
 361  ggcgcgtgct gcgtggacga ctacacagcg cgggctctgg gtgctgactt cttggtgcac
 421  tatggacaca gctgcctgat ccccatcgat gccacgcgtg gctgaagat gctctacgtc
 481  ttcgtggaca tcaagattga cacatcccat ttcctcgaca ccatccgctt caacttcgcc
 541  gtgggctctt ccctggccct ggtcagcacc atccagttcg tggcagcagt gcaggcggcc
 601  tcacaggagc tgcagtcaca gtacaaggtg tgcgtgcccc agtgcaagcc gctgtcccct
 661  ggtgagatac tgggctgcac atcgccccgg ctcgcacggg acaccgatgc cattgtctat
 721  ttggggatg ccgtttcca cctggagtcc atcatgatcg ccaacccggg ataccccgcc
 781  tacaggtatg atccctacag caaggtcttc tcgcaggagc attatgccca tgaccgcatg
 841  cgtgaagccc ggcaggctgc catccgctcc gccgcccgcg cccggtgctg ggggctgctg
 901  ctgggcaccc tggggcgaca gggatccccc gccatcctac agcacctgga gtcacggctg
 961  cgtgccctgg gccggccctt tgtgcgggtg ctgctgtctg agatcttccc cagcaagctg
1021  cagctctttg acagcgtgga tgcgtgggtg cagatcgcct gtccccggct ctccatcgac
1081  tgggggagg cattcagcaa accactgctg acaccctatg aggcagcggt ggctcttggg
1141  gacatcgagt ggcaacagcc gtaccccatg gacttctatg ccagtcaatc cctggggccg
```

TABLE 1-continued

```
1201    tggacggcca accacacagc gcggcccgcc caggtaggct ctgggggtg ggggggccc 1261    ccctgtgtcc cctggtgctc gctgccatgt ggcacaagcg ccacccagtg gctcgctccc 1321    tggagagcag ggctggcgcc cacccggtgc cctccatcgg ggcacacatg gccccatctt 1381    tgcttacccc atgtctgtcc ctacaggaga agccacccgc aaccccagc ctga
```

SEQ ID NO: 22 *Gallus gallus* (chicken) diphthamide biosynthesis 1 (DPH1) amino acid sequence, isoform X1 (XP_015151238)
```
  1   MFDGAAVNNG ALPPFPPPRR LWGRTLLSAR WWEGGRAPRR TARQVPEELL NNVELREAMG

61   ALPSNYNFEI PKTIWRIQQA GAKKVALQMP EGLLMFACTI ADIIERFTDA KAVVMGDVTY

121   GACCVDDYTA RALGADFLVH YGHSCLIPID ATRGLKMLYV FVDIKIDTSH FLDTIRFNFA

181   VGSSLALVST IQFVAAVQAA SQELQSQYKV CVPQCKPLSP GEILGCTSPR LARDTDAIVY

241   LGDGRFHLES IMIANPGIPA YRYDPYSKVF SQEHYAHDRM REARQAAIRS AARARCWGLL

301   LGTLGRQGSP AILQHLESRL RALGRPFVRV LLSEIFPSKL QLFDSVDAWV QIACPRLSID

361   WGEAFSKPLL TPYEAAVALG DIEWQQPYPM DFYASQSLGP WTANHTARPA QVGSGGWGGP

421   PCVPWCSLPC GTSATQWLAP WRAGLAPTRC PPSGHTWPHL CLPHVCPYRR SHPQPPA
```

SEQ ID NO: 23 *Gallus gallus* (chicken) diphthamide biosynthesis 1 (DPH1) cDNA, transcript variant X2 (XM_015295753)
```
  1    atggccgcac cgcagcgttc cggcagcgcg gctcttctgc cctccgccaa cggcgcaggc 61    cgagcccac gtcgcactgc ccgccaggtc cccgaggagc tgctgaacaa tgtggagctg 121    cggaggcga tggggctct gccctccaac tacaacttcg agatccccaa aaccatctgg 181    cggatccagc aggcgggagc caaaaggtg gccctgcaga tgccggaggg gctgctcatg 241    tttgcctgca ccatcgcaga tatcattgag cggttcacgg acgccaaggc ggtggtgatg 301    ggcgatgtga cctacggcgc gtgctgcgtg gacgactaca gcgcgggc tctgggtgct 361    gacttcttgg tgcactatgg cacagctgc ctgatcccca tcgatgccac gcgtgggctg 421    aagatgctct acgtcttcgt ggacatcaag attgacacat cccatttcct cgacaccatc 481    cgcttcaact tcgccgtggg ctcttccctg gccctggtca gcaccatcca gttcgtggca 541    gcagtgcagg cggcctcaca ggagctgcag tcacagtaca aggtgtgcgt gccccagtgc 601    aagccgctgt ccctggtga gatactgggc tgcacatcgc ccggctcgc acgggacacc 661    gatgccattg tctatttggg ggatggccgt ttccacctgg agtccatcat gatcgccaac 721    ccggggatac ccgcctacag gtatgatccc tacagcaagg tcttctcgca ggagcattat 781    gcccatgacc gcatgcgtga agcccggcag gctgccatcc gctccgccgc ccgcgcccgg 841    tgctgggggc tgctgctggg caccctgggg cgacagggat cccccgccat cctacagcac 901    ctggagtcac ggctgcgtgc cctgggccgg ccctttgtgc gggtgctgct gtctgagatc 961    ttccccagca agctgcagct ctttgacagc gtggatgcgt gggtgcagat cgcctgtccc 1021   cggctctcca tcgactgggg ggaggcattc agcaaaccac tgctgacacc ctatgaggca 1081   gcggtggctc ttggggacat cgagtggcaa cagccgtacc ccatggactt ctatgccagt 1141   caatccctgg ggccgtggac ggccaaccac acagcgcggc ccgcccaggt aggctctggg 1201   gggtggggg gccccccctg tgtccctgg tgctcgctgc catgtggcac aagcgccacc 1261   cagtggctcg ctccctggag agcagggctg gcgccaccc ggtgccctcc atcggggcac 1321   acatgccccc atctttgctt accccatgtc tgtccctaca ggagaagcca cccgcaaccc 1381   ccagcctga
```

TABLE 1-continued

SEQ ID NO: 24 *Gallus gallus* (chicken) diphthamide biosynthesis 1 (DPH1)
amino acid sequence, isoform X2 (XP_015151239)

```
  1  MAAPQRSGSA ALLPSANGAG RAPRRTARQV PEELLNNVEL REAMGALPSN YNFEIPKTIW
 61  RIQQAGAKKV ALQMPEGLLM FACTIADIIE RFTDAKAVVM GDVTYGACCV DDYTARALGA
121  DFLVHYGHSC LIPIDATRGL KMLYVFVDIK IDTSHFLDTI RFNFAVGSSL ALVSTIQFVA
181  AVQAASQELQ SQYKVCVPQC KPLSPGEILG CTSPRLARDT DAIVYLGDGR FHLESIMIAN
241  PGIPAYRYDP YSKVFSQEHY AHDRMREARQ AAIRSAARAR CWGLLLGTLG RQGSPAILQH
301  LESRLRALGR PFVRVLLSEI FPSKLQLFDS VDAWVQIACP RLSIDWGEAF SKPLLTPYEA
361  AVALGDIEWQ QPYPMDFYAS QSLGPWTANH TARPAQVGSG GWGGPPCVPW CSLPCGTSAT
421  QWLAPWRAGL APTRCPPSGH TWPHLCLPHV CPYRRSHPQP PA
```

SEQ ID NO: 25 *Gallus gallus* (chicken) diphthamide biosynthesis 1 (DPH1)
cDNA, transcript variant X3 (XM_015295754)

```
   1  atgttcgacg gggcggcggt gaataacgga gcgctgcccc ccttcccacc ccccgccgg
  61  ctgtggggga gaacgctgct gagtgcccgc tggtgggaag ggggccgagc ccacgtcgc
 121  actgcccgcc aggtccccga ggagctgctg aacaatgtgg agctgcggga ggcgatgggg
 181  gctctgccct ccaactacaa cttcgagatc cccaaaacca tctggcggat ccagcaggcg
 241  ggagccaaaa aggtggccct gcagatgccg gaggggctgc tcatgtttgc ctgcaccatc
 301  gcagatatca ttgagcggtt cacggacgcc aaggcggtgg tgatgggcga tgtgacctac
 361  ggcgcgtgct cgtggacga ctacacagcg cgggctctgg gtgctgactt cttggtgcac
 421  tatggacaca gctgcctgat ccccatcgat gccacgcgtg ggctgaagat gctctacgtc
 481  ttcgtggaca tcaagattga cacatcccat ttcctcgaca ccatccgctt caacttcgcc
 541  gtgggctctt ccctggccct ggtcagcacc atccagttcg tggcagcagt gcaggcggcc
 601  tcacaggagc tgcagtcaca gtacaaggtg tgcgtgcccc agtgcaagcc gctgtcccct
 661  ggtgagatac tgggctgcac atcgccccgg ctcgcacggg accgatgc cattgtctat
 721  ttgggggatg gccgtttcca cctggagtcc atcatgatcg ccaacccggg gataccgcc
 781  tacaggtatg atccctacag caaggtcttc tcgcaggagc attatgccca tgaccgcatg
 841  cgtgaagccc ggcaggctgc catccgctcc gccgccgcg cccggtgctg ggggctgctg
 901  ctgggcaccc tggggcgaca gggatccccc gccatcctac agcacctgga gtcacggctg
 961  cgtgccctgg gccggccctt tgtgcgggtg ctgctgtctg agatcttccc cagcaagctg
1021  cagctctttg acagcgtgga tgcgtgggtg cagatcgcct gtcccggct ctccatcgac
1081  tgggggagg cattcagcaa accactgctg acaccctatg aggtgagcag tccccggtgg
1141  gtttcgggag accccctccc agccctgcgc gtggcactca gccccttatc ccctcctcac
1201  aggcagcgt ggctcttggg gacatcgagt ggcaacagcc gtaccccatg gacttctatg
1261  ccagtcaatc cctggggccg tggacggcca accacacagc gcggcccgcc caggagaagc
1321  cacccgcaac cccagcctg a
```

SEQ ID NO: 26 *Gallus gallus* (chicken) diphthamide biosynthesis 1 (DPH1)
amino acid sequence, isoform X3 (XP_015151240)

```
  1  MFDGAAVNNG ALPPFPPPRR LWGRTLLSAR WWEGGRAPRR TARQVPEELL NNVELREAMG
 61  ALPSNYNFEI PKTIWRIQQA GAKKVALQMP EGLLMFACTI ADIIERFTDA KAVVMGDVTY
121  GACCVDDYTA RALGADFLVH YGHSCLIPID ATRGLKMLYV FVDIKIDTSH FLDTIRFNFA
181  VGSSLALVST IQFVAAVQAA SQELQSQYKV CVPQCKPLSP GEILGCTSPR LARDTDAIVY
241  LGDGRFHLES IMIANPGIPA YRYDPYSKVF SQEHYAHDRM REARQAAIRS AARARCWGLL
301  LGTLGRQGSP AILQHLESRL RALGRPFVRV LLSEIFPSKL QLFDSVDAWV QIACPRLSID
```

TABLE 1-continued

```
361  WGEAFSKPLL TPYEVSSPRW VSGGPLPALR VALSPLSPPH RQRWLLGTSS GNSRTPWTSM

421  PVNPWGRGRP TTQRGPPRRS HPQPPA
```

SEQ ID NO: 27 Gallus gallus (chicken) diphthamide biosynthesis 1 (DPH1)
cDNA, transcript variant X4 (XM_015295755)
```
   1  atgttcgacg gggcggcggt gaataacgga gcgctgcccc ccttcccacc ccccgccgg 61  ctgtggggga gaacgctgct gagtgcccgc tggtgggaag ggggccgagc ccacgtcgc 121  actgcccgcc aggtccccga ggagctgctg aacaatgtgg agctgcggga ggcgatgggg 181  gctctgccct ccaactacaa cttcgagatc cccaaaacca tctggcggat ccagcaggcg 241  ggagccaaaa aggtggccct gcagatgccg gaggggctgc tcatgtttgc ctgcaccatc 301  gcagatatca ttgagcggtt cacggacgcc aaggcggtgg tgatgggcga tgtgacctac 361  ggcgcgtgct gcgtggacga ctacacagcg cgggctctgg gtgctgactt cttggtgcac 421  tatggacaca gctgcctgat ccccatcgat gccacgcgtg ggctgaagat gctctacgtc 481  ttcgtggaca tcaagattga cacatcccat tcctcgaca ccatccgctt caacttcgcc 541  gtgggctctt ccctggccct ggtcagcacc atccagttcg tggcagcagt gcaggcggcc 601  tcacaggagc tgcagtcaca gtacaaggtg tgcgtgcccc agtgcaagcc gctgtcccct 661  ggtgagatac tgggctgcac atcgccccgg ctcgcacggg acaccgatgc cattgtctat 721  ttgggggatg ccgtttcca cctggagtcc atcatgatcg ccaacccggg gataccgcc 781  tacaggtatg atccctacag caaggtcttc tcgcaggagc attatgccca tgaccgcatg 841  cgtgaagccc ggcaggctgc catccgctcc gccgcccgcg cccggtgctg ggggctgctg 901  ctgggcaccc tggggcgaca gggatccccc gccatcctac agcacctgga gtcacggctg 961  cgtgccctgg gccggccctt tgtgcgggtg ctgctgtctg agatcttccc cagcaagctg 1021  cagctctttg acagcgtgga tgcgtgggtg cagatcgcct gtccccggct ctccatcgac 1081  tggggggagg cattcagcaa accactgctg acaccctatg aggcagcggt ggctcttggg 1141  gacatcgagt ggcaacagcc gtaccccatg gacttctatg ccagtcaatc cctggggccg 1201  tggacgggca accacacagc gcggcccgcc caggagaagc caccgcaac ccccagcctg 1261  aagaatggca ctgagggggtc ccgcagtgcc caccgcctg aggacacggc cacctcctg
```

SEQ ID NO: 28 Gallus gallus (chicken) diphthamide biosynthesis 1 (DPH1)
amino acid sequence, isoform X4 (XP_015151241)
```
   1  MFDGAAVNNG ALPPFPPPRR LWGRTLLSAR WWEGGRAPRR TARQVPEELL NNVELREAMG

61  ALPSNYNFEI PKTIWRIQQA GAKKVALQMP EGLLMFACTI ADIIERFTDA KAVVMGDVTY

121  GACCVDDYTA RALGADFLVH YGHSCLIPID ATRGLKMLYV FVDIKIDTSH FLDTIRFNFA

181  VGSSLALVST IQFVAAVQAA SQELQSQYKV CVPQCKPLSP GEILGCTSPR LARDTDAIVY

241  LGDGRFHLES IMIANPGIPA YRYDPYSKVF SQEHYAHDRM REARQAAIRS AARARCWGLL

301  LGTLGRQGSP AILQHLESRL RALGRPFVRV LLSEIFPSKL QLFDSVDAWV QIACPRLSID

361  WGEAFSKPLL TPYEAAVALG DIEWQQPYPM DFYASQSLGP WTANHTARPA QEKPPATPSL

421  KNGTEGSRSA HPPEDTATS
```

SEQ ID NO: 29 Xenopus tropicalis (frog) diphthamide biosynthesis 1 (DPH1)
cDNA (XM_012956575)
```
   1  atgtcagaga tggcggaaga gccggttggg ttggagactg cgactgggac ggatcctcag 61  ctgggaatga tggctccggc gagaagccag tcagtagcac tgacacctgc ggctcccagt 121  aatgcaggcc gtgcacccat ccgtcgcgtg gctaaccaga tccctgatga aatctcccac 181  aatcctcttc tgctggaagc catgaaagtg ctgccgaaa actacaattt tgaaataccc 241  aagacaatat ggagaattca gcaagcctca gccaaaagag ttgctttgca gatgccagaa
```

TABLE 1-continued

```
 301    gggcttctca tgtttgcctg tactattgct gatatcatag aaaggttcac atcagcagag
 361    acagtagtga tgggcgatgt gacgtatgga gcatgctgtg tggatgatta cactgcacaa
 421    gcgctaggag ctgactttat ggtacattat ggacacagct gcctcatccc gattgatgcc
 481    acgcatgggg tgcgtatgtt atatgttttt gtcgacataa agattgacac gtctcatttt
 541    gtggacacca ttcgcttcaa cttcaaccg ggagcatcac tagcgcttgt cagcacggtg
 601    cagtttgtgt cagcacttca ggcagctcac caagcttac gtatggacta caaagtgact
 661    gttccacagt gcaagccgct gtcacctgga gaaatcttag gttgcacctc tccaaagctg
 721    gacaagtctg tggatgccgt agtgtatctg ggagatggac gctttcacct ggagtctgtt
 781    atgatttcca accctgatac aaaagcttac aggtatgatc catacagcaa ggtattctct
 841    cgggaatatt atgaccacag tgccatgctt aaacagagag gggaggccat ctcagctgct
 901    gccggtgcaa aaacatgggg gcttatcctg ggtactctgg gtcgtcaggg atctcccaaa
 961    atcctggagc acctggagtc acgtctgcag gcactcggct gtcgttacgt gcggctgctg
1021    ctgtcggaaa tcttccctaa taaactcaag ctgttcccag aggtggaagt gtgggtgcag
1081    gttgcctgcc caagactatc cattgattgg gggacagcat ctccaggcct tttgcttact
1141    ccatatgagg cctcagtggc tctgaaagaa gcagaatggc agcatactta tccaatggat
1201    ttctacgcca atgagtccct tggtccgtgg accgtgaacc atgaatccca ccgccccacc
1261    cgtgcaacag tccagcgcac acagaaatca gagcagagaa agcttcggag cacagacata
1321    agtgcaaagg ttgaagaatg ccctgtcag gataaggag agaccaagac tgagtga
```

SEQ ID NO: 30 *Xenopus tropicalis* (frog) diphthamide biosynthesis 1 (DPH1) amino acid sequence (XP_012812029)

```
   1    MSEMAEEPVG LETATGTDPQ LGMMAPARSQ SVALTPAAPS NAGRAPIRRV ANQIPDEISH
  61    NPLLLEAMKV LPENYNFEIP KTIWRIQQAS AKRVALQMPE GLLMFACTIA DIIERFTSAE
 121    TVVMGDVTYG ACCVDDYTAQ ALGADFMVHY GHSCLIPIDA THGVRMLYVF VDIKIDTSHF
 181    VDTIRFNFQP GASLALVSTV QFVSALQAAH QALRMDYKVT VPQCKPLSPG EILGCTSPKL
 241    DKSVDAVVYL GDGRFHLESV MISNPDTKAY RYDPYSKVFS REYYDHSAML KHRGEAISAA
 301    AGAKTWGLIL GTLGRQGSPK ILEHLESRLQ ALGCRYVRLL LSEIFPNKLK LFPEVEVWVQ
 361    VACPRLSIDW GTAFSRPLLT PYEASVALKE AEWQHTYPMD FYANESLGPW TVNHESHRPT
 421    RATVQRTQKS EQRKLRSTDI SAKVEECPCQ DKGETKTE
```

SEQ ID NO: 31 *Homo sapiens* diphthamide biosynthesis 2 (DPH2) cDNA, transcript variant 1 (NM_001384.4)

```
   1    atggagtcga tgtttagcag ccctgccgag gcggcgctgc agcgagagac cggggtgcca
  61    ggactgctta ctcctcttcc ggacctggac ggagtgtacg agctggagcg agtcgctgga
 121    tttgtccgcg acctggggtg tgaacgagtt gccttgcagt ccctgaccag gctattggga
 181    gatgctgtgg ctgtggctgc acgactggag gagacgacag gtcaaagat gttcattctg
 241    ggtgacacag cctacggcag ctgctgcgtg gatgtgctgg gtgctgagca agctggagct
 301    caggctctca tacattttgg ccctgcctgc ttaagccctc cagcccgccc actgcccgtt
 361    gccttcgtgc ttcgtcaacg ttctgtggcc ttgagctct gtgtcaaggc ctttgaggcc
 421    cagaacccag accccaaagc gcctgtggtg ctgctgagtg agccggcctg tgcccatgcc
 481    ctggaggctt tggctactct cctgcgccca cggtacctgg acctgctagt ctccagccca
 541    gcttttcccc aaccagtggg ttccctgagt ccagagccta tgccctaga gcgttttggg
 601    cgccgcttcc cccttgcccc agggaggcgt ctagaagagt atggtgcctt ctatgtaggg
 661    ggctctaagg ccagccctga cccagacctt gacccagacc tgagtcggct gctcttgggg
```

TABLE 1-continued

```
 721   tgggcaccag gtcaaccctt ctcctcctgc tgtccagata cagggaagac tcaggatgag
 781   ggtgcccggg ctggacggct aagggcacga agacgatatc tggtagagag ggccagagat
 841   gcccgcgtgg tagggctgct ggcaggcaca ctgggtgtag cccaacaccg tgaggcactg
 901   gcccacttgc ggaacctgac tcaggctgct ggcaagcgta gctatgtgtt ggcctgggg
 961   cggcccaccc ctgccaagct tgccaacttc cctgaggtgg atgtctttgt gctattagcc
1021   tgtcctctgg gtgctctagc cccccagctt tctggtagct tcttccagcc tatactggca
1081   ccatgtgagc tggaagctgc ctgcaaccct gcctggccac tccaggcct ggctccccac
1141   ctcacacatt atgcggactt attgcctggc tctcccttcc acgtggctct cccaccacct
1201   gagtcagagc tgtgggaaac cccagacgtg tcactcatta ctggagatct ccgaccccca
1261   cctgcctgga agtcatcaaa tgatcatgga agcttggctc tgaccccacg gccccagctg
1321   gagctggctg agagcagtcc tgcagcctca ttccttagtt cccggagctg gcaagggctg
1381   gagccccgcc tgggtcagac gccagtgaca gaagctgtga gtggaagacg agggattgcc
1441   atcgcctatg aggatgaggg aagcggctga
```

SEQ ID NO: 32 Homo sapiens diphthamide biosynthesis 2 (DPH2) cDNA, transcript variant 2 (NM_001039589.1)

```
   1   atggagtcga tgtttagcag ccctgccgag gcggcgctgc agcgagagac cggggtgcca
  61   ggactgctta ctcctcttcc ggacctggac ggagtgtacg agctggagcg agtcgctgga
 121   tttgtccgcg acctggggtg tgaacgagtt gccttgcagt ccctgacca gctattggga
 181   gatgctgtgg ctgtggctgc acgactggag gagacgacag ggtcaaagat gttcattctg
 241   ggtgacacag cctacggcag ctgctgcgtg gatgtgctgg gtgctgagca agctggagct
 301   caggctctca tacattttgg ccctgcctgc ttaagccctc agcccgccc actgcccgtt
 361   gccttcgtgc ttcgtcaacg ttctgtggcc ttggagctct gtgtcaaggc ctttgaggcc
 421   cagaacccag accccaaagc gcctgtggtg ctgctgagtg agccggcctg tgcccatgcc
 481   ctgggctctc ccttccacgt ggctctccca ccacctgagt cagagctgtg gaaaccccca
 541   gacgtgtcac tcattactgg agatctccga ccccaccctg cctggaagtc atcaaatgat
 601   catggaagct tggctctgac cccacgccc cagctggagc tggctgagag cagtcctgca
 661   gcctcattcc ttagttcccg gagctggcaa gggctggagc ccgcctggg tcagacgcca
 721   gtgacagaag ctgtgagtgg aagacgaggg attgccatcg cctatgagga tgagggaagc
 781   ggctga
```

SEQ ID NO: 33 Homo sapiens diphthamide biosynthesis 2 (DPH2) cDNA, transcript variant 3 (NM_001319165.1)

```
   1   atgttcattc tgggtgacac agcctacggc agctgctgcg tggatgtgct gggtgctgag
  61   caagctggag ctcaggctct catacatttt ggccctgcct gcttaagccc tccagcccgc
 121   ccactgcccg ttgccttcgt gcttcgtcaa cgttctgtgg ccttggagct ctgtgtcaag
 181   gcctttgagg cccagaaccc agaccccaaa gcgcctgtgg tgctgctgag tgagccggcc
 241   tgtgcccatg ccctggaggc tttggctact ctcctgcgcc acggtacct ggacctgcta
 301   gtctccagcc agctttttcc ccaaccagtg ggttccctga gtccagaagcc tatgccccta
 361   gagcgttttg gcgccgcctt cccccttgcc ccagggaggc gtctagaaga gtatggtgcc
 421   ttctatgtag ggggctctaa ggccagccct gacccagacc ttgacccaga cctgagtcgg
 481   ctgctcttgg ggtgggcacc aggtcaaccc ttctcctcct gctgtccaga tacagggaag
 541   actcaggatg agggtgcccg ggctggacgg ctaagggcac gaagacgata tctggtagag
 601   agggccagag atgcccgcgt ggtagggctg ctggcaggca cactgggtgt agcccaacac
```

TABLE 1-continued

```
 661   cgtgaggcac tggcccactt gcggaacctg actcaggctg ctggcaagcg tagctatgtg
 721   ttggccctgg ggcggccac  ccctgccaag cttgccaact ccctgaggt  ggatgtcttt
 781   gtgctattag cctgtcctct gggtgctcta gcccccagc  tttctggtag cttcttccag
 841   cctatactgg caccatgtga gctggaagct gcctgcaacc ctgcctggcc acctccaggc
 901   ctggctcccc acctcacaca ttatgcggac ttattgcctg gctctccctt ccacgtggct
 961   ctcccaccac ctgagtcaga gctgtgggaa accccagacg tgtcactcat tactggagat
1021   ctccgacccc cacctgcctg aagtcatca  aatgatcatg gaagcttggc tctgacccca
1081   cggccccagc tggagctggc tgagagcagt cctgcagcct cattccttag ttcccggagc
1141   tggcaagggc tggagccccg cctgggtcag acgccagtga cagaagctgt gagtggaaga
1201   cgagggattg ccatcgccta tgaggatgag ggaagcggct ga
```

SEQ ID NO: 34 *Homo sapiens* diphthamide biosynthesis 2 (DPH2) cDNA,
transcript variant 4 (NM_001319166.1)

```
   1   atggagtcga tgtttagcag ccctgccgag gcggcgctgc agcgagagac cggggtgcca
  61   ggactgctta ctcctcttcc ggacctggac ggagtgtacg agctggagcg agtcgctgga
 121   tttgtccgcg acctggggtg tgaacgagtt gccttgcagt ccctgacca  gctattggga
 181   gatgctgtgg ctgtggctgc acgactggag gagacgacag ggtcaaagat gttcattctg
 241   ggtgacacag cctacggcag ctgctgcgtg gatgtgctgg gtgctgagca agctggagct
 301   caggctctca tacattttgg ccctgcctgc ttaagccctc cagcccgccc actgcccgtt
 361   gccttcgtgc ttcgtcaacg ttctgtggcc ttgagctctc tgtcaaggc  ctttgaggcc
 421   cagaacccag accccaaagc gcctgtggtg ctgctgagtg agccggcctg tgcccatgcc
 481   ctggatacag ggaagactca ggatgagggt gcccgggctg gacggctaag ggcacgaaga
 541   cgatatctgg tagagagggc cagagatgcc cgcgtggtag ggctgctggc aggcacactg
 601   ggtgtagccc aacaccgtga ggcactggcc cacttgcgga acctgactca ggctgctggc
 661   aagcgtagct atgtgttggc cctggggcgg cccacccctg ccaagcttgc caacttccct
 721   gaggtggatg tctttgtgct attagcctgt cctctgggtg ctctagcccc ccagctttct
 781   ggtagcttct tccagcctat actggcacca tgtgagctgg aagctgcctg caaccctgcc
 841   tggccaccte caggcctggc tccccacctc acacattatg cggacttatt gcctggctct
 901   cccttccacg tggctctccc accacctgag tcagagctgt gggaaacccc agacgtgtca
 961   ctcattactg gagatctccg accccacct  gcctggaagt catcaaatga tcatggaagc
1021   ttggctctga ccccacgcc  ccagctggag ctggctgaga gcagtcctgc agcctcattc
1081   cttagttccc ggagctggca agggctggag cccgcctgg  gtcagacgcc agtgacagaa
1141   gctgtgagtg gaagacgagg gattgccatc gcctatgagg atgagggaag cggctga
```

SEQ ID NO: 35 *Homo sapiens* diphthamide biosynthesis 2 (DPH2) cDNA,
transcript variant 5 (NM_001319167.1)

```
   1   atgccctag  agcgttttgg gcgccgcttc ccccttgccc cagggaggcg tctagaagag
  61   tatggtgcct tctatgtagg gggctctaag gccagccctg acccagacct tgacccagac
 121   ctgagtcggc tgctcttggg gtgggcacca ggtcaaccct ctcctcctg  ctgtccagat
 181   acagggaaga ctcaggatga gggtgcccgg gctggacggc taagggcacg aagacgatat
 241   ctggtagaga gggccagaga tgcccgcgtg gtagggctgc tggcaggcac actgggtgta
 301   gcccaacacc gtgaggcact ggcccacttg cggaacctga ctcaggctgc tggcaagcgt
 361   agctatgtgt tggccctggg gcggcccacc cctgccaagc ttgccaactt ccctgaggtg
 421   gatgtctttg tgctattagc ctgtcctctg ggtgctctag ccccccagct ttctggtagc
```

TABLE 1-continued

| | |
|---|---|
| 481 | ttcttccagc ctatactggc accatgtgag ctggaagctg cctgcaaccc tgcctggcca |
| 541 | cctccaggcc tggctcccca cctcacacat tatgcggact tattgcctgg ctctcccttc |
| 601 | cacgtggctc tcccaccacc tgagtcagag ctgtgggaaa ccccagacgt gtcactcatt |
| 661 | actggagatc tccgacccc acctgcctgg aagtcatcaa atgatcatgg aagcttggct |
| 721 | ctgaccccac ggccccagct ggagctggct gagagcagtc ctgcagcctc attccttagt |
| 781 | tcccggagct ggcaagggct ggagccccgc ctgggtcaga cgccagtgac agaagctgtg |
| 841 | agtggaagac gagggattgc catcgcctat gaggatgagg gaagcggctg a |

SEQ ID NO: 36 Homo sapiens diphthamide biosynthesis 2 (DPH2) cDNA, transcript variant 6 (NM_001319168.1)

| | |
|---|---|
| 1 | atgttcattc tgggtgacac agcctacggc agctgctgcg tggatgtgct gggtgctgag |
| 61 | caagctggag ctcaggctct catacatttt ggccctgcct gcttaagccc tccagcccgc |
| 121 | ccactgcccg ttgccttcgt gcttcgtcaa cgttctgtgg ccttggagct ctgtgtcaag |
| 181 | gcctttgagg cccagaaccc agacccaaa gcgcctgtgg tgctgctgag tgagccggcc |
| 241 | tgtgcccatg ccctggaggc tttggctact ctcctgcgcc acggtacct ggacctgcta |
| 301 | gtctccagcc cagcttttcc ccaaccagtg ggttccctga gtccagagcc tatgccccta |
| 361 | gagcgttttg ggcgccgctt ccccttgcc ccagggaggc gtctagaaga gtatggtgcc |
| 421 | ttctatgtag ggggctctaa ggccagccct gacccagacc ttgacccaga cctgagtcgg |
| 481 | ctgctcttgg ggtgggcacc aggtcaaccc ttctcctcct gctgtccaga tacagggaag |
| 541 | actcaggatg agggtgcccg ggctggacgg ctaagggcac gaagacgata tctggtagag |
| 601 | agggccagag atgcccgcgt ggtagggctg ctggcaggca cactgggtgt agcccaacac |
| 661 | cgtgaggcac tggcccactt gcggaacctg actcaggctg ctggcaagc tagctatgtg |
| 721 | ttggccctgg ggcggccac ccctgccaag cttgccaact tccctgaggt ggatgtcttt |
| 781 | gtgctattag cctgtcctct gggtgctcta gccccccagc tttctggtag cttcttccag |
| 841 | cctatactgg caccatgtga gctggaagct gcctgcaacc ctgcctggcc acctccaggc |
| 901 | ctggctcccc acctcacaca ttatgcggac ttattgcctg gctctccctt ccacgtggct |
| 961 | ctcccaccac ctgagtcaga gctgtgggaa accccagacg tgtcactcat tactggagat |
| 1021 | ctccgacccc acctgcctg gaagtcatca aatgatcatg gaagcttggc tctgacccca |
| 1081 | cggccccagc tggagctggc tgagagcagt cctgcagcct cattccttag ttcccggagc |
| 1141 | tggcaagggc tggagccccg cctgggtcag acgccagtga cagaagctgt gagtggaaga |
| 1201 | cgagggattg ccatcgccta tgaggatgag ggaagcggct ga |

SEQ ID NO: 37 Homo sapiens diphthamide biosynthesis 2 (DPH2) cDNA, transcript variant 7 (NM_001319169.1)

| | |
|---|---|
| 1 | atgctgtggc tgtggctgca cgactggagg agacgacagg gtcaaagatg ttcattctgg |
| 61 | gtgacacagc ctacggcaga ggctttggct actctcctgc cccacggta cctggacctg |
| 121 | ctagtctcca gcccagcttt tccccaacca gtgggttccc tgagtccaga gcctatgccc |
| 181 | ctagagcgtt ttgggcgccg cttccccctt gccccaggga ggcgtctaga agagtatggt |
| 241 | gccttctatg tagggggctc taaggccagc cctgacccag accttgaccc agacctgagt |
| 301 | cggctgctct tggggtgggc accaggtcaa cccttctcct cctgctgtcc agatacaggg |
| 361 | aagactcagg atgagggtgc ccgggctgga cggctaaggg cacgaagacg atatctggta |
| 421 | gagagggcca gagatgcccg cgtggtaggg ctgctggcag gcacactggg tgtagcccaa |
| 481 | caccgtgagg cactggccca cttgcggaac ctgactcagg ctgctggcaa gcgtagctat |
| 541 | gtgttggccc tggggcggcc cacccctgcc aagcttgcca acttccctga ggtggatgtc |

TABLE 1-continued

```
 601   tttgtgctat tagcctgtcc tctgggtgct ctagccccccc agctttctgg tagcttcttc
 661   cagcctatac tggcaccatg tgagctggaa gctgcctgca accctgcctg gccacctcca
 721   ggcctggctc cccacctcac acattatgcg gacttattgc ctggctctcc cttccacgtg
 781   gctctcccac cacctgagtc agagctgtgg gaaacccag acgtgtcact cattactgga
 841   gatctccgac ccccacctgc ctggaagtca tcaaatgatc atggaagctt ggctctgacc
 901   ccacggcccc agctggagct ggctgagagc agtcctgcag cctcattcct tagttcccgg
 961   agctggcaag ggctggagcc ccgcctgggt cagacgccag tgacagaagc tgtgagtgga
1021   agacgaggga ttgccatcgc ctatgaggat gagggaagcg gctga
```

SEQ ID NO: 38 Homo sapiens diphthamide biosynthesis 2 (DPH2) cDNA, transcript variant 8 (NM_001319170.1)

```
   1   atgcccctag agcgtttttgg gcgccgcttc cccttgccc cagggaggcg tctagaagag
  61   tatggtgcct tctatgtagg gggctctaag gccagccctg acccagacct tgacccagac
 121   ctgagtcggc tgctcttggg gtgggcacca ggtcaaccct ctcctcctg ctgtccagat
 181   acagggaaga ctcaggatga gggtgcccgg gctggacggc taagggcacg aagacgatat
 241   ctggtagaga gggccagaga tgcccgcgtg gtagggctgc tggcaggcac actgggtgta
 301   gcccaacacc gtgaggcact ggcccacttg cggaacctga ctcaggctgc tggcaagcgt
 361   agctatgtgt tggccctggg gcggcccacc cctgccaagc ttgccaactt ccctgaggtg
 421   gatgtctttg tgctattagc ctgtcctctg ggtgctctag cccccccagct ttctggtagc
 481   ttcttccagc ctatactggc accatgtgag ctggaagctg cctgcaaccc tgcctggcca
 541   cctccaggcc tggctcccca cctcacacat tatgcggact tattgcctgg ctctcccttc
 601   cacgtggctc tcccaccacc tgagtcagag ctgtgggaaa ccccagacgt gtcactcatt
 661   actggagatc tccgaccccc acctgcctgg aagtcatcaa atgatcatgg aagcttggct
 721   ctgaccccac ggccccagct ggagctggct gagagcagtc ctgcagcctc attccttagt
 781   tcccggagct ggcaagggct ggagcccgc ctgggtcaga cgccagtgac agaagctgtg
 841   agtggaagac gagggattgc catcgcctat gaggatgagg gaagcggctg a
```

SEQ ID NO: 39 Homo sapiens diphthamide biosynthesis 2 (DPH2) cDNA, transcript variant 9 (NM_001319171.1)

```
   1   atgccctggg taaggggttt tgcctgtgta tgcacaaagg aggctttggc tactctcctg
  61   cgcccacggt acctggacct gctagtctcc agcccagctt ttccccaacc agtgggttcc
 121   ctgagtccag agcctatgcc cctagagcgt tttgggcgcc gcttccccct tgccccaggg
 181   aggcgtctag aagagtatgg tgccttctat gtagggggct ctaaggccag ccctgaccca
 241   gaccttgacc cagacctgag tcggctgctc ttggggtggg caccaggtca accttctcc
 301   tcctgctgtc cagatacagg gaagactcag gatgagggtg cccggctgg acggctaagg
 361   gcacgaagac gatatctggt agagagggcc agagatgccc gcgtggtagg gctgctggca
 421   ggcacactgg gtgtagccca acaccgtgag gcactggccc acttgcggaa cctgactcag
 481   gctgctggca agcgtagcta tgtgttggcc ctggggcggc ccaccctgc caagcttgcc
 541   aacttccctg aggtggatgt ctttgtgcta ttagcctgtc ctctgggtgc tctagccccc
 601   cagctttctg gtagcttctt ccagcctata ctggcaccat gtgagctgga agctgcctgc
 661   aaccctgcct ggccacctcc aggcctggct ccccacctca cacattatgc ggacttattg
 721   cctggctctc ccttccacgt ggctctccca ccactgagt cagagctgtg ggaaacccca
 781   gacgtgtcac tcattactgg agatctccga ccccacctg cctggaagtc atcaaatgat
 841   catggaagct tggctctgac cccacggccc cagctggagc tggctgagag cagtcctgca
```

TABLE 1-continued

```
901    gcctcattcc ttagttcccg gagctggcaa gggctggagc cccgcctggg tcagacgcca 961    gtgacagaag ctgtgagtgg aagacgaggg attgccatcg cctatgagga tgagggaagc 1021   ggctga
```

SEQ ID NO: 40 *Homo sapiens* diphthamide biosynthesis 2 (DPH2) amino acid sequence, isoform 1 (NP_001375.2)
```
  1    mesmfsspae aalqretgvp glltplpdld gvyelervag fvrdlgcerv alqfpdqllg 61    davavaarle ettgskmfil gdtaygsccv dvlgaeqaga qalihfgpac lspparplpv 121    afvlrqrsva lelcvkafea qnpdpkapvv llsepacaha lealatllrp ryldllvssp 181    afpqpvgsls pepmplerfg rrfplapgrr leeygafyvg gskaspdpdl dpdlsrlllg 241    wapgqpfssc cpdtgktqde garagrlrar rrylverard arvvgllagt lgvaqhreal 301    ahlrnitqaa gkrsyvlalg rptpaklanf pevdvfvlla cplgalapql sgsffqpila 361    pceleaacnp awpppglaph lthyadllpg spfhvalppp eselwetpdv slitgdlrpp 421    pawkssndhg slaltprpql elaesspaas flssrswqgl eprlgqtpvt eaysgrrgia 481    iayedegsg
```

SEQ ID NO: 41 *Homo sapiens* diphthamide biosynthesis 2 (DPH2) amino acid sequence, isoform 2 (NP_001034678.1)
```
  1    mesmfsspae aalqretgvp glltplpdld gvyelervag fvrdlgcerv alqfpdqllg 61    davavaarle ettgskmfil gdtaygsccv dvlgaeqaga qalihfgpac lspparplpv 121    afvlrqrsva lelcvkafea qnpdpkapvv llsepacaha lgspfhvalp ppeselwetp 181    dvslitgdlr pppawkssnd hgslaltprp qlelaesspa asflssrswq gleprlgqtp 241    vteavsgrrg iaiayedegs g
```

SEQ ID NO: 42 *Homo sapiens* diphthamide biosynthesis 2 (DPH2) amino acid sequence, isoform 3 (NP_001306094.1 and NP_001306097.1)
```
  1    mfilgdtayg sccvdvlgae qagaqalihf gpaclsppar plpvafvlrq rsvalelcvk 61    afeaqnpdpk apvvllsepa cahalealat llrpryldll vsspafpqpv gslspepmpl 121    erfgrrfpla pgrrleeyga fyvggskasp dpdldpdlsr lllgwapgqp fssccpdtgk 181    tqdegaragr lrarrrylve rardarvvgl lagtlgvaqh realahlrnl tqaagkrsyv 241    lalgrptpak lanfpevdvf vllacplgal apqlsgsffq pilapcelea acnpawpppg 301    laphlthyad llpgspfhva lpppeselwe tpdvslitgd lrpppawkss ndhgslaltp 361    rpqlelaess paasflssrs wqgleprlgq tpvteavsgr rgiaiayede gsg
```

SEQ ID NO: 43 *Homo sapiens* diphthamide biosynthesis 2 (DPH2) amino acid sequence, isoform 4 (NP_001306095.1)
```
  1    mesmfsspae aalqretgvp glltplpdld gvyelervag fvrdlgcerv alqfpdqllg 61    davavaarle ettgskmfil gdtaygsccv dvlgaeqaga qalihfgpac lspparplpv 121    afvlrqrsva lelcvkafea qnpdpkapvv llsepacaha ldtgktqdeg aragrlrarr 181    rylverarda rvvgllagtl gvaqhreala hlrnltqaag krsyvlalgr ptpaklanfp 241    evdvfvllac plgalapqls gsffqpilap celeaacnpa wpppglaphl thyadllpgs 301    pfhvalpppe selwetpdvs litgdlrppp awkssndhgs laltprpqle laesspaasf 361    lssrswqgle prlgqtpvte avsgrrgiai ayedegsg
```

SEQ ID NO: 44 *Homo sapiens* diphthamide biosynthesis 2 (DPH2) amino acid sequence, isoform 5 (NP_001306096.1 and NP_001306099.1)
```
  1    mplerfgrrf plapgrrlee ygafyvggsk aspdpdldpd lsrlllgwap gqpfssccpd 61    tgktqdegar agrlrarrry lverardarv vgllagtlgv aqhrealahl rnltqaagkr 121    syvlalgrpt paklanfpev dvfvllacpl galapqlsgs ffqpilapce leaacnpawp
```

TABLE 1-continued

```
 181    ppglaphlth yadllpgspf hvalpppese lwetpdvsli tgdlrpppaw kssndhgsla 241    ltprpqlela esspaasfls srswqglepr lgqtpvteav sgrrgiaiay edegsg
```

SEQ ID NO: 45 *Homo sapiens* diphthamide biosynthesis 2 (DPH2) amino acid sequence, isoform 6 (NP_001306098.1)
```
   1    mlwlwlhdwr rrqgqrcsfw vtqptaeala tllrpryldl lvsspafpqp vgslspepmp 61    lerfgrrfpl apgrrleeyg afyvggskas pdpdldpdls rlllgwapgq pfssccpdtg 121    ktqdegarag rlrarrrylv erardarvvg llagtlgvaq hrealahlrn ltqaagkrsy 181    vlalgrptpa klanfpevdv fvllacplga lapqlsgsff qpilapcele aacnpawppp 241    glaphlthya dllpgspfhv alpppeselw etpdvslitg dlrpppawks sndhgslalt 301    prpqlelaes spaasflssr swqgleprlg qtpvteaysg rrgiaiayed egsg
```

SEQ ID NO: 46 *Homo sapiens* diphthamide biosynthesis 2 (DPH2) amino acid sequence, isoform 7 (NP_001306100.1)
```
   1    mpwvrgfacv ctkealatll rpryldllvs spafpqpvgs lspepmpler fgrrfplapg 61    rrleeygafy vggskaspdp dldpdlsrll lgwapgqpfs sccpdtgktq degaragrlr 121    arrrylvera rdarvvglla gtlgvaqhre alahlrnltq aagkrsyvla lgrptpakla 181    nfpevdvfvl lacplgalap qlsgsffqpi lapceleaac npawpppgla phlthyadll 241    pgspfhvalp ppeselwetp dvslitgdlr pppawkssnd hgslaltprp qlelaesspa 301    asflssrswq gleprlgqtp vteaysgrrg iaiayedegs g
```

SEQ ID NO: 47 *Homo sapiens* diphthamide biosynthesis 2 (DPH2) cDNA, (NM_026344.3)
```
   1    atggagtcta cgttcagcag ccctgcggag gcagccctgc aacgggaggc gggcgttcca 61    ggacagttca ctcctcctga agacctggac cgcgtgtatg agctggagcg agttacgaaa 121    tttgtctgcg atttaggttg tcagcgggtg actttgcagt ccctgaccag gttactagga 181    gatgcgggag cggtggctgc ccggctggag gaagtcacag gagctaagat gttcatttta 241    ggggacacag cttatggcag ctgctgtgtg gatgtgctgg gcgccgagca ggctggagct 301    caagcccttg tgcacttcgg tcctgcctgc ttaagccccc cagcctcgca gctgcccatc 361    acctttgtcc ttggtcagcg acccgttgct ttagagctct gtgcaaaggc ctttgaagcc 421    cagaacccag atccgacagc cccggtggta ctgctgagtg agccagcttg tgcccatgcc 481    ctagagcctt tggccatgct cctgctccca aagtaccaag atctgctcat ctcccgccca 541    gctcttcccc tgccagtggg atccccgagc tcacagcctg agtccctgga gcgttttggg 601    cgctgcttcc ccctgaatcc agggagacgt ctggaagaat atggtgcctt ctatgtaggg 661    gcttctcaag caagctcgga ctccagcctt gatcccgacc tgagcagact gctcttgggt 721    tggacaccag gcggcccctt cttttcctgt tgtccagata caggacagac acaagaccag 781    ggtgccaagg ctgggagact aagagcacga agactgtatc tcatagagag gccagagat 841    gcccgtgtgg ttgggctgct ggcaggcaca ttaggtgtgg ctcgacaccg tgaggcactg 901    gcacacttgc ggaaactgac ggaagctgct ggaaaacgta gctatgtgtt agccgtgggg 961    aagcccacac ccgccaagct tgccaacttc cctgagatgg acgtctttgt gctgttagcc 1021    tgtccctggg ggcactagc ccccagcct cgggtggct tctttcggcc tgtattgacg 1081    ccatgtgaat tggaggctgc ctgcaaccct gcctggcccc cgccaggcct ggctccccac 1141    ctcacacatt atgcagagct gttgcctggt tctcccttcc atgtgccact ccctccacct 1201    gagtcagagt gtgggatac ccagatgtg tcactcattt ctggggagct ccgaccacca 1261    cctccttgga agtcatcaga tgacactaga tgttcggcct taattccgag gccccaactg 1321    gagctggcgg agagcagccc tgcagcttca ttccttagtt ctcggaactg cagggggctg
```

TABLE 1-continued

```
1381    gagccacgct tgggccagac accagtgaaa gaagccgtca gaggaagacg aggtatcgcc 1441    atcgcctacg aggatgaggg gagcagctga
```

SEQ ID NO: 48 Mus musculus diphthamide biosynthesis 2 (DPH2) amino acid
sequence, (NP_080620.1)
```
  1    mestfsspae aalqreagvp gqftppedld rvyelervtk fvcdlgcqrv tlqfpdqllg 61    dagavaarle evtgakmfil gdtaygsccv dvlgaeqaga qalvhfgpac lsppasqlpi 121    tfvlgqrpva lelcakafea qnpdptapvv llsepacaha leplamlllp kyqdllisrp 181    alplpvgsps sqpeslerfg rcfplnpgrr leeygafyvg asqassdssl dpdlsrlllg 241    wtpgrpffsc cpdtgqtqdq gakagrlrar rlylierard arvvgllagt lgvarhreal 301    ahlrklteaa gkrsyvlavg kptpaklanf pemdvfvlla cplgalapqp sggffrpvlt 361    pceleaacnp awpppglaph lthyaellpg spfhvplppp eselwdtpdv slisgelrpp 421    ppwkssddtr csaliprpql elaesspaas flssrnwqgl eprlgqtpvk eavrgrrgia 481    iayedegss
```

SEQ ID NO: 49 Homo sapiens diphthamide biosynthesis 3 (DPH3) cDNA,
transcript variant 1 (NM_206831.2)
```
  1    atggcagtgt tcatgacga ggtggaaatc gaggacttcc aatatgacga ggactcggag 61    acgtatttct atccctgccc atgtggagat aacttctcca tcaccaagga agatttggag 121    aatggggaag acgtggcaac gtgtcctagc tgctctctca ttataaaagt gatttatgac 181    aaagatcagt ttgtgtgtgg agaaacagtc ccagccccct cagccaacaa agaattagtt 241    aaatgctga
```

SEQ ID NO: 50 Homo sapiens diphthamide biosynthesis 3 (DPH3) cDNA,
transcript variant 2 (NM_001047434.2)
```
  1    atggcagtgt tcatgacga ggtggaaatc gaggacttcc aatatgacga ggactcggag 61    acgtatttct atccctgccc atgtggagat aacttctcca tcaccaagga tcagtttgtg 121    tgtggagaaa cagtcccagc cccttcagcc aacaaagaat tagttaaatg ctga
```

SEQ ID NO: 51 Homo sapiens diphthamide biosynthesis 3 (DPH3) amino acid
sequence, isoform 1 (NP_996662.1)
```
  1    mavfhdevei edfqydedse tyfypcpcgd nfsitkedle ngedvatcps csliikviyd 61    kdqfvcgetv papsankelv kc
```

SEQ ID NO: 52 Homo sapiens diphthamide biosynthesis 3 (DPH3) amino acid
sequence, isoform 2 (NP_001040899.1)
```
  1    mavfhdevei edfqydedse tyfypcpcgd nfsitkdqfv cgetvpapsa nkelvkc
```

SEQ ID NO: 53 Mus musculus diphthamide biosynthesis 3 (DPH3) cDNA,
transcript variant 1 (NM_172254.4)
```
  1    atggcggtgt tcacgacga ggtggagatc gaggactttc aatatgacga ggactcggag 61    acatatttct acccttgccc ctgtggggat aactttgcca tcaccaagga agatttggaa 121    aatggagaag atgtggccac gtgtcctagc tgctcactca ttataaaagt gatttatgac 181    aaagatcagt tcatgtgtgg agaaacagtc ccagcacctt caaccaacaa ggagttagtt 241    aaatgctga
```

SEQ ID NO: 54 Mus musculus diphthamide biosynthesis 3 (DPH3) cDNA,
transcript variant 2 (NM_001047433.2)
```
  1    atggcggtgt tcacgacga ggtggagatc gaggactttc aatatgacga ggactcggag 61    acatatttct acccttgccc ctgtggggat aactttgcca tcaccaagga tcagttcatg 121    tgtggagaaa cagtcccagc accttcaacc aacaaggagt tagttaaatg ctga
```

SEQ ID NO: 55 Mus musculus diphthamide biosynthesis 3 (DPH3) cDNA,
transcript variant 3 (NM_001284346.1)
```
  1    atggcggtgt tcacgacga ggtggagatc gaggactttc aatatgacga ggactcggag 61    acatatttct acccttgccc ctgtggggat aactttgcca tcaccaagga agatttggaa
```

TABLE 1-continued

```
121    aatggagaag atgtggccac gtgtcctagc tgctcactca ttataaaagt gatttatgac 181    aaagatcagt tcatgtgtgg agaaacagtc ccagcacctt caaccaacaa ggagttagtt 241    aaatgctga
```

SEQ ID NO: 56 *Mus musculus* diphthamide biosynthesis 3 (DPH3) amino acid sequence, isoform 1 (NP_758458.1 and NP_001271275.1)
```
  1    mavfhdevei edfqydedse tyfypcpcgd nfaitkedle ngedvatcps csliikviyd 61    kdqfmcgetv papstnkelv kc
```

SEQ ID NO: 57 *Mus musculus* diphthamide biosynthesis 3 (DPH3) amino acid sequence, isoform 2 (NP_001040898.1)
```
  1    mavfhdevei edfqydedse tyfypcpcgd nfaitkdqfm cgetvpapst nkelvkc
```

SEQ ID NO: 58 *Homo sapiens* diphthamide biosynthesis 4 (DPH4) cDNA, (NM_181706.4)
```
  1    atgatggcgg ttgagcagat gccaaaaaag gattggtaca gcatcctggg agcagaccca 61    tctgcaaata tatcagacct aaaacaaaaa tatcaaaaac tcatattaat gtatcatcca 121    gataaacaaa gtacagatgt accagcagga acagtggagg aatgtgtaca gaagttcatc 181    gaaattgatc aagcatggaa aattctagga aatgaagaga caaaaagaga gtatgacctg 241    cagcggtgtg aagatgatct aagaaatgta ggaccagtag atgctcaagt atatcttgaa 301    gaaatgtctt ggaatgaagg tgatcactct ttttatctga gttgcagatg tggtggaaaa 361    tacagtgttt ccaaggatga agcggaagaa gttagcctga tttcttgtga tacatgttca 421    ctaattatag aactccttca ttataactaa
```

SEQ ID NO: 59 *Homo sapiens* diphthamide biosynthesis 4 (DPH4) amino acid sequence, (NP_859057.4)
```
  1    mmaveqmpkk dwysilgadp sanisdlkqk yqklilmyhp dkqstdvpag tveecvqkfi 61    eidqawkilg neetkreydl qrceddlrnv gpvdaqvyle emswnegdhs fylscrcggk 121    ysvskdeaee vsliscdtcs liiellhyn
```

SEQ ID NO: 60 *Mus musculus* diphthamide biosynthesis 4 (DPH4) cDNA, (NM_026992.3)
```
  1    atggctttgg agcagacact caaaaaggat tggtacagca ttctgggtgc agacccatct 61    gcaaatatgt cagacctaaa acaaaaatat cagaaactca tattactgta tcatccagat 121    aaacaaagtg cagatgtgcc agctggaacc atggaggagt gtatgcagaa gtttattgaa 181    attgatcagg catggaaaat tctagggaat gaagaaacca gaaaaagta tgacctgcag 241    cggcatgaag atgagctaag aaatgtgggg ccagtagatg cacaggtgcg ccttgaagag 301    atgtcctgga accaaggtga tgaatctttc tttctgagct gtcgatgtgg tgggaaatac 361    actgtctcca aggatgaagc acaagaagcc accctcatct cctgtgacgc gtgctcgctg 421    attgtggagc tcctccatca gagctga
```

SEQ ID NO: 61 *Mus musculus* diphthamide biosynthesis 4 (DPH4) amino acid sequence, (NP_081268.1)
```
  1    maleqtlkkd wysilgadps anmsdlkqky qklilllyhpd kqsadvpagt meecmqkfie 61    idqawkilgn eetkkkydlq rhedelrnvg pvdaqvrlee mswnqgdesf flscrcggky 121    tvskdeaqea tliscdacsl ivellhqs
```

SEQ ID NO: 62 *Homo sapiens* diphthamide biosynthesis 5 (DPH5) cDNA, transcript variant 1 (NM_001077394.1)
```
  1    atgctttatc tcatcgggtt gggcctggga gatgccaagg acatcacagt caagggcctg 61    gaagttgtta gacgctgcag tcgagtgtat ctggaagcct acacctcagt cctaactgta 121    gggaaggaag ccttggaaga gttttatgga agaaaattgg ttgttgctga tagagaagaa 181    gtggaacaag aagcagataa tattttaaag gatgctgata tcagtgatgt tgcattcctt 241    gtggttggtg atccatttgg ggccacaaca cacagtgatc ttgttctaag agcaacaaag
```

TABLE 1-continued

```
301    ctgggaattc cttatagagt tattcacaat gcctccataa tgaatgctgt aggctgctgt
361    ggtttacagt tatataagtt tggagagaca gtttctattg ttttttggac agacacttgg
421    agaccagaaa gcttctttga caaagtgaag aagaacagac aaaatggcat gcacacatta
481    tgtttactag acatcaaagt aaaggagcag tctttggaaa atctaatcaa gggaaggaag
541    atctatgaac ctccacggta tatgagtgta aaccaagcag cccagcagct tctggagatt
601    gttcaaaatc aaagaatacg aggagaagaa ccagcagtta ccgaggagac actttgtgtt
661    ggcttagcca gggttggagc cgacgaccag aaaattgcag caggcacttt aaggcaaatg
721    tgcactgtgg acttgggaga accattgcat tccttgatca tcacaggagg cagcatacat
781    ccaatggaga tggagatgct aagtctgttt tccataccag aaaatagctc agaatctcaa
841    agcatcaatg gactttga
```

SEQ ID NO: 63 *Homo sapiens* diphthamide biosynthesis 5 (DPH5) cDNA, transcript variant 2 (NM_001077395.1)

```
1      atgctttatc tcatcgggtt gggcctggga gatgccaagg acatcacagt caagggcctg
61     gaagttgtta gacgctgcag tcgagtgtat ctggaagcct acacctcagt cctaactgta
121    gggaaggaag ccttggaaga gttttatgga agaaaattgg ttgttgctga tagagaagaa
181    gtggaacaag aagcagataa tattttaaag gatgctgata tcagtgatgt tgcattcctt
241    gtggttggtg atccattggg ggccacaaca cacagtgatc ttgttctaag agcaacaaag
301    ctgggaattc cttatagagt tattcacaat gcctccataa tgaatgctgt aggctgctgt
361    ggtttacagt tatataagtt tggagagaca gtttctattg ttttttggac agacacttgg
421    agaccagaaa gcttctttga caaagtgaag aagaacagac aaaatggcat gcacacatta
481    tgtttactag acatcaaagt aaaggagcag tctttggaaa atctaatcaa gggaaggaag
541    atctatgaac ctccacggta tatgagtgta aaccaagcag cccagcagct tctggagatt
601    gttcaaaatc aaagaatacg aggagaagaa ccagcagtta ccgaggagac actttgtgtt
661    ggcttagcca gggttggagc cgacgaccag aaaattgcag caggcacttt aaggcaaatg
721    tgcactgtgg acttgggaga accattgcat tccttgatca tcacaggagg cagcatacat
781    ccaatggaga tggagatgct aagtctgttt tccataccag aaaatagctc agaatctcaa
841    agcatcaatg gactttga
```

SEQ ID NO: 64 *Homo sapiens* diphthamide biosynthesis 5 (DPH5) cDNA, transcript variant 3 (NM_015958.2)

```
1      atgctttatc tcatcgggtt gggcctggga gatgccaagg acatcacagt caagggcctg
61     gaagttgtta gacgctgcag tcgagtgtat ctggaagcct acacctcagt cctaactgta
121    gggaaggaag ccttggaaga gttttatgga agaaaattgg ttgttgctga tagagaagaa
181    gtggaacaag aagcagataa tattttaaag gatgctgata tcagtgatgt tgcattcctt
241    gtggttggtg atccattggg ggccacaaca cacagtgatc ttgttctaag agcaacaaag
301    ctgggaattc cttatagagt tattcacaat gcctccataa tgaatgctgt aggctgctgt
361    ggtttacagt tatataagtt tggagagaca gtttctattg ttttttggac agacacttgg
421    agaccagaaa gcttctttga caaagtgaag aagaacagac aaaatggcat gcacacatta
481    tgtttactag acatcaaagt aaaggagcag tctttggaaa atctaatcaa gggaaggaag
541    atctatgaac ctccacggta tatgagtgta aaccaagcag cccagcagct tctggagatt
601    gttcaaaatc aaagaatacg aggagaagaa ccagttaccg aggagacact tgtgttggc
661    ttagccaggg ttggagccga cgaccagaaa attgcagcag gcactttaag gcaaatgtgc
721    actgtggact tgggagaacc attgcattcc ttgatcatca caggaggcag catacatcca
```

TABLE 1-continued

```
781   atggagatgg agatgctaag tctgttttcc ataccagaaa atagctcaga atctcaaagc 841   atcaatggac tttga
```

SEQ ID NO: 65 *Homo sapiens* diphthamide biosynthesis 5 (DPH5) amino acid sequence, isoform 1 (NP_057042.2)

```
  1   mlyliglglg dakditvkgl evvrrcsrvy leaytsvltv gkealeefyg rklvvadree 61   veqeadnilk dadisdvafl vvgdpfgatt hsdlvlratk lgipyrvihn asimnavgcc 121   glqlykfget vsivfwtdtw rpesffdkvk knrqngmhtl clldikvkeq slenlikgrk 181   iyepprymsv nqaaqqllei vqnqrirgee pavteetlcv glarvgaddq kiaagtlrqm 241   ctvdlgeplh sliitggsih pmememlslf sipenssesq singl
```

SEQ ID NO: 66 *Homo sapiens* diphthamide biosynthesis 5 (DPH5) amino acid sequence, isoform 2 (NP_001070863.1)

```
  1   mlyliglglg dakditvkgl evvrrcsrvy leaytsvltv gkealeefyg rklvvadree 61   veqeadnilk dadisdvafl vvgdpfgatt hsdlvlratk lgipyrvihn asimnavgcc 121   glqlykfget vsivfwtdtw rpesffdkvk knrqngmhtl clldikvkeq slenlikgrk 181   iyepprymsv nqaaqqllei vqnqrirgee pvteetlcvg larvgaddqk iaagtlrqmc 241   tvdlgeplhs liitggsihp mememlslfs ipenssesqs ingl
```

SEQ ID NO: 67 *Mus musculus* diphthamide biosynthesis 5 (DPH5) cDNA, (NM_027193.2)

```
  1   atgctttact tgatcggctt gggcctggga gatgccaagg acatcacagt caagggcctg 61   gaagttgtga cgcgatgcag tcgcgtgtat ctggaagcct acacctcagt cctgactgta 121   gggaaggaag ccctggaaga gttttatgga agaaaattga ttcttgctga cagagaagaa 181   gtagaacaag aagcagataa tattttttaag gatgcagatg tcagtgatgt tgcgttcctt 241   gtggttggtg atccatttgg ggctacaaca cacagtgatc ttattctgag agcaacaaag 301   ttgggcatcc cttatcaagt tattcacaat gcctccataa tgaacgctgt aggctgctgt 361   ggtttgcagt tgtacaggtt tggagaaaca gtttctattg tgttttggac ggacacttgg 421   cgaccagaga gcttctttga caaggtgaag aggaaccggg ccaatggcat gcacacgctg 481   tgcttactcg atatcaaagt gaaggagcag tctctggaga acctcatcag aggaagaaag 541   atctatgaac cccctcggta catgagtgtg aaccaggcgg cccagcagct tctagagatt 601   gttcagaatc acagagcacg cggggaggaa ccagcaatca ctgaggagac actctgtgtc 661   ggcttagcca gagtgggagc tgaagatcag aaaattgcag caggcacgtt acagcagatg 721   tgcacagtga gcttgggaga accactgcat tctttggtca ttacaggggg caacctgcac 781   ccactggaga tggagatgct aagtctcttc tctataccgg aatcccagag tactgatgga 841   ctctga
```

SEQ ID NO: 68 *Mus musculus* diphthamide biosynthesis 5 (DPH5) amino acid sequence, (NP_081469.2)

```
  1   mlyliglglg dakditvkgl evvrrcsrvy leaytsvltv gkealeefyg rkliladree 61   veqeadnifk dadvsdvafl vvgdpfgatt hsdlilratk lgipyqvihn asimnavgcc 121   glqlyrfget vsivfwtdtw rpesffdkvk rnrangmhtl clldikvkeq slenlirgrk 181   iyepprymsv nqaaqqllei vqnhrargee paiteetlcv glarvgaedq kiaagtlqqm 241   ctvslgeplh slvitggnlh plememlslf sipesqstdg l
```

SEQ ID NO: 69 *Homo sapiens* diphthamide biosynthesis 6 (DPH6) cDNA, transcript variant 1 (NM_080650.3)

```
  1   atgagggtcg cggctctgat cagtggtggg aaggacagct gctataatat gatgcagtgc 61   attgctgctg ggcatcgatc gttgcttta gcaaatcaa gaccagctga aaaccaagtg 121   gggtctgatg aactggatag ctacatgtat cagacagtgg ggcaccatgc cattgacttg
```

| | |
|---|---|
| 181 | tatgcagaag caatggctct tcccctctat cgccgaacca taagaggaag gagcttggat |
| 241 | acaagacaag tgtacaccaa atgtgaaggt gatgaggttg aagatctcta tgagcttttg |
| 301 | aaacttgtta aggaaaaaga agaagtagag gggatatcag taggtgctat actttctgac |
| 361 | tatcagcgta ttcgagtgga aaatgtgtgt aaaaggctta atctccagcc tttagcttat |
| 421 | ctttggcaga gaaaccagga agatttgctc agagagatga tatcatctaa cattcaagca |
| 481 | atgatcatca aagtagcagc tttgggttta gatcctgata agcatcttgg gaaaaccctg |
| 541 | gatcaaatgg agccttatct catagagctt tctaagaagt atggagtaca tgtttgtgga |
| 601 | gaaggtggag agtatgaaac tttcactttg gattgccctc tatttaagaa gaaaataatt |
| 661 | gtggattcat cagaagtagt catacattca gctgatgcat ttgcacctgt ggcttatcta |
| 721 | cgcttttag aattgcactt ggaggacaag gtgtcctcag tgcctgacaa ctacagaaca |
| 781 | tctaattata tatataattt ttga |

SEQ ID NO: 70 Homo sapiens diphthamide biosynthesis 6 (DPH6) cDNA, transcript variant 2 (NM_001141972.1)

| | |
|---|---|
| 1 | atgagggtcg cggctctgat cagtggtggg aaggacagct gctataatat gatgcagtgc |
| 61 | attgctgctg ggcatcagat cgttgcttta gcaaatctaa gaccagctga aaaccaagtg |
| 121 | gggtctgatg aactggatag ctacatgtat cagacagtgg ggcaccatgc cattgacttg |
| 181 | tatgcagaag caatggctct tcccctctat cgccgaacca taagaggaag gagcttggat |
| 241 | acaagacaag tgtacaccaa atgtgaaggt gatgaggttg aagatctcta tgagcttttg |
| 301 | aaacttgtta agggcatcac tagaatgacc ttgcttgctg aatatgatgc tctgaatctc |
| 361 | caagattttc acatgcattt gaaagtgggc agccaggcga ttgtttacag gactccaaat |
| 421 | gaactgtgca ctcacagcaa gtttgataaa cacacatttc ctcctttat cagtgagatt |
| 481 | gcaaaatgtg aagtatga |

SEQ ID NO: 71 Homo sapiens diphthamide biosynthesis 6 (DPH6) amino acid sequence, isoform 1 (NP_542381.1)

| | |
|---|---|
| 1 | mrvaalisgg kdscynmmqc iaaghqival anlrpaenqv gsdeldsymy qtvghhaidl |
| 61 | yaeamalply rrtirgrsld trqvytkceg devedlyell klvkekeeve gisvgailsd |
| 121 | yqrirvenvc krlnlqplay lwqrnqedll remissniqa miikvaalgl dpdkhlgktl |
| 181 | dqmepyliel skkygvhvcg eggeyetftl dcplfkkkii vdssevvihs adafapvayl |
| 241 | rflelhledk vssvpdnyrt snyiynf |

SEQ ID NO: 72 Homo sapiens diphthamide biosynthesis 6 (DPH6) amino acid sequence, isoform 2 (NP_001135444.1)

| | |
|---|---|
| 1 | mrvaalisgg kdscynmmqc iaaghqival anlrpaenqv gsdeldsymy qtvghhaidl |
| 61 | yaeamalply rrtirgrsld trqvytkceg devedlyell klvkgitrmt llaeydalnl |
| 121 | qdfhmhlkvg sqaivyrtpn elcthskfdk htfppfisei akcev |

SEQ ID NO: 73 Mus musculus diphthamide biosynthesis 6 (DPH6) cDNA, transcript variant 1 (NM_001356438.1)

| | |
|---|---|
| 1 | atgagggtcg cggccctgat cagtggtggg aaggacagct gttacaacat gatgcagtgc |
| 61 | attgctgagg ggcatcaaat tgttgcatta gcaaatctaa gaccagatga aaaccaagtg |
| 121 | gagtcagatg aactggatag ctatatgtat cagacagtgg gtcaccatgc cattgacttg |
| 181 | tatgctgaag caatggcgct gcccctgtat cgcagagcca tcagaggaag gagcttggag |
| 241 | acaggaagag tttatacgca atgtgaaggt gacgaggttg aagatctcta tgaactgttg |
| 301 | aaacttgtta aggaaaaaga agaaatcgaa ggggtatcag taggtgctat actctctgac |
| 361 | tatcaacgtg gacgagtaga aaatgtatgt aaacgactca atctccagcc tttagcttat |
| 421 | ctttggcaaa gaaaccagga agatttgctc cgagagatga tagcttctaa tatcaaggcc |

TABLE 1-continued

```
481    attatcatca aagtagcagc tttgggctta gatcctgata agcatcttgg gaaaaccctg 541    gttgaaatgg agccttatct tttagagctt tctaagaagt acggtgtcca cgtgtgtgga 601    gaaggtggag agtatgagac attcacgttg gactgccctc tattcaagaa gaagattgtt 661    gtggactctt cagaagcagt catgcactca gcggatgcat cgcacctgt ggcttatctg 721    cggctctccc ggctgcactt ggaagagaaa gtgagtaaag ctcagatggc agagattcca 781    aggcgagtga gaggtgtcgt cagtacctgc ggatga
```

SEQ ID NO: 74 *Mus musculus* diphthamide biosynthesis 6 (DPH6) cDNA, transcript variant 2 (NM_025675.5)

```
  1    atgagggtcg cggccctgat cagtggtggg aaggacagct gttacaacat gatgcagtgc 61    attgctgagg ggcatcaaat tgttgcatta gcaaatctaa gaccagatga aaaccaagtg 121    gagtcagatg aactggatag ctatatgtat cagacagtgg gtcaccatgc cattgacttg 181    tatgctgaag caatggcgct gcccctgtat cgcagagcca tcagaggaag gagcttggag 241    acaggaagag tttatacgca atgtgaaggt gacgaggttg aagatctcta tgaactgttg 301    aaacttgtta aggaaaaaga agaaatcgaa ggggtatcag taggtgctat actctctgac 361    tatcaacgtg gacgagtaga aaatgtatgt aaacgactca atctccagcc tttagcttat 421    ctttggcaaa gaaaccagga agatttgctc cgagagatga tagcttctaa tatcaaggcc 481    attatcatca aagtagcagc tttgggctta gatcctgata agcatcttgg gaaaaccctg 541    gttgaaatgg agccttatct tttagagctt tctaagaagt acggtgtcca cgtgtgtgga 601    gaaggtggag agtatgagac attcacgttg gactgccctc tattcaagaa gaagattgtt 661    gtggactctt cagaagcagt catgcactca gcggatgcat cgcacctgt ggcttatctg 721    cggctctccc ggctgcactt ggaagagaaa gtgtcgtcag tacctgcgga tgatgaaaca 781    gctaactcta tacacagctc ttaa
```

SEQ ID NO: 75 *Mus musculus* diphthamide biosynthesis 6 (DPH6) cDNA, transcript variant 3 (NM_001356439.1)

```
  1    atgagggtcg cggccctgat cagtggtggg aaggacagct gttacaacat gatgcagtgc 61    attgctgagg ggcatcaaat tgttgcatta gcaaatctaa gaccagatga aaaccaagtg 121    gagtcagatg aactggatag ctatatgtat cagacagtgg gtcaccatgc cattgacttg 181    tatgctgaag caatggcgct gcccctgtat cgcagagcca tcagaggaag gagcttggag 241    acaggaagag tttatacgca atgtgaaggt gacgaggttg aagatctcta tgaactgttg 301    aaacttgtta aggaaaaaga agaaatcgaa ggggtatcag taggtgctat actctctgac 361    tatcaacgtg gacgagtaga aaatgtatgt aaacgactca atctccagcc tttagcttat 421    ctttggcaaa gaaaccagga agatttgctc cgagagatga tagcttctaa tatcaaggcc 481    attatcatca aagtagcagc tttgggctta gatcctgata agcatcttgg gaaaaccctg 541    gttgaaatgg agccttatct tttagaggga ctcttcagaa gcagtcatgc actcagcgga 601    tgcattcgca cctgtggctt atctgcggct ctcccggctg cacttggaag agaaagtgtc 661    gtcagtacct gcggatga
```

SEQ ID NO: 76 *Mus musculus* diphthamide biosynthesis 6 (DPH6) amino acid sequence, isoform 1 (NP_001343367.1)

```
  1    mrvaalisgg kdscynmmqc iaeghqival anlrpdenqv esdeldsymy qtvghhaidl 61    yaeamalply rrairgrsle tgrvytqceg devedlyell klvkekeeie gvsvgailsd 121    yqrgrvenvc krlnlqplay lwqrnqedll remiasnika iiikvaalgl dpdkhlgktl 181    vemepyllel skkygvhvcg eggeyetftl dcplfkkkiv vdsseavmhs adafapvayl 241    rlsrlhleek vskaqmaeip rrvrgvvstc g
```

TABLE 1-continued

SEQ ID NO: 77 *Mus musculus* diphthamide biosynthesis 6 (DPH6) amino acid
sequence, isoform 2 (NP_079951.1)
```
  1  mrvaalisgg kdscynmmqc iaeghqival anlrpdenqv esdeldsymy qtvghhaidl
 61  yaeamalply rrairgrsle tgrvytqceg devedlyell klvkekeeie gvsvgailsd
121  yqrgrvenvc krlnlqplay lwqrnqedll remiasnika iiikvaalgl dpdkhlgktl
181  vemepyllel skkygvhvcg eggeyetftl dcplfkkkiv vdsseavmhs adafapvayl
241  rlsrlhleek vssvpaddet ansihss
```

SEQ ID NO: 78 *Mus musculus* diphthamide biosynthesis 6 (DPH6) amino acid
sequence, isoform 3 (NP_001343368.1)
```
  1  mrvaalisgg kdscynmmqc iaeghqival anlrpdenqv esdeldsymy qtvghhaidl
 61  yaeamalply rrairgrsle tgrvytqceg devedlyell klvkekeeie gvsvgailsd
121  yqrgrvenvc krlnlqplay lwqrnqedll remiasnika iiikvaalgl dpdkhlgktl
181  vemepylleg lfrsshalsg cirtcglsaa lpaalgresv vstcg
```

SEQ ID NO: 79 *Homo sapiens* diphthamide biosynthesis 7 (DPH7) cDNA,
transcript variant 1 (NM_138778.4)
```
   1  atgatgggct gtttcgccct gcaaacggtg acaccgagc tgaccgcgga ctcggtggag
  61  tggtgcccgc tgcaaggctg caggcacctg ctggcgtgcg ggacctacca gctgcggcgg
 121  ccggaggacc ggcctgccgg cccccagaac aagggtggaa tggaagttaa ggagcctcag
 181  gtccgtttag gccgtctctt cctgtacagt ttcaatgaca caactctat tcaccctctg
 241  gtcgaggtcc aaagaaaaga tacttctgca atcctggaca tgaaatggtg tcacatcccg
 301  gtggctggac atgccctctt gggcttggca gatgccagtg gatccataca actgctccgc
 361  ctggtggaat ctgagaagag ccacgtgctg gagccattgt ccagccttgc cctggaggag
 421  cagtgtctgg ctttgtccct agattggtcc actgggaaaa ctggaagggc cggggaccag
 481  cccttgaaga tcatcagcag tgactccaca gggcagctcc acctcctgat ggtgaatgag
 541  acgaggccca ggctgcagaa agtggcctca tggcaggcac atcaattcga ggcctggatt
 601  gctgctttca attactggca tccagaaatt gtgtattcag ggggcgacga tggccttctg
 661  aggggctggg acaccagggt acccggcaaa tttctcttca ccagcaaaag acacaccatg
 721  ggtgtgtgca gcatccagag cagccctcat cgggagcaca tcctggccac gggaagctat
 781  gatgaacaca tcctactgtg ggacacacga aacatgaagc agccgttggc agatacgcct
 841  gtgcagggtg gggtatggag aatcaagtgg caccctttcc accaccacct gctcctggcc
 901  gcctgcatgc acagtggctt taagatcctc aactgccaaa aggcaatgga ggagaggcag
 961  gaggcgacgg tcctgacatc tcacacattg cccgactcgc tggtgtatgg agccgactgg
1021  tcctggctgc tcttccgttc tctgcagcgg gcccctcgt ggtccttcc tagcaaccta
1081  ggaaccaaga cggcagacct gaagggtgca agcgagttgc aacaccctg tcatgaatgc
1141  agagaggata cgatgggga gggccatgcc agacccaga gtggaatgaa gccactcaca
1201  gagggcatga ggaagaatgg cacctggctg caggctacag cagccaccac acgtgactgt
1261  ggcgtgaacc cagaagaagc agactcagcc ttcagcctcc tggccacctg ctccttctat
1321  gaccatgcgc tccacctctg ggagtgggag gggaactga
```

SEQ ID NO: 80 *Homo sapiens* diphthamide biosynthesis 7 (DPH7) cDNA,
transcript variant 2 (NM_001346370.1)
```
   1  atgatgggct gtttcgccct gcaaacggtg acaccgagc tgaccgcgga ctcggtggag
  61  tggtgcccgc tgcaaggctg caggcacctg ctggcgtgcg ggacctacca gctgcggcgg
 121  ccggaggacc ggcctgccgg cccccagaac aagggtggaa tggaagttaa ggagcctcag
 181  gtccgtttag gccgtctctt cctgtacagt ttcaatgaca caactctat tcaccctctg
```

TABLE 1-continued

```
 241    gtcgaggtcc aaagaaaaga tacttctgca atcctggaca tgaaatggtg tcacatcccg
 301    gtggctggac atgccctctt gggcttggca gatgccagtg gatccataca actgctccgc
 361    ctggtggaat ctgagaagag ccacgtgctg gagccattgt ccagccttgc cctggaggag
 421    cagtgtctgg ctttgtccct agattggtcc actgggaaaa ctggaagggc cggggaccag
 481    cccttgaaga tcatcagcag tgactccaca gggcagctcc acctcctgat ggtgaatgag
 541    acgaggccca ggctgcagaa agtggcctca tggcaggcac atcaattcga ggcctggatt
 601    gctgctttca attactggca tccagaaatt gtgtattcag ggggcgacga tggccttctg
 661    agggctggg acaccagggt acccggcaaa tttctcttca ccagcaaaag ctatgatgaa
 721    cacatcctac tgtgggacac acgaaacatg aagcagccgt ggcagatac gcctgtgcag
 781    ggtggggtat ggagaatcaa gtggcaccct ttccaccacc acctgctcct ggccgcctgc
 841    atgcacagtg gctttaagat cctcaactgc caaaaggcaa tggaggagag caggaggcg
 901    acggtcctga catctcacac attgcccgac tcgctggtgt atggagccga ctggtcctgg
 961    ctgctcttcc gttctctgca gcgggccccc tcgtggtcct ttcctagcaa cctaggaacc
1021    aagacggcag acctgaaggg tgcaagcgag ttgccaacac cctgtcatga atgcagagag
1081    gataacgatg gggagggcca tgccagaccc cagagtggaa tgaagccact cacagagggc
1141    atgaggaaga atggcacctg gctgcaggct acagcagcca ccacgtga ctgtggcgtg
1201    aacccagaag aagcagactc agccttcagc ctcctggcca cctgctcctt ctatgaccat
1261    gcgctccacc tctgggagtg ggaggggaac tga
```

SEQ ID NO: 81 *Homo sapiens* diphthamide biosynthesis 7 (DPH7) cDNA, transcript variant 3 (NM_001346371.1)

```
   1    atgatgggct gtttcgccct gcaaacggtg gacaccgagc tgaccgcgga ctcggtggag
  61    tggtgcccgc tgcaaggctg caggcacctg ctggcgtgcg ggacctacca gctgcggcgg
 121    ccggaggacc ggcctgccgg cccccagaac aagggtggaa tggaagttaa ggagcctcag
 181    gtccgtttag gccgtctctt cctgtacagt ttcaatgaca caactctat tcaccctctg
 241    gtcgaggtcc aaagaaaaga tacttctgca atcctggaca tgaaatggtg tcacatcccg
 301    gtggctggac atgccctctt gggcttggca gatgccagtg gatccataca actgctccgc
 361    ctggtggaat ctgagaagag ccacgtgctg gagccattgt ccagccttgc cctggaggag
 421    cagtgtctgg ctttgtccct agattggtcc actgggaaaa ctggaagggc cggggaccag
 481    cccttgaaga tcatcagcag tgactccaca gggcagctcc acctcctgat ggtgaatgag
 541    acgaggccca ggctgcagaa agtggcctca tggcaggcac atcaattcga ggcctggatt
 601    gctgctttca attactggca tccagaaatt gtgtattcag ggggcgacga tggccttctg
 661    agggctggg acaccagggt acccggcaaa tttctcttca ccagcaaaag acacaccatg
 721    ggtgtgtgca gcatccagag cagccctcat cgggagcaca tcctggccac gggaagctat
 781    gatgaacaca tcctactgtg gacacacga aacatgaagc agccgttggc agatacgcct
 841    gtgcagggtg gggtatggag aatcaagtgg cacccttttcc accaccacct gctcctggcc
 901    gcctgcatgc acagtggctt taagatcctc aactgccaaa aggcaatggc tgtagaagag
 961    gtcctgctgg cccgagtgga cgtgttgagc gattgctgga tgaaagacta g
```

SEQ ID NO: 82 *Homo sapiens* diphthamide biosynthesis 7 (DPH7) cDNA, transcript variant 4 (NM_001346372.1)

```
   1    atgatgggct gtttcgccct gcaaacggtg gacaccgagc tgaccgcgga ctcggtggag
  61    tggtgcccgc tgcaaggctg caggcacctg ctggcgtgcg ggacctacca gctgcggcgg
 121    ccggaggacc ggcctgccgg cccccagaac aagggtggaa tggaagttaa ggagcctcag
```

TABLE 1-continued

```
181    gtccgtttag gccgtctctt cctgtacagt ttcaatgaca acaactctat tcaccctctg
241    gtcgaggtcc aaagaaaaga tacttctgca atcctggaca tgaaatggtg tcacatcccg
301    gtggctggac atgccctctt gggcttggca gatgccagtg gatccataca actgctccgc
361    ctggtggaat ctgagaagag ccacgtgctg gagccattgt ccagccttgc cctggaggag
421    cagtgtctgg ctttgtccct agattggtcc actgggaaaa ctggaagggc cggggaccag
481    cccttgaaga tcatcagcag tgactccaca gggcagctcc acctcctgat ggtgaatgag
541    acgaggccca ggctgcagaa agtggcctca tggcaggcac atcaattcga ggcctggatt
601    gctgctttca attactggca tccagaaatt gtgtattcag ggggcgacga tggccttctg
661    aggggctggg acaccagggt acccggcaaa tttctcttca ccagcaaaag acacaccatg
721    ggtgtgtgca gcatccagag cagccctcat cggagcacat cctggccac gggaagctat
781    gatgaacaca tcctactgtg ggacacacga aacatgaagc agccgttggc agatacgcct
841    gtgcagggtg gggtatggag aatcaagtgg caccctttcc accaccacct gctcctggcc
901    gcctgcatgc acagtggctt taagatcctc aactgccaaa aggcaatggg ctgtggctct
961    ctgagggctt ag
```

SEQ ID NO: 83 Homo sapiens diphthamide biosynthesis 7 (DPH7) cDNA, transcript variant 5 (NM_001346373.1)

```
1      atgccctctt gggcttggca gatgccagtg gatccataca actgctccgc ctggtggaat
61     ctgagggccg gggaccagcc cttgaagatc atcagcagtg actccacagg gcagctccac
121    ctcctgatgg tgaatgagac gaggcccagg ctgcagaaag tggcctcatg gcaggcacat
181    caattcgagg cctggattgc tgctttcaat tactggcatc cagaaattgt gtattcaggg
241    ggcgacgatg gccttctgag gggctgggac accagggtac ccggcaaatt tctcttcacc
301    agcaaaagac acaccatggg tgtgtgcagc atccagagca gccctcatcg ggagcacatc
361    ctggccacgg gaagctatga tgaacacatc ctactgtggg acacacgaaa catgaagcag
421    ccgttggcag atacgcctgt gcagggtggg gtatggagaa tcaagtggca ccctttccac
481    caccacctgc tcctggccgc ctgcatgcac agtggcttta agatcctcaa ctgccaaaag
541    gcaatggagg agaggcagga ggcgacggtc ctgacatctc acacattgcc cgactcgctg
601    gtgtatggag ccgactggtc ctggctgctc ttccgttctc tgcagcgggc cccctcgtgg
661    tcctttccta gcaacctagg aaccaagacg gcagacctga agggtgcaag cgagttgcca
721    acaccctgtc atgaatgcag agaggataac gatggggagg ccatgccag acccccagagt
781    ggaatgaagc cactcacaga gggcatgagg aagaatggca cctggctgca ggctacagca
841    gccaccacac gtgactgtgg cgtgaaccca aagaagcag actcagcctt cagcctcctg
901    gccacctgct ccttctatga ccatgcgctc cacctctggg agtgggaggg aactga
```

SEQ ID NO: 84 Homo sapiens diphthamide biosynthesis 7 (DPH7) cDNA, transcript variant 6 (NM_001346374.1)

```
1      atgatgggct gtttcgccct gcaaacggtg acaccgagc tgaccgcgga ctcggtggag
61     tggtgcccgc tgcaaggctg caggcacctg ctggcgtgcg ggacctacca gctgcggcgg
121    ccggaggacc ggcctgccgg cccccagaac aagggtggaa tggaagttaa ggagcctcag
181    gtccgtttag gccgtctctt cctgtacagt ttcaatgaca acaactctat tcaccctctg
241    gtcgaggtcc aaagaaaaga tacttctgca atcctggaca tgaaatggtg tcacatcccg
301    gtggctggac atgccctctt gggcttggca gatgccagtg gatccataca actgctccgc
361    ctggtggaat ctgagaagag ccacgtgctg gagccattgt ccagccttgc cctggaggag
421    cagtgtctgg ctttgtccct agattggtcc actgggaaaa ctggaagggc cggggaccag
```

TABLE 1-continued

```
481   cccttgaaga tcatcagcag tgactccaca gggcagctcc acctcctgat ggtgaatgag 541   acgaggccca ggctgcagaa agtggcctca tggcaggcac atcaattcga ggcctggatt 601   gctgctttca attactggca tccagaaatt gtgtattcag ggggcgacga tggccttctg 661   aggggctggg acaccagggt acccggcaaa tttctcttca ccagcaaaag ctatgatgaa 721   cacatcctac tgtgggacac acgaaacatg aagcagccgt ggcagatac gcctgtgcag 781   ggtggggtat ggagaatcaa gtggcaccct ttccaccacc acctgctcct ggccgcctgc 841   atgcacagtg ctttaagat cctcaactgc caaaaggcaa tgggctgtgg ctctctgagg 901   gcttag
```

SEQ ID NO: 85 *Homo sapiens* diphthamide biosynthesis 7 (DPH7) cDNA, transcript variant 7 (NM_001346375.1)

```
  1   atggtgaatg agacgaggcc caggctgcag aaagtggcct catggcaggc acatcaattc 61   gaggcctgga ttgctgcttt caattactgg catccagaaa ttgtgtattc aggggggcgac 121   gatggccttc tgaggggctg ggacaccagg gtacccggca aatttctctt caccagcaaa 181   agacacacca tgggtgtgtg cagcatccag agcagccctc atcgggagca catcctggcc 241   acgggaagct atgatgaaca catcctactg tgggacacac gaaacatgaa gcagccgttg 301   gcagatacgc ctgtgcaggg tggggtatgg agaatcaagt ggcacccttt ccaccaccac 361   ctgctcctgg ccgcctgcat gcacagtggc tttaagatcc tcaactgcca aaaggcaatg 421   gaggagaggc aggaggcgac ggtcctgaca tctcacacat gcccgactc gctggtgtat 481   ggagccgact ggtcctggct gctcttccgt tctctgcagc gggccccctc gtggtccttt

541   cctagcaacc taggaaccaa gacggcagac ctgaagggtg caagcgagtt gccaacaccc 601   tgtcatgaat gcagagagga taacgatggg gagggccatg ccagacccca gagtggaatg 661   aagccactca cagagggcat gaggaagaat ggcacctggc tgcaggctac agcagccacc 721   acacgtgact gtggcgtgaa cccagaagaa gcagactcag ccttcagcct cctggccacc 781   tgctccttct atgaccatgc gctccacctc tgggagtggg aggggaactg a
```

SEQ ID NO: 86 *Homo sapiens* diphthamide biosynthesis 7 (DPH7) cDNA, transcript variant 8 (NM_001346376.1)

```
  1   atggtgaatg agacgaggcc caggctgcag aaagtggcct catggcaggc acatcaattc 61   gaggcctgga ttgctgcttt caattactgg catccagaaa ttgtgtattc aggggggcgac 121   gatggccttc tgaggggctg ggacaccagg gtacccggca aatttctctt caccagcaaa 181   agacacacca tgggtgtgtg cagcatccag agcagccctc atcgggagca catcctggcc 241   acgggaagct atgatgaaca catcctactg tgggacacac gaaacatgaa gcagccgttg 301   gcagatacgc ctgtgcaggg tggggtatgg agaatcaagt ggcacccttt ccaccaccac 361   ctgctcctgg ccgcctgcat gcacagtggc tttaagatcc tcaactgcca aaaggcaatg 421   gaggagaggc aggaggcgac ggtcctgaca tctcacacat gcccgactc gctggtgtat 481   ggagccgact ggtcctggct gctcttccgt tctctgcagc gggccccctc gtggtccttt

541   cctagcaacc taggaaccaa gacggcagac ctgaagggtg caagcgagtt gccaacaccc 601   tgtcatgaat gcagagagga taacgatggg gagggccatg ccagacccca gagtggaatg 661   aagccactca cagagggcat gaggaagaat ggcacctggc tgcaggctac agcagccacc 721   acacgtgact gtggcgtgaa cccagaagaa gcagactcag ccttcagcct cctggccacc 781   tgctccttct atgaccatgc gctccacctc tgggagtggg aggggaactg a
```

TABLE 1-continued

SEQ ID NO: 87 *Homo sapiens* diphthamide biosynthesis 7 (DPH7) cDNA, transcript variant 9 (NM_001346377.1)

```
  1  atggtgaatg agacgaggcc caggctgcag aaagtggcct catggcaggc acatcaattc
 61  gaggcctgga ttgctgcttt caattactgg catccagaaa ttgtgtattc aggggcgac
121  gatggccttc tgagggctg ggacaccagg gtacccggca aatttctctt caccagcaaa
181  agacacacca tgggtgtgtg cagcatccag agcagccctc atcgggagca catcctggcc
241  acgggaagct atgatgaaca catcctactg tgggacacac gaaacatgaa gcagccgttg
301  gcagatacgc ctgtgcaggg tggggtatgg agaatcaagt ggcacccttt ccaccaccac
361  ctgctcctgg ccgcctgcat gcacagtggc tttaagatcc tcaactgcca aaaggcaatg
421  gaggagaggc aggaggcgac ggtcctgaca tctcacacat gcccgactc gctggtgtat
481  ggagccgact ggtcctggct gctcttccgt tctctgcagc gggccccctc gtggtccttt
541  cctagcaacc taggaaccaa gacggcagac ctgaagggtg caagcgagtt gccaacaccc
601  tgtcatgaat gcagagagga taacgatggg gagggccatg ccagaccca gagtggaatg
661  aagccactca cagagggcat gaggaagaat ggcacctggc tgcaggctac agcagccacc
721  acacgtgact gtggcgtgaa cccagaagaa gcagactcag ccttcagcct cctggccacc
781  tgctccttct atgaccatgc gctccacctc tgggagtggg agggaactg a
```

SEQ ID NO: 88 *Homo sapiens* diphthamide biosynthesis 7 (DPH7) cDNA, transcript variant 10 (NM_001346378.1)

```
  1  atggtgaatg agacgaggcc caggctgcag aaagtggcct catggcaggc acatcaattc
 61  gaggcctgga ttgctgcttt caattactgg catccagaaa ttgtgtattc aggggcgac
121  gatggccttc tgagggctg ggacaccagg gtacccggca aatttctctt caccagcaaa
181  agacacacca tgggtgtgtg cagcatccag agcagccctc atcgggagca catcctggcc
241  acgggaagct atgatgaaca catcctactg tgggacacac gaaacatgaa gcagccgttg
301  gcagatacgc ctgtgcaggg tggggtatgg agaatcaagt ggcacccttt ccaccaccac
361  ctgctcctgg ccgcctgcat gcacagtggc tttaagatcc tcaactgcca aaaggcaatg
421  gaggagaggc aggaggcgac ggtcctgaca tctcacacat gcccgactc gctggtgtat
481  ggagccgact ggtcctggct gctcttccgt tctctgcagc gggccccctc gtggtccttt
541  cctagcaacc taggaaccaa gacggcagac ctgaagggtg caagcgagtt gccaacaccc
601  tgtcatgaat gcagagagga taacgatggg gagggccatg ccagaccca gagtggaatg
661  aagccactca cagagggcat gaggaagaat ggcacctggc tgcaggctac agcagccacc
721  acacgtgact gtggcgtgaa cccagaagaa gcagactcag ccttcagcct cctggccacc
781  tgctccttct atgaccatgc gctccacctc tgggagtggg agggaactg a
```

SEQ ID NO: 89 *Homo sapiens* diphthamide biosynthesis 7 (DPH7) cDNA, transcript variant 11 (NM_001346379.1)

```
  1  atggtgaatg agacgaggcc caggctgcag aaagtggcct catggcaggc acatcaattc
 61  gaggcctgga ttgctgcttt caattactgg catccagaaa ttgtgtattc aggggcgac
121  gatggccttc tgagggctg ggacaccagg gtacccggca aatttctctt caccagcaaa
181  agacacacca tgggtgtgtg cagcatccag agcagccctc atcgggagca catcctggcc
241  acgggaagct atgatgaaca catcctactg tgggacacac gaaacatgaa gcagccgttg
301  gcagatacgc ctgtgcaggg tggggtatgg agaatcaagt ggcacccttt ccaccaccac
361  ctgctcctgg ccgcctgcat gcacagtggc tttaagatcc tcaactgcca aaaggcaatg
421  gaggagaggc aggaggcgac ggtcctgaca tctcacacat gcccgactc gctggtgtat
481  ggagccgact ggtcctggct gctcttccgt tctctgcagc gggccccctc gtggtccttt
```

TABLE 1-continued

```
541  cctagcaacc taggaaccaa dacggcagac ctgaagggtg caagcgagtt gccaacaccc 601  tgtcatgaat gcagagagga taacgatggg gagggccatg ccagacccca gagtggaatg 661  aagccactca cagagggcat gaggaagaat ggcacctggc tgcaggctac agcagccacc 721  acacgtgact gtggcgtgaa cccagaagaa gcagactcag ccttcagcct cctggccacc 781  tgctccttct atgaccatgc gctccacctc tgggagtggg aggggaactg a
```

SEQ ID NO: 90 Homo sapiens diphthamide biosynthesis 7 (DPH7) cDNA,
transcript variant 12 (NM_001346380.1)
```
  1  atggtgaatg agacgaggcc caggctgcag aaagtggcct catggcaggc acatcaattc 61  gaggcctgga ttgctgcttt caattactgg catccagaaa ttgtgtattc aggggggcgac 121  gatggccttc tgaggggctg ggacaccagg gtacccggca aatttctctt caccagcaaa 181  agacacacca tgggtgtgtg cagcatccag agcagccctc atcgggagca catcctggcc 241  acgggaagct atgatgaaca catcctactg tgggacacac gaaacatgaa gcagccgttg 301  gcagatacgc ctgtgcaggg tggggtatgg agaatcaagt ggcacccttt ccaccaccac 361  ctgctcctgg ccgcctgcat gcacagtggc tttaagatcc tcaactgcca aaaggcaatg 421  gaggagaggc aggaggcgac ggtcctgaca tctcacacat gcccgactc gctggtgtat 481  ggagccgact ggtcctggct gctcttccgt tctctgcagc gggcccctc gtggtccttt 541  cctagcaacc taggaaccaa dacggcagac ctgaagggtg caagcgagtt gccaacaccc 601  tgtcatgaat gcagagagga taacgatggg gagggccatg ccagacccca gagtggaatg 661  aagccactca cagagggcat gaggaagaat ggcacctggc tgcaggctac agcagccacc 721  acacgtgact gtggcgtgaa cccagaagaa gcagactcag ccttcagcct cctggccacc 781  tgctccttct atgaccatgc gctccacctc tgggagtggg aggggaactg a
```

SEQ ID NO: 91 Homo sapiens diphthamide biosynthesis 7 (DPH7) cDNA,
transcript variant 13 (NM_001346381.1)
```
  1  atggtgaatg agacgaggcc caggctgcag aaagtggcct catggcaggc acatcaattc 61  gaggcctgga ttgctgcttt caattactgg catccagaaa ttgtgtattc aggggggcgac 121  gatggccttc tgaggggctg ggacaccagg gtacccggca aatttctctt caccagcaaa 181  agacacacca tgggtgtgtg cagcatccag agcagccctc atcgggagca catcctggcc 241  acgggaagct atgatgaaca catcctactg tgggacacac gaaacatgaa gcagccgttg 301  gcagatacgc ctgtgcaggg tggggtatgg agaatcaagt ggcacccttt ccaccaccac 361  ctgctcctgg ccgcctgcat gcacagtggc tttaagatcc tcaactgcca aaaggcaatg 421  gaggagaggc aggaggcgac ggtcctgaca tctcacacat gcccgactc gctggtgtat 481  ggagccgact ggtcctggct gctcttccgt tctctgcagc gggcccctc gtggtccttt 541  cctagcaacc taggaaccaa dacggcagac ctgaagggtg caagcgagtt gccaacaccc 601  tgtcatgaat gcagagagga taacgatggg gagggccatg ccagacccca gagtggaatg 661  aagccactca cagagggcat gaggaagaat ggcacctggc tgcaggctac agcagccacc 721  acacgtgact gtggcgtgaa cccagaagaa gcagactcag ccttcagcct cctggccacc 781  tgctccttct atgaccatgc gctccacctc tgggagtggg aggggaactg a
```

SEQ ID NO: 92 Homo sapiens diphthamide biosynthesis 7 (DPH7) cDNA,
transcript variant 14 (NM_001346382.1)
```
  1  atggtgaatg agacgaggcc caggctgcag aaagtggcct catggcaggc acatcaattc 61  gaggcctgga ttgctgcttt caattactgg catccagaaa ttgtgtattc aggggggcgac 121  gatggccttc tgaggggctg ggacaccagg gtacccggca aatttctctt caccagcaaa 181  agacacacca tgggtgtgtg cagcatccag agcagccctc atcgggagca catcctggcc
```

TABLE 1-continued

| | |
|---|---|
| 241 | acgggaagct atgatgaaca catcctactg tgggacacac gaaacatgaa gcagccgttg |
| 301 | gcagatacgc ctgtgcaggg tggggtatgg agaatcaagt ggcacccttt ccaccaccac |
| 361 | ctgctcctgg ccgcctgcat gcacagtggc tttaagatcc tcaactgcca aaaggcaatg |
| 421 | gaggagaggc aggaggcgac ggtcctgaca tctcacacat gcccgactc gctggtgtat |
| 481 | ggagccgact ggtcctggct gctcttccgt tctctgcagc gggcccctc gtggtccttt |
| 541 | cctagcaacc taggaaccaa gacggcagac ctgaagggtg caagcgagtt gccaacaccc |
| 601 | tgtcatgaat gcagagagga taacgatggg gagggccatg ccagacccca gagtggaatg |
| 661 | aagccactca cagagggcat gaggaagaat ggcacctggc tgcaggctac agcagccacc |
| 721 | acacgtgact gtggcgtgaa cccagaagaa gcagactcag ccttcagcct cctggccacc |
| 781 | tgctccttct atgaccatgc gctccacctc tgggagtggg aggggaactg a |

SEQ ID NO: 93 Homo sapiens diphthamide biosynthesis 7 (DPH7) cDNA, transcript variant 15 (NM_001346383.1)

| | |
|---|---|
| 1 | atggtgaatg agacgaggcc caggctgcag aaagtggcct catggcaggc acatcaattc |
| 61 | gaggcctgga ttgctgcttt caattactgg catccagaaa ttgtgtattc aggggggcgac |
| 121 | gatggccttc tgaggggctg ggacaccagg gtacccggca aatttctctt caccagcaaa |
| 181 | agacacacca tgggtgtgtg cagcatccag agcagccctc atcgggagca catcctggcc |
| 241 | acgggaagct atgatgaaca catcctactg tgggacacac gaaacatgaa gcagccgttg |
| 301 | gcagatacgc ctgtgcaggg tggggtatgg agaatcaagt ggcacccttt ccaccaccac |
| 361 | ctgctcctgg ccgcctgcat gcacagtggc tttaagatcc tcaactgcca aaaggcaatg |
| 421 | gaggagaggc aggaggcgac ggtcctgaca tctcacacat gcccgactc gctggtgtat |
| 481 | ggagccgact ggtcctggct gctcttccgt tctctgcagc gggcccctc gtggtccttt |
| 541 | cctagcaacc taggaaccaa gacggcagac ctgaagggtg caagcgagtt gccaacaccc |
| 601 | tgtcatgaat gcagagagga taacgatggg gagggccatg ccagacccca gagtggaatg |
| 661 | aagccactca cagagggcat gaggaagaat ggcacctggc tgcaggctac agcagccacc |
| 721 | acacgtgact gtggcgtgaa cccagaagaa gcagactcag ccttcagcct cctggccacc |
| 781 | tgctccttct atgaccatgc gctccacctc tgggagtggg aggggaactg a |

SEQ ID NO: 94 Homo sapiens diphthamide biosynthesis 7 (DPH7) cDNA, transcript variant 16 (NM_001346384.1)

| | |
|---|---|
| 1 | atggtgaatg agacgaggcc caggctgcag aaagtggcct catggcaggc acatcaattc |
| 61 | gaggcctgga ttgctgcttt caattactgg catccagaaa ttgtgtattc aggggggcgac |
| 121 | gatggccttc tgaggggctg ggacaccagg gtacccggca aatttctctt caccagcaaa |
| 181 | agacacacca tgggtgtgtg cagcatccag agcagccctc atcgggagca catcctggcc |
| 241 | acgggaagct atgatgaaca catcctactg tgggacacac gaaacatgaa gcagccgttg |
| 301 | gcagatacgc ctgtgcaggg tggggtatgg agaatcaagt ggcacccttt ccaccaccac |
| 361 | ctgctcctgg ccgcctgcat gcacagtggc tttaagatcc tcaactgcca aaaggcaatg |
| 421 | gaggagaggc aggaggcgac ggtcctgaca tctcacacat gcccgactc gctggtgtat |
| 481 | ggagccgact ggtcctggct gctcttccgt tctctgcagc gggcccctc gtggtccttt |
| 541 | cctagcaacc taggaaccaa gacggcagac ctgaagggtg caagcgagtt gccaacaccc |
| 601 | tgtcatgaat gcagagagga taacgatggg gagggccatg ccagacccca gagtggaatg |
| 661 | aagccactca cagagggcat gaggaagaat ggcacctggc tgcaggctac agcagccacc |
| 721 | acacgtgact gtggcgtgaa cccagaagaa gcagactcag ccttcagcct cctggccacc |
| 781 | tgctccttct atgaccatgc gctccacctc tgggagtggg aggggaactg a |

TABLE 1-continued

SEQ ID NO: 95 *Homo sapiens* diphthamide biosynthesis 7 (DPH7) cDNA, transcript variant 17 (NM_001346385.1)

```
  1   atggtgaatg agacgaggcc caggctgcag aaagtggcct catggcaggc acatcaattc
 61   gaggcctgga ttgctgcttt caattactgg catccagaaa ttgtgtattc aggggggcgac
121   gatggccttc tgaggggctg ggacaccagg gtacccggca aatttctctt caccagcaaa
181   agacacacca tgggtgtgtg cagcatccag agcagccctc atcgggagca catcctggcc
241   acgggaagct atgatgaaca catcctactg tgggacacac gaaacatgaa gcagccgttg
301   gcagatacgc ctgtgcaggg tggggtatgg agaatcaagt ggcacccttt ccaccaccac
361   ctgctcctgg ccgcctgcat gcacagtggc tttaagatcc tcaactgcca aaaggcaatg
421   gaggagaggc aggaggcgac ggtcctgaca tctcacacat gcccgactc gctggtgtat
481   ggagccgact ggtcctggct gctcttccgt tctctgcagc gggcccctc gtggtccttt
541   cctagcaacc taggaaccaa gacggcagac ctgaagggtg caagcgagtt gccaacaccc
601   tgtcatgaat gcagagagga taacgatggg gagggccatg ccagacccca gagtggaatg
661   aagccactca cagagggcat gaggaagaat ggcacctggc tgcaggctac agcagccacc
721   acacgtgact gtggcgtgaa cccagaagaa gcagactcag ccttcagcct cctggccacc
781   tgctccttct atgaccatgc gctccacctc tgggagtggg aggggaactg a
```

SEQ ID NO: 96 *Homo sapiens* diphthamide biosynthesis 7 (DPH7) cDNA, transcript variant 18 (NM_001346386.1)

```
  1   atggtgaatg agacgaggcc caggctgcag aaagtggcct catggcaggc acatcaattc
 61   gaggcctgga ttgctgcttt caattactgg catccagaaa ttgtgtattc aggggggcgac
121   gatggccttc tgaggggctg ggacaccagg gtacccggca aatttctctt caccagcaaa
181   agacacacca tgggtgtgtg cagcatccag agcagccctc atcgggagca catcctggcc
241   acgggaagct atgatgaaca catcctactg tgggacacac gaaacatgaa gcagccgttg
301   gcagatacgc ctgtgcaggg tggggtatgg agaatcaagt ggcacccttt ccaccaccac
361   ctgctcctgg ccgcctgcat gcacagtggc tttaagatcc tcaactgcca aaaggcaatg
421   gaggagaggc aggaggcgac ggtcctgaca tctcacacat gcccgactc gctggtgtat
481   ggagccgact ggtcctggct gctcttccgt tctctgcagc gggcccctc gtggtccttt
541   cctagcaacc taggaaccaa gacggcagac ctgaagggtg caagcgagtt gccaacaccc
601   tgtcatgaat gcagagagga taacgatggg gagggccatg ccagacccca gagtggaatg
661   aagccactca cagagggcat gaggaagaat ggcacctggc tgcaggctac agcagccacc
721   acacgtgact gtggcgtgaa cccagaagaa gcagactcag ccttcagcct cctggccacc
781   tgctccttct atgaccatgc gctccacctc tgggagtggg aggggaactg a
```

SEQ ID NO: 97 *Homo sapiens* diphthamide biosynthesis 7 (DPH7) cDNA, transcript variant 19 (NM_001346387.1)

```
  1   atggtgaatg agacgaggcc caggctgcag aaagtggcct catggcaggc acatcaattc
 61   gaggcctgga ttgctgcttt caattactgg catccagaaa ttgtgtattc aggggggcgac
121   gatggccttc tgaggggctg ggacaccagg gtacccggca aatttctctt caccagcaaa
181   agacacacca tgggtgtgtg cagcatccag agcagccctc atcgggagca catcctggcc
241   acgggaagct atgatgaaca catcctactg tgggacacac gaaacatgaa gcagccgttg
301   gcagatacgc ctgtgcaggg tggggtatgg agaatcaagt ggcacccttt ccaccaccac
361   ctgctcctgg ccgcctgcat gcacagtggc tttaagatcc tcaactgcca aaaggcaatg
421   gaggagaggc aggaggcgac ggtcctgaca tctcacacat gcccgactc gctggtgtat
481   ggagccgact ggtcctggct gctcttccgt tctctgcagc gggcccctc gtggtccttt
```

TABLE 1-continued

```
541   cctagcaacc taggaaccaa gacggcagac ctgaagggtg caagcgagtt gccaacaccc 601   tgtcatgaat gcagagagga taacgatggg gagggccatg ccagacccca gagtggaatg 661   aagccactca cagagggcat gaggaagaat ggcacctggc tgcaggctac agcagccacc 721   acacgtgact gtggcgtgaa cccagaagaa gcagactcag ccttcagcct cctggccacc 781   tgctccttct atgaccatgc gctccacctc tgggagtggg aggggaactg a
```

SEQ ID NO: 98 *Homo sapiens* diphthamide biosynthesis 7 (DPH7) cDNA, transcript variant 20 (NM_001346388.1)

```
  1   atggtgaatg agacgaggcc caggctgcag aaagtggcct catggcaggc acatcaattc 61   gaggcctgga ttgctgcttt caattactgg catccagaaa ttgtgtattc aggggcgac 121   gatggccttc tgaggggctg ggacaccagg gtacccggca aatttctctt caccagcaaa 181   agacacacca tgggtgtgtg cagcatccag agcagccctc atcgggagca catcctggcc 241   acgggaagct atgatgaaca catcctactg tgggacacac gaaacatgaa gcagccgttg 301   gcagatacgc ctgtgcaggg tggggtatgg agaatcaagt ggcacccttt ccaccaccac 361   ctgctcctgg ccgcctgcat gcacagtggc tttaagatcc tcaactgcca aaaggcaatg 421   gaggagaggc aggaggcgac ggtcctgaca tctcacacat gcccgactc gctggtgtat 481   ggagccgact ggtcctggct gctcttccgt tctctgcagc gggccccctc gtggtccttt 541   cctagcaacc taggaaccaa gacggcagac ctgaagggtg caagcgagtt gccaacaccc 601   tgtcatgaat gcagagagga taacgatggg gagggccatg ccagacccca gagtggaatg 661   aagccactca cagagggcat gaggaagaat ggcacctggc tgcaggctac agcagccacc 721   acacgtgact gtggcgtgaa cccagaagaa gcagactcag ccttcagcct cctggccacc 781   tgctccttct atgaccatgc gctccacctc tgggagtggg aggggaactg a
```

SEQ ID NO: 99 *Homo sapiens* diphthamide biosynthesis 7 (DPH7) cDNA, transcript variant 21 (NM_001346389.1)

```
  1   atggtgaatg agacgaggcc caggctgcag aaagtggcct catggcaggc acatcaattc 61   gaggcctgga ttgctgcttt caattactgg catccagaaa ttgtgtattc aggggcgac 121   gatggccttc tgaggggctg ggacaccagg gtacccggca aatttctctt caccagcaaa 181   agacacacca tgggtgtgtg cagcatccag agcagccctc atcgggagca catcctggcc 241   acgggaagct atgatgaaca catcctactg tgggacacac gaaacatgaa gcagccgttg 301   gcagatacgc ctgtgcaggg tggggtatgg agaatcaagt ggcacccttt ccaccaccac 361   ctgctcctgg ccgcctgcat gcacagtggc tttaagatcc tcaactgcca aaaggcaatg 421   gaggagaggc aggaggcgac ggtcctgaca tctcacacat gcccgactc gctggtgtat 481   ggagccgact ggtcctggct gctcttccgt tctctgcagc gggccccctc gtggtccttt 541   cctagcaacc taggaaccaa gacggcagac ctgaagggtg caagcgagtt gccaacaccc 601   tgtcatgaat gcagagagga taacgatggg gagggccatg ccagacccca gagtggaatg 661   aagccactca cagagggcat gaggaagaat ggcacctggc tgcaggctac agcagccacc 721   acacgtgact gtggcgtgaa cccagaagaa gcagactcag ccttcagcct cctggccacc 781   tgctccttct atgaccatgc gctccacctc tgggagtggg aggggaactg a
```

SEQ ID NO: 100 *Homo sapiens* diphthamide biosynthesis 7 (DPH7) cDNA, transcript variant 22 (NM_001346390.1)

```
  1   atggtgaatg agacgaggcc caggctgcag aaagtggcct catggcaggc acatcaattc 61   gaggcctgga ttgctgcttt caattactgg catccagaaa ttgtgtattc aggggcgac 121   gatggccttc tgaggggctg ggacaccagg gtacccggca aatttctctt caccagcaaa 181   agacacacca tgggtgtgtg cagcatccag agcagccctc atcgggagca catcctggcc
```

TABLE 1-continued

```
241   acgggaagct atgatgaaca catcctactg tgggacacac gaaacatgaa gcagccgttg
301   gcagatacgc ctgtgcaggg tggggtatgg agaatcaagt ggcacccttt ccaccaccac
361   ctgctcctgg ccgcctgcat gcacagtggc tttaagatcc tcaactgcca aaaggcaatg
421   gaggagaggc aggaggcgac ggtcctgaca tctcacacat gcccgactc gctggtgtat
481   ggagccgact ggtcctggct gctcttccgt tctctgcagc gggcccctc gtggtccttt
541   cctagcaacc taggaaccaa gacggcagac ctgaagggtg caagcgagtt gccaacaccc
601   tgtcatgaat gcagagagga taacgatggg gagggccatg ccagacccca gagtggaatg
661   aagccactca cagagggcat gaggaagaat ggcacctggc tgcaggctac agcagccacc
721   acacgtgact gtggcgtgaa cccagaagaa gcagactcag ccttcagcct cctggccacc
781   tgctccttct atgaccatgc gctccacctc tgggagtggg aggggaactg a
```

SEQ ID NO: 101 Homo sapiens diphthamide biosynthesis 7 (DPH7) cDNA, transcript variant 23 (NM_001346391.1)

```
  1   atggtgaatg agacgaggcc caggctgcag aaagtggcct catggcaggc acatcaattc
 61   gaggcctgga ttgctgcttt caattactgg catccagaaa ttgtgtattc aggggggcgac
121   gatggcc ttc tgaggggctg ggacaccagg gtaccggca aatttctctt caccagcaaa
181   agacacacca tgggtgtgtg cagcatccag agcagccctc atcgggagca catcctggcc
241   acgggaagct atgatgaaca catcctactg tgggacacac gaaacatgaa gcagccgttg
301   gcagatacgc ctgtgcaggg tggggtatgg agaatcaagt ggcacccttt ccaccaccac
361   ctgctcctgg ccgcctgcat gcacagtggc tttaagatcc tcaactgcca aaaggcaatg
421   gaggagaggc aggaggcgac ggtcctgaca tctcacacat gcccgactc gctggtgtat
481   ggagccgact ggtcctggct gctcttccgt tctctgcagc gggcccctc gtggtccttt
541   cctagcaacc taggaaccaa gacggcagac ctgaagggtg caagcgagtt gccaacaccc
601   tgtcatgaat gcagagagga taacgatggg gagggccatg ccagacccca gagtggaatg
661   aagccactca cagagggcat gaggaagaat ggcacctggc tgcaggctac agcagccacc
721   acacgtgact gtggcgtgaa cccagaagaa gcagactcag ccttcagcct cctggccacc
781   tgctccttct atgaccatgc gctccacctc tgggagtggg aggggaactg a
```

SEQ ID NO: 102 Homo sapiens diphthamide biosynthesis 7 (DPH7) cDNA, transcript variant 24 (NM_001346392.1)

```
  1   atggtgaatg agacgaggcc caggctgcag aaagtggcct catggcaggc acatcaattc
 61   gaggcctgga ttgctgcttt caattactgg catccagaaa ttgtgtattc aggggggcgac
121   gatggcc ttc tgaggggctg ggacaccagg gtaccggca aatttctctt caccagcaaa
181   agacacacca tgggtgtgtg cagcatccag agcagccctc atcgggagca catcctggcc
241   acgggaagct atgatgaaca catcctactg tgggacacac gaaacatgaa gcagccgttg
301   gcagatacgc ctgtgcaggg tggggtatgg agaatcaagt ggcacccttt ccaccaccac
361   ctgctcctgg ccgcctgcat gcacagtggc tttaagatcc tcaactgcca aaaggcaatg
421   gaggagaggc aggaggcgac ggtcctgaca tctcacacat gcccgactc gctggtgtat
481   ggagccgact ggtcctggct gctcttccgt tctctgcagc gggcccctc gtggtccttt
541   cctagcaacc taggaaccaa gacggcagac ctgaagggtg caagcgagtt gccaacaccc
601   tgtcatgaat gcagagagga taacgatggg gagggccatg ccagacccca gagtggaatg
661   aagccactca cagagggcat gaggaagaat ggcacctggc tgcaggctac agcagccacc
721   acacgtgact gtggcgtgaa cccagaagaa gcagactcag ccttcagcct cctggccacc
781   tgctccttct atgaccatgc gctccacctc tgggagtggg aggggaactg a
```

TABLE 1-continued

SEQ ID NO: 103 *Homo sapiens* diphthamide biosynthesis 7 (DPH7) cDNA, transcript variant 25 (NM_001346393.1)

```
  1  atggtgaatg agacgaggcc caggctgcag aaagtggcct catggcaggc acatcaattc
 61  gaggcctgga ttgctgcttt caattactgg catccagaaa ttgtgtattc aggggggcgac
121  gatggccttc tgaggggctg ggacaccagg gtacccggca aatttctctt caccagcaaa
181  agctatgatg aacacatcct actgtgggac acacgaaaca tgaagcagcc gttggcagat
241  acgcctgtgc agggtggggt atggagaatc aagtggcacc ctttccacca ccacctgctc
301  ctggccgcct gcatgcacag tggctttaag atcctcaact gccaaaaggc aatggaggag
361  aggcaggagg cgacggtcct gacatctcac acattgcccg actcgctggt gtatggagcc
421  gactggtcct ggctgctctt ccgttctctg cagcgggccc cctcgtggtc ctttcctagc
481  aacctaggaa ccaagacggc agacctgaag ggtgcaagcg agttgccaac accctgtcat
541  gaatgcagag aggataacga tggggagggc catgccagac cccagagtgg aatgaagcca
601  ctcacagagg gcatgaggaa gaatggcacc tggctgcagg ctacagcagc caccacacgt
661  gactgtggcg tgaacccaga agaagcagac tcagccttca gcctcctggc cacctgctcc
721  ttctatgacc atgcgctcca cctctgggag tgggagggga actga
```

SEQ ID NO: 104 *Homo sapiens* diphthamide biosynthesis 7 (DPH7) cDNA, transcript variant 26 (NM_001346394.1)

```
  1  atggtgaatg agacgaggcc caggctgcag aaagtggcct catggcaggc acatcaattc
 61  gaggcctgga ttgctgcttt caattactgg catccagaaa ttgtgtattc aggggggcgac
121  gatggccttc tgaggggctg ggacaccagg gtacccggca aatttctctt caccagcaaa
181  agctatgatg aacacatcct actgtgggac acacgaaaca tgaagcagcc gttggcagat
241  acgcctgtgc agggtggggt atggagaatc aagtggcacc ctttccacca ccacctgctc
301  ctggccgcct gcatgcacag tggctttaag atcctcaact gccaaaaggc aatggaggag
361  aggcaggagg cgacggtcct gacatctcac acattgcccg actcgctggt gtatggagcc
421  gactggtcct ggctgctctt ccgttctctg cagcgggccc cctcgtggtc ctttcctagc
481  aacctaggaa ccaagacggc agacctgaag ggtgcaagcg agttgccaac accctgtcat
541  gaatgcagag aggataacga tggggagggc catgccagac cccagagtgg aatgaagcca
601  ctcacagagg gcatgaggaa gaatggcacc tggctgcagg ctacagcagc caccacacgt
661  gactgtggcg tgaacccaga agaagcagac tcagccttca gcctcctggc cacctgctcc
721  ttctatgacc atgcgctcca cctctgggag tgggagggga actga
```

SEQ ID NO: 105 *Homo sapiens* diphthamide biosynthesis 7 (DPH7) cDNA, transcript variant 27 (NM_001346395.1)

```
  1  atggtgaatg agacgaggcc caggctgcag aaagtggcct catggcaggc acatcaattc
 61  gaggcctgga ttgctgcttt caattactgg catccagaaa ttgtgtattc aggggggcgac
121  gatggccttc tgaggggctg ggacaccagg gtacccggca aatttctctt caccagcaaa
181  agctatgatg aacacatcct actgtgggac acacgaaaca tgaagcagcc gttggcagat
241  acgcctgtgc agggtggggt atggagaatc aagtggcacc ctttccacca ccacctgctc
301  ctggccgcct gcatgcacag tggctttaag atcctcaact gccaaaaggc aatggaggag
361  aggcaggagg cgacggtcct gacatctcac acattgcccg actcgctggt gtatggagcc
421  gactggtcct ggctgctctt ccgttctctg cagcgggccc cctcgtggtc ctttcctagc
481  aacctaggaa ccaagacggc agacctgaag ggtgcaagcg agttgccaac accctgtcat
541  gaatgcagag aggataacga tggggagggc catgccagac cccagagtgg aatgaagcca
601  ctcacagagg gcatgaggaa gaatggcacc tggctgcagg ctacagcagc caccacacgt
```

TABLE 1-continued

```
661    gactgtggcg tgaacccaga agaagcagac tcagccttca gcctcctggc cacctgctcc 721    ttctatgacc atgcgctcca cctctgggag tgggagggga actga
```

SEQ ID NO: 106 *Homo sapiens* diphthamide biosynthesis 7 (DPH7) cDNA, transcript variant 28 (NM_001346396.1)

```
  1    atggtgaatg agacgaggcc caggctgcag aaagtggcct catggcaggc acatcaattc 61    gaggcctgga ttgctgcttt caattactgg catccagaaa ttgtgtattc aggggggcgac 121    gatggccttc tgaggggctg ggacaccagg gtacccggca aatttctctt caccagcaaa 181    agctatgatg aacacatcct actgtgggac acacgaaaca tgaagcagcc gttggcagat 241    acgcctgtgc agggtggggt atggagaatc aagtggcacc ctttccacca ccacctgctc 301    ctggccgcct gcatgcacag tggctttaag atcctcaact gccaaaaggc aatggaggag 361    aggcaggagc gacggtcctg acatctcaca cattgcccg actcgctggt gtatggagcc 421    gactggtcct ggctgctctt ccgttctctg cagcgggccc cctcgtggtc ctttcctagc 481    aacctaggaa ccaagacggc agacctgaag ggtgcaagcg agttgccaac accctgtcat 541    gaatgcagag aggataacga tggggagggc catgccagac ccagagtgg aatgaagcca 601    ctcacagagg gcatgaggaa gaatggcacc tggctgcagg ctacagcagc caccacacgt 661    gactgtggcg tgaacccaga agaagcagac tcagccttca gcctcctggc cacctgctcc 721    ttctatgacc atgcgctcca cctctgggag tgggagggga actga
```

SEQ ID NO: 107 *Homo sapiens* diphthamide biosynthesis 7 (DPH7) amino acid sequence, isoform 1 (NP_620133.1)

```
  1    mmgcfalqtv dteltadsve wcplqgcrhl lacgtyqlrr pedrpagpqn kggmevkepq 61    vrlgrlflys fndnnsihpl vevqrkdtsa ildmkwchip vaghallgla dasgsiqllr 121    lvesekshvl eplsslalee qclalsldws tgktgragdq plkiissdst gqlhllmvne 181    trprlqkvas wqahqfeawi aafnywhpei vysggddgll rgwdtrvpgk flftskrhtm 241    gvcsiqssph rehilatgsy dehillwdtr nmkqpladtp vqggvwrikw hpfhhhllla 301    acmhsgfkil ncqkameerq eatvltshtl pdslvygadw swllfrslqr apswsfpsnl 361    gtktadlkga selptpchec redndgegha rpqsgmkplt egmrkngtwl qataattrdc 421    gvnpeeadsa fsllatcsfy dhalhlwewe gn
```

SEQ ID NO: 108 *Homo sapiens* diphthamide biosynthesis 7 (DPH7) amino acid sequence, isoform 2 (NP_001333299.1)

```
  1    mmgcfalqtv dteltadsve wcplqgcrhl lacgtyqlrr pedrpagpqn kggmevkepq 61    vrlgrlflys fndnnsihpl vevqrkdtsa ildmkwchip vaghallgla dasgsiqllr 121    lvesekshvl eplsslalee qclalsldws tgktgragdq plkiissdst gqlhllmvne 181    trprlqkvas wqahqfeawi aafnywhpei vysggddgll rgwdtrvpgk flftsksyde 241    hillwdtrnm kqpladtpvq ggvwrikwhp fhhhlllaac mhsgfkilnc qkameerqea 301    tvltshtlpd slvygadwsw llfrslqrap swsfpsnlgt ktadlkgase lptpchecre 361    dndgegharp qsgmkplteg mrkngtwlqa taattrdcgv npeeadsafs llatcsfydh 421    alhlwewegn
```

SEQ ID NO: 109 *Homo sapiens* diphthamide biosynthesis 7 (DPH7) amino acid sequence, isoform 3 (NP_001333300.1)

```
  1    mmgcfalqtv dteltadsve wcplqgcrhl lacgtyqlrr pedrpagpqn kggmevkepq 61    vrlgrlflys fndnnsihpl vevqrkdtsa ildmkwchip vaghallgla dasgsiqllr 121    lvesekshvl eplsslalee qclalsldws tgktgragdq plkiissdst gqlhllmvne 181    trprlqkvas wqahqfeawi aafnywhpei vysggddgll rgwdtrvpgk flftskrhtm
```

TABLE 1-continued

```
    241 gvcsiqssph rehilatgsy dehillwdtr nmkqpladtp vqggvwrikw hpfhhhllla 301 acmhsgfkil ncqkamavee vllarvdvls dcwmkd
```

SEQ ID NO: 110 *Homo sapiens* diphthamide biosynthesis 7 (DPH7) amino acid sequence, isoform 4 (NP_001333301.1)

```
      1 mmgcfalqtv dteltadsve wcplqgcrhl lacgtyqlrr pedrpagpqn kggmevkepq 61 vrlgrlflys fndnnsihpl vevqrkdtsa ildmkwchip vaghallgla dasgsiqllr 121 lvesekshvl eplsslalee qclalsldws tgktgragdq plkiissdst gqlhllmvne 181 trprlqkvas wqahqfeawi aafnywhpei vysggddgll rgwdtrvpgk flftskrhtm 241 gvcsiqssph rehilatgsy dehillwdtr nmkqpladtp vqggvwrikw hpfhhhllla 301 acmhsgfkil ncqkamgcgs lra
```

SEQ ID NO: 111 *Homo sapiens* diphthamide biosynthesis 7 (DPH7) amino acid sequence, isoform 5 (NP_001333302.1)

```
      1 mpswawqmpv dpyncsawwn lragdqplki issdstgqlh llmvnetrpr lqkvaswqah 61 qfeawiaafn ywhpeivysg gddgllrgwd trvpgkflft skrhtmgvcs iqssphrehi 121 latgsydehi llwdtrnmkg pladtpvqgg vwrikwhpfh hhllaacmh sgfkilncqk 181 ameerqeatv ltshtlpdsl vygadwswll frslqrapsw sfpsnlgtkt adlkgaselp 241 tpchecredn dgegharpqs gmkpltegmr kngtwlqata attrdcgvnp eeadsafsll 301 atcsfydhal hlwewegn
```

SEQ ID NO: 112 *Homo sapiens* diphthamide biosynthesis 7 (DPH7) amino acid sequence, isoform 6 (NP_001333303.1)

```
      1 mmgcfalqtv dteltadsve wcplqgcrhl lacgtyqlrr pedrpagpqn kggmevkepq 61 vrlgrlflys fndnnsihpl vevqrkdtsa ildmkwchip vaghallgla dasgsiqllr 121 lvesekshvl eplsslalee qclalsldws tgktgragdq plkiissdst gqlhllmvne 181 trprlqkvas wqahqfeawi aafnywhpei vysggddgll rgwdtrvpgk flftsksyde 241 hillwdtrnm kqpladtpvq ggvwrikwhp fhhhlllaac mhsgfkilnc qkamgcgslr 301 a
```

SEQ ID NO: 113 *Homo sapiens* diphthamide biosynthesis 7 (DPH7) amino acid sequence, isoform 7 (NP_001333304.1, NP_001333305.1, NP_001333306.1, NP_001333307.1, NP_001333308.1, NP_001333309.1, NP_001333310.1, NP_001333311.1, NP_001333312.1, NP_001333313.1, NP_001333314.1, NP_001333315.1, NP_001333316.1, NP_001333317.1, NP_001333318.1, NP_001333319.1, NP_001333320.1, and NP_001333321.1)

```
      1 mvnetrprlq kvaswqahqf eawiaafnyw hpeivysggd dgllrgwdtr vpgkflftsk 61 rhtmgvcsiq ssphrehila tgsydehill wdtrnmkqpl adtpvqggvw rikwhpfhhh 121 lllaacmhsg fkilncqkam eerqeatvlt shtlpdslvy gadwswllfr slqrapswsf 181 psnlgtktad lkgaselptp checredndg egharpqsgm kpltegmrkn gtwlqataat 241 trdcgvnpee adsafsllat csfydhalhl wewegn
```

SEQ ID NO: 114 *Homo sapiens* diphthamide biosynthesis 7 (DPH7) amino acid sequence, isoform 8 (NP_001333322.1, NP_001333323.1, NP_001333324.1, and NP_001333325.1)

```
      1 mvnetrprlq kvaswqahqf eawiaafnyw hpeivysggd dgllrgwdtr vpgkflftsk 61 sydehillwd trnmkqplad tpvqggvwri kwhpfhhhll laacmhsgfk ilncqkamee 121 rqeatvltsh tlpdslvyga dwswllfrsl qrapswsfps nlgtktadlk gaselptpch 181 ecredndgeg harpqsgmkp ltegmrkngt wlqataattr dcgvnpeead safsllatcs 241 fydhalhlwe wegn
```

SEQ ID NO: 115 *Mus musculus* diphthamide biosynthesis 7 (DPH7) cDNA, transcript variant 1 (NM_026044.4)

```
      1 atggcgggta gccacgcagg gacgttgcga gtcctgcagg cagtagacac tgagcttacc 61 gcggactcgg tggaatggtg cccagtagaa ggttaccagc atctgctggc ctgcggaacc
```

TABLE 1-continued

```
 121   taccagctgc gagcgcccag ggaccagcct gcactggatg gcagtgagcc tcaagttcgt
 181   ttaggtcgtc tctacctgtt cagcttcagt gagcacaaca cggctaaacc tctgcttgag
 241   gtccaaagaa gggactcttc tgctgtcctg gacatgaaat ggtgccacat cccagtctct
 301   ggccatgtgc ttttaggctt ggcaaacgcc agtggatcca tagggctgct ccgcctgatg
 361   gaatgtgaga acaacagtta caccctgcag ccaatatcca gcctcgccct ggatgagaat
 421   tgtctgtcct tgtcaatgga ttggtccact gggaaatctg tcagggccag agaacagccc
 481   ttgaagatca ttagcagtga ttctaagggg cagttgcacc tcctgatggt gaatgagggc
 541   acagctgaac tacagctagt agcatcttgg ccagcccatc actttgaggc ctggattgct
 601   gctttcaatt actggcagac agaactcgtg tattcagggg gagatgactg ccttctgaga
 661   ggctgggaca ctaggatgct gggcacacct gtcttcacta gcaaaagaca ttgcatgggt
 721   gtgtgcagca tccagagcag cccccatcag gagcatatac tggcaactgg aagctatgat
 781   gagcatgttc tgctgtggga cactcgaaac ataagacagc cattggcgga tgtaccagtg
 841   caaggaggtg tgtggaggct caagtggcac ccagttcacc accatctact cctggcggcc
 901   tgcatgcaca atggcttcaa gattctcaac tgccagaagg ccattgagga aagcaggac
 961   ataactgttt taacatccca cgaaatgcct aactcattag tatatggggc tgactggtcc
1021   tggcttttcc attccatgaa gcccactcct acctggttct ttgatcagaa tgcatggga
1081   gtcaaagcag cagaccactc tagcctaaag gtcacagagg agccaccaat acattctcag
1141   gaacaaacca tggatcgcca agtggaaggc cccgctaacg ctcataccag agctgaactg
1201   aaggcttctc tccttccatt aacagaggac atgaaaaaca gcaaagactg ctcctcatcc
1261   tcagtcaaga ctcgtgatct tagccactgc tctggtgggc agagctttga caatagcctc
1321   ctggccacct gctccttta tgaccatgtt ctccaccttt ggaagtggga gacgaatcaa
1381   gctcgcactc tttgcagtgg cactggatgt gatttgggga gtgctgacca ttga
```
SEQ ID NO: 116 *Mus musculus* diphthamide biosynthesis 7 (DPH7) cDNA, transcript variant 2 (NM_001355554.1)
```
   1   atgaacaaca gttacaccct gcagccaata tccagcctcg ccctggatga gaattgtctg
  61   tccttgtcaa tggattggtc cactgggaaa tctgtcaggg ccagagaaca gcccttgaag
 121   atcattagca gtgattctaa ggggcagttg cacctcctga tggtgaatga gggcacagct
 181   gaactacagc tagtagcatc ttggccagcc catcactttg aggcctggat tgctgctttc
 241   aattactggc agacagaact cgtgtattca gggggagatg actgccttct gagaggctgg
 301   gacactagga tgctgggcac acctgtcttc actagcaaaa gacattgcat gggtgtgtgc
 361   agcatccaga gcagccccca tcaggagcat atactggcaa ctggaagcta tgatgagcat
 421   gttctgctgt gggacactcg aaacataaga cagccattgg cggatgtacc agtgcaagga
 481   ggtgtgtgga ggctcaagtg cacccagtt caccaccatc tactcctggc ggcctgcatg
 541   cacaatggct tcaagattct caactgccag aaggccattg aggagaagca ggacataact
 601   gttttaacat cccacgaaat gcctaactca ttagtatatg gggctgactg gtcctggctt
 661   ttccattcca tgaagcccac tcctacctgg ttctttgatc agaatgcat gggagtcaaa
 721   gcagcagacc actctagcct aaaggtcaca gaggagccac caatacattc tcaggaacaa
 781   accatggatc gccaagtgga aggccccgct aacgctcata ccagagctga actgaaggct
 841   tctctccttc cattaacaga ggacatgaaa aacagcaaag actgctcctc atcctcagtc
```

TABLE 1-continued

```
 901    aagactcgtg atcttagcca ctgctctggt gggcagagct ttgacaatag cctcctggcc
 961    acctgctcct tttatgacca tgttctccac ctttggaagt gggagacgaa tcaagctcgc
1021    actctttgca gtggcactgg atgtgatttg gggagtgctg accattga
```

SEQ ID NO: 117 Mus musculus diphthamide biosynthesis 7 (DPH7) cDNA, transcript variant 3 (NM_001355556.1)
```
   1    atggattggt ccactgggaa atctgtcagg ccagagaac agcccttgaa gatcattagc
  61    agtgattcta agggcagtt gcacctcctg atggtgaatg agggcacagc tgaactacag
 121    ctagtagcat cttggccagc ccatcacttt gaggcctgga ttgctgcttt caattactgg
 181    cagacagaac tcgtgtattc agggggagat gactgccttc tgagaggctg gacactagg
 241    atgctgggca cctgtctt cactagcaaa agacattgca tgggtgtgtg cagcatccag
 301    agcagccccc atcaggagca tatactggca actggaagct atgatgagca tgttctgctg
 361    tgggacactc gaaacataag acagccattg gcggatgtac cagtgcaagg aggtgtgtgg
 421    aggctcaagt ggcacccagt tcaccaccat ctactcctgg cggcctgcat gcacaatggc
 481    ttcaagattc tcaactgcca gaaggccatt gaggagaagc aggacataac tgttttaaca
 541    tcccacgaaa tgcctaactc attagtatat ggggctgact ggtcctggct tttccattcc
 601    atgaagccca ctcctacctg gttctttgat cagaatgaca tgggagtcaa agcagcagac
 661    cactctagcc taaaggtcac agaggagcca ccaatacatt ctcaggaaca aaccatggat
 721    cgccaagtgg aaggcccccgc taacgctcat accagagctg aactgaaggc ttctctcctt
 781    ccattaacag aggacatgaa aaacagcaaa gactgctcct catcctcagt caagactcgt
 841    gatcttagcc actgctctgg tgggcagagc tttgacaata gcctcctggc cacctgctcc
 901    ttttatgacc atgttctcca cctttggaag tgggagacga atcaagctcg cactctttgc
 961    agtggcactg gatgtgattt ggggagtgct gaccattga
```

SEQ ID NO: 118 Mus musculus diphthamide biosynthesis 7 (DPH7) cDNA, transcript variant 4 (NM_001355557.1)
```
   1    atggattggt ccactgggaa atctgtcagg ccagagaac agcccttgaa gatcattagc
  61    agtgattcta agggcagtt gcacctcctg atggtgaatg agggcacagc tgaactacag
 121    ctagtagcat cttggccagc ccatcacttt gaggcctgga ttgctgcttt caattactgg
 181    cagacagaac tcgtgtattc agggggagat gactgccttc tgagaggctg gacactagg
 241    atgctgggca cctgtctt cactagcaaa agacattgca tgggtgtgtg cagcatccag
 301    agcagccccc atcaggagca tatactggca actggaagct atgatgagca tgttctgctg
 361    tgggacactc gaaacataag acagccattg gcggatgtac cagtgcaagg aggtgtgtgg
 421    aggctcaagt ggcacccagt tcaccaccat ctactcctgg cggcctgcat gcacaatggc
 481    ttcaagattc tcaactgcca gaaggccatt gaggagaagc aggacataac tgttttaaca
 541    tcccacgaaa tgcctaactc attagtatat ggggctgact ggtcctggct tttccattcc
 601    atgaagccca ctcctacctg gttctttgat cagaatgaca tgggagtcaa agcagcagac
 661    cactctagcc taaaggtcac agaggagcca ccaatacatt ctcaggaaca aaccatggat
 721    cgccaagtgg aaggcccccgc taacgctcat accagagctg aactgaaggc ttctctcctt
 781    ccattaacag aggacatgaa aaacagcaaa gactgctcct catcctcagt caagactcgt
 841    gatcttagcc actgctctgg tgggcagagc tttgacaata gcctcctggc cacctgctcc
 901    ttttatgacc atgttctcca cctttggaag tgggagacga atcaagctcg cactctttgc
 961    agtggcactg gatgtgattt ggggagtgct gaccattga
```

TABLE 1-continued

SEQ ID NO: 119 Mus musculus diphthamide biosynthesis 7 (DPH7) cDNA, transcript variant 5 (NM_001355558.1)

```
  1  atggattggt ccactgggaa atctgtcagg gccagagaac agcccttgaa gatcattagc
 61  agtgattcta aggggcagtt gcacctcctg atggtgaatg agggcacagc tgaactacag
121  ctagtagcat cttggccagc ccatcacttt gaggcctgga ttgctgcttt caattactgg
181  cagacagaac tcgtgtattc aggggagat gactgccttc tgagaggctg ggacactagg
241  atgctgggca cacctgtctt cactagcaaa agacattgca tgggtgtgtg cagcatccag
301  agcagccccc atcaggagca tatactggca actggaagct atgatgagca tgttctgctg
361  tgggacactc gaaacataag acagccattg gcggatgtac cagtgcaagg aggtgtgtgg
421  aggctcaagt ggcacccagt tcaccaccat ctactcctgg cggcctgcat gcacaatggc
481  ttcaagattc tcaactgcca gaaggccatt gaggagaagc aggacataac tgttttaaca
541  tcccacgaaa tgcctaactc attagtatat ggggctgact ggtcctggct tttccattcc
601  atgaagccca ctcctacctg gttctttgat cagaatgaca tgggagtcaa agcagcagac
661  cactctagcc taaaggtcac agaggagcca ccaatacatt ctcaggaaca aaccatggat
721  cgccaagtgg aaggccccgc taacgctcat accagagctg aactgaaggc ttctctcctt
781  ccattaacag aggacatgaa aaacagcaaa gactgctcct catcctcagt caagactcgt
841  gatcttagcc actgctctgg tgggcagagc tttgacaata gcctcctggc cacctgctcc
901  ttttatgacc atgttctcca cctttggaag tgggagacga atcaagctcg cactctttgc
961  agtggcactg gatgtgattt ggggagtgct gaccattga
```

SEQ ID NO: 120 Mus musculus diphthamide biosynthesis 7 (DPH7) cDNA, transcript variant 6 (NM_001355559.1)

```
  1  atggattggt ccactgggaa atctgtcagg gccagagaac agcccttgaa gatcattagc
 61  agtgattcta aggggcagtt gcacctcctg atggtgaatg agggcacagc tgaactacag
121  ctagtagcat cttggccagc ccatcacttt gaggcctgga ttgctgcttt caattactgg
181  cagacagaac tcgtgtattc aggggagat gactgccttc tgagaggctg ggacactagg
241  atgctgggca cacctgtctt cactagcaaa agacattgca tgggtgtgtg cagcatccag
301  agcagccccc atcaggagca tatactggca actggaagct atgatgagca tgttctgctg
361  tgggacactc gaaacataag acagccattg gcggatgtac cagtgcaagg aggtgtgtgg
421  aggctcaagt ggcacccagt tcaccaccat ctactcctgg cggcctgcat gcacaatggc
481  ttcaagattc tcaactgcca gaaggccatt gaggagaagc aggacataac tgttttaaca
541  tcccacgaaa tgcctaactc attagtatat ggggctgact ggtcctggct tttccattcc
601  atgaagccca ctcctacctg gttctttgat cagaatgaca tgggagtcaa agcagcagac
661  cactctagcc taaaggtcac agaggagcca ccaatacatt ctcaggaaca aaccatggat
721  cgccaagtgg aaggccccgc taacgctcat accagagctg aactgaaggc ttctctcctt
781  ccattaacag aggacatgaa aaacagcaaa gactgctcct catcctcagt caagactcgt
841  gatcttagcc actgctctgg tgggcagagc tttgacaata gcctcctggc cacctgctcc
901  ttttatgacc atgttctcca cctttggaag tgggagacga atcaagctcg cactctttgc
961  agtggcactg gatgtgattt ggggagtgct gaccattga
```

SEQ ID NO: 121 Mus musculus diphthamide biosynthesis 7 (DPH7) cDNA, transcript variant 7 (NM_001355560.1)

```
  1  atgagaattg tctgtccttg tcaatggatt ggtccactgg gaaatctgtc aggggagat
 61  gactgccttc tgagaggctg ggacactagg atgctgggca cacctgtctt cactagcaaa
121  agacattgca tgggtgtgtg cagcatccag agcagccccc atcaggagca tatactggca
```

TABLE 1-continued

```
181    actggaagct atgatgagca tgttctgctg tgggacactc gaaacataag acagccattg
241    gcggatgtac cagtgcaagg aggtgtgtgg aggctcaagt ggcacccagt tcaccaccat
301    ctactcctgg cggcctgcat gcacaatggc ttcaagattc tcaactgcca gaaggccatt
361    gaggagaagc aggacataac tgttttaaca tcccacgaaa tgcctaactc attagtatat
421    gggctgact ggtcctggct tttccattcc atgaagccca ctcctacctg gttctttgat
481    cagaatgaca tgggagtcaa agcagcagac cactctagcc taaaggtcac agaggagcca
541    ccaatacatt ctcaggaaca aaccatggat cgccaagtgg aaggccccgc taacgctcat
601    accagagctg aactgaaggc ttctctcctt ccattaacag aggacatgaa aaacagcaaa
661    gactgctcct catcctcagt caagactcgt gatcttagcc actgctctgg tgggcagagc
721    tttgacaata gcctcctggc cacctgctcc ttttatgacc atgttctcca cctttggaag
781    tgggagacga atcaagctcg cactctttgc agtggcactg gatgtgattt ggggagtgct
841    gaccattga
```

SEQ ID NO: 123 *Mus musculus* diphthamide biosynthesis 7 (DPH7) cDNA, transcript variant 8 (NM_001355561.1)

```
  1    atggacttct gtcttccac aggggagat gactgccttc tgagaggctg ggacactagg
 61    atgctgggca cacctgtctt cactagcaaa agacattgca tgggtgtgtg cagcatccag
121    agcagccccc atcaggagca tatactggca actggaagct atgatgagca tgttctgctg
181    tgggacactc gaaacataag acagccattg gcggatgtac cagtgcaagg aggtgtgtgg
241    aggctcaagt ggcacccagt tcaccaccat ctactcctgg cggcctgcat gcacaatggc
301    ttcaagattc tcaactgcca gaaggccatt gaggagaagc aggacataac tgttttaaca
361    tcccacgaaa tgcctaactc attagtatat gggctgact ggtcctggct tttccattcc
421    atgaagccca ctcctacctg gttctttgat cagaatgaca tgggagtcaa agcagcagac
481    cactctagcc taaaggtcac agaggagcca ccaatacatt ctcaggaaca aaccatggat
541    cgccaagtgg aaggccccgc taacgctcat accagagctg aactgaaggc ttctctcctt
601    ccattaacag aggacatgaa aaacagcaaa gactgctcct catcctcagt caagactcgt
661    gatcttagcc actgctctgg tgggcagagc tttgacaata gcctcctggc cacctgctcc
721    ttttatgacc atgttctcca cctttggaag tgggagacga atcaagctcg cactctttgc
781    agtggcactg gatgtgattt ggggagtgct gaccattga
```

SEQ ID NO: 124 *Mus musculus* diphthamide biosynthesis 7 (DPH7) amino acid sequence, isoform 1 (NP_080320.1)

```
  1    magshagtlr vlqavdtelt adsvewcpve gyqhllacgt yqlraprdqp aldgsepqvr
 61    lgrlylfsfs ehntakplle vqrrdssavl dmkwchipvs ghvllglana sgsigllrlm
121    ecennsytlq pisslalden clslsmdwst gksvrareqp lkiissdskg qlhllmvneg
181    taelqlvasw pahhfeawia afnywqtelv ysggddcllr gwdtrmlgtp vftskrhcmg
241    vcsiqssphq ehilatgsyd ehvalwdtrn irqpladvpv qggvwrlkwh pvhhhlllaa
301    cmhngfkiln cqkaieekqd itvltshemp nslvygadws wlfhsmkptp twffdqndmg
361    vkaadhsslk vteeppihsq eqtmdrqveg panahtrael kaslllplted mknskdcsss
421    svktrdlshc sggqsfdnsl latcsfydhv lhlwkwetnq articsgtgc dlgsadh
```

SEQ ID NO: 125 *Mus musculus* diphthamide biosynthesis 7 (DPH7) amino acid sequence, isoform 2 (NP_001342483.1)

```
  1    mnnsytlqpi sslaldencl slsmdwstgk svrareqplk iissdskgql hllmvnegta
 61    elqlvaswpa hhfeawiaaf nywqtelvys ggddcllrgw dtrmlgtpvf tskrhcmgvc
121    siqssphgeh ilatgsydeh vilwdtrnir qpladvpvqg gvwrlkwhpv hhhlllaacm
```

TABLE 1-continued

```
181     hngfkilncq  kaieekqdit  vltshempns  lvygadwswl  fhsmkptptw  ffdqndmgvk 241     aadhsslkvt  eeppihsqeq  tmdrqvegpa  nahtraelka  sllpltedmk  nskdcssssv 301     ktrdlshcsg  gqsfdnslla  tcsfydhvlh  lwkwetnqar  ticsgtgcdl  gsadh SEQ ID NO: 126 Mus musculus diphthamide biosynthesis 7 (DPH7) amino acid
sequence, isoform 3 (NP_001342485.1, NP_001342486.1, NP_001342487.1, and
NP_001342488.1)
  1     mdwstgksvr  areqplkiis  sdskgqlhll  mvnegtaelq  lvaswpahhf  eawiaafnyw 61     qtelvysggd  dcllrgwdtr  mlgtpvftsk  rhcmgvcsiq  ssphqehila  tgsydehvll 121     wdtrnirqpl  advpvqggvw  rlkwhpvhhh  lllaacmhng  fkilncqkai  eekqditvlt 181     shempnslvy  gadwswlfhs  mkptptwffd  qndmgvkaad  hsslkvteep  pihsqeqtmd 241     rqvegpanah  traelkasll  pltedmknsk  dcssssvktr  dlshcsggqs  fdnsllatcs 301     fydhvlhlwk  wetnqartic  sgtgcdlgsa  dh SEQ ID NO: 127 Mus musculus diphthamide biosynthesis 7 (DPH7) amino acid
sequence, isoform 4 (NP_001342489.1)
  1     mrivcpcqwi  gplgnlsggd  dcllrgwdtr  mlgtpvftsk  rhcmgvcsiq  ssphqehila 61     tgsydehvll  wdtrnirqpl  advpvqggvw  rlkwhpvhhh  lllaacmhng  fkilncqkai 121     eekqditvlt  shempnslvy  gadwswlfhs  mkptptwffd  qndmgvkaad  hsslkvteep 181     pihsqeqtmd  rqvegpanah  traelkasll  pltedmknsk  dcssssvktr  dlshcsggqs 241     fdnsllatcs  fydhvlhlwk  wetnqartic  sgtgcdlgsa  dh SEQ ID NO: 128 Mus musculus diphthamide biosynthesis 7 (DPH7) amino acid
sequence, isoform 5 (NP_001342490.1)
  1     mdfclptggd  dcllrgwdtr  mlgtpvftsk  rhcmgvcsiq  ssphqehila  tgsydehvll 61     wdtrnirqpl  advpvqggvw  rlkwhpvhhh  lllaacmhng  fkilncqkai  eekqditvlt 121     shempnslvy  gadwswlfhs  mkptptwffd  qndmgvkaad  hsslkvteep  pihsqeqtmd 181     rqvegpanah  traelkasll  pltedmknsk  dcssssvktr  dlshcsggqs  fdnsllatcs 241     fydhvlhlwk  wetnqartic  sgtgcdlgsa  dh
```

*Included in Table 1 are RNA nucleic acid molecules (e.g., thymines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof Such nucleic acid molecules can have a function of the full-length nucleic acid as described further herein.
*Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.
*Included in Table 1 are DPH1, DPH2, DPH3, DPH4, DPH5, DPH6, and DPH7 null mutations, missense mutations, nonsense mutations, frameshift mutations, insertion mutation, deletion mutations, and rearrangement mutations.

II. Subjects

In one embodiment, the subject for whom predicted likelihood of resistance to an ADP-ribosylating toxin is determined, is a mammal (e.g., mouse, rat, primate, non-human mammal, domestic animal, such as a dog, cat, cow, horse, and the like), and is preferably a human. In one embodiment, the subject for whom the ADP-ribosylating toxin in combination with an agent that increases the copy number, amount, and/or activity of at least one member of the diphthamide synthesis pathway is administered, is a mammal (e.g., mouse, rat, primate, non-human mammal, domestic animal, such as a dog, cat, cow, horse, and the like), and is preferably a human. In another embodiment, the subject is an animal model of a condition (e.g., cancer, such as CD123+ cancer, including AML, MDS, and BPDCN). For example, the animal model can be an orthotopic xenograft animal model of a human-derived cancer, such as CD123+ cancer including AML, MDS, and BPDCN.

In another embodiment of the methods of the present invention, the subject has not undergone treatment, such as hypomethylating agent, chemotherapy, radiation therapy, targeted therapy, and/or an ADP-ribosylating toxin. In still another embodiment, the subject has undergone treatment, such as hypomethylating agent, chemotherapy, radiation therapy, targeted therapy, and/or an ADP-ribosylating toxin.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the efficacy of an agent for treating many different conditions (e.g., cancers, such as CD123+ cancers) that are resistant to the ADP-ribosylating toxin in subjects such as those described herein.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be resistant to an ADP-ribosylating toxin, and/or evaluate a response to the combination of the ADP-ribosylating toxin with an agent that increases the copy number, amount, and/or activity of at least one member of the diphthamide synthesis pathway. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising ADP-ribosylating toxin alone or in combination with other anti-cancer agents, such as an agent that increases the copy number, amount, and/or activity of at least one member of the diphthamide synthesis pathway.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement. In some embodiments of the present invention the change of biomarker amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. IN another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermeable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids (e.g., DPH1-7 and/or CD123) that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In Gene Expression Technology: Methods in Enzymology vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. The absence of at least one biomarker listed in Table 1 is predictive of poorer outcome of the ADP-ribosylating toxin treatment. A copy number of at least 3, 4, 5, 6, 7, 8, 9, or 10 of at least one biomarker listed in Table 1 is predictive of likely responsive to the ADP-ribosylating toxin treatment.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization arrays are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. NatlAcad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of afflicted cells (e.g., CD123+ cancer cells) are obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos. 6,618,679; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}$P and $^{35}$S. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an ADP-ribosylating toxin treatment. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker proteinantibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify DPH1 protein that is overexpressed, overfunctional, and the like.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) Mutat. Res. 285:125-144 and Hayashi (1992) Genet. Anal. Tech. Appl. 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

VI. Anti-Cancer Therapies

The response of a condition in a subject to an ADP-ribosylating toxin treatment is predicted according to the methods described herein. In one embodiment, such ADP-ribosylating toxin treatment or combinations of therapies (e.g., ADP-ribosylating toxin in combination with an agent that increases the copy number, amount, and/or activity of at least one member of the diphthamide synthesis pathway) can be administered once a subject is indicated as being a likely responder to an ADP-ribosylating toxin. In another embodiment, such ADP-ribosylating toxin treatment can be avoided once a subject is indicated as not being a likely responder to an ADP-ribosylating toxin and an alternative treatment regimen, such as targeted and/or untargeted therapies can be administered. In some embodiments, the condition is a cancer (e.g., CD123+ cancer), and anti-cancer therapies may be used. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with the ADP-ribosylating toxin. The ADP-ribosylating toxin and exemplary agents useful for increasing the copy number, amount, and/or activity of at least one member of the diphthamide synthesis pathway described herein, have been described above.

The term "targeted therapy" refers to administration of agents that selectively interact with a chosen biomolecule to thereby treat the condition (e.g., cancer). For example, SL-401 is a targeted therapy for treating CD123+ AML.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, mitochondrial cofactor therapy is useful. For example, vitamin E is known to block cell death via ferroptosis such that mitochondrial cofactor therapy can alleviate or improve any toxicity associated with ISC biosynthesis pathway inhibition. Mitochondrial cofactor therapies are well known in the art and include, for example, coenzyme Q10 (ubiquinone), riboflavin, thiamin, niacin, vitamin K (phylloquinone and menadione), creatine, carnitine, and other antioxidants such as ascorbic acid and lipoic acid (see, for example, Marriage et al. (2003) *J. Am. Diet. Assoc.* 103:1029-1038 and Parikh et al. (2009) *Curr. Treat. Options Neurol.* 11:414-430).

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, pro-apoptotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; pro-apoptotic agents: venetoclax (ABT-199), navitoclax and Obatoclax; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside (cytarabine); purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of 0-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. In addition to its use to destroy the cancer, laser surgery is also used to help relieve symptoms caused by cancer (palliative care). It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with an ADP-ribosylating toxin in combination with an agent that increases the copy number, amount, and/or activity of at least one member of the diphthamide synthesis pathway may vary according to the particular ADP-ribosylating toxin, agent, or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

VII. Clinical Efficacy

Clinical efficacy can be measured by any method known in the art. For example, the response to a therapy, such as the combination of an ADP-ribosylating toxin and an agent that increases the copy number, amount, and/or activity of at least one member of the diphthamide synthesis pathway, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular combination of an ADP-ribosylating toxin and an agent that increases the copy number, amount, and/or activity of at least one member of the diphthamide synthesis pathway regimen is at least 25%, 30%, 35%, 40%, 45%, 50%, 55%, 60%, 65%, 70%, 75%, 80%, 85%, or more.

Additional criteria for evaluating the response to the combination of an ADP-ribosylating toxin and an agent that increases the copy number, amount, and/or activity of at least one member of the diphthamide synthesis pathway is related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular combination of an ADP-ribosylating toxin and an agent that increases the copy number, amount, and/or activity of at least one member of the diphthamide synthesis pathway therapeutic regimen can be administered to a population of subjects and the outcome can be correlated to biomarker measurements that were determined prior to administration of any combination therapy of an ADP-ribosylating toxin and an agent that increases the copy number, amount, and/or activity of at least one member of the diphthamide synthesis pathway. The outcome measurement may be pathologic response to therapy given in the neoadjuvant setting. Alternatively, outcome measures, such as overall survival and disease-free survival can be monitored over a period of time for subjects following the combination therapy of an ADP-ribosylating toxin and an agent that increases the copy number, amount, and/or activity of at least one member of the diphthamide synthesis pathway for whom biomarker measurement values are known. In certain embodiments, the same doses of ADP-ribosylating toxins and agents that increase the copy number, amount, and/or activity of at least one member of the diphthamide synthesis pathway are administered to each subject. In related embodiments, the doses administered are standard doses known in the art for ADP-ribosylating toxins and agents that increase the copy number, amount, and/or activity of at least one member of the diphthamide synthesis pathway. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an combination therapy of an ADP-ribosylating toxin and an agent that increases the copy number, amount, and/or activity of at least one member of the diphthamide synthesis pathway can be determined using methods such as those described in the Examples section.

VIII. Further Uses and Methods of the Present Invention

The methods described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays. The compositions described herein can be used in a variety of diagnostic, prognostic, and therapeutic applications regarding biomarkers described herein, such as those listed in Table 1. Moreover, any method of diagnosis, prognosis, prevention, and the like described herein can be applied to a therapy or test agent of interest, such as IL3-conjugated toxin treatment, combination therapy of an ADP-ribosylating toxin and an agent that increases the copy number, amount, and/or activity of at least one member of the diphthamide synthesis pathway, and the like.

a. Screening Methods

One aspect of the present invention relates to screening assays, including non-cell based assays. In one embodiment, the assays provide a method for identifying whether a condition (e.g., CD123+ cancer) is likely to respond to an ADP-ribosylating toxin (e.g., IL3-conjugated toxin) and/or whether an agent can inhibit the growth of or kill a cell (e.g., CD123+ cancer cell) that is unlikely to respond to an ADP-ribosylating toxin (e.g., IL3-conjugated toxin).

In one embodiment, the invention relates to assays for screening test agents which have a cytotoxic or cytostatic effect on cells (e.g., CD123+ cancer cells) that are resistant to an ADP-ribosylating toxin. In one embodiment, a method for identifying such an agent entails determining the ability of the agent to agent to increase the copy number, amount, and/or activity of at least one member of the diphthamide synthesis pathway.

In one embodiment, an assay is a cell-free or cell-based assay, comprising contacting at least one biomarker listed in Table 1, with a test agent, and determining the ability of the test agent to modulate (e.g. upregulate) the enzymatic activity of the biomarker, such as by measuring direct binding of substrates or by measuring indirect parameters as described below.

In another embodiment, an assay is a cell-free or cell-based assay, comprising contacting at least one biomarker listed in Table 1, with a test agent, and determining the ability of the test agent to modulate (e.g. upregulate) the ability of the biomarker to regulate translation of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and its natural binding partner can be accomplished by determining the ability of the test agent to modulate the activity of a polypeptide or other product that functions downstream or upstream of its position within the same pathway of the biomarker.

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker listed in Table 1 in the context of a biological sample (e.g., blood, serum, cells, or tissue) to thereby determine whether an individual afflicted with a codition (e.g., CD123+ cancer) is likely to respond to an ADP-ribosylating toxin, whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers listed in Table 1.

Another aspect of the present invention pertains to monitoring the influence of agents (e.g., drugs, compounds, and small nucleic acid-based molecules) on the expression or activity of a biomarker listed in Table 1. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to ADP-ribosylating toxin. In some embodiments, the present invention is useful for classifying a sample (e.g., from a subject) as associated with or at risk for responding to or not responding to ADP-ribosylating toxin using a statistical algorithm and/or empirical data (e.g., the amount or activity of a biomarker listed in Table 1).

An exemplary method for detecting the amount or activity of a biomarker listed in Table 1, and thus useful for classifying whether a sample is likely or unlikely to respond to an ADP-ribosylating toxin involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely IL3-conjugated toxin responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%0, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to an IL3-conjugated toxin treatment), a biological sample from the subject during remission, or a biological sample from the subject during treatment for developing a cancer progressing despite an ADP-ribosylating toxin treatment.

d. Prognostic Assays

The diagnostic methods described herein can furthermore be utilized to identify subjects having or at risk of developing a cancer that is likely or unlikely to be responsive to an ADP-ribosylating toxin. The assays described herein, such as the preceding diagnostic assays or the following assays, can be utilized to identify a subject having or at risk of developing a disorder associated with a misregulation of the amount or activity of at least one biomarker described in Table 1, such as in cancer. Alternatively, the prognostic assays can be utilized to identify a subject having or at risk for developing a disorder associated with a misregulation of the at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The compositions described herein (including dual binding antibodies and derivatives and conjugates thereof) can be used in a variety of in vitro and in vivo therapeutic applications using the formulations and/or combinations described herein. In one embodiment, ADP-ribosylating toxin can be used to treat cancers determined to be responsive thereto. For example, SL-401 can be used to treat CD123+ cancer such as AML, MDS, or BPDCN in subjects identified as likely responders thereto.

Another aspect of the invention pertains to methods of modulating the expression or activity of one or more biomarkers described herein (e.g., those listed in Table 1 and the Examples or fragments thereof) for therapeutic purposes. The biomarkers of the present invention have been demonstrated to correlate with cancers (e.g., CD123+ cancers). Accordingly, in some embodiment, the activity and/or expression of the biomarker, as well as the interaction between one or more biomarkers or a fragment thereof and its natural binding partner(s) or a fragment(s) thereof, can be modulated in order to treat cancers (e.g., CD123+ cancers).

Another aspect of the invention pertains to methods of modulating the expression or activity of one or more biomarkers described herein (e.g., those listed in Table 1 and the Examples or fragments thereof,) for therapeutic purposes. The biomarkers of the present invention have been demonstrated to correlate with cancers. Accordingly, the activity and/or expression of the biomarker, as well as the interaction between one or more biomarkers or a fragment thereof and its natural binding partner(s) or a fragment(s) thereof, can be modulated in order to treat cancers.

Modulatory methods of the invention involve contacting a cell with one or more biomarkers of the invention, including one or more biomarkers of the invention, including one or more biomarkers listed in Table 1 and the Examples or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the invention, including one or more biomarkers listed in Table 1 and the Examples or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the invention, including one or more biomarkers listed in Table 1 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the present invention listed in Table 1 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and can be determined by the physician.

IX. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Other embodiments of the present invention are described in the following Examples. The present invention is further illustrated by the following examples which should not be construed as further limiting.

EXEMPLIFICATION

Example 1: CD123+ Cancers Resistant to IL3-Conjugated Toxins Display Reduced DPH1

The results described herein demonstrate that resistance of CD123+ cancers to an IL3 polypeptide conjugated to toxin that inhibits eEF2 (IL3-conjugated toxin) is associated with reduction of the dipthamide synthesis pathway enzyme, DPH1, and is reversible with a hypomethylating agent. For example, in one embodiment, SL-401, which is a recombinant interleukin 3 (IL3) polypeptide fused to a truncated diphtheria toxin (DT) polypeptide payload, was used to deliver DT to cells expressing the IL3 receptor (CD123). After internalization, DT catalyzes ADP ribosylation of eukaryotic elongation factor 2 (eEF2), blocking protein synthesis and killing target cells. SL-401 is currently in clinical trials for CD123+ cancers, including acute myeloid leukemia (AML) and blastic plasmacytoid dendritic cell neoplasm (BPDCN). Other than CD123 expression, the determinants of response are largely unknown. The results described herein elucidate the mechanisms of such de novo and acquired resistance.

Figure 1B:
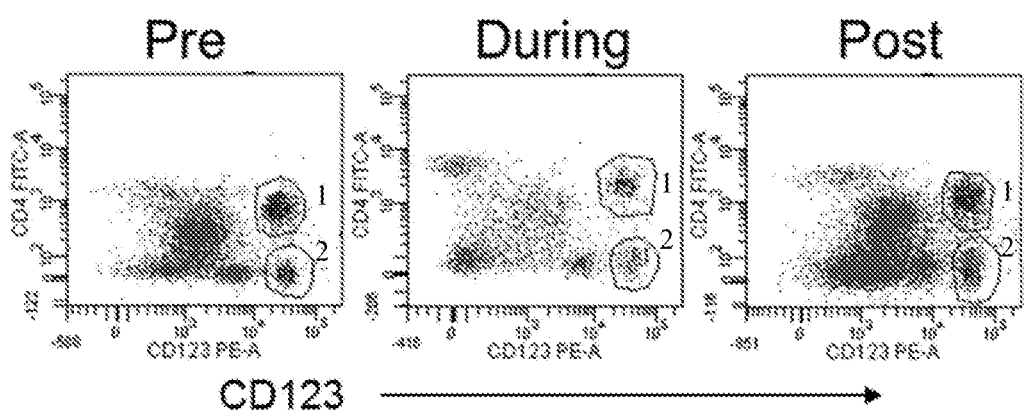
Figure 1C:
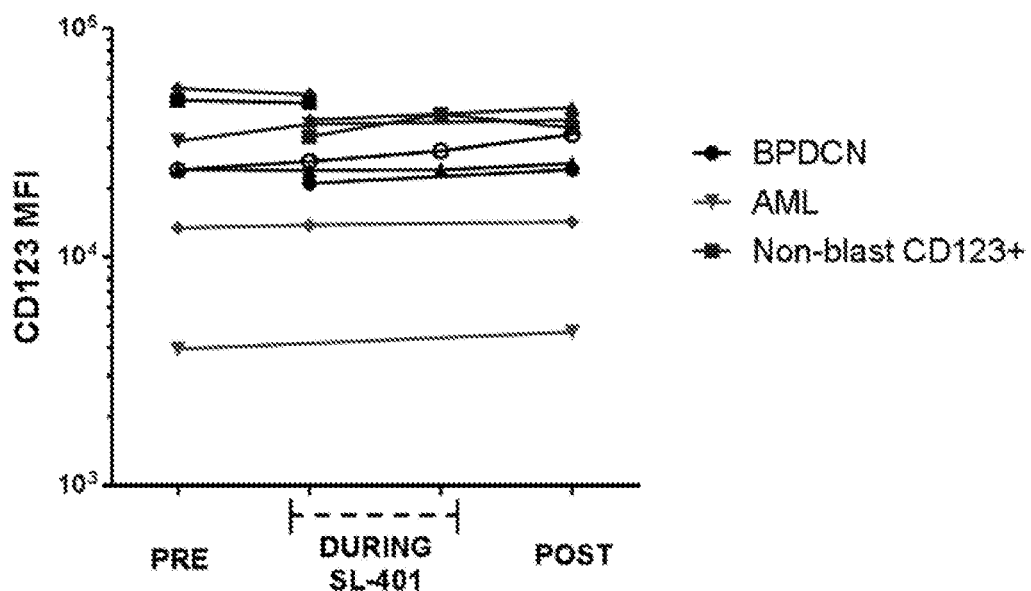
Figure 1D:
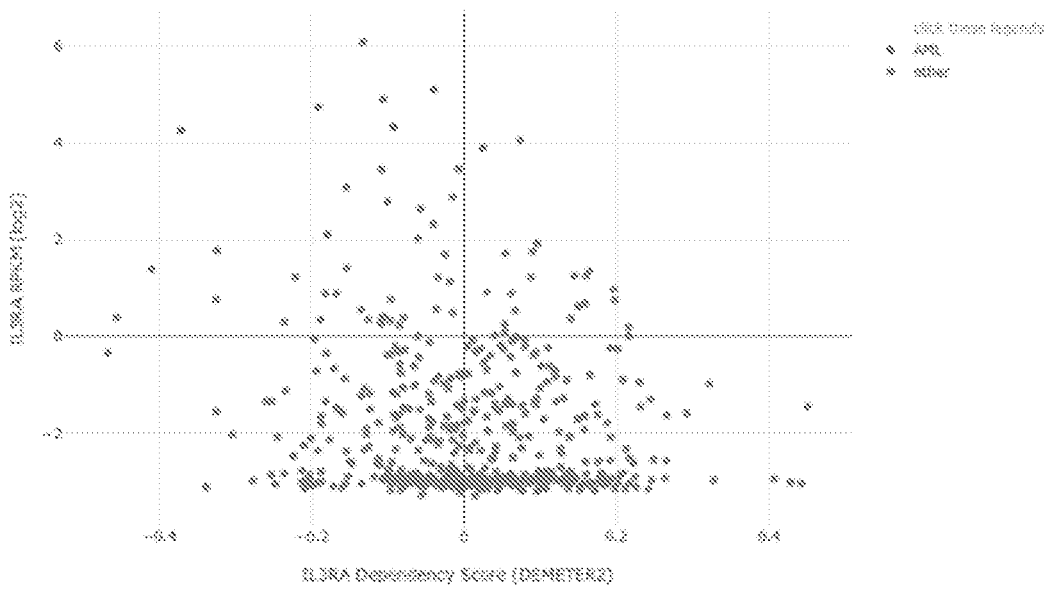

Resistance to some cell surface-targeted therapies in other hematologic malignancies is associated with loss of expression or downregulation of the target, such as CD19 or CD22 in B cell acute lymphoblastic leukemia [blina, CART for 19; moxetumomab for CD22]. The level of CD123 on the surface of AML and BPDCN cells in the bone marrow of patients was measured before, during, and after exposure to tagraxofusp in an ongoing phase 1-2 clinical trial. No decrease in CD123 associated with therapy was observed, in the malignant cell population or on the surface of presumed "non-blast," normal CD123-positive cells (FIGS. 1B and 1D). In one illustrative patient, the CD123 level on the BPDCN malignant population was maintained even in the setting of significant changes in the relative blast percentage during initial response and continued treatment (FIG. 1A). In 16 AML and BPDCN patients enrolled in a phase 1-2 trial, a decreased expression of CD123 by flow cytometry during or after SL-401 treatment was not observed. CD123 levels on the surface of patient (FIG. 1A and FIG. 1B) and patient-derived xenografts from AML and BPDCN (FIG. 1C) before, during, and at progression after treatment with CD123 were examined. Patients received SL-401 on a phase 1-2 clinical trial at 12 ug/kg/day intravenously on days 1-5 of a 21-day cycle until disease progression, intolerance of treatment, or until they withdrew from the study. For staining, cells were incubated in PBS with 2% fetal calf serum with antibody at 1:100 dilution for 20 minutes on ice, then washed once in PBS, and measured by flow cytometry. Antibodies included CD123 PE (BD Pharmingen™ Cat. 55644), CD45 APC (BD Pharmingen™ Cat. 340943), and PE Isotype (BD Pharmingen™ Cat. 550617). Representative examples from 16 patients/PDXs tested are shown in FIG. 1A-FIG. 1B. In no case was loss of CD123 during SL-401 treatment or at the time of progression/resistance to SL-401 observed. CD123 surface staining (labeled "1") and % bone marrow involvement with BPDCN blasts at the indicated times before, during, and after SL-401 treatment are shown in FIG. 1A. CD123 expression level is maintained in the setting of response, and in blasts that began to grow at the time of resistance. CD123 and CD4 flow cytometry in the bone marrow from another representative patient is shown in FIG. 1B. Cells marked with "1" (CD123+/CD4+) are the presumptive leukemia blasts, whereas the designation "2" (CD123+/CD4−) are presumptive normal marrow cells (e.g., basophils) that are CD123+. Panels from left to right correspond to the following conditions, respectively, as pre-treatment, during SL-401 (cycle 2), and at the time of progressive disease while on SL-401. Loss or decrease in CD123 expression level was observed in neither the leukemia blasts nor in the normal CD123+ cells.

It is believed that that CD123 itself can be required for growth and/or survival of AML and BPDCN cells. Data from genome-wide RNAi screening in 547 cell lines representing diverse cancer types from the Cancer Cell Line Encyclopedia (CCLE) were analyzed for evidence of relative growth disadvantage upon knock-down. For CD123 (IL3RA), only two lineages, AML and multiple myeloma, were enriched (P<0.0005) among all cells for relative dependency on CD123 (FIG. 1D). There were no BPDCN cell lines analyzed in the CCLE. These data indicate that myeloid lineage cancers, like AML and BPDCN, can be unlikely to lose expression of CD123, even during therapy with a CD123-targeted agent, because loss is associated with a growth disadvantage.

Figure 17A:
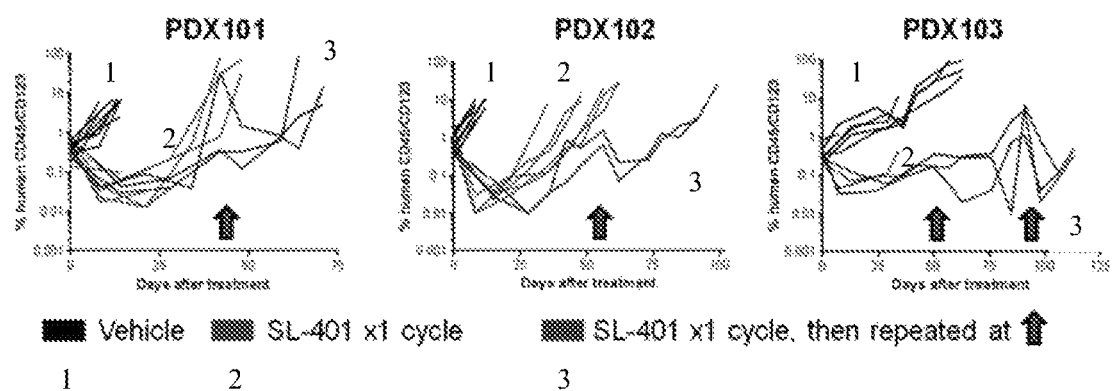
FIG. 17A-FIG. 17H show that tagraxofusp and azacitidine are an effective combination in treating patient-derived xenografts (PDXs) in vivo.
Figure 17B:
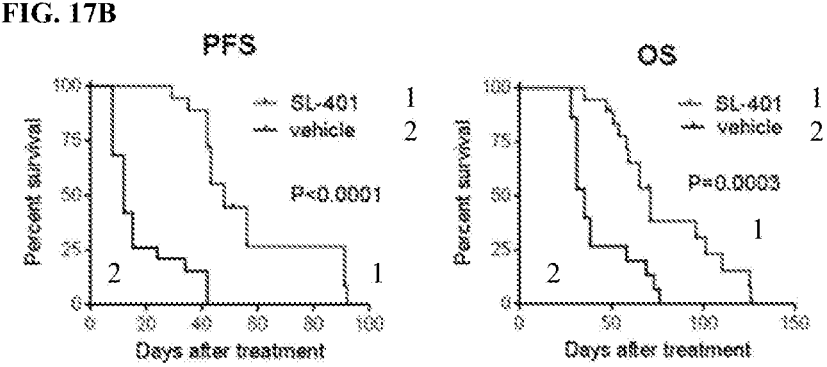
Figure 17C:
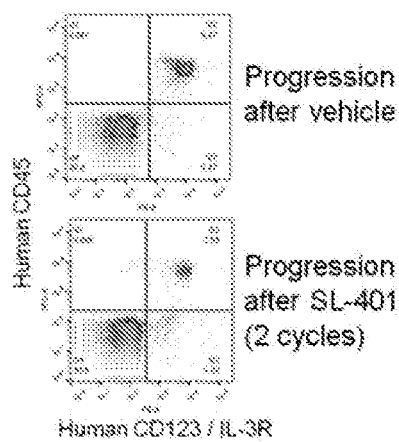

SL-401 was administered to three cohorts (n=20 mice each) of NSG immunodeficient animals engrafted with human BPDCN patient-derived xenografts. To generate the xenograft models, bone marrow blasts from patients with active, newly diagnosed BPDCN were injected into primary NSG mouse receipients. When cells were engrafted, as detected by human CD123+CD45+ cells in the peripheral blood, mice were sacrificed and human BPDCN patient-derived xenografts (PDX) were harvested from bone marrow and spleens. For treatment experiments, 1 million BPDCN PDX cells were injected into each NSG recipient intravenously. Perpiheral blood was monitored weekly for human CD123+CD45+ cells by flow cytometry. When BPDCN cells were detectable (>0.2% of peripheral blood), treatment was started with SL-401 or vehicle. Mice harboring BPDCN PDXs received 100 ug/kg/day intraperitoneally x5 days. In some animals the cycle was repeated 1-2 times after 40-50 days, when peripheral blood BPDCN (CD123+ CD45+) cells became detectable. PDX cells were harvested for analysis from mice at the time they became moribund with fatal BPDCN. As shown in FIG. 17C, all responded to SL-401 with prolonged progression-free and overall survival. CD123 was maintained in all leukemias (representative flow shown in FIG. 17C) at the same level before and after SL-401.

Example 2: Mechanisms of Resistance of CD123+ Cancers to IL3-Conjugated Toxins

Figure 2:
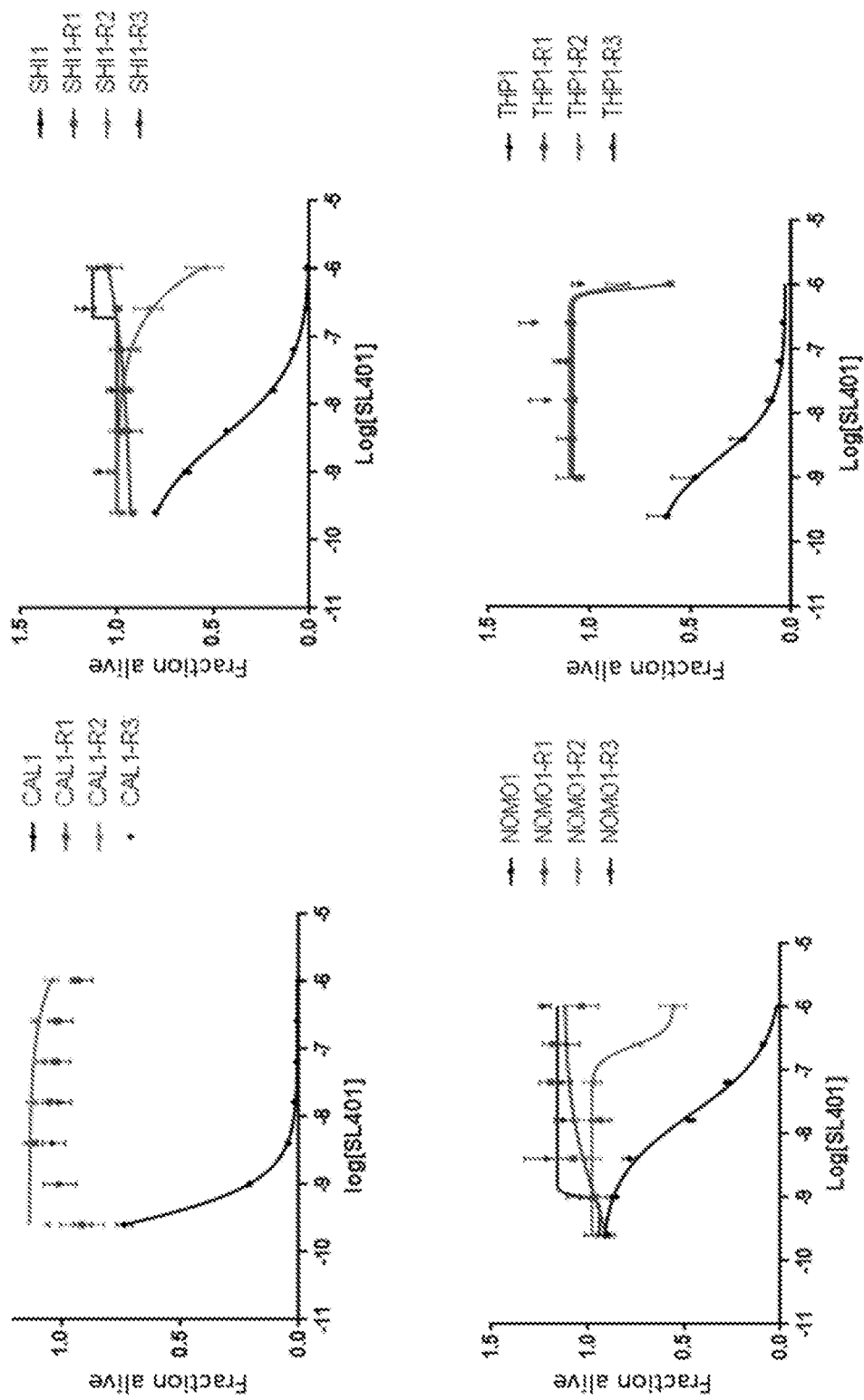
FIG. 2 shows the generation of SL-401 resistant AML and BPDCN cell lines. BPDCN (CAL1) and AML (SHI1, NOMO1, THP1) parental (black) and tagraxofusp-resistant (red, green, blue; R1-3) cultures were tested for sensitivity to five-fold decreasing concentrations of tagraxofusp in an MTT assay. Each point was assessed in triplicate and plotted relative to cells growing in vehicle alone.

To study alternative resistance mechanisms, 3-6 independent SL-401 resistant clones from each of 4 CD123+ AML (THP1, NOMO1, EOL1) or BPDCN (CAL1) cell lines were generated. These cells were treated with the $LD_{95}$ (lethal dose to 95%), and retreated upon recovery. Specifically, 0.2 μg/ml of SL-401 was used for the initial treatment, then 1 μg/ml of SL-401 for retreatment. Within one to three treatment cycles, several biologically-independent subcultures of each line that were at least 2 logs less sensitive to tagraxofusp were generated, including some that were completely insensitive to tagraxofusp up to concentrations of 1 μg/ml (FIG. 2). All lines developed >2-3 log resistance to SL-401 within 28 days. As shown in FIG. 2, 8-point dose response curves over >4 log concentration ranges for SL-401 in parental CAL1 (BPDCN), SHI1, THP1, and NOMO1 (AML) cell lines were determined. Each cell line was then treated with the $LD_{95}$ (i.e., dose that kills 95% of cells), and the surviving cells were allowed to recover and grow. The $LD_{95}$ treatment was repeated, and then SL-401 dose response curves were determined for parental cell lines and at least 3 independent resistant subclones. All cell lines had developed significant resistance to SL-401.

Figure 3:
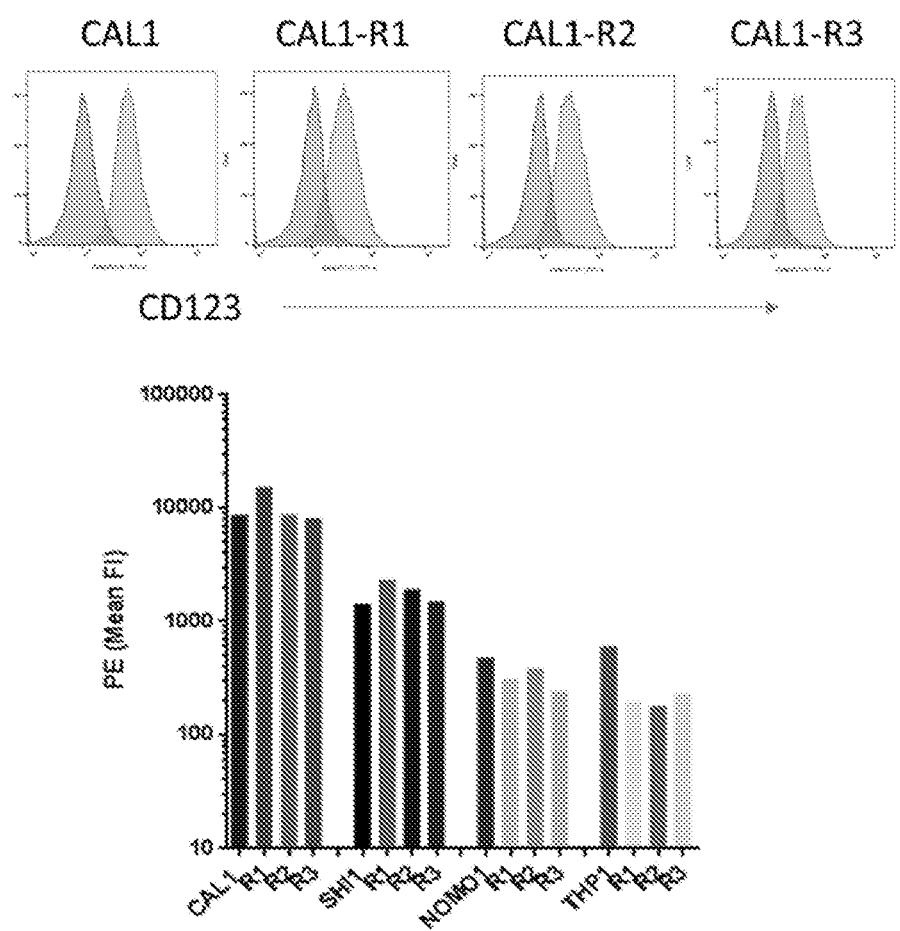
FIG. 3 shows that SL-401 resistant AML and BPDCN cell lines maintain CD123 expression. The top panel of FIG. 3 shows the CD123 (blue) and isotype control (red) staining as measured by flow cytometry for parental CAL1 cells and three independent tagraxofusp-resistant CAL1 subcultures. The bottom panel of FIG. 3 shows the MFI of CD123 in the indicated BPDCN and AML parental and tagraxofusp-resistant cell lines.

All resistant clones maintained CD123 surface expression, consistent with what was observed in patients. Flow cytometry was performed as described above for CD123 compared to isotype control in parental and 3 resistant subclones in each of 4 cell lines (FIG. 3). There was no loss of CD123 expression in the resistant cells compared to their corresponding parental lines. Maintenance of CD123 levels were consistent across all cell lines, even considering that the parental lines have a >1 log range of CD123 expression and baseline tagraxofusp $IC_{50}$ values ranging from sub nM to >10 nM.

Figure 4:
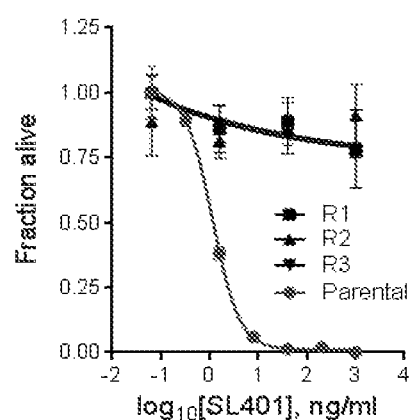
FIG. 4 shows that SL-401 is internalized equivalently into parental and SL-401 resistant CAL1 cells.
Figure 4:
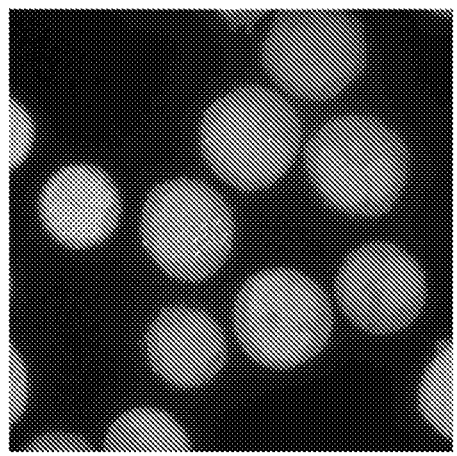
Figure 4:
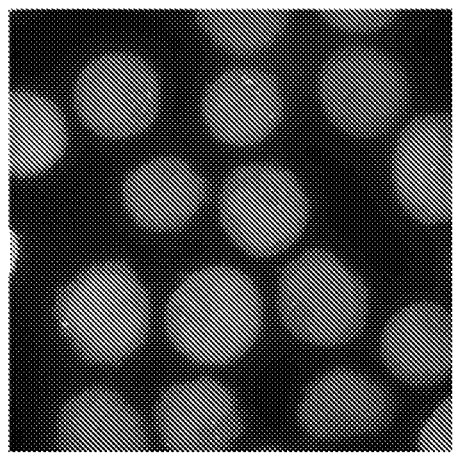

The cytotoxic activity of full-length diphtheria toxin (DT) requires cell entry, escape from endosomes into the cytoplasm, and ADP ribosylation of eEF2. Confocal microscopy was used with a fluorescently-tagged tagraxofusp to test if there was a difference in drug internalization into resistant cells. At early timepoints (30-60 minutes) after exposure to APC-tagged tagraxofusp, a fluorescently tagged SL-401 was found to be internalized equally in resistant and parental cells (FIG. 4). Tagraxofusp-APC killed parental cell lines with equal efficiency as the untagged drug but had no activity against resistant subclones. The subcellular localization of SL-401 in parental (sensitive) and SL-401 resistant cell lines was measured using a fluorescently labeled SL-401 with confocal microscopy (FIG. 4). Cells were treated with 1 µg/ml SL-401 and confocal microscopy was performed at baseline and at 30, 60, and 120 minutes later. A representative confocal image is shown in FIG. 4, demonstrating that SL-401 enters resistant cells equivalently to sensitive cells.

Figure 5:
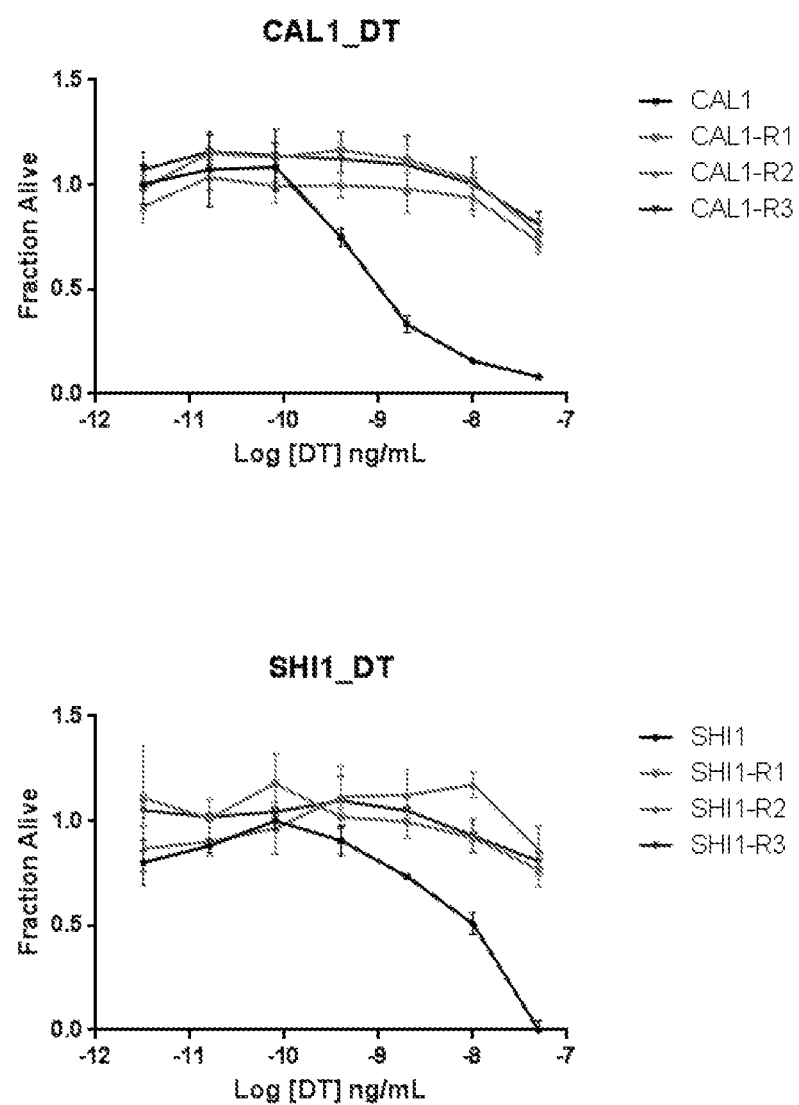
FIG. 5 shows that SL-401 resistant AML and BPDCN cell lines are also resistant to full-length diphtheria toxin.

Some AML cell lines express the DT ligand-binding domain cell-surface receptor, proheparin-binding EGF-like growth factor precursor. Accordingly, the cytotoxic activity of full-length DT in parental and tagraxofusp-resistant cells was tested. SL-401 resistant cells were also resistant to full-length DT (FIG. 5), indicating that the mechanism of resistance involved DT rather than IL3 binding/internalization. Sensitive and resistant AML and BPDCN cell lines were treated with DT and it was found that SL-401 resistant cells were also relatively resistant to DT compared to parental sensitive cells (FIG. 5). These data indicated that the mechanism of resistance was not based on the IL3 portion of the fusion protein. Together, these data indicate that tagraxofusp resistance in AML and BPDCN cells is due to a defect in either endocytic escape or susceptibility to DT catalytic activity, rather than due to loss of the cell surface target or defective internalization after ligand binding.

Next, experiments were performed to determine whether there was a therapeutically-exploitable phenotype associated with cells that had acquired tagraxofusp resistance. BH3 profiling is an assay that measures the "apoptotic priming" of cells by measuring mitochondrial depolarization or cytochrome c release after stimulation of permeabilized cells with BH3 domain-containing peptides. Depolarization after broadly-active peptides, such as those derived from the pro-apoptotic BH3 protein BIM, measures the "overall priming" of the cells, or its general propensity to undergo cell death via mitochondrial apoptosis after a toxic stimulus. In contrast, measuring depolarization with other peptides, such as derived from BAD, PUMA, or HRK, that bind to and block specific subsets of anti-apoptotic BCL2-family proteins, assesses the relative dependence of cells on a given anti-apoptotic pathway for survival. BH3 profiling has been used to predict sensitivity to conventional chemotherapy and targeted therapy, and results also correlate with activity of BCL2-family antagonists such as venetoclax.

Figure 6:
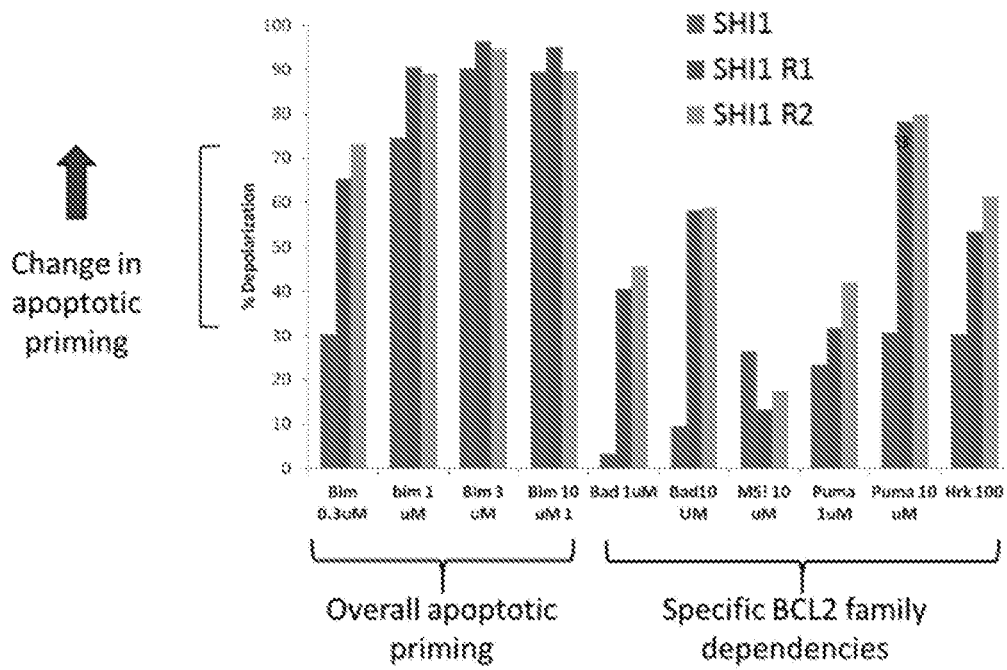
FIG. 6 shows that SL-401 resistant cells are more "primed" for apoptosis.
Figure 6:
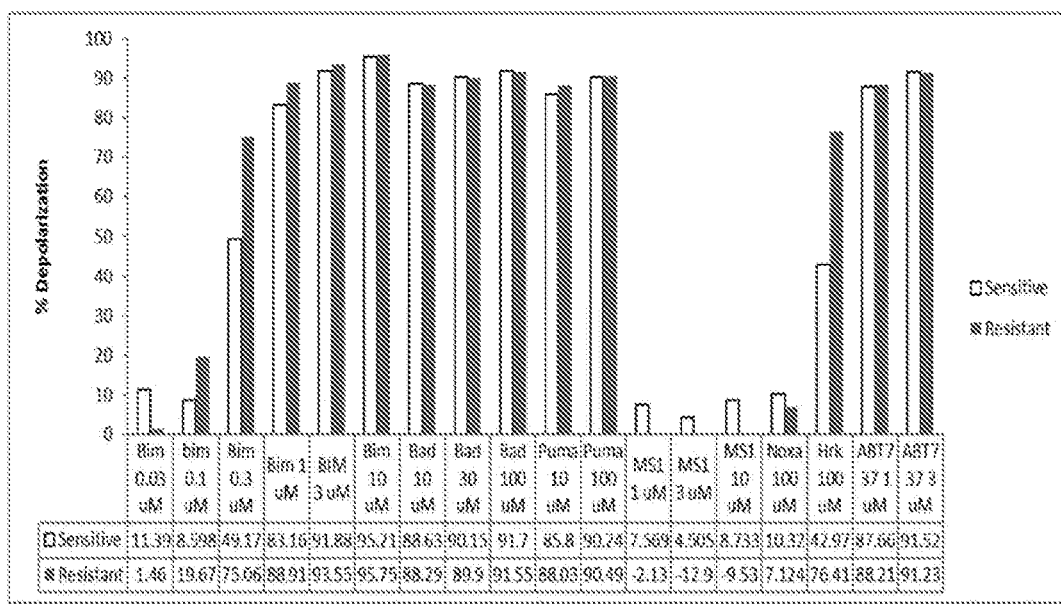

BH3 profiling was performed on parental cells and those with acquired resistance to tagraxofusp. BH3 profiling was performed as described previously in Ryan and Letai (2013) *Methods* 61:156. The profiling was applied to SL-401 sensitive and resistant cells, using BIM peptide stimulation to measure overall apoptotic priming, and assessed specific anti-apoptotic pathways using peptides of BAD (measures BCL-2 and BCL-XL), MS1 (MCL-1), PUMA (BCL-2, BCL-XL, and MCL-1), and HRK (BCL-XL). It was found that AML and BPDCN cells (SHI1 shown in FIG. 6; similar results were observed in CAL1) became more primed for apoptosis in the setting of resistance to SL-401 (FIG. 6). When most cancer cells become resistant to most cancer therapies, they usually become less primed, i.e., less likely to die in response to any other anti-cancer therapy. In this case, the cells were more primed, which indicated that they are believed to be more sensitive to other anti-cancer agents in the setting of SL-401 resistance.

Figure 7:
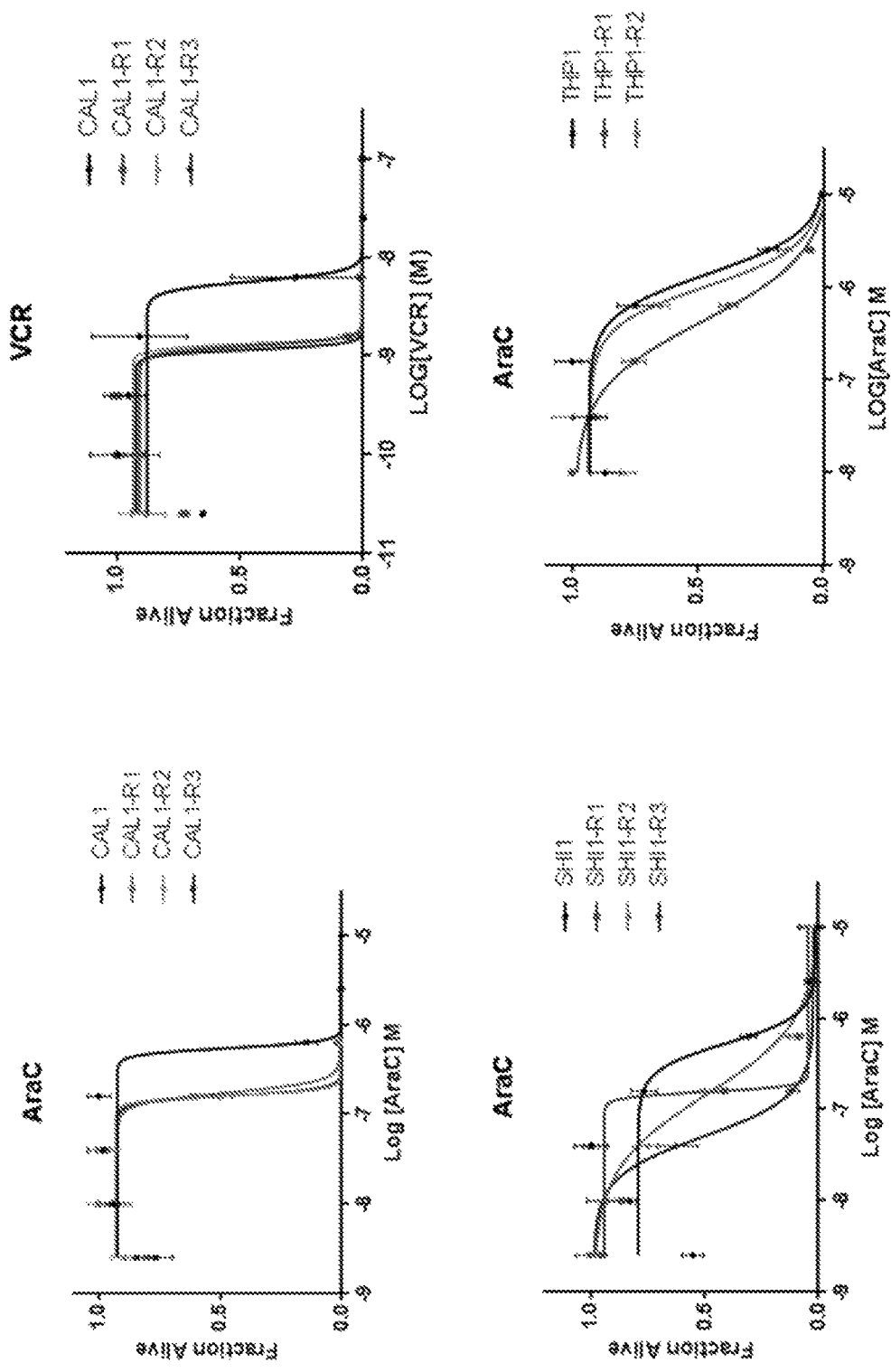
FIG. 7 shows that SL-401 resistant cells have increased sensitivity to conventional chemotherapy. CAL1, SHI1, and THP1 parental and tagraxofusp-resistant cells were tested in MTT viability assays after exposure to increasing doses of cytarabine (AraC) or vincristine (VCR).
Figure 8:
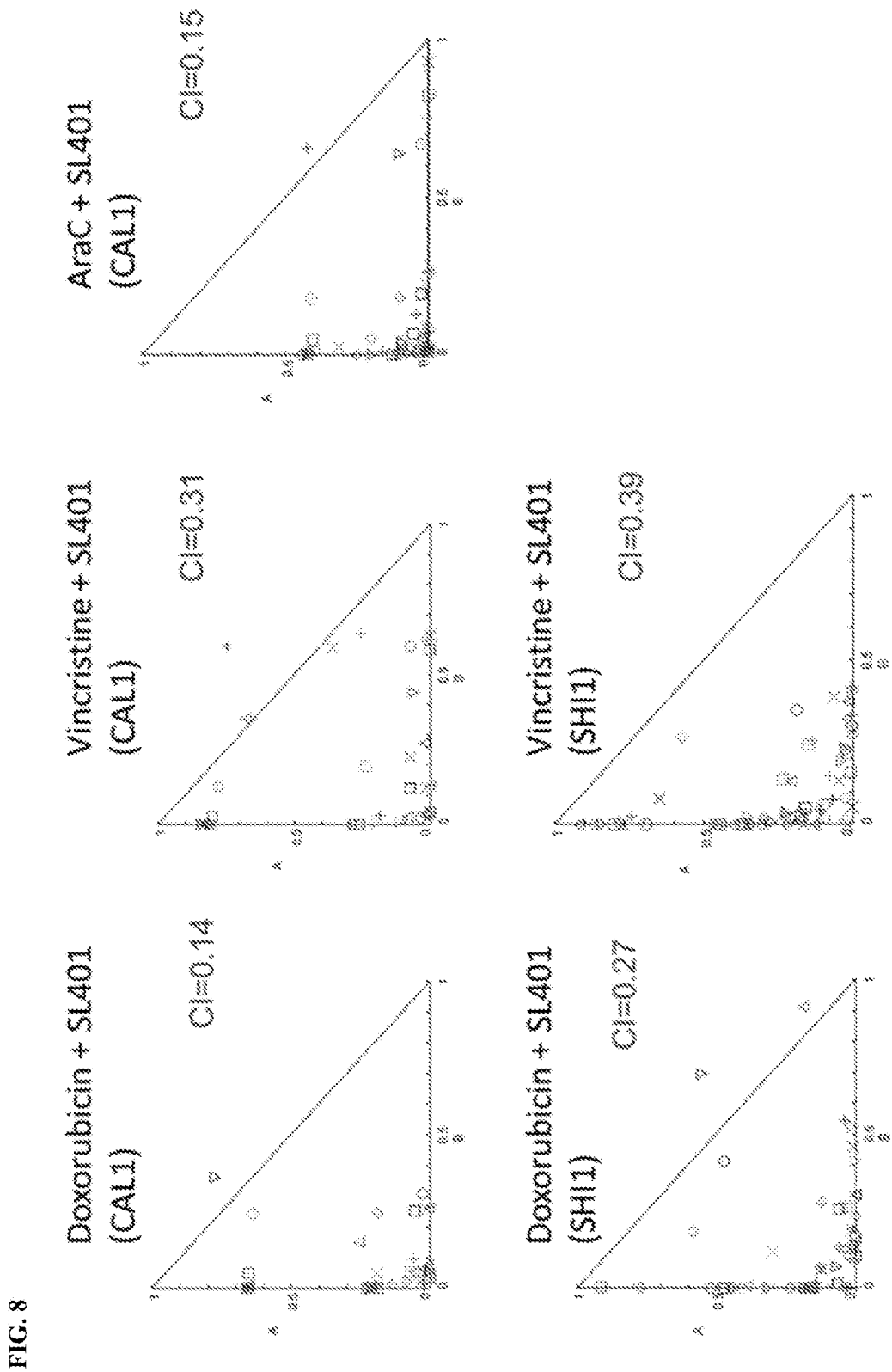
FIG. 8 shows that SL-401 and chemotherapy are synergistic. BPDCN (CAL1) and AML (SHI1) parental cell lines were tested for synergistic cell death with combinations of tagraxofusp with doxorubicin, vincristine, or cytarabine, each varied over five-fold dilution series plotted using an isobologram, where the points on the diagonal line indicate additivity, to the right of the line indicate antagonism, and to the left of the line indicate synergy. Combination indices (CI) are also shown for each drug pair, calculated using the method of Chou-Tallalay, where CI<1 indicates synergy.

In support of the results shown in FIG. 6 (BH3 profiling), parental and SL-401 resistant subclones of CAL1, SHI1, and THP1 cell lines were tested for their sensitivity to conventional leukemia chemotherapy drugs cytarabine (AraC) and vincristine (VCR). In all cases, the SL-401 resistant cells were more sensitive to chemotherapy compared to the parental cells (FIG. 7). CAL1 and SHI1 cells were treated with 96 different concentration combinations of SL-401 and either doxorubicin, vincristine, or cytarabine (AraC). Experiments were performed to determine whether there was also up-front synergy between tagraxofusp and conventional chemotherapy. Testing all combinations of each drug over 5-fold dilutions across 8 dose levels and the method of Chou-Talalay to calculate the combination index (CI), it was found that tagraxofusp and chemotherapy were synergistic (CI<1) with all cytotoxic compounds in all cell lines tested (FIG. 8). All combinations showed overall marked synergy, as calculated using CompuSyn software (available on the World Wide Web at combosyn.com/) which relies on the method of Chou-Talalay (Chou and Talalay (1984) *Adv Enzyme Regul* 22:27-55), and as shown in the isobologram plots in FIG. 8 (points below or inside the diagonal line indicate synergy, points on the line indicate additive effects, points above the line indicate antagonism). All combinations had a composite combination index (CI) of less than 0.4. These data indicate that tagraxofusp is synergistic with conventional chemotherapy, and in sum, support clinical testing of tagraxofusp in combination with chemotherapy, either in first-line therapy or after progression on single-agent tagraxofusp.

Figure 16A:
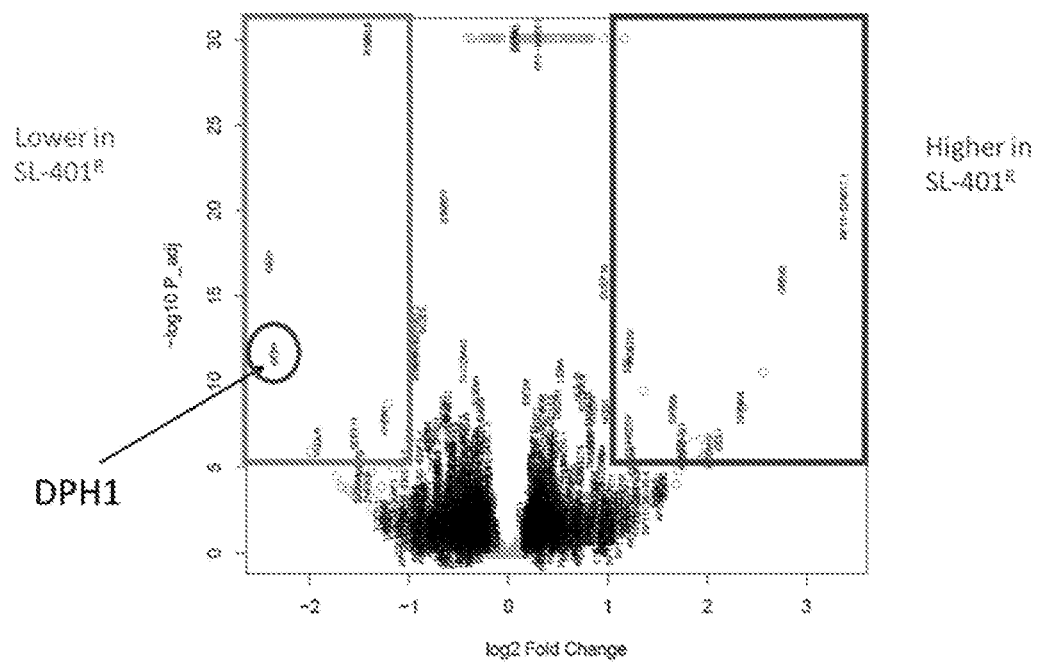
FIG. 16A-FIG. 16F show that tagraxofusp resistance is mediated by loss of the diphthamide synthesis pathway enzyme DPH1.
Figure 16B:
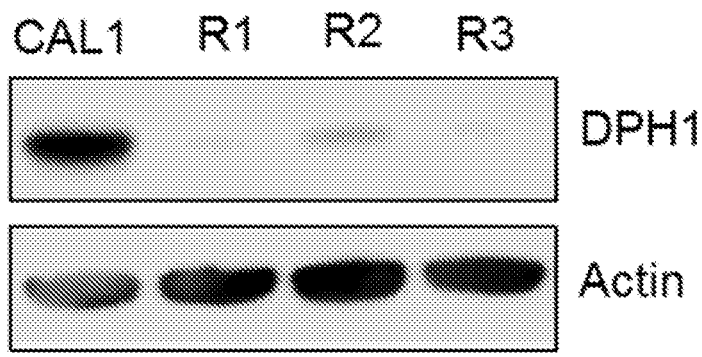

Example 3: Loss of DPH1 Alone is Sufficient to Promote Resistance to Il3-Conjugated Toxins To elucidate mechanisms of tagraxofusp resistance, whole exome sequencing (WES) and whole transcriptome RNA-sequencing (RNA-seq) were performed on parental and resistant BPDCN and AML cell lines. There were no recurrently mutated genes at the DNA level among six resistant subclones (n=3 CAL1 and n=3 SHI1) by WES. Among the relatively small number of genes with significantly altered expression in the combined CAL1 and SHI1 resistant cells compared to parental (n=6 resistant, n=6 parental), one of the most downregulated genes was DPH1 (7.53-fold decrease, P<0.0001; FIG. 16A). DPH1 encodes the first protein in an enzymatic pathway containing at least 7 members known as the diphthamide synthesis pathway, which is responsible for catalyzing the conversion of histidine 715 on eEF2 to the variant amino acid diphthamide. Diphthamide-715 on eEF2 is the site of ADP ribosylation by diphtheria toxin as well as other ADP-ribosylating bacterial toxins such as *Pseudomonas* exotoxin A. Loss of DPH1 protein in resistant cells was confirmed by Western blotting (FIG. 16B).

Figure 16C:
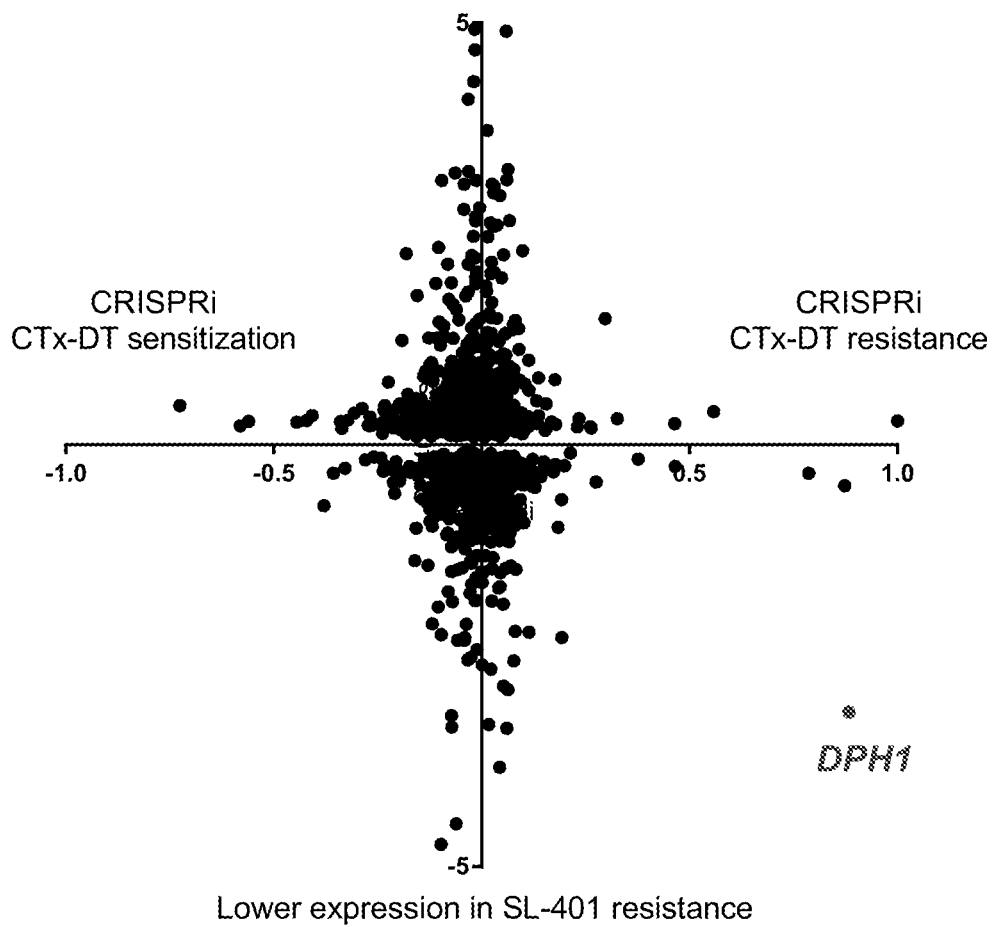

Diphthamide synthesis proteins are known to be required for cytotoxicity of full-length DT, but their role in tagraxofusp sensitivity and resistance has not been studied. Given that several other genes' expression was also affected in the setting of tagraxofusp resistance, RNA-seq data were integrated with a prior dataset that measured the influence of gene expression on sensitivity to a cholera toxin-diphtheria toxin hybrid protein (CTx-DTA). In that experiment, a genome-wide CRISPR sgRNA library was introduced into human cells with expression of a catalytically-inactive Cas9 nuclease fused to either a transcriptional activator or repressor (so-called "CRISPRa" or "CRISPRi") and then relative sgRNA abundance was compared before and after exposure to CTx-DTA. When tagraxofusp resistance-associated gene expression versus the CRISPRi score was plotted on a per-gene basis, only one gene, DPH1, was a "hit" in both assays—i.e., lower in tagraxofusp-resistant cells and knockdown was advantageous in the setting of CTx-DT exposure (FIG. 16C).

Figure 16D:
Figure 16E:
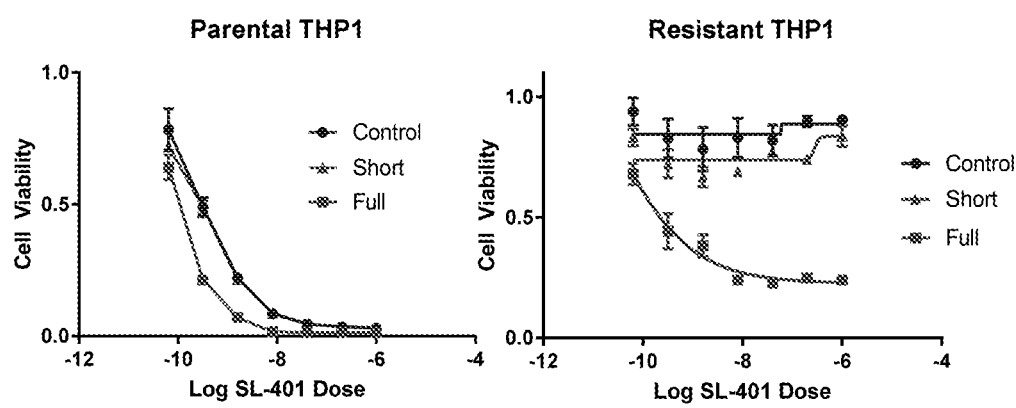
Figure 16F:
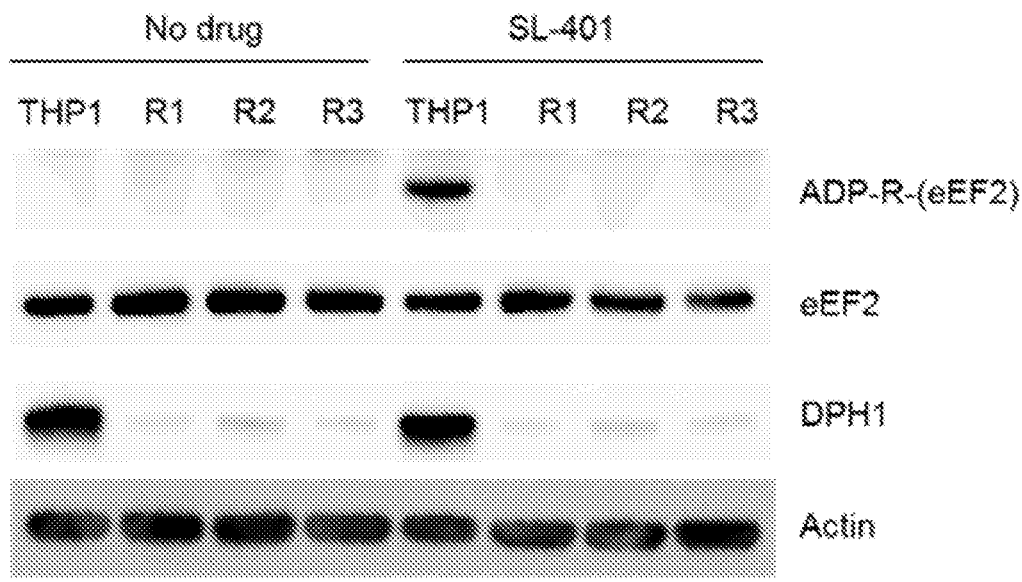

A biochemical assay was next performed to test the ability of tagraxofusp to catalyze ADP-ribosylation in cellular lysates in the presence of exogenous biotin-tagged nicotine-adenine-dinucleotide (NAD) as a source of ADP-ribose. In parental cells, tagraxofusp caused ADP-ribosylation of a single protein detectable on streptavidin-HRP Western blotting at the expected molecular weight of eEF2. In contrast, tagraxofusp-resistant cells had significantly decreased DPH1 expression and tagraxofusp was unable to catalyze ADP-ribosylation of any proteins in the lysate (FIG. 16F). Together, these data indicated that loss of DPH1 was associated with resistance to tagraxofusp cytotoxicity and loss of tagraxofusp-induced ADP-ribosylation activity in BPDCN and AML cells.

Whole transcriptome RNA-sequencing and whole exome sequencing (WES) were performed for 12 samples, which included 3 biological replicates of each parental cell line CAL1 (BPDCN) and SHI1 (AML) and 3 independent SL-401 resistant subclones of each. RNA-seq and WES were performed as described below. For RNA-seq, total RNA was prepared using a MiRNeasy kit (Qiagen). Illumnia sequencing libraries were prepared using Illumina TruSeq® Stranded mRNA sample preparation kits from 500 ng of purified total RNA according to the manufacturer's protocol. The finished dsDNA libraries were quantified by Qubit™ fluorometer, Agilent TapeStation 2200, and RT-qPCR using the Kapa Biosystems library quantification kit according to manufacturer's protocols. Uniquely indexed libraries were pooled in equimolar ratios and sequenced on an Illumina NextSeq® 500 with single-end 75 bp reads. Reads were aligned to the hg19 reference genome assembly using STAR (v25.1b) (available on the World Wide Web at github.com/alexdobin/STAR). FPKM expression values were calculated using cufflinks (v2.2.1) (available on the World Wide Web at cole-trapnell-lab.github.io/cufflinks/). For WES, DNA preparation, target capture, and sequencing were performed as described previously (Fisher et al. (2011) *Genome Biol.* 12:R1). Data analysis was performed using the MuTect algorithm as described in Cibulskis et al. (2013) *Nat. Biotech.* 31:213.

Figure 9:
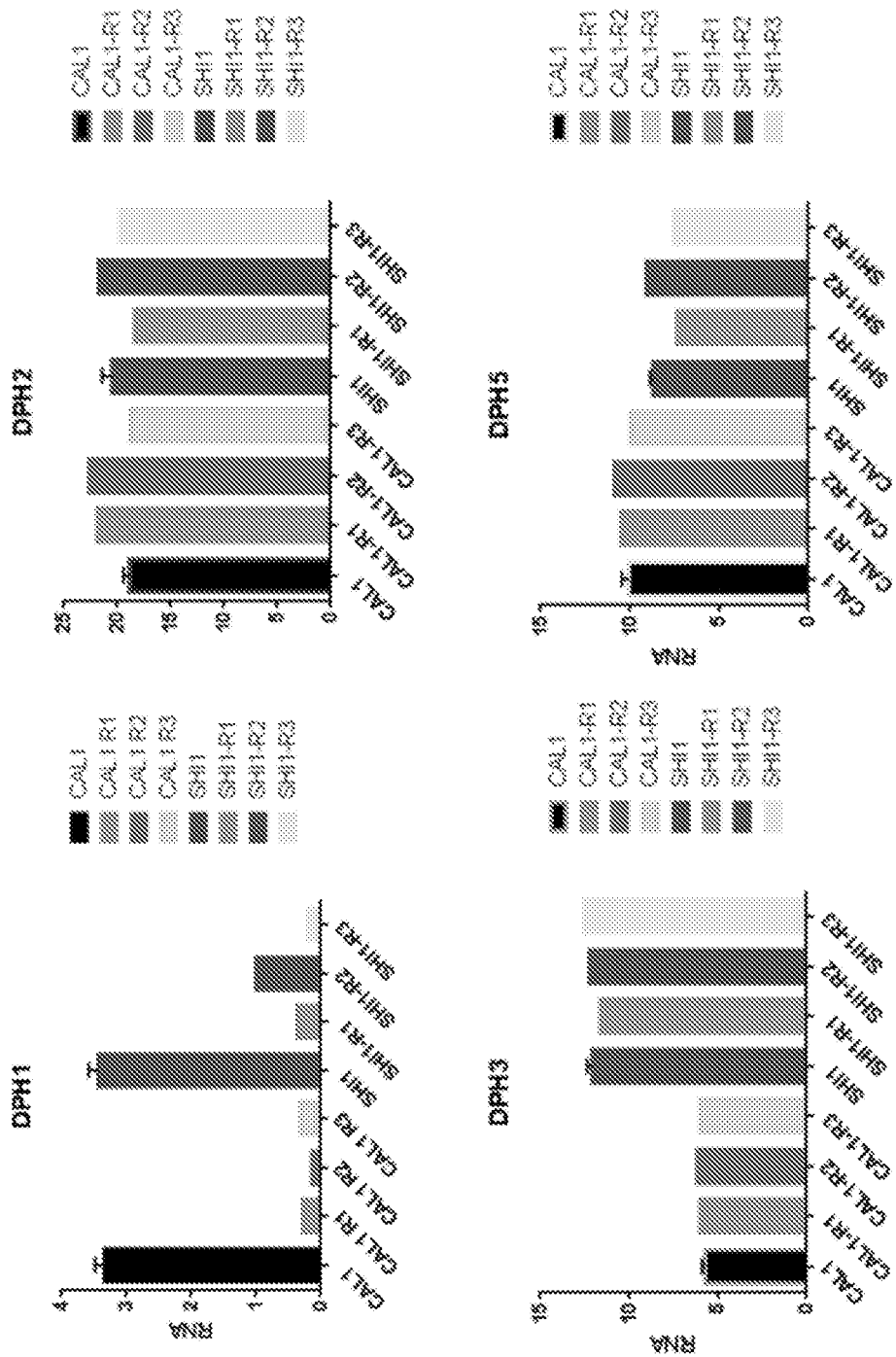
FIG. 9 shows that DPH1 is significantly downregulated in SL-401 resistance BPDCN and AML cells.
Figure 10A:
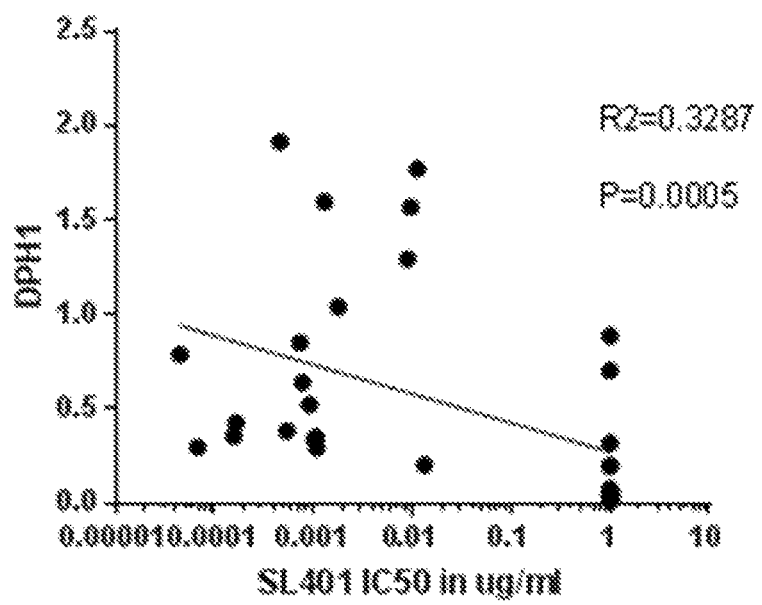
FIG. 10A-FIG. 10B show that the level of DPH1 is anti-correlated with sensitivity to SL-401 across leukemia cells and patients' AMLs.
Figure 10B:
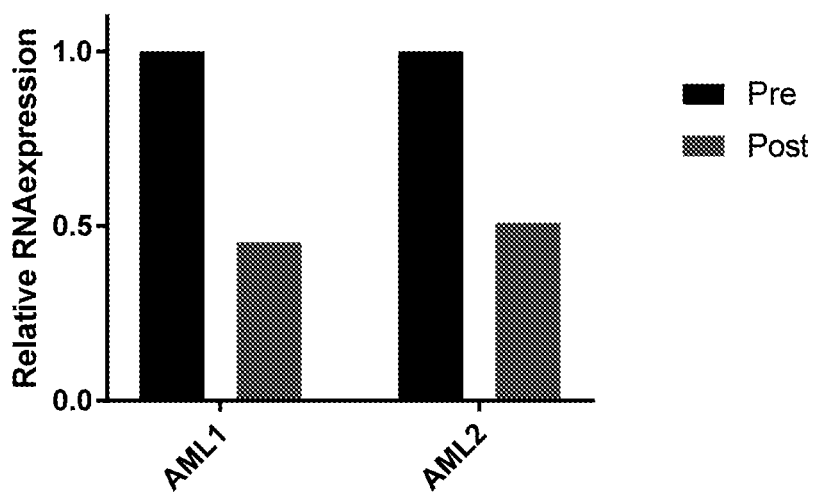

The most downregulated gene combination of fold-change and significance by t-test was DPH1. There were no recurrent acquired DNA mutations. However, in RNA-seq the most downregulated gene in 6 independent clones from 2 lines was DPH1 (FC −7.5, FDR<0.0001). Plotted in FIG. 9 are the expression levels by RNA of DPH family members (fragments per kilobase per million reads mapped, FPKM, are plotted). DPH1 is the first enzyme in a cascade that converts histidine 715 on eEF2 to diphthamide, the direct target for ADP ribosylation by DT. Quantitative RT-PCR for DPH1 was performed in >20 AML and BPDCN cells, normalized to actin. Decreased expression of DPH1 was confirmed in the 6 resistant clones by qRT-PCR, and in 3 clones from an additional line. The IC50 for SL-401 was also determined using an 8 point 4-log dose curve in the same cells. SL-401 IC50 vs relative DPH1 expression level was plotted in FIG. 10A, and a significant correlation (P=0.0005) was calculated. Across 33 cell lines and subclones, there was an inverse linear correlation between DPH1 level and SL-401 IC50 (P=0.0005). These data indicate that DPH1 level is inversely correlated with sensitivity to SL-401 in univariate analysis. To validate this finding in patients, paired RNA-seq was performed on CD45+CD123+ sorted blasts from 2 AMLs pre & post 2 cycles of SL-401. Both patients' AMLs had reduced DPH1 after exposure to SL-401 (mean −2.1 fold; FIG. 10B).

It was next tested whether DPH1 level and SL-401 sensitivity were causally linked, rather than simply associated. Three AML and BDPCN cell lines with stable expression of the Cas9 nuclease were generated by transducing them with a lentivirus that expresses a FLAG-tagged Cas9 nuclease (available on the World Wide Web at addgene.org/52961/), and then selecting them in puromycin. Puro-resistant cell clones were tested by western blot for FLAG-Cas9 using anti-FLAG® M2 antibody (Sigma F1804). Next, cas9-expressing clones were transduced with a lentivirus to express the CRISPR guide RNAs with GFP (available on the World Wide Web at addgene.org/57822/). Lentiviral vectors that express 4 independent CRISPR sgRNAs targeting human DPH1, or two control guides that do not recognize any sequence in the human genome were generated. The specific guide RNA sequences were shown below:

Control Guides:

```
Control 1:
ACGGAGGCTAAGCGTCGCAA;

Control 2:
CGCTTCCGCGGCCCGTTCAA;
```

DPH1 Guides:

```
g2:
GTCTTGAACGGAGGTGTCCA g3:
AGCTGTGACCATAGTGCACC g5:
GTTGACTTCCTGGTGCACTA g6:
GGGTTGTTCAGGACCTCAGG
```

Figure 11:
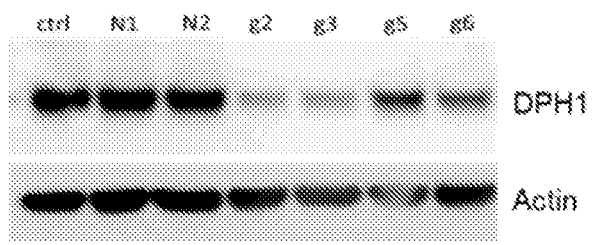
FIG. 11 shows that loss of DPH1 alone is sufficient to confer resistance to SL-401 in AML and BPDCN cells. The top panel of FIG. 11 shows the results of Western blotting for DPH1 and actin in parental THP1 cells (ctrl), and cells transduced with independent non-targeting (N1-2) and DPH1-targeted (g2, g3, g5, g6) sgRNAs. The bottom panel of FIG. 11 shows the percent GFP+ cells in culture is plotted over time after treatment with tagraxofusp in cells transduced with the same CRISPR sgRNA-containing lentiviruses as described in the top panel, each co-expressing GFP.
Figure 11:
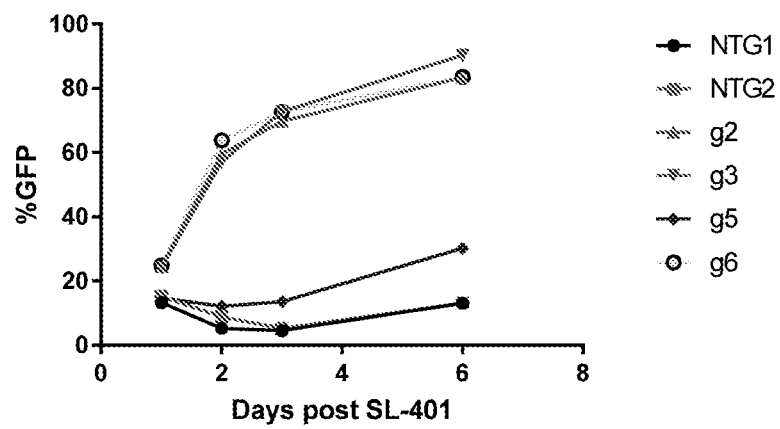

The Cas9-expression cell lines were transduced with the sgRNA viruses, also marked by GFP expression, at high MOI (>80% transduction efficiency). At high multiplicity of infection (MOI), resulting in >80% GFP-positivity, Knockdown of DPH1 was first validated by Western blot in NOMO1-Cas9 cells (FIG. 11, top panel). The control is parental NOMO1-Cas9, N1 and N2 are control non-targeting guides, and g2, g3, g5, and g6 target DPH1. All except g5 substantially knocked down DPH1. The low-MOI sgRNA-transduced cells (target 20% transduction efficiency) were treated with SL-401 at the LD95 for NOMO1 cells. As seen in the bottom panel of FIG. 11, GFP-positive cells expressing the DPH1 guides that knocked down DPH1 had a rapid and distinct growth advantage, as determined by the enriched GFP-positive fraction over time. The control guides had no enrichment, and g5 (partial knockdown) had only partial enrichment. These data indicate that loss of DPH1 alone is sufficient to promote SL-401 resistance, and that the degree of DPH1 loss may correlate with degree of SL-401 resistance.

Next, a full-length DPH1 cDNA or a N-terminal truncated cDNA deleting a domain known to be required for DPH1 catalytic activity, was cloned into a doxycycline-inducible lentiviral expression vector. Full-length or truncated dox-on DPH1, or empty vector-containing viruses was transduced into parental or tagraxofusp-resistant THP1 AML cells and selected with puromycin. First, Western blotting and the in vitro ADP-ribosylation biochemical assay was performed in cell lysates after doxycycline-induction. It was found that expression of the full-length DPH1, but not the enzymatic activity-deficient DPH1 or empty vector, restored ADP-ribosylation activity of tagraxofusp in resistant cells (FIG. 16D). Re-expression of full-length DPH1 restored the cytotoxic activity of tagraxofusp in resistant cells to $IC_{50}$ values comparable to that parental cells (FIG. 16E). Of interest, overexpression of DPH1 in parental cells was also associated with modestly increased sensitivity to tagraxofusp, indicating that DPH1 level and/or diphthamide synthesis pathway activity can be at least one determinant of upfront sensitivity to tagraxofusp.

Figure 12:
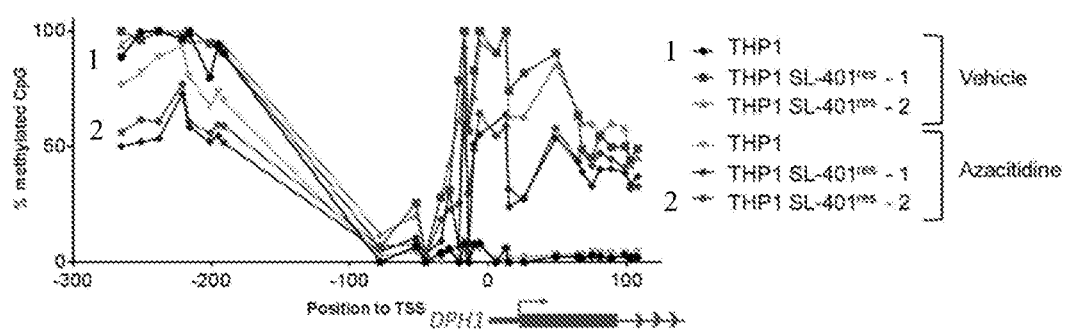
FIG. 12 shows that SL-401 resistance is associated with DPH1 promoter hypermethylation of DNA at CpG sites, and that hypermethylation is reversible by azacitidine. The Fraction of methylated CpGs in the DPH1 locus is shown for the indicated genomic positions in parental THP1 cells and two independent tagraxofusp-resistant subclones, before and after 2 weeks of pulsatile treatment with non-cytotoxic doses of azacitidine.
Figure 14A:
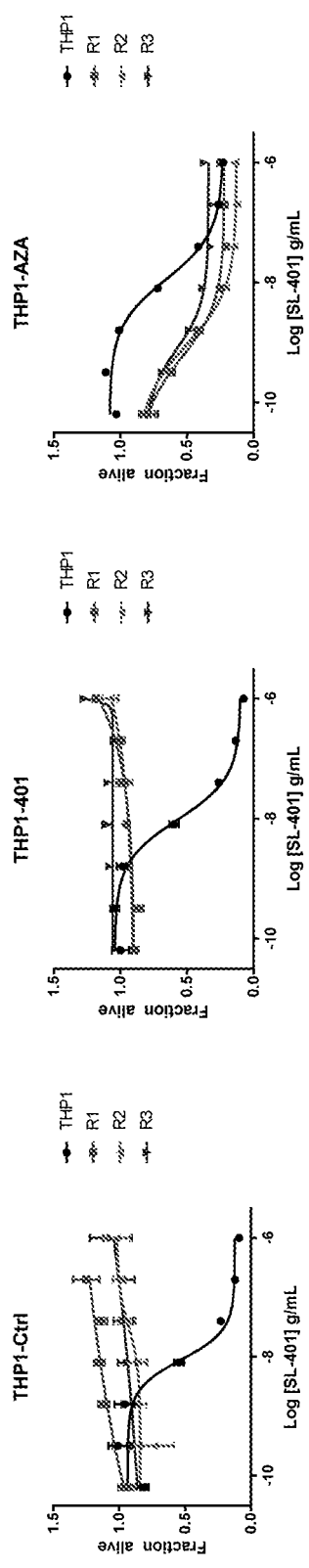
FIG. 14A-FIG. 14C show that prolonged, pulsatile, non-cytotoxic treatment with azacitidine reverses SL-401 resistance in association with causing increased levels of DPH1.
Figure 14B:
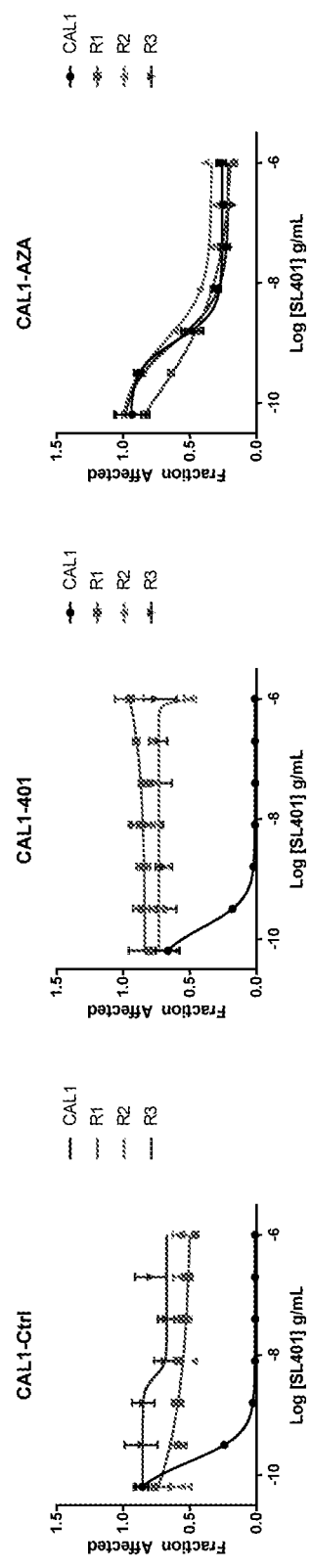
Figure 14C:
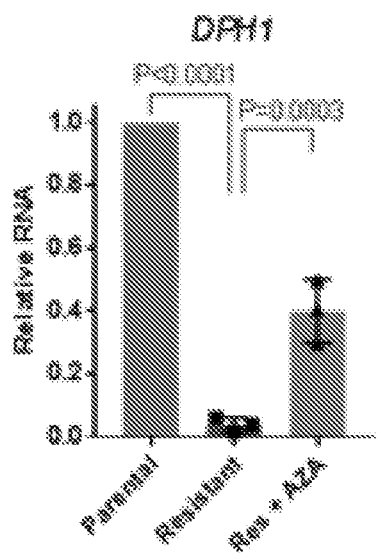

Example 4: Synergistic Cytotoxicity was Observed in Cancer Cells Treated with Il3-Conjugated Toxins and a Hypomethylating Agent DPH1 expression is known to be regulated by DNA methylation and sensitivity to *Pseudomonas* exotoxin A was previously shown to be modulated by CpG methylation in the DPH1 locus. To test whether loss of DPH1 is mediated by DNA methylation, bisulfite pyrosequencing of the DPH1 locus in CpG islands (30 individual CpG sites) was performed by EpigenDx analysis (available on the World Wide Web at epigendx.com/d/service/pyrosequencing/) and the % methylated cytosine at each CpG site was quantitated. This analysis was performed in THP1 parental and 2 SL-401 resistant subclones, and CAL1 parental and 2 SL-401 resistant subclones. Data plotted in FIG. 12 are from THP1 cells, and are representative of CAL1. Dramatic hypermethylation of the DPH1 locus CpGs was observed in the setting of SL-401 resistance (black to red/orange), consistent with gene expression silencing. An upstream CpG island between −300 and −200 baes from the transcription start site had not change in methylation, indicating that increased DPH1 promoter methylation associated with tagraxofusp resistance was specific. Given this finding, it was believed that 5-azacitidine, a DNA methyltransferase inhibitor or "DNA hypomethylating agent" can reverse the aberrant DPH1 hypermethylation and restore DPH1 expression. The parental and resistant cells were also treated with non-cytotoxic, low doses of azacitidine, so called "epigenetic dosing" (300 nM, 2 days on/2 days off) over 2 weeks to determine if the hypermethylation was reversible by DNA methyltransferase inhibition. Low dose azacitidine treatment resulted in reduction in the DPH1 CpG DNA hypermethylation associated with SL-401 resistance, and partially restored mRNA expression as measured by quantitative RT-PCR (FIG. 12 and FIG. 14C).

Figure 13A:
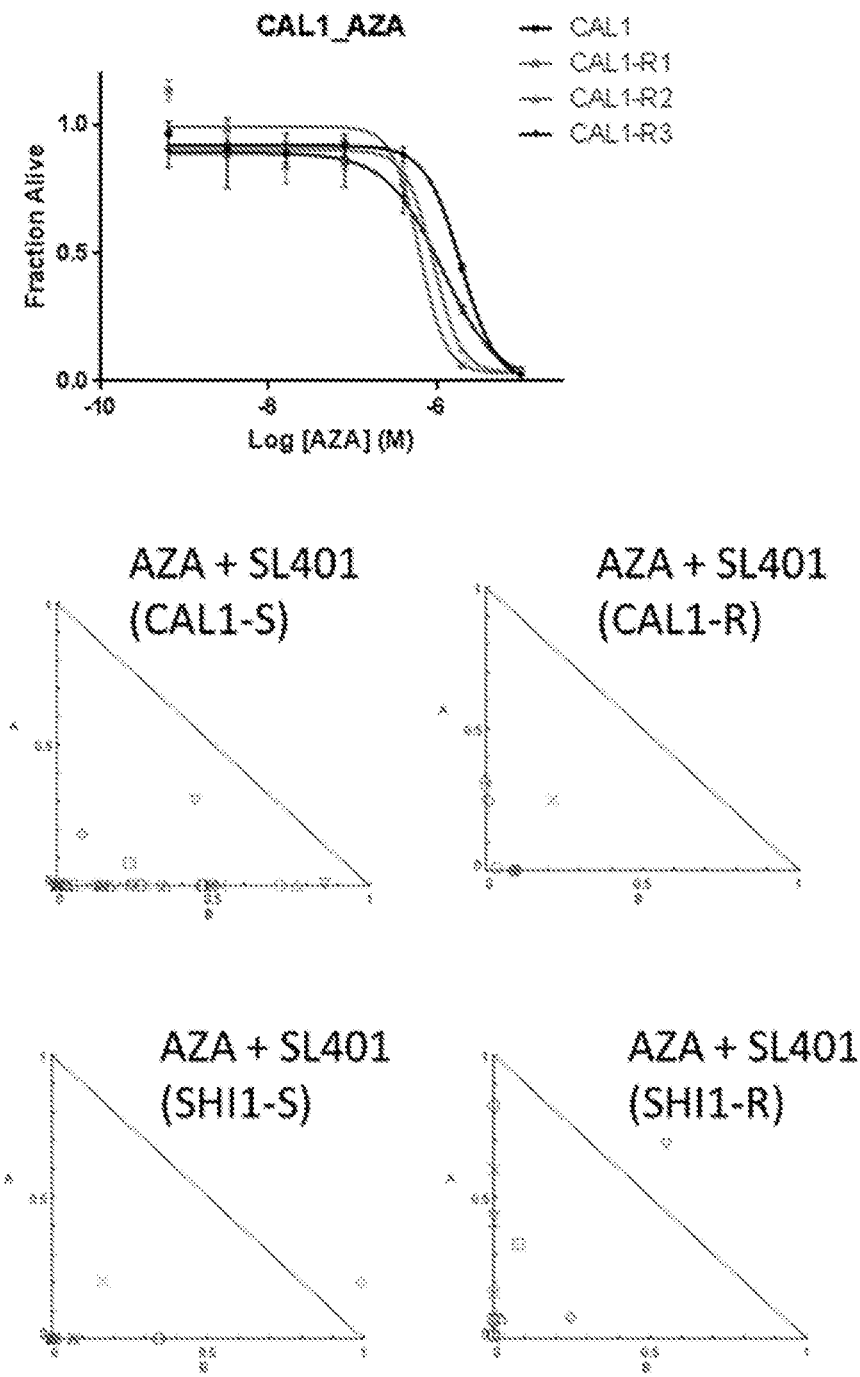
FIG. 13A shows that SL-401 resistant cells are more sensitive to cytotoxic doses of azacitidine, and SL-401 and azacitidine are synergistic both in naïve parental cells and in the setting of SL-401 resistance.

The DNA methyltransferase inhibitor azacitidine in combination with SL-401 was tested and synergistic cytotoxicity was observed, in naïve (combination index (CI)=0.45; <1 indicates synergy) and SL-401 resistant (CI=0.55) cells. Dose response curves (FIG. 13A, top panel) for azacitidine (AZA) in parental SL-401 sensitive and 3 independent SL-401 resistant subclones of CAL1 show increased sensitivity in resistant cells. This is consistent with the increased apoptotic priming and increased sensitivity to cytotoxic chemotherapy as shown above. In addition, there is a striking synergy (FIG. 13, bottom panel) between azacitidine and SL-401 in causing cytotoxicity both in parental SL-401 sensitive CAL1 and SHI1 cells (CAL1-S and SHI1-S) and in SL-401 resistant cells (CAL1-R and SHI1-R). Synergy calculated by the method of Chou-Talalay and plotted on isobolograms as above, with points below the diagonal line indicating synergy. These data show that azacitidine and SL-401 are not simply additive, but have true synergistic effect.

Figure 13B:
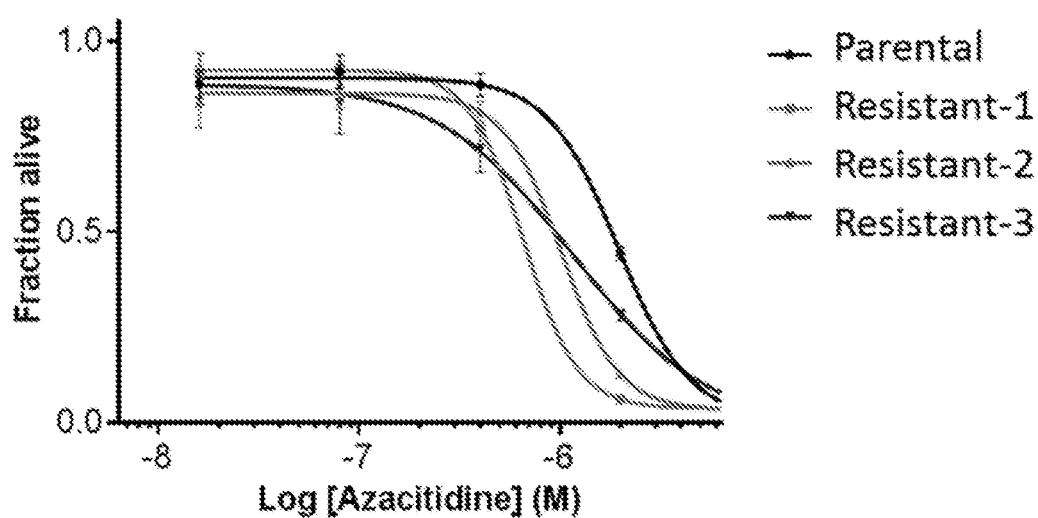
FIG. 13B shows the results of short-term (72 hour) cytotoxicity assays of parental and tagraxofusp-resistant THP1 cells treated with 5-fold decreasing concentrations of azacitidine.

Next, it was tested if azacitidine cooperated with tagraxofusp in AML and BPDCN cells. First, given that azacitidine acts as a cytotoxic chemotherapy at higher doses, experiments were performed to determine whether tagraxofusp-resistant cells were more sensitive to short-term treatment, similar to what was described above (FIGS. 6-8). All independent subclones of tagraxofusp-resistant THP1 cells were more sensitive to cytotoxic doses of azacitidine than parental cells (FIG. 13B).

Regarding long-term, "epigenetic" dosing of azacitidine, experiments were performed to determine whether the partial restoration of DPH1 mRNA observed (FIG. 14C) was sufficient to resensitize cells to tagraxofusp. Most strikingly, 4-week pulsatile treatment with non-lethal "epigenetic" doses of azacitidine (300 nM 2d on/2d off) fully reversed SL-401 resistance in 6 CAL1 and THP1 clones that were insensitive at baseline. Controls grown in vehicle or with weekly SL-401 challenge showed no reversion, indicating that azacitidine had a specific sensitizing effect. Restoration of SL-401 sensitivity was accompanied by an increase in DPH1 expression compared to resistant clones. FIG. 14A shows the viability after SL-401 treatment in parental THP1 cells and 3 independent resistant subclones (R1-3). Cells from FIG. 14A were treated with 4 weeks of azacitidine at a non-lethal dose (300 nM 2d on/2d off), then re-treated with SL-401 (FIG. 14B). FIG. 14C shows quantitative RT-PCR for DPH1 in cells from FIG. 14A and FIG. 14B. Similar findings as in panels FIG. 14A-FIG. 14C were observed in CAL1 cells and resistant subclones. These data indicated that tagraxofusp and azacitidine are synergistic in combination up-front and in the setting of tagraxofusp resistance.

Figure 15:
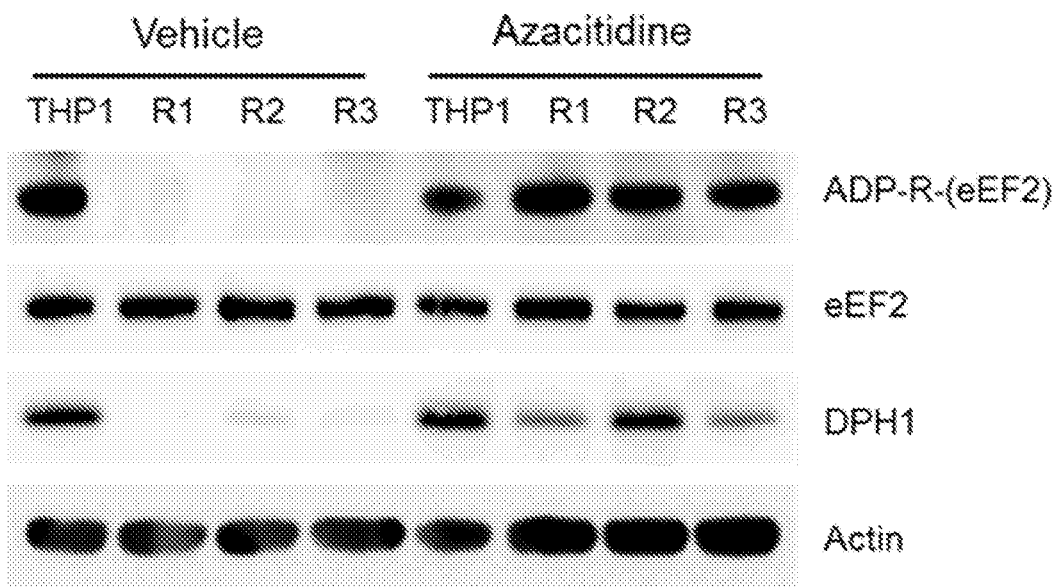
FIG. 15 shows that SL-401 resistance results in loss of ability of SL-401 to promote transfer of ADP-ribose to eEF2, and this defect is reversed by azacitidine treatment. The figure shows the results of an in vitro ADP-ribosylation assay in the presence of tagraxofusp (top row) and Western blotting for eEF2, DPH1, and actin (bottom rows) for parental THP1 and 3 independent tagraxofusp-resistant subclones (R1-3) after 2 weeks of pulsatile treatment with non-cytotoxic doses of azacitidine.

To determine the biochemical mechanism of SL-401 resistance and restoration of sensitivity upon non-cytotoxic treatment with azacitidine, an in vitro ADP-ribosylation assay was developed to perform lysates harvested from human leukemia cells. Briefly, 50 µg of cell lysates were harvested and mixed with 5 uM NAD+-Biotin (R&D Systems; 4670-500-01), in the presence or absence of 100 ng of SL-401 (or DT) in 35 uL of reaction buffer containing 20 mM Tris-HCl pH 7.4, 1 mM EDTA, and 50 mM DTT. The mixture is incubated for 15 minutes at room temperature and then the reaction is halted by boiling in SDS loading buffer. An SDS polyacrylamide gel is run and proteins are transferred to a PVDF membrane as in a Western blot. Protein levels are determined by traditional western blot. ADP-ribosylation of target proteins is detected by streptavidin-HRP (Abcam ab7403). FIG. 15 shows blots from THP1 AML cells, parental and 3 independent SL-401 resistant clones (R1-R3), before and after 2 weeks of pulsatile, non-cytotoxic treatment with azacitidine (300 nM, 2d on/2d off). Top blot is ADP-ribose, presumably on eEF2 (band is at same position as eEF2 protein detected by antibody); next, are levels of eEF2, DPH1, and beta-actin protein. Using the in vitro biochemical assay, it was found that long-term azacitidine-treated THP cells had complete restoration of tagraxofusp-mediated ADP ribosylation activity (FIG. 15). These data show that ADP-ribosylation of eEF2 is lost in SL-401 resistant cells, in association with significant decrease/loss of DPH1 protein. After azacitidine treatment, DPH1 levels are partially or fully restored, and those levels of restoration are sufficient to completely restore ADP-ribosylation of eEF2. Together, these data confirm the mechanism of resistance to SL-401, and the mechanism of azacitidine treatment to reverse SL-401 resistance.

Figure 17D:
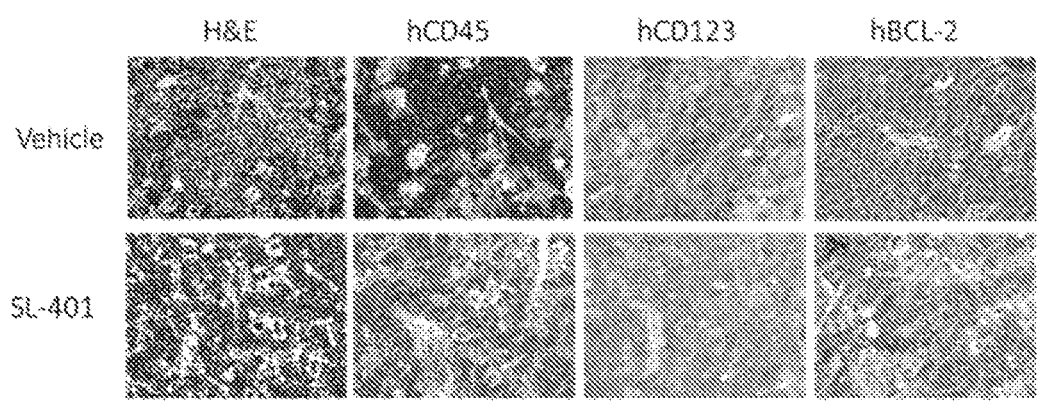
Figure 17E:
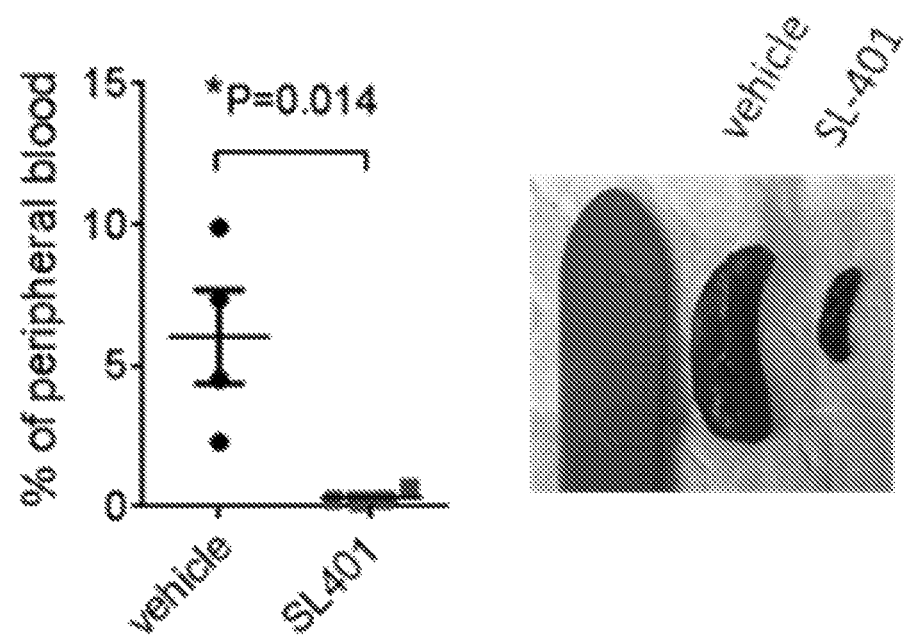

To test these predictions in primary human leukemia cells in vivo, therapeutic models were established using BPDCN patient-derived xenografts (PDXs). First, the activity of single-agent tagraxofusp was tested in three independent BPDCN PDXs. Each PDX was injected into a cohort of recipients as a secondary transplant from previously cryopreserved cells. Peripheral blood disease burden was monitored by weekly flow cytometry, and when the average CD45+CD123+ measurement reached 0.2% of peripheral blood, animals were randomized to receive vehicle or tagraxofusp, given daily for 5 days to mimic the phase 1-2 trial dosing being tested in patients. The peripheral blood leukemia burden was followed by weekly flow cytometry and observed a significant pharmacodynamic effect of tagraxofusp (FIG. 17A). In a subset of tagraxofusp-treated animals, one to two additional cycles of therapy were given at the time of overt progressive disease. To confirm disease response, a subset of vehicle or tagraxofusp-treated animals were sacrificed after 14 days from initiation of treatment and observed decreased splenic infiltration of human BPDCN cells (human CD45, CD123, BCL-2 positive) with lower peripheral blood circulating leukemia blasts and reduction in splenomegaly (FIG. 17D and FIG. 17E). Treatment with tagraxofusp was also associated with restoration of normal hematopoietic elements, such as megakaryocytes, in the spleen (FIG. 17D). Tagraxofusp treatment resulted in prolonged progression-free (48 vs 12 days, P<0.0001) and overall survival (71 vs 35 days, P=0.0003; FIG. 17B).

Figure 17F:
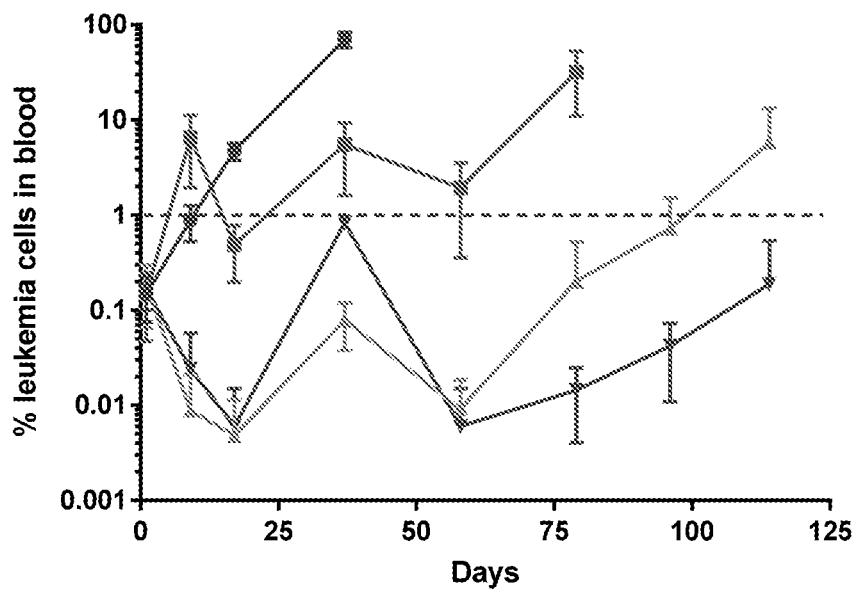
Figure 17G:
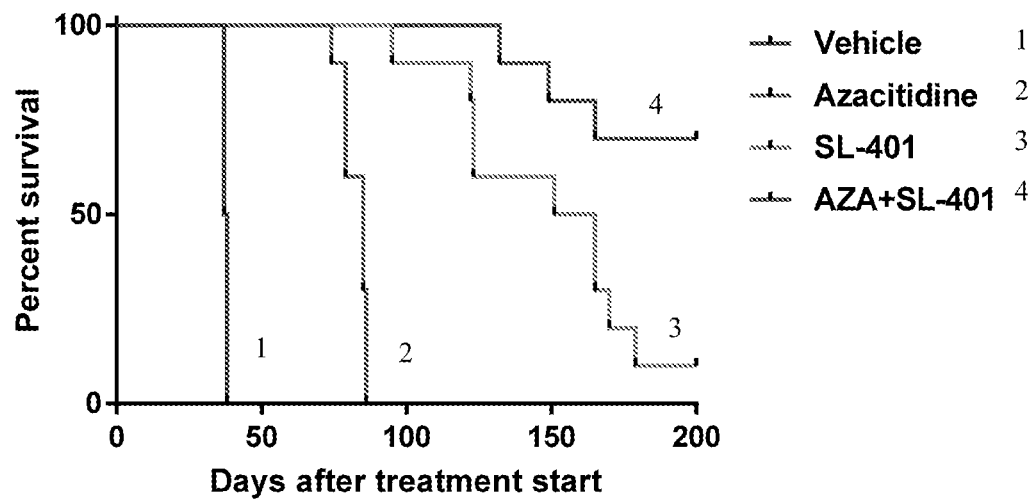
Figure 17H:
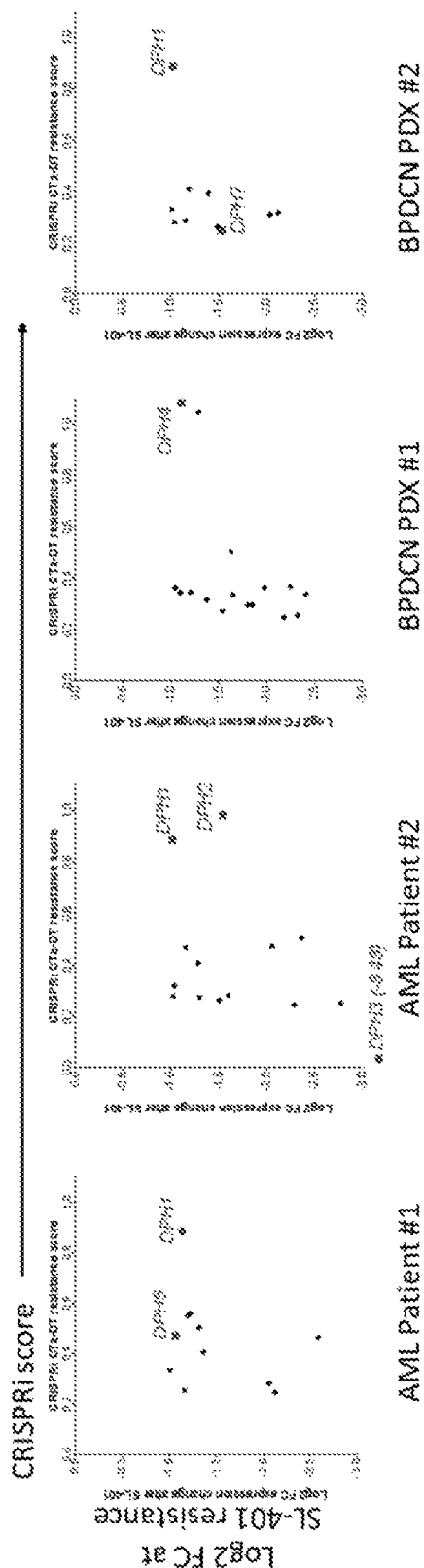
Figure 18A:
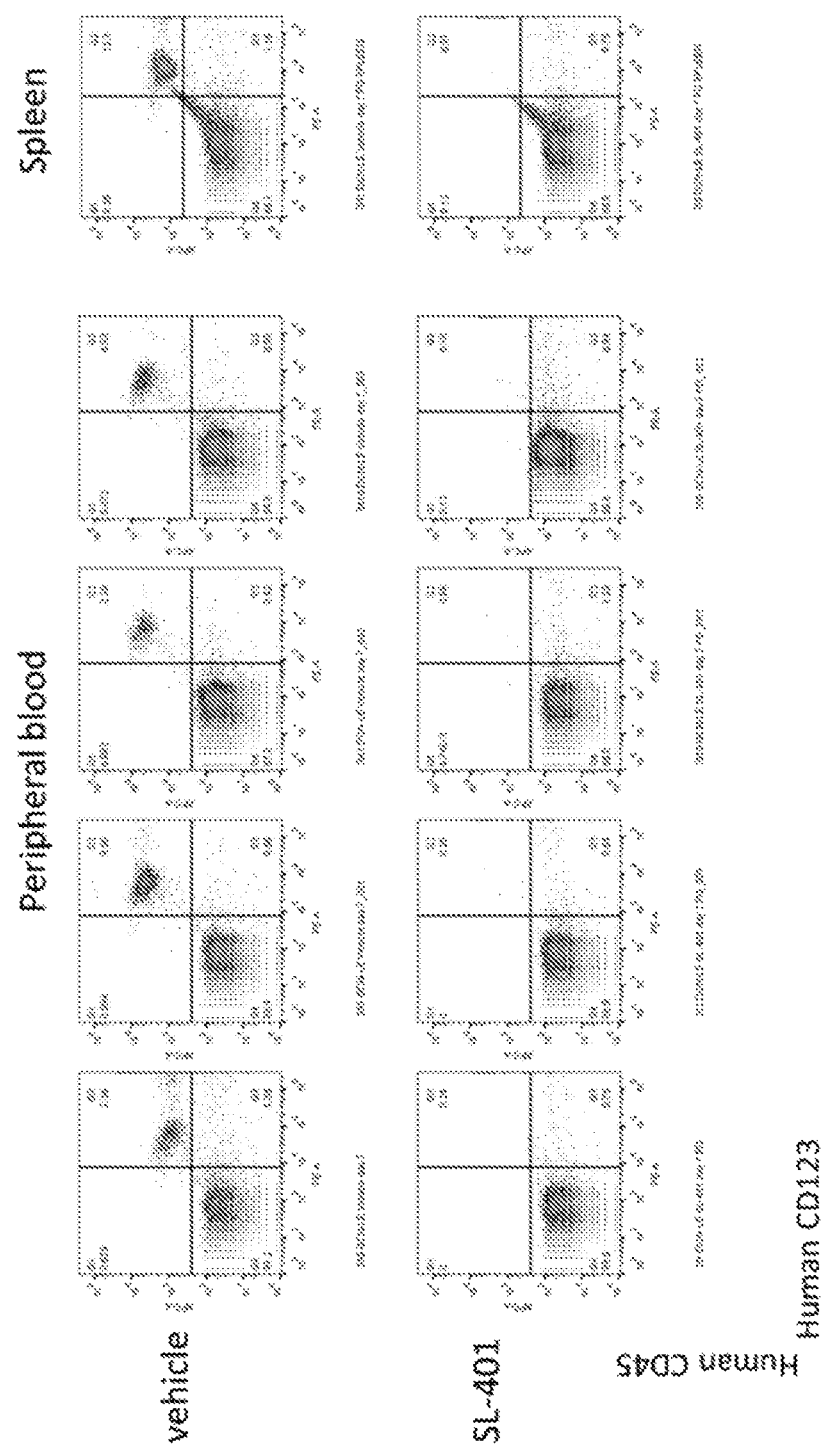
FIG. 18A shows reduction in peripheral blood and spleen human leukemia cells in mice bearing BPDCN PDXs treated with vehicle or SL-401. Peripheral blood was harvested from 8 mice on day 7 after treatment with SL-401 and flow cytometry was performed for human CD45 and human CD123 to measure leukemia cell burden (left). Spleen flow cytometery from two animals, one treated with vehicle and the other with SL-401, for human CD123/CD45 is shown (right).
Figure 18B:
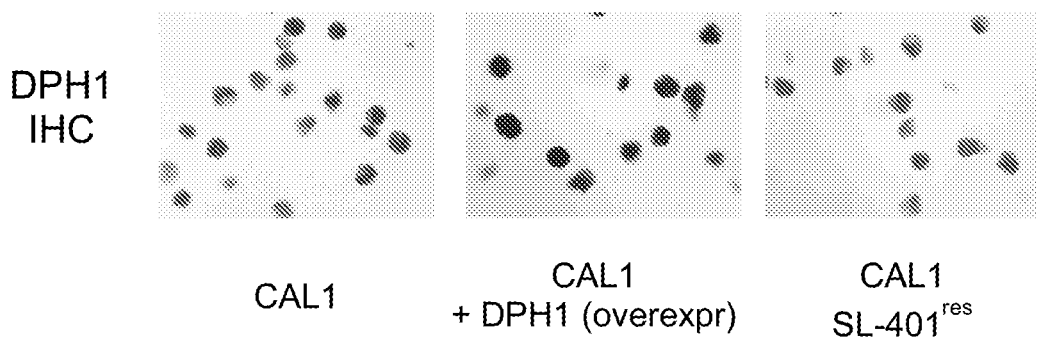
FIG. 18B shows the results of CAL1 cells stained with an antibody recognizing human DPH1 in an immunohistochemistry assay using CAL1 cells as follows: CAL1 parental cells (left), CAL1 parental cells overexpressing a DPH1 cDNA by lentiviral transduction (middle), CAL1 cells that were resistant to SL-401 (right).
Figure 18C:
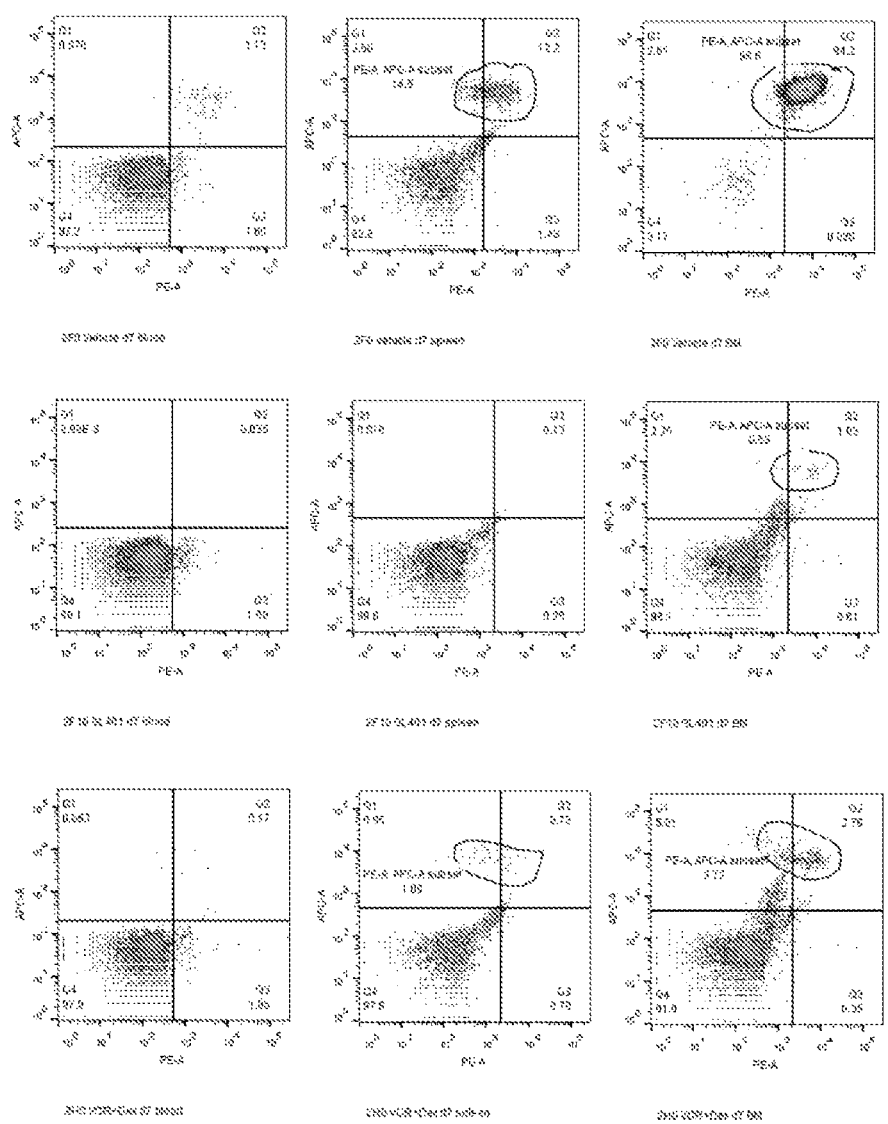
FIG. 18C shows flow cytometry for human CD123 and human CD45 to measure tumor burden from mice bearing BPDCN PDXs at 7 days after treatment with vehicle (top row), SL-401 (middle row), or chemotherapy with vincristine and dexamethasone (bottom row). Tissues analyzed were peripheral blood (left column), spleen (middle column), and bone marrow (right column).
Figure 18D:
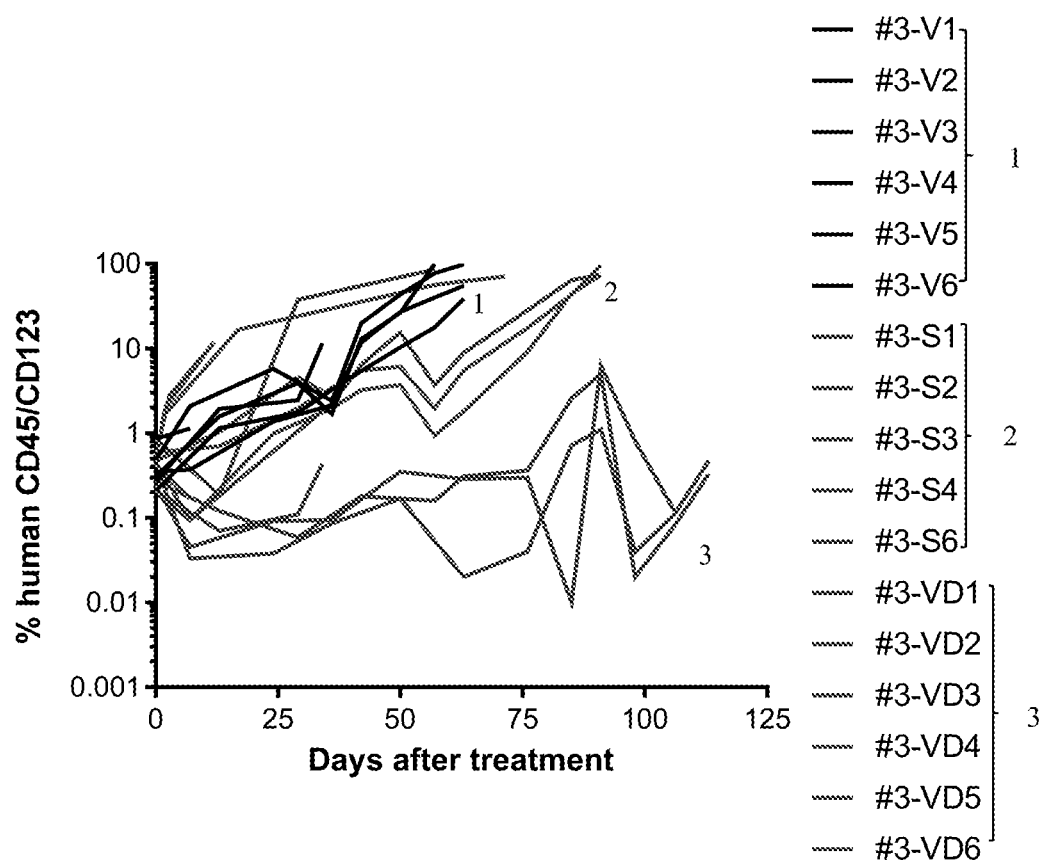
FIG. 18D shows peripheral blood flow cytometry results for human CD123 and CD45 in mice bearing BPDCN PDXs after treatment with vehicle (black), vincristine/dexamethasone (purple), or SL-401 (red) showing that in most animals, SL-401 resulted in a longer sustained reduction in human BPDCN leukemia burden.
Figure 18E:
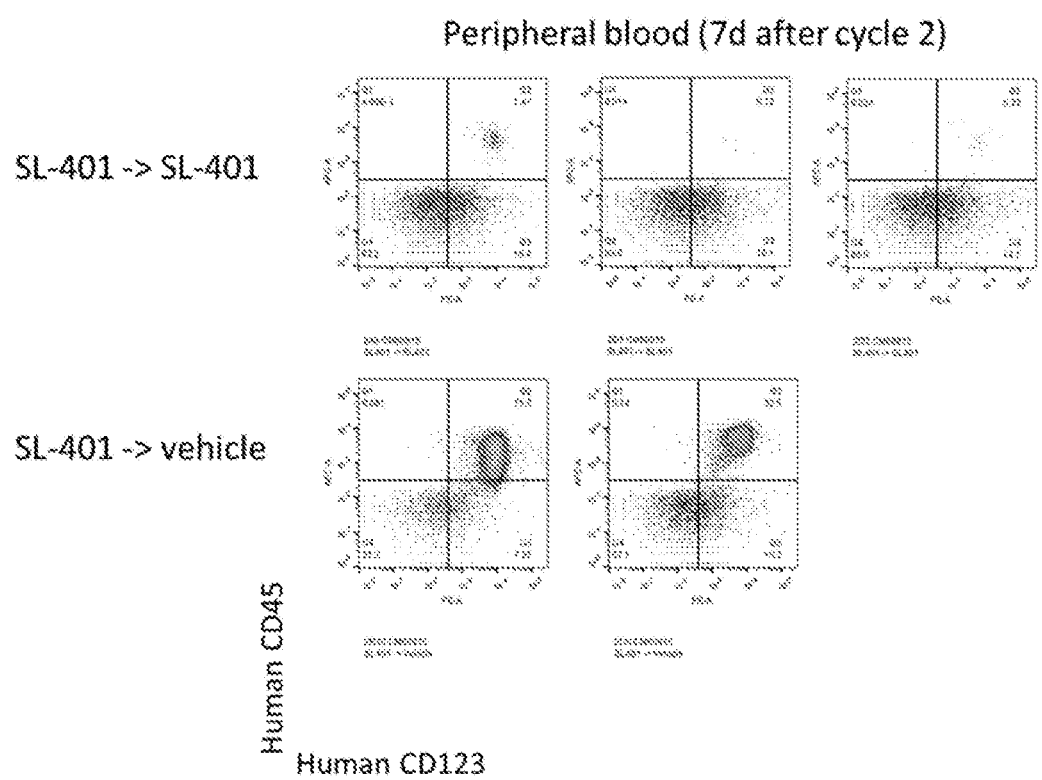
FIG. 18E demonstrates that a second cycle of SL-401 is effective in mice bearing BPDCN PDXs. Flow cytometry is shown for human CD123 and human CD45 in 5 animals that received one cycle of SL-401. At the time of progress (re-emergence of peripheral blood leukemia cell burden of average >2%, three mice received a second cycle of SL-401 (top row) whereas two mice received vehicle only (bottom row). Flow is shown from peripheral blood 7 days after receiving the second cycle of SL-401.

Finally, experiments were performed to determine whether the changes observed after tagraxofusp exposure in cell lines were observed in primary samples. Like in patients treated with tagraxofusp and in resistant cell lines, there was no decrease in CD123 expression on the surface of PDX blasts at the time of progression after tagraxofusp (FIG. 17C). RNA-sequencing was also performed on CD123+ sorted cells from two PDXs and two AML patients after treatment with tagraxofusp. The results were analyzed in the context of the CTx-DTA CRISPRi-resistance screen score as in FIG. 16C, to highlight genes most likely to influence tagraxofusp sensitivity. Interestingly, there was modest downregulation of DPH1 (approximately 2-fold) in three of four samples, but also downregulation of other diphthamide synthesis pathway genes (FIG. 17H). It is unknown whether these (or other downregulated genes that overlapped with the CRISPRi screen) are direct mediators of tagraxofusp-resistance in vivo, but experiments were performed to determine whether tagraxofusp and azacitidine, like in cell lines, were an effective combination in human leukemias.

Forty recipient mice were injected with 1 million PDX cells each and followed for engraftment as above. When the average peripheral blood leukemia burden was 0.2%, the animals were randomized to one of four treatment groups: vehicle, azacitidine alone, tagraxofusp alone, or azacitidine/tagraxofusp in combination, for two cycles of each. Both azacitidine and tagraxofusp prolonged the time to progression of peripheral blood leukemia burden, but the combination was more effective (FIG. 17F). This correlated with a prolongation of overall survival after treatment with tagraxofusp plus azacitidine that was greater than either single agent alone (FIG. 17G). At 200 days, the remaining one tagraxofusp-treated mouse and the six tagraxofusp plus azacitidine-treated mice were sacrificed and CD45+CD123+ human leukemia cell burden in peripheral blood, spleen, and bone marrow was measured. Whereas the one remaining tagraxofusp-treated animal had detectable leukemia cells in spleen and bone marrow, only one of five combination-treated mice had any measurable residual disease. Accordingly, it was concluded that the combination of tagraxofusp and azacitidine is effective in vivo.

In this study, the mechanisms of response and resistance to tagraxofusp, an interleukin 3-diphtheria toxin fusion protein that targets DT to cells expressing the IL3 receptor alpha chain, or CD123 was investigated. These results are important in optimizing use of tagraxofusp in AML, MDS, and other hematologic malignancies that express CD123. No evidence of loss of CD123 as a mechanism of resistance in cell lines, patient-derived xenografts, or in leukemias from patients treated with tagraxofusp was found. Rather, resistance was associated with loss of activity in the diphthamide synthesis pathway and resistance to DT, at least in some cases via DNA methylation-mediated downregulation of DPHL. Tagraxofusp-resistant cells had increased apoptotic priming and were hypersensitive to cytotoxic chemotherapy. It was also found that treatment with the DNA hypomethylating agent azacitidine restored DPH1 expression and reversed tagraxofusp resistance. Tagraxofusp and azacitidine decreased leukemia burden and prolonged survival in vivo, compared to either agent alone. In summary, DPH1 is a biomarker of SL-401 activity and acquired resistance, and resistance is reversible by azacitidine. Based on these data, a multicenter phase 1 trial of the combination of SL-401 and azacitidine in patients with AML or MDS (NCT03113643) have initiated with correlative laboratory studies.

Other bacterial toxin conjugates are in various stages of development for cancer therapy, including moxetumomab pasudotox, an anti-CD22-*pseudomonas* exotoxin (PT) conjugate recently approved for treatment of relapsed/refractory hairy cell leukemia and in trials for other cancer types that express the B cell antigen CD22. Both DT and PT catalyze ADP-ribosylation of eEF2 to inhibit protein synthesis, and deletion or loss of diphthamide synthesis genes is known to promote resistance to both toxins. Accordingly, it is believed that resistance mechanisms and biomarkers for response may be shared across this class of toxin immunoconjugates. However, while in vitro resistance to moxetumomab pasudotox in cell lines was associated with downregulation of diphthamide synthesis genes, this did not seem to be the mechanism of resistance in patients with B-cell acute lymphoblastic leukemia (B-ALL) or in PDX models of B-ALL. In that study, resistant cells underwent a developmental state change associated with karyotypic abnormalities and loss of surface CD22 expression. Given that it was found that CD123 loss was associated with lineage-restricted growth disadvantage in genome-wide pan-cancer screens, it is believed that myeloid lineage-related malignancies such as AML, MDS, and BPDCN are forced to evolve alternative resistance mechanisms to tagraxofusp such as in the diphthamide synthesis pathway.

Maintenance of CD123 expression during and after treatment with tagraxofusp or other CD123-targeting agents and evolution of non-CD123-associated mechanism of resistance can be particularly important in the current pre-clinical and clinical development surrounding this target. In addition to tagraxofusp, there are anti-CD123 antibody-drug conjugates, CD123-CD3 bispecific antibodies, and CD123-targeted chimeric antigen receptor T (CAR-T) cells in development for treatment of AML, MDS, BPDCN, and other hematologic malignancies. If resistance to any given agent is more likely to be related to the payload or immune activity, rather than loss of the CD123 target, then there can not be significant cross-resistance to different classes of agents. This should be considered when designing entry criteria for clinical trials, specifically that prior therapy with another CD123-targeted agent should not necessarily exclude eligibility for fear of target loss. However, more subtle resistance mechanisms in the target itself, such as point mutations or alternative splicing, are possible and thus, one component of optimal therapy selection can include testing for specific binding of the CD123-targeted agent to the epitope of interest, rather than relying on a generic "expression" analysis that can miss some changes that abolish target engagement.

Thus, it is described herein that tagraxofusp resistance is associated with increased apoptotic priming and sensitivity to several conventional chemotherapy agents with distinct mechanisms of action. Since resistant cells had lost diphthamide genes, this can be consistent with prior reports that engineered knock-out of any one of DPH1-4 resulted in hypersensitivity to cell death induced by tumor necrosis factor-alpha. The normal function of diphthamide-eEF2 is thought to be in regulating protein translation, specifically to prevent "ribosomal slippage" and −1 frameshifting. In one study, loss of Dph3 resulted in decreased expression of the anti-apoptotic protein XIAP by impairing translation fidelity, which can be one explanation for increased apoptotic priming. On the other hand, DPH1 is also described as a tumor suppressor gene frequently co-deleted with TP53 on chromosome 17 in several human cancers, and haploinsufficiency of Dph1 promoted spontaneous tumor development in mice, alone or in concert with Tp53 deletion. Accordingly, the consequences of acquired loss of the diphthamide pathway due to tagraxofusp resistance can have complex consequences on tumor cell biology but indicates that the resulting global changes in gene expression and or protein abundance may create novel targets for therapy. Given that these changes can be tumor type-, lineage restricted-, and/or patient-specific, the consequences of resistance can be best assessed using combined genomic, proteomic, and functional assays in each situation.

Figure 19:
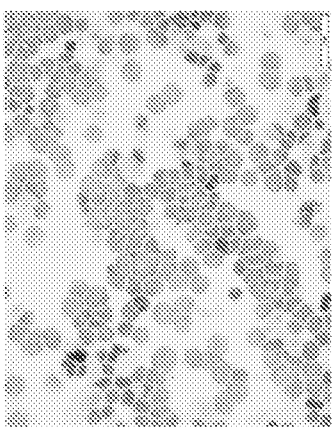
FIG. 19 shows the results of an immunohistochemical assay for SL-401-dependent ADP ribosylation activity in leukemia cells. THP1 human AML cells are shown that are parental SL-401 sensitive (top row) and SL-401 resistant (bottom row). The in situ ADP-riboslyation assay was performed without (left) and with (SL-401) present, showing an SL-401-dependent ADP ribosylation activity that is diminished in the SL-401 resistant cells.
Figure 19:
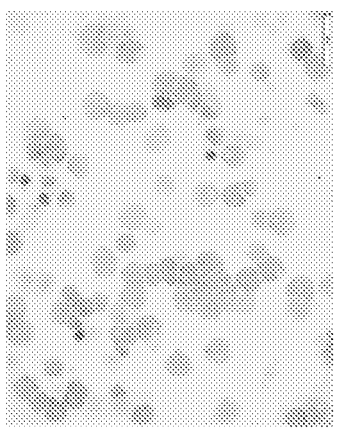
Figure 19:
Figure 19:
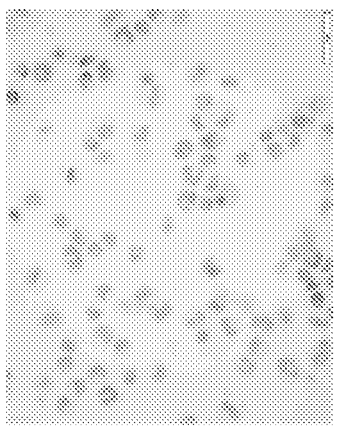

Example 5: ADP Ribosylation Assays were Developed to Measure the Functional Copy Number, Amount, and/or Activity of at Least One Member of the Diphthamide Synthesis Pathway It was found herein that sensitivity to SL-401, a DT-interleukin 3 fusion, and to full-length DT itself, was determined by the level of gene expression and protein expression of several members of the diphthamide synthesis pathway (DPH1 through DPH7). Rather than having to measure each individual DPH gene or protein level, it was unexpectedly determined that diphthamide synthesis pathway output (e.g., the ability to ADP ribosylate cellular proteins) could be used as a biomarker of ADP ribosylating toxin sensitivity or resistance determination as well (e.g., was not subject to compensatory mechanisms). For example, it was unclear whether an observed downregulation (e.g., 2-fold) of one or more DPH pathway genes would be sufficient to mediate loss of ADP ribosylation ability sufficient to render a cell resistant to ADP ribosylating toxins like full-length DT, partial DT, SL-401, and the like as DPH pathway member research used knockout mutants of DPH pathway members. This assay measures the functional activity of the entire diphthamide synthesis pathway by assessing the presence of a biomarker that assesses the output of the entire pathway. An in situ histochemical assay that marks cells with a biotinylated ADP-ribose only in the presence of a diphtheria toxin fusion protein was designed and optimized (FIG. 19). In one embodiment, this assay may be performed as follows. A wax circle was drawn around the sample with a pap pen and the tissue was covered in PBS after the circle was drawn. The slides were placed in 3% paraformaldehyde, pH 7.0 for 15 min at room temperature (RT) and then rinsed five times in PBS. The slides were next incubated in cold methanol at −20° C. for 1 min and rinsed five times in PBS. 3% Hydrogen Peroxide (dilute 30% $H_2O_2$ Stock 1:10) was prepared and added to cover the tissue on the slides. The slides were incubated for 10 minutes, rinsed with PBS-T briefly, and then washed with PBS-T three times. Each wash was for 5 minutes. Novolink™ Protein Block (RE7102) (cover) was applied to the slides for 30 min at RT. The slides were rinsed with PBS-T briefly, and then washed with PBS-T three times. Each wash was for 5 minutes. Primary ADP immunostaining reagents were prepared according to the recipe shown in Table 2 and Table 3.

TABLE 2

In the absence of SL-401 and presence of 50 µM Biotin NAD+

| Component | Final Concentration | 1X | 3X |
|---|---|---|---|
| 250 µM Biotinylated NAD+ (Trevigen) | 50 µM | 20 µL | 60 µL |
| 5X Ribosylation Buffer (100 mM Tris-HCL pH 7.4, 5 mM EDTA] | 1X | 20 µL | 60 µL |
| 1M DTT | 50 mM | 5 µL | 15 µL |
| Nuclease-Free Water | | 65 µL | 195 µL |

TABLE 3

In the presence of SL-401 (19.04 ng/µL) and 50 µM Biotin NAD+

| Component | Final Concentration | 1X | 3X |
|---|---|---|---|
| [100 ng/µL] SL-401 | 19.04 ng/µL | 19.04 µL | 57.12 µL |
| 250 µM Biotinylated NAD+ | 50 µM | 20 µL | 60 µL |
| 5X Ribosylation Buffer (100 mM Tris-HCL pH 7.4, 5 mM EDTA] | 1X | 20 µL | 60 µL |
| 1M DTT | 50 mM | 5 µL | 15 µL |
| Nuclease-Free Water | | 45.96 µL | 137.88 µL |

50 to 100 µL of above primary ADP immunostaining reagents were added to cover the slides, which were then incubated at 37° C. in a humid box for 1 hour. After the incubation, the slides were rinsed with PBS-T briefly, and then washed with PBS-T three times. Each wash was for 5 minutes. Streptavidin-poly HRP (Thermo, 21140) was diluted in PBS with 1% BSA diluent by adding 6 µL of strep poly-HIRP to 1494 µL of diluent (1:250). 1% BSA diluent was made by adding 10 mg BSA to 1 mL PBS. About 100 µL diluted streptavidin-poly HRP was added to cells for 30 min at RT in a humid box. The slides were washed with PBS-T (R/5/5/5 min). DAB Chromogen was diluted in DAB Diluent (Vector Labs, #SK-4105) by Adding 1 drop of DAB Chromogen to 1 mL of DAB Diluent. Slides were developed with about 100 L DAB for a period of time. The time was determined by observing the slides under microscope. The slides were rinsed with PBS-T briefly, and then washed with PBS-T three times. Each wash was for 5 minutes. The slides were counterstained with Hematoxylin (RE7164) (cover) for 3 minutes. The stained slides were washed in tap water, and then observed under microscope. To dehydrate and mount the slides, the slides were rinsed with cold tap water for three times, then with 100% EtOH for four times, and with Xylene for four times before allowing to dry for a minimum of 15 minutes to 1 hour. Xylene rinsing was performed in the fume hood with lightly shaking and drip drying. One drop of Cytoseal™ Mounting Media (Thermo, 8312-4) was added to the slide, and a singular glass coverslip was Affixed. The level of ADP staining was observed under a microscope.

Positivity in this assay also correlates with the sensitivity of the cell to death induced by the same bacterial toxin/toxin conjugate. This assay can be used as a predictive biomarker or a companion diagnostic test to determine if a given patient/tumor/cell population responds to a toxin conjugate therapy. Also, by coupling the assay with microscopy or flow cytometry, with or without additional marker co-staining, the test can be used to evaluate single cells and/or subpopulations of cells within a heterogeneous sample to predict toxin sensitivity in relevant tumor cells or other cell populations of interest.

For example, in another embodiment, a flow ADP ribosylation assay may be used to measure the functional activity of the entire diphthamide synthesis pathway (FIG. 20). As a representative demonstration, 300,000 cells were plated per FACS tube and washed with 2% FACS (PBS with 2% FBS) buffer for 5 minutes. The cells were stained with antibodies (e.g., CD45-APC, CD123-PE) at concentration of 1:100, incubated for 30 min at 4° C., and then washed with FACS buffer 5 minutes. The cells were fixed with 3% paraformaldehyde (PFA), incubated for 20 min at RT, and washed with PBS for 5 minutes. The cells were permeabilized with Saponin (1:10 in H2O, BD Biosciences-"Perm/Wash" solution) for 20 min at 4° C., washed with PBS for 5 minutes, and applied with endogenous Streptavidin block (BD Biosciences) for 20 min at RT. The cells were then washed with PBS for 5 minutes and applied with endogenous Biotin block (BD Biosciences) for 20 min at RT. The cells were then washed with PBS for 5 minutes and applied with protein block for 30 min at RT. The cells were washed twice with FACS buffer. Each wash was for 5 minutes. SL-401/biotin solution was added to the samples and the samples was incubated for 30 min at RT. The SL401/Biotin solution contains 20 ng/ul SL401, 1 uM Biotin NAD+ (Trivigen), 1x Buffer (20 mM Tris-HCL, PH=7.4; 1 mM EDTA) and 50 mM DTT at final concentration. DdH2O was in place of SL401 in conditions without SL401. The cells were washed twice with FACS buffer, each time for 5 minutes, before staining with Streptavidin BV510 at 1:100 dilution for 30 min at 4° C. The cells were washed 5 minutes in FACS buffer, resuspended in 300 µl FACS buffer and level of the ADP was detected with the flow assay.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. A method of treating a subject afflicted with a condition that is resistant to an IL3-conjugated diphtheria (IL3-DT) toxin comprising administering to the subject a therapeutically effective amount of the IL3-DT toxin in combination with a therapeutically effective amount of an agent that increases the copy number, amount, and/or activity of DPH1, thereby treating the subject afflicted with the condition that is resistant to the IL3-DT toxin.

2. The method of claim 1, wherein the subject is an animal model of cancer.

3. The method of claim 2, wherein the subject is a mouse model of cancer.

4. The method of claim 1, wherein the subject is a mammal.

5. The method of claim 4, wherein the mammal is a mouse or a human.

6. The method of claim 1, wherein the copy number, amount, and/or activity of DPH1 is determined by detecting the ADP ribosylation by the IL3-DT toxin.

7. The method of claim 6, wherein the ADP ribosylation detection is by Western blot, immunohistochemistry, microscopy, and/or flow cytometry.

8. The method of claim 6, wherein the ADP ribosylation detection is by detecting ADP ribosylation of eEF2.

9. The method of claim 6, wherein the ADP ribosylation detection is by detecting using streptavidin-conjugated enzyme, dye, or fluorescent marker.

10. The method of claim 1, wherein the IL3-DT toxin ribosylates eEF2.

11. The method of claim 1, wherein the IL3-DT toxin uses NAD+ as the source of ADP ribose.

12. The method of claim 11, wherein the NAD+ is conjugated with a label, optionally wherein the label is a biotin.

13. The method of claim 1, wherein the IL3-DT toxin is conjugated to an antibody or a cytokine.

14. The method of claim 1, wherein the IL3-DT toxin comprises a full-length IL3 polypeptide.

15. The method of claim 1, wherein the IL3-DT toxin comprises a full-length DT.

16. The method of claim 1, wherein the IL3-DT toxin comprises a truncated DT.

17. The method of claim 1, wherein the IL3-DT toxin is SL-4011.

18. The method of claim 1, wherein the IL3-DT toxin inhibits the function of eEF2.

19. The method of claim 1, wherein the agent comprises a hypomethylating agent (HMA).

20. The method of claim 19, wherein the HMA dose is a sub-cytotoxic dose.

21. The method of claim 19, wherein the HMA is selected from the group consisting of azacitidine, decitabine, guadecitabine (SGI-110), zebularine, and MG98.

22. The method of claim 1, wherein the agent comprises a DPH1 polypeptide molecule, or biologically active fragment thereof.

23. The method of claim 22, wherein the DPH1 polypeptide molecule is at least 80% identical over its full length to a polypeptide selected from SEQ ID Nos: 5-8, 10, 12, 14, 16, 18, 20, 22, 24, 26, 28, 30, 40-46, 48, 51, 52, 56, 57, 59, 61, 65, 66, 68, 71, 72, 76-78, 107-114, and 124-128, or a biologically active fragment thereof.

24. The method of claim 1, wherein the agent comprises a nucleic acid encoding a DPH1 polypeptide molecule, or biologically active fragment thereof.

25. The method of claim 24, wherein the nucleic acid encoding the DPH1 polypeptide molecule is at least 80% identical over its full length to a nucleic acid selected from SEQ ID Nos: 1-4, 9, 11, 13, 15, 17, 19, 21, 23, 25, 27, 29, 31-39, 47, 49, 50, 53-55, 58, 60, 62-64, 67, 69, 70, 73-75, 79-106, and 115-123, or a portion thereof that encodes the biologically active fragment.

26. The method of claim 1, wherein the condition is a cancer and the agent reduces the number of proliferating cells in the cancer and/or reduces the volume or size of a cancerous tumor.

27. The method of claim 1, wherein the agent is administered before the IL3-DT toxin.

28. The method of claim 1, wherein the agent is administered after the IL3-DT toxin.

29. The method of claim 1, wherein the agent is administered concurrently with the IL3-DT toxin.

30. The method of claim 1, wherein the condition is a cancer.

31. The method of claim 30, wherein the cancer is a CD123+ cancer.

32. The method of claim 30, wherein the cancer is selected from the group consisting of acute myeloid leukemia (AML), blastic plasmacytoid dendritic cell neoplasm (BPDCN), myelodysplastic syndromes (MDS), Myeloproliferative neoplasms (MPN), acute lymphoblastic leukemia (ALL), chronic myeloid leukemia (CML), chronic myelomonocytic leukemia (CMML), hairy cell leukemia, non-Hodgkin lymphoma (NHL), and Hodgkin lymphoma.

33. The method of claim 1, further comprising administering to the subject anti-cancer therapy, wherein the anti-cancer therapy is selected from the group consisting of targeted therapy, chemotherapy, radiation therapy, and hormonal therapy.

34. The method of claim 33, wherein the targeted therapy is selected from the group consisting of immunotherapy, cell-based immunotherapy, a cancer vaccine, a virus, and an immune checkpoint inhibitor.

35. The method of claim 34, wherein the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR.

\* \* \* \* \*

SEQUENCE LISTING

```
<160> NUMBER OF SEQ ID NOS: 134

<210> SEQ ID NO 1
<211> LENGTH: 1332
<212> TYPE: DNA
<213> ORGANISM: Homo sapiens

<400> SEQUENCE: 1
atgcgcaggc aggtgatggc ggcgctggtc gtatccgggg cagcggagca gggcggccga      60
gacggccctg gcagaggtcg ggcccctcgg ggccgcgtgg ccaatcagat ccccctgag     120 atcctgaaga accctcagct gcaggcagca atccgggtcc tgccttccaa ctacaacttt     180
gagatcccca agaccatctg gaggatccaa caagcccagg ccaagaaggt ggccttgcaa     240
atgccggaag gcctcctcct ctttgcctgt accattgtgg atatcttgga aaggttcacg     300
gaggccgaag tgatggtgat gggtgacgtg acctacgggg cttgctgtgt ggatgacttc     360
acagcgaggg ccctgggagc tgacttcttg gtgcactacg gccacagttg cctgattccc     420
```

-continued

| | |
|---|---|
| atggacacct cggcccaaga cttccgggtg ctgtacgtct ttgtggacat ccggatagac | 480 |
| actacacacc tcctggactc tctccgcctc acctttcccc cagccactgc ccttgccctg | 540 |
| gtcagcacca ttcagtttgt gtcgaccttg caggcagccg cccaggagct gaaagccgag | 600 |
| tatcgtgtga gtgtcccaca gtgcaagccc ctgtcccctg agagatcct gggctgcaca | 660 |
| tcccccgac tgtccaaaga ggtggaggcc gttgtgtatc ttggagatgg ccgcttccat | 720 |
| ctggagtctg tcatgattgc caaccccaat gtccccgctt accggtatga cccatatagc | 780 |
| aaagtcctat ccagagaaca ctatgaccac cagcgcatgc aggctgctcg ccaagaagcc | 840 |
| atagccactg cccgctcagc taagtcctgg ggccttattc tgggcacttt gggccgccag | 900 |
| ggcagtccta agatcctgga gcacctggaa tctcgactcc gagccttggg cctttccttt | 960 |
| gtgaggctgc tgctctctga gatcttcccc agcaagctta gcctacttcc tgaggtggat | 1020 |
| gtgtgggtgc aggtggcatg tccacgtctc tccattgact ggggcacagc cttccccaag | 1080 |
| ccgctgctga cacccatga ggcggccgtg gctctgaggg acatttcctg gcagcagccc | 1140 |
| tacccgatgg acttctacgc tggcagctcc ttggggccct ggacggtgaa ccacggccag | 1200 |
| gaccgccgtc cccacgcccc gggccggccc gcgcggggga aggtgcagga ggggtccgcg | 1260 |
| cgtccccctt cggccgtggc ttgcgaggac tgcagctgca gggacgagaa ggtggcgccg | 1320 |
| ctggctcctt ga | 1332 |

<210> SEQ ID NO 2
<211> LENGTH: 1269
<212> TYPE: DNA
<213> ORGANISM: Homo sapiens

<400> SEQUENCE: 2

| | |
|---|---|
| atgcgcaggc aggtgatggc ggcgctggtc gtatccgggg cagcggagca gggcggccga | 60 |
| gacggccctg gcagaggtcg ggcccctcgg ggccgcgtgg ccaatcagat ccccccctgag | 120 |
| atcctgaaga accctcagct gcaggcagca atccgggtcc tgccttccaa ctacaacttt | 180 |
| gagatcccca gaccatctg gaggatccaa caagcccagg ccaagaaggt ggccttgcaa | 240 |
| atgccggaag gcctcctcct ctttgcctgt accattgtgg atatcttgga aaggttcacg | 300 |
| gaggccgaag tgatggtgat gggtgacgtg acctacgggg cttgctgtgt ggatgacttc | 360 |
| acagcgaggg ccctggagc tgacttcttg gtgcactacg ccacagttg cctgattccc | 420 |
| atggacacct cggcccaaga cttccgggtg ctgtacgtct ttgtggacat ccggatagac | 480 |
| actacacacc tcctggactc tctccgcctc acctttcccc cagccactgc ccttgccctg | 540 |
| gtcagcacca ttcagtttgt gtcgaccttg caggcagccg cccaggagct gaaagccgag | 600 |
| tatcgtgtga gtgtcccaca gtgcaagccc ctgtcccctg agagatcct gggctgcaca | 660 |
| tcccccgac tgtccaaaga ggtggaggcc gttgtgtatc ttggagatgg ccgcttccat | 720 |
| ctggagtctg tcatgattgc caaccccaat gtccccgctt accggtatga cccatatagc | 780 |
| aaagtcctat ccagagaaca ctatgaccac cagcgcatgc aggctgctcg ccaagaagcc | 840 |
| atagccactg cccgctcaca cctggaatct cgactccgag ccttgggcct ttcctttgtg | 900 |
| aggctgctgc tctctgagat cttccccagc aagcttagcc tacttcctga ggtggatgtg | 960 |
| tgggtgcagg tggcatgtcc acgtctctcc attgactggg gcacagcctt ccccaagccg | 1020 |
| ctgctgacac cctatgaggc ggccgtggct ctgagggaca tttcctggca gcagccctac | 1080 |
| ccgatggact tctacgctgg cagctccttg gggccctgga cggtgaacca cggccaggac | 1140 |

```
cgccgtcccc acgcccgggg ccggcccgcg cggggggaagg tgcaggaggg gtccgcgcgt    1200 ccccccttcgg ccgtggcttg cgaggactgc agctgcaggg acgagaaggt ggcgccgctg   1260
gctccttga                                                             1269

<210> SEQ ID NO 3
<211> LENGTH: 1236
<212> TYPE: DNA
<213> ORGANISM: Homo sapiens

<400> SEQUENCE: 3
atgcgcaggc aggtgatggc ggcgctggtc gtatccgggg cagcggagca gggcggccga      60
gacggccctg gcagaggtcg ggcccctcgg ggccgcgtgg ccaatcagat ccccccctgag   120 atcctgaaga accctcagct gcaggcagca atccgggtcc tgccttccaa ctacaacttt    180
gagatcccca agaccatctg gaggatccaa caagcccagg ccaagaaggt ggccttgcaa    240
atgccggaag gcctcctcct ctttgcctgt accattgtgg atatcttgga aaggttcacg    300
gaggccgaag tgatggtgat gggtgacgtg acctacgggg cttgctgtgt ggatgacttc    360
acagcgaggg ccctgggagc tgacttcttg gtgcactacg ccacagttg cctgattccc    420 atggacacct cggcccaaga cttccgggtg ctgtacgtct tgtggacat ccggatagac    480 actacacacc tcctggactc tctccgcctc accttttcccc cagccactgc ccttgccctg   540
gcagccgccc aggagctgaa agccgagtat cgtgtgagtg tcccacagtg caagcccctg    600
tcccctggag agatcctggg ctgcacatcc cccgactgt ccaaagaggt ggaggccgtt    660
gtgtatcttg agatggccg cttccatctg gagtctgtca tgattgccaa ccccaatgtc    720
cccgcttacc ggtatgaccc atatagcaaa gtcctatcca gagaacacta tgaccaccag    780
cgcatgcagg ctgctcgcca agaagccata gccactgccc gctcacacct ggaatctcga    840
ctccgagcct tgggcctttc ctttgtgagg ctgctgctct ctgagatctt cccagcaag    900 cttagcctac ttcctgaggt ggatgtgtgg gtgcaggtgg catgtccacg tctctccatt    960
gactggggca cagccttccc caagccgctg ctgacaccct atgaggcggc cgtggctctg   1020
agggacattt cctggcagca gccctacccg atggacttct acgctggcag ctccttgggg    1080
ccctggacgg tgaaccacgg ccaggaccgc cgtccccacg ccccgggccg gccgcgcgg    1140 gggaaggtgc aggaggggtc cgcgcgtccc ccttcggccg tggcttgcga ggactgcagc    1200
tgcagggacg agaaggtggc gccgctggct ccttga                               1236

<210> SEQ ID NO 4
<211> LENGTH: 912
<212> TYPE: DNA
<213> ORGANISM: Homo sapiens

<400> SEQUENCE: 4
atggacacct cggcccaaga cttccgggtg ctgtacgtct tgtggacat ccggatagac       60 actacacacc tcctggactc tctccgcctc accttttcccc cagccactgc ccttgccctg    120
gtcagcacca ttcagtttgt gtcgaccttg caggcagccg cccaggagct gaaagccgag   180
tatcgtgtga gtgtcccaca gtgcaagccc tgtcccctg agagatcct gggctgcaca    240 tcccccccgac tgtccaaaga ggtggaggcc gttgtgtatc ttggagatgg ccgcttccat    300
ctggagtctg tcatgattgc caaccccaat gtccccgctt accggtatga cccatatagc    360
aaagtcctat ccagagaaca ctatgaccac cagcgcatgc aggctgctcg ccaagaagcc    420
atagccactg cccgctcagc taagtcctgg ggccttattc tgggcacttt gggccgccag    480
```

-continued

```
ggcagtccta agatcctgga gcacctggaa tctcgactcc gagccttggg cctttccttt        540
gtgaggctgc tgctctctga gatcttcccc agcaagctta gcctacttcc tgaggtggat        600
gtgtgggtgc aggtggcatg tccacgtctc tccattgact ggggcacagc cttccccaag        660
ccgctgctga cacccgatga ggcggccgtg gctctgaggg acatttcctg gcagcagccc        720
tacccgatgg acttctacgc tggcagctcc ttggggccct ggacggtgaa ccacggccag        780
gaccgccgtc cccacgcccc gggccggccc gcgcggggga aggtgcagga gggggtccgcg       840 cgtccccctt cggccgtggc ttgcgaggac tgcagctgca gggacgagaa ggtggcgccg        900
ctggctcctt ga                                                            912
```

<210> SEQ ID NO 5
<211> LENGTH: 443
<212> TYPE: PRT
<213> ORGANISM: Homo sapiens

<400> SEQUENCE: 5

```
Met Arg Arg Gln Val Met Ala Ala Leu Val Ser Gly Ala Ala Glu
1               5                   10                  15

Gln Gly Gly Arg Asp Gly Pro Gly Arg Gly Arg Ala Pro Arg Gly Arg
            20                  25                  30

Val Ala Asn Gln Ile Pro Pro Glu Ile Leu Lys Asn Pro Gln Leu Gln
        35                  40                  45

Ala Ala Ile Arg Val Leu Pro Ser Asn Tyr Asn Phe Glu Ile Pro Lys
    50                  55                  60

Thr Ile Trp Arg Ile Gln Ala Gln Ala Lys Val Ala Leu Gln
65                  70                  75                  80

Met Pro Glu Gly Leu Leu Leu Phe Ala Cys Thr Ile Val Asp Ile Leu
                85                  90                  95

Glu Arg Phe Thr Glu Ala Glu Val Met Val Met Gly Asp Val Thr Tyr
            100                 105                 110

Gly Ala Cys Cys Val Asp Asp Phe Thr Ala Arg Ala Leu Gly Ala Asp
        115                 120                 125

Phe Leu Val His Tyr Gly His Ser Cys Leu Ile Pro Met Asp Thr Ser
    130                 135                 140

Ala Gln Asp Phe Arg Val Leu Tyr Val Phe Val Asp Ile Arg Ile Asp
145                 150                 155                 160

Thr Thr His Leu Leu Asp Ser Leu Arg Leu Thr Phe Pro Pro Ala Thr
                165                 170                 175

Ala Leu Ala Leu Val Ser Thr Ile Gln Phe Val Ser Thr Leu Gln Ala
            180                 185                 190

Ala Ala Gln Glu Leu Lys Ala Glu Tyr Arg Val Ser Val Pro Gln Cys
        195                 200                 205

Lys Pro Leu Ser Pro Gly Glu Ile Leu Gly Cys Thr Ser Pro Arg Leu
    210                 215                 220

Ser Lys Glu Val Glu Ala Val Val Tyr Leu Gly Asp Gly Arg Phe His
225                 230                 235                 240

Leu Glu Ser Val Met Ile Ala Asn Pro Asn Val Pro Ala Tyr Arg Tyr
                245                 250                 255

Asp Pro Tyr Ser Lys Val Leu Ser Arg Glu His Tyr Asp His Gln Arg
            260                 265                 270

Met Gln Ala Ala Arg Gln Glu Ala Ile Ala Thr Ala Arg Ser Ala Lys
        275                 280                 285
```

```
Ser Trp Gly Leu Ile Leu Gly Thr Leu Gly Arg Gln Gly Ser Pro Lys
        290                 295                 300
Ile Leu Glu His Leu Glu Ser Arg Leu Arg Ala Leu Gly Leu Ser Phe
305                 310                 315                 320
Val Arg Leu Leu Leu Ser Glu Ile Phe Pro Ser Lys Leu Ser Leu Leu
                    325                 330                 335
Pro Glu Val Asp Val Trp Val Gln Val Ala Cys Pro Arg Leu Ser Ile
                340                 345                 350
Asp Trp Gly Thr Ala Phe Pro Lys Pro Leu Leu Thr Pro Tyr Glu Ala
            355                 360                 365
Ala Val Ala Leu Arg Asp Ile Ser Trp Gln Gln Pro Tyr Pro Met Asp
370                 375                 380
Phe Tyr Ala Gly Ser Ser Leu Gly Pro Trp Thr Val Asn His Gly Gln
385                 390                 395                 400
Asp Arg Arg Pro His Ala Pro Gly Arg Pro Ala Arg Gly Lys Val Gln
                405                 410                 415
Glu Gly Ser Ala Arg Pro Pro Ser Ala Val Ala Cys Glu Asp Cys Ser
            420                 425                 430
Cys Arg Asp Glu Lys Val Ala Pro Leu Ala Pro
            435                 440

<210> SEQ ID NO 6
<211> LENGTH: 422
<212> TYPE: PRT
<213> ORGANISM: Homo sapiens

<400> SEQUENCE: 6

Met Arg Arg Gln Val Met Ala Ala Leu Val Val Ser Gly Ala Ala Glu
1               5                   10                  15
Gln Gly Gly Arg Asp Gly Pro Gly Arg Gly Arg Ala Pro Arg Gly Arg
                20                  25                  30
Val Ala Asn Gln Ile Pro Pro Glu Ile Leu Lys Asn Pro Gln Leu Gln
                35                  40                  45
Ala Ala Ile Arg Val Leu Pro Ser Asn Tyr Asn Phe Glu Ile Pro Lys
50                  55                  60
Thr Ile Trp Arg Ile Gln Gln Ala Gln Ala Lys Lys Val Ala Leu Gln
65                  70                  75                  80
Met Pro Glu Gly Leu Leu Leu Phe Ala Cys Thr Ile Val Asp Ile Leu
                85                  90                  95
Glu Arg Phe Thr Glu Ala Glu Val Met Val Met Gly Asp Val Thr Tyr
                100                 105                 110
Gly Ala Cys Cys Val Asp Asp Phe Thr Ala Arg Ala Leu Gly Ala Asp
            115                 120                 125
Phe Leu Val His Tyr Gly His Ser Cys Leu Ile Pro Met Asp Thr Ser
130                 135                 140
Ala Gln Asp Phe Arg Val Leu Tyr Val Phe Val Asp Ile Arg Ile Asp
145                 150                 155                 160
Thr Thr His Leu Leu Asp Ser Leu Arg Leu Thr Phe Pro Pro Ala Thr
                165                 170                 175
Ala Leu Ala Leu Val Ser Thr Ile Gln Phe Val Ser Thr Leu Gln Ala
                180                 185                 190
Ala Ala Gln Glu Leu Lys Ala Glu Tyr Arg Val Ser Val Pro Gln Cys
            195                 200                 205
Lys Pro Leu Ser Pro Gly Glu Ile Leu Gly Cys Thr Ser Pro Arg Leu
210                 215                 220
```

```
Ser Lys Glu Val Glu Ala Val Val Tyr Leu Gly Asp Gly Arg Phe His
225                 230                 235                 240

Leu Glu Ser Val Met Ile Ala Asn Pro Asn Val Pro Ala Tyr Arg Tyr
                245                 250                 255

Asp Pro Tyr Ser Lys Val Leu Ser Arg Glu His Tyr Asp His Gln Arg
            260                 265                 270

Met Gln Ala Ala Arg Gln Glu Ala Ile Ala Thr Ala Arg Ser His Leu
        275                 280                 285

Glu Ser Arg Leu Arg Ala Leu Gly Leu Ser Phe Val Arg Leu Leu Leu
    290                 295                 300

Ser Glu Ile Phe Pro Ser Lys Leu Ser Leu Leu Pro Glu Val Asp Val
305                 310                 315                 320

Trp Val Gln Val Ala Cys Pro Arg Leu Ser Ile Asp Trp Gly Thr Ala
                325                 330                 335

Phe Pro Lys Pro Leu Leu Thr Pro Tyr Glu Ala Ala Val Ala Leu Arg
            340                 345                 350

Asp Ile Ser Trp Gln Gln Pro Tyr Pro Met Asp Phe Tyr Ala Gly Ser
        355                 360                 365

Ser Leu Gly Pro Trp Thr Val Asn His Gly Gln Asp Arg Arg Pro His
    370                 375                 380

Ala Pro Gly Arg Pro Ala Arg Gly Lys Val Gln Glu Gly Ser Ala Arg
385                 390                 395                 400

Pro Pro Ser Ala Val Ala Cys Glu Asp Cys Ser Cys Arg Asp Glu Lys
                405                 410                 415

Val Ala Pro Leu Ala Pro
            420

<210> SEQ ID NO 7
<211> LENGTH: 411
<212> TYPE: PRT
<213> ORGANISM: Homo sapiens

<400> SEQUENCE: 7

Met Arg Arg Gln Val Met Ala Ala Leu Val Val Ser Gly Ala Ala Glu
1               5                   10                  15

Gln Gly Gly Arg Asp Gly Pro Gly Arg Gly Arg Ala Pro Arg Gly Arg
                20                  25                  30

Val Ala Asn Gln Ile Pro Pro Glu Ile Leu Lys Asn Pro Gln Leu Gln
            35                  40                  45

Ala Ala Ile Arg Val Leu Pro Ser Asn Tyr Asn Phe Glu Ile Pro Lys
    50                  55                  60

Thr Ile Trp Arg Ile Gln Gln Ala Gln Ala Lys Lys Val Ala Leu Gln
65                  70                  75                  80

Met Pro Glu Gly Leu Leu Leu Phe Ala Cys Thr Ile Val Asp Ile Leu
                85                  90                  95

Glu Arg Phe Thr Glu Ala Glu Val Met Val Met Gly Asp Val Thr Tyr
            100                 105                 110

Gly Ala Cys Cys Val Asp Asp Phe Thr Ala Arg Ala Leu Gly Ala Asp
        115                 120                 125

Phe Leu Val His Tyr Gly His Ser Cys Leu Ile Pro Met Asp Thr Ser
    130                 135                 140

Ala Gln Asp Phe Arg Val Leu Tyr Val Phe Val Asp Ile Arg Ile Asp
145                 150                 155                 160

Thr Thr His Leu Leu Asp Ser Leu Arg Leu Thr Phe Pro Pro Ala Thr
```

```
              165                 170                 175
Ala Leu Ala Leu Ala Ala Gln Glu Leu Lys Ala Glu Tyr Arg Val
            180                 185                 190

Ser Val Pro Gln Cys Lys Pro Leu Ser Pro Gly Glu Ile Leu Gly Cys
            195                 200                 205

Thr Ser Pro Arg Leu Ser Lys Glu Val Glu Ala Val Val Tyr Leu Gly
            210                 215                 220

Asp Gly Arg Phe His Leu Glu Ser Val Met Ile Ala Asn Pro Asn Val
225                 230                 235                 240

Pro Ala Tyr Arg Tyr Asp Pro Tyr Ser Lys Val Leu Ser Arg Glu His
                245                 250                 255

Tyr Asp His Gln Arg Met Gln Ala Ala Arg Gln Glu Ala Ile Ala Thr
            260                 265                 270

Ala Arg Ser His Leu Glu Ser Arg Leu Arg Ala Leu Gly Leu Ser Phe
            275                 280                 285

Val Arg Leu Leu Leu Ser Glu Ile Phe Pro Ser Lys Leu Ser Leu Leu
        290                 295                 300

Pro Glu Val Asp Val Trp Val Gln Val Ala Cys Pro Arg Leu Ser Ile
305                 310                 315                 320

Asp Trp Gly Thr Ala Phe Pro Lys Pro Leu Leu Thr Pro Tyr Glu Ala
                325                 330                 335

Ala Val Ala Leu Arg Asp Ile Ser Trp Gln Gln Pro Tyr Pro Met Asp
            340                 345                 350

Phe Tyr Ala Gly Ser Ser Leu Gly Pro Trp Thr Val Asn His Gly Gln
            355                 360                 365

Asp Arg Arg Pro His Ala Pro Gly Arg Pro Ala Arg Gly Lys Val Gln
            370                 375                 380

Glu Gly Ser Ala Arg Pro Pro Ser Ala Val Ala Cys Glu Asp Cys Ser
385                 390                 395                 400

Cys Arg Asp Glu Lys Val Ala Pro Leu Ala Pro
                405                 410

<210> SEQ ID NO 8
<211> LENGTH: 303
<212> TYPE: PRT
<213> ORGANISM: Homo sapiens

<400> SEQUENCE: 8

Met Asp Thr Ser Ala Gln Asp Phe Arg Val Leu Tyr Val Phe Val Asp
1               5                   10                  15

Ile Arg Ile Asp Thr Thr His Leu Leu Asp Ser Leu Arg Leu Thr Phe
                20                  25                  30

Pro Pro Ala Thr Ala Leu Ala Leu Val Ser Thr Ile Gln Phe Val Ser
            35                  40                  45

Thr Leu Gln Ala Ala Ala Gln Glu Leu Lys Ala Glu Tyr Arg Val Ser
        50                  55                  60

Val Pro Gln Cys Lys Pro Leu Ser Pro Gly Glu Ile Leu Gly Cys Thr
65                  70                  75                  80

Ser Pro Arg Leu Ser Lys Glu Val Glu Ala Val Val Tyr Leu Gly Asp
                85                  90                  95

Gly Arg Phe His Leu Glu Ser Val Met Ile Ala Asn Pro Asn Val Pro
            100                 105                 110

Ala Tyr Arg Tyr Asp Pro Tyr Ser Lys Val Leu Ser Arg Glu His Tyr
        115                 120                 125
```

Asp His Gln Arg Met Gln Ala Ala Arg Gln Glu Ala Ile Ala Thr Ala
130                 135                 140

Arg Ser Ala Lys Ser Trp Gly Leu Ile Leu Gly Thr Leu Gly Arg Gln
145                 150                 155                 160

Gly Ser Pro Lys Ile Leu Glu His Leu Glu Ser Arg Leu Arg Ala Leu
                165                 170                 175

Gly Leu Ser Phe Val Arg Leu Leu Leu Ser Glu Ile Phe Pro Ser Lys
                180                 185                 190

Leu Ser Leu Leu Pro Glu Val Asp Val Trp Val Gln Val Ala Cys Pro
            195                 200                 205

Arg Leu Ser Ile Asp Trp Gly Thr Ala Phe Pro Lys Pro Leu Leu Thr
210                 215                 220

Pro Tyr Glu Ala Ala Val Ala Leu Arg Asp Ile Ser Trp Gln Gln Pro
225                 230                 235                 240

Tyr Pro Met Asp Phe Tyr Ala Gly Ser Ser Leu Gly Pro Trp Thr Val
                245                 250                 255

Asn His Gly Gln Asp Arg Arg Pro His Ala Pro Gly Arg Pro Ala Arg
                260                 265                 270

Gly Lys Val Gln Glu Gly Ser Ala Arg Pro Pro Ser Ala Val Ala Cys
            275                 280                 285

Glu Asp Cys Ser Cys Arg Asp Glu Lys Val Ala Pro Leu Ala Pro
290                 295                 300

<210> SEQ ID NO 9
<211> LENGTH: 1317
<212> TYPE: DNA
<213> ORGANISM: Mus musculus

<400> SEQUENCE: 9

| | |
|---|---|
| atggcggcgc tggttgtgtc cgagactgcg gagccaggaa gccgagtcgg ccctggcaga | 60 |
| ggtcgcatct ctcgggggcg actggccaat cagatccccc tgaggtcct gaacaacccc | 120 |
| cagttacagg ctgctgtcca agttctgcct tctaactaca actttgagat ccccaaaacc | 180 |
| atctggagaa tccagcaggc ccaggccaag aaggtggcct acaaatgcc agaaggcctc | 240 |
| ctcctctttg cctgcactat tgtggatatc ttggaaaggt tcacagaggc tgaggtgatg | 300 |
| gtgatgggtg atgtcaccta tggggcttgc tgtgtggatg acttcactgc aagggccttg | 360 |
| ggagttgact tcctggtgca ctatggtcac agctgtctag tccccatgga cacctccgtt | 420 |
| caagacttcc gagtcttgta tgtcttcgtg gatatccgga tagacactgc ccaccttctg | 480 |
| gactcggtcc gcctcacctt taccccaggc agctcactcg ctctggtcag caccattcag | 540 |
| tttgtgtcaa ccttacaggc agctgcacag gagctgaaag ctgattatca catcagtgtc | 600 |
| ccacagtgca agccctgtc ccctggggag atcctaggct gcacatcccc tcggctatcc | 660 |
| aaggaagtgg aagctgttgt gtatcttgga gatggccgct tcatctgga gtctgtcatg | 720 |
| attgccaacc ctaatatacc tgcttaccgg tatgacccat atggcaaagt cctatccaga | 780 |
| gaatactatg accatcagcg catgcaggcc actcgccagg aagccattgc tgctgcacgc | 840 |
| tcagccaaat cctggggcct tattctggga accttgggcc gccagggcag tcccaagatc | 900 |
| ctggagcact ggaatctca gctcagaaac ttggacttc ctttcgtgag ctgttgctc | 960 |
| tctgagatct ccccagcaa gctcagtcta cttcctgagg tggatgtgtg ggtgcaggtg | 1020 |
| gcatgtccac gcctctccat tgactgggt tcagccttc ccaagccact gctgacaccg | 1080 |
| tacgaggcag ctgtggccct gaaggacatt tcttggcagc aaccctaccc catggacttc | 1140 |

```
tactctggca gctccttagg gccatggaca gtgaactacg gtcgggaccg agcacctcgg    1200
ggtctctgcc agcctgcatc tgacaaggtg cagcaagggt ccagaggcgg ctctccagcc    1260
ccagcctgtg agagttgcaa ctgcgcagac cagaaggcta cttcgccggc tccctga      1317
```

```
<210> SEQ ID NO 10
<211> LENGTH: 438
<212> TYPE: PRT
<213> ORGANISM: Mus musculus

<400> SEQUENCE: 10
```

```
Met Ala Ala Leu Val Val Ser Glu Thr Ala Glu Pro Gly Ser Arg Val
1               5                   10                  15

Gly Pro Gly Arg Gly Arg Ile Ser Arg Gly Arg Leu Ala Asn Gln Ile
            20                  25                  30

Pro Pro Glu Val Leu Asn Asn Pro Gln Leu Gln Ala Ala Val Gln Val
        35                  40                  45

Leu Pro Ser Asn Tyr Asn Phe Glu Ile Pro Lys Thr Ile Trp Arg Ile
    50                  55                  60

Gln Gln Ala Gln Ala Lys Lys Val Ala Leu Gln Met Pro Glu Gly Leu
65                  70                  75                  80

Leu Leu Phe Ala Cys Thr Ile Val Asp Ile Leu Glu Arg Phe Thr Glu
                85                  90                  95

Ala Glu Val Met Val Met Gly Asp Val Thr Tyr Gly Ala Cys Cys Val
            100                 105                 110

Asp Asp Phe Thr Ala Arg Ala Leu Gly Val Asp Phe Leu Val His Tyr
        115                 120                 125

Gly His Ser Cys Leu Val Pro Met Asp Thr Ser Val Gln Asp Phe Arg
    130                 135                 140

Val Leu Tyr Val Phe Val Asp Ile Arg Ile Asp Thr Ala His Leu Leu
145                 150                 155                 160

Asp Ser Val Arg Leu Thr Phe Thr Pro Gly Ser Ser Leu Ala Leu Val
                165                 170                 175

Ser Thr Ile Gln Phe Val Ser Thr Leu Gln Ala Ala Ala Gln Glu Leu
            180                 185                 190

Lys Ala Asp Tyr His Ile Ser Val Pro Gln Cys Lys Pro Leu Ser Pro
        195                 200                 205

Gly Glu Ile Leu Gly Cys Thr Ser Pro Arg Leu Ser Lys Glu Val Glu
    210                 215                 220

Ala Val Val Tyr Leu Gly Asp Gly Arg Phe His Leu Glu Ser Val Met
225                 230                 235                 240

Ile Ala Asn Pro Asn Ile Pro Ala Tyr Arg Tyr Asp Pro Tyr Gly Lys
                245                 250                 255

Val Leu Ser Arg Glu Tyr Tyr Asp His Gln Arg Met Gln Ala Thr Arg
            260                 265                 270

Gln Glu Ala Ile Ala Ala Arg Ser Ala Lys Ser Trp Gly Leu Ile
        275                 280                 285

Leu Gly Thr Leu Gly Arg Gln Gly Ser Pro Lys Ile Leu Glu His Leu
    290                 295                 300

Glu Ser Gln Leu Arg Asn Leu Gly Leu Pro Phe Val Arg Leu Leu Leu
305                 310                 315                 320

Ser Glu Ile Phe Pro Ser Lys Leu Ser Leu Leu Pro Glu Val Asp Val
                325                 330                 335

Trp Val Gln Val Ala Cys Pro Arg Leu Ser Ile Asp Trp Gly Ser Ala
            340                 345                 350
```

```
        Phe Pro Lys Pro Leu Leu Thr Pro Tyr Glu Ala Ala Val Ala Leu Lys
                355                 360                 365

Asp Ile Ser Trp Gln Gln Pro Tyr Pro Met Asp Phe Tyr Ser Gly Ser
            370                 375                 380

Ser Leu Gly Pro Trp Thr Val Asn Tyr Gly Arg Asp Arg Ala Pro Arg
        385                 390                 395                 400

Gly Leu Cys Gln Pro Ala Ser Asp Lys Val Gln Gln Gly Ser Arg Gly
                        405                 410                 415

Gly Ser Pro Ala Pro Ala Cys Glu Ser Cys Asn Cys Ala Asp Gln Lys
                    420                 425                 430

Ala Thr Ser Pro Ala Pro
                    435

<210> SEQ ID NO 11
<211> LENGTH: 1332
<212> TYPE: DNA
<213> ORGANISM: Pan troglodytes

<400> SEQUENCE: 11
atgcgcaggc aggtgatggc ggcgctggtt gtatccgggg cagcggagca gggcggccga        60
aacggccctg gcagaggtcg ggcccctcgg ggccgcgtgg ccaatcagat ccccccctgag      120 atcctgaaga accctcagct gcaggcagca atgcgggtcc tgccttccaa ctacaacttt       180
gagatcccca agaccatctg gaggatccaa caagcccagg ccaagaaggt ggccttgcag       240
atgccggaag gctcctcct ctttgcctgt accattgtgg atatcttgga aaggttcacg        300
gaggccgaag tgatggtgat gggtgacgtg acctacgggg cttgctgtgt ggatgacttc       360
acagcgaggg ccctgggagc tgacttcttg gtgcactacg ccacagttg cctgattccc        420 atggacacct cggcccaaga cttccgggtg ctgtacgtct ttgtggacat ccggatagac       480
actacgcacc tcctggactc tctccgcctc acctttcccc cagccactgc ccttgccctg      540
gtcagcacca ttcagtttgt gtcgaccttg caggcagccg cccaggagct gaaagccgag       600
tatcgtgtga gtgtcccaca gtgcaagccc ctgtcccctg agagatcct gggctgcaca       660 tccccccgac tgtccaaaga ggtggaggcc gttgtgtatc ttggagatgg ccgcttccat       720
ctggagtctg tcatgattgc caaccccaat gtccccgctt accggtatga cccatatagc      780
aaagtcctat ccagagaaca ctatgaccac cagcgcatgc aggctgctcg ccaagaagcc      840
atagccactg cccgctcagc taagtcctgg ggccttattc tgggcacttt gggccgccag      900
ggcagtccta agatcctgga gcacctggaa tctcaactcc gagccttggg cctttccttt      960
gtgaggctgc tgctctctga gatcttcccc agcaagctta gcctacttcc gaggtggat      1020 gtgtgggtgc aggtggcatg tccacgtctc tccattgact ggggcacagc cttcccaag     1080 ccgctgctga caccctatga ggcggccgtg gctctgaggg acatttcctg gcagcagccc     1140
tacccgatgg acttctacgc tggcagctct ttggggccct ggacggtgaa ccacggccag     1200
gaccgccgtc cccacgcccc gggccggccc gcgcggggga aggtgcagga ggggtccgcg     1260
cgtccccctt cagccgtggc ttgcgaggat tgcagctgca gggacgagaa ggtggcgccg     1320
ctggctcctt ga                                                         1332

<210> SEQ ID NO 12
<211> LENGTH: 443
<212> TYPE: PRT
<213> ORGANISM: Pan troglodytes
```

```
<400> SEQUENCE: 12

Met Arg Arg Gln Val Met Ala Ala Leu Val Val Ser Gly Ala Ala Glu
1               5                   10                  15

Gln Gly Gly Arg Asn Gly Pro Gly Arg Gly Ala Pro Arg Gly Arg
            20                  25                  30

Val Ala Asn Gln Ile Pro Pro Glu Ile Leu Lys Asn Pro Gln Leu Gln
            35                  40                  45

Ala Ala Met Arg Val Leu Pro Ser Asn Tyr Asn Phe Glu Ile Pro Lys
        50                  55                  60

Thr Ile Trp Arg Ile Gln Gln Ala Gln Ala Lys Lys Val Ala Leu Gln
65                  70                  75                  80

Met Pro Glu Gly Leu Leu Leu Phe Ala Cys Thr Ile Val Asp Ile Leu
                85                  90                  95

Glu Arg Phe Thr Glu Ala Glu Val Met Val Met Gly Asp Val Thr Tyr
            100                 105                 110

Gly Ala Cys Cys Val Asp Asp Phe Thr Ala Arg Ala Leu Gly Ala Asp
            115                 120                 125

Phe Leu Val His Tyr Gly His Ser Cys Leu Ile Pro Met Asp Thr Ser
            130                 135                 140

Ala Gln Asp Phe Arg Val Leu Tyr Val Phe Val Asp Ile Arg Ile Asp
145                 150                 155                 160

Thr Thr His Leu Leu Asp Ser Leu Arg Leu Thr Phe Pro Pro Ala Thr
                165                 170                 175

Ala Leu Ala Leu Val Ser Thr Ile Gln Phe Val Ser Thr Leu Gln Ala
            180                 185                 190

Ala Ala Gln Glu Leu Lys Ala Glu Tyr Arg Val Ser Val Pro Gln Cys
            195                 200                 205

Lys Pro Leu Ser Pro Gly Glu Ile Leu Gly Cys Thr Ser Pro Arg Leu
        210                 215                 220

Ser Lys Glu Val Glu Ala Val Val Tyr Leu Gly Asp Gly Arg Phe His
225                 230                 235                 240

Leu Glu Ser Val Met Ile Ala Asn Pro Asn Val Pro Ala Tyr Arg Tyr
                245                 250                 255

Asp Pro Tyr Ser Lys Val Leu Ser Arg Glu His Tyr Asp His Gln Arg
            260                 265                 270

Met Gln Ala Ala Arg Gln Glu Ala Ile Ala Thr Ala Arg Ser Ala Lys
        275                 280                 285

Ser Trp Gly Leu Ile Leu Gly Thr Leu Gly Arg Gln Gly Ser Pro Lys
        290                 295                 300

Ile Leu Glu His Leu Glu Ser Gln Leu Arg Ala Leu Gly Leu Ser Phe
305                 310                 315                 320

Val Arg Leu Leu Leu Ser Glu Ile Phe Pro Ser Lys Leu Ser Leu Leu
                325                 330                 335

Pro Glu Val Asp Val Trp Val Gln Val Ala Cys Pro Arg Leu Ser Ile
            340                 345                 350

Asp Trp Gly Thr Ala Phe Pro Lys Pro Leu Leu Thr Pro Tyr Glu Ala
            355                 360                 365

Ala Val Ala Leu Arg Asp Ile Ser Trp Gln Pro Tyr Pro Met Asp
        370                 375                 380

Phe Tyr Ala Gly Ser Ser Leu Gly Pro Trp Thr Val Asn His Gly Gln
385                 390                 395                 400

Asp Arg Arg Pro His Ala Pro Gly Arg Pro Ala Arg Gly Lys Val Gln
            405                 410                 415
```

-continued

Glu Gly Ser Ala Arg Pro Pro Ser Ala Val Ala Cys Glu Asp Cys Ser
            420                 425                 430

Cys Arg Asp Glu Lys Val Ala Pro Leu Ala Pro
            435                 440

<210> SEQ ID NO 13
<211> LENGTH: 1317
<212> TYPE: DNA
<213> ORGANISM: Macaca mulatta

<400> SEQUENCE: 13
atggcggcgc tggttgtgtc ccgggcagcg gagcagggcg gccgaaacgg ccctggcaga      60
gttcgggccc ctcggggccg cgtggccaat cagatccccc ctgagatcct gaagaactcc     120
cagctgcagg cagcaatcca ggtcctgcct tccaactaca actttgagat ccccaagacc     180
atctggagga tccaacaagc ccaggccaag aaggtggcct tgcaaatgcc ggaaggcctc     240
ctcctctttg cctgtaccat cgtggatatc ttggaaaggt tcacggaggc tgaagtgatg     300
gtgatgggtg acgtgaccta tgggcttgc tgtgtggatg acttcacggc gagggccctg     360
ggagctgact tcttggtgca ctatggccac agttgcctgg ttcccatgga cacctcggcc     420
caagacttcc gggtgctgta cgtctttgtg gacatccgga tagacactgc ccacctcctg     480
gactctctcc gcctcacctt tcccccagcc accgcccttg ccctggtcag caccattcag     540
tttgtgtcga ccttgcaggc agccgcccag gagctgaaag ctgagtaccg tgtgagtgtc     600
ccacagtgca agcccctgtc ccctggagag attctgggct gcacatcccc ccgactgccc     660
gaagaggtgg aggccgttgt gtatcttgga gatggccgct tccatctgga gtctgtcatg     720
attgccaacc ccaatgtccc cgcttaccgg tatgacccgt acagcaaagt cctgtccaga     780
gagcactatg accaccagcg catgcgggct gctcgccagg aagccatagc caccgcccgc     840
tccgctaagt cctggggcct tattctgggc actctgggcc gccagggcag tcctaagatc     900
ctggagcacc tggaatctcg actccgagcc ttgggccttt ccttcgtgag ctgctgctc      960 tctgagatct cccccagcaa gcttggccta cttcccgagg tggatgtgtg ggtgcaggtg    1020
gcatgtccac gtctctccat tgactgggc acagccttcc ccaagcctct gctgacaccc    1080
tatgaggcgg ccgtggctct gagggacatt tcctggcagc agccctaccc gatggacttc    1140
tacgctggca gctccttggg gccctggacg gtgaaccacg gcctggaccg cgtccccag    1200 accccgggcc gacccacgcg ggggaaggtg caggaggggt ccacgcatcc cccttcagcc    1260
gtggcttgcg aggactgcag ctgcagagac aagaaggtgg cgccgcttgc tccttga      1317

<210> SEQ ID NO 14
<211> LENGTH: 438
<212> TYPE: PRT
<213> ORGANISM: Macaca mulatta

<400> SEQUENCE: 14

Met Ala Ala Leu Val Val Ser Arg Ala Ala Glu Gln Gly Gly Arg Asn
1               5                   10                  15

Gly Pro Gly Arg Val Arg Ala Pro Arg Gly Arg Val Ala Asn Gln Ile
            20                  25                  30

Pro Pro Glu Ile Leu Lys Asn Ser Gln Leu Gln Ala Ala Ile Gln Val
        35                  40                  45

Leu Pro Ser Asn Tyr Asn Phe Glu Ile Pro Lys Thr Ile Trp Arg Ile
    50                  55                  60

```
Gln Gln Ala Gln Ala Lys Val Ala Leu Gln Met Pro Glu Gly Leu
 65                  70                  75                  80

Leu Leu Phe Ala Cys Thr Ile Val Asp Ile Leu Glu Arg Phe Thr Glu
                 85                  90                  95

Ala Glu Val Met Val Met Gly Asp Val Thr Tyr Gly Ala Cys Cys Val
                100                 105                 110

Asp Asp Phe Thr Ala Arg Ala Leu Gly Ala Asp Phe Leu Val His Tyr
                115                 120                 125

Gly His Ser Cys Leu Val Pro Met Asp Thr Ser Ala Gln Asp Phe Arg
    130                 135                 140

Val Leu Tyr Val Phe Val Asp Ile Arg Ile Asp Thr Ala His Leu Leu
145                 150                 155                 160

Asp Ser Leu Arg Leu Thr Phe Pro Pro Ala Thr Ala Leu Ala Leu Val
                165                 170                 175

Ser Thr Ile Gln Phe Val Ser Thr Leu Gln Ala Ala Ala Gln Glu Leu
                180                 185                 190

Lys Ala Glu Tyr Arg Val Ser Val Pro Gln Cys Lys Pro Leu Ser Pro
                195                 200                 205

Gly Glu Ile Leu Gly Cys Thr Ser Pro Arg Leu Pro Glu Glu Val Glu
    210                 215                 220

Ala Val Val Tyr Leu Gly Asp Gly Arg Phe His Leu Glu Ser Val Met
225                 230                 235                 240

Ile Ala Asn Pro Asn Val Pro Ala Tyr Arg Tyr Asp Pro Tyr Ser Lys
                245                 250                 255

Val Leu Ser Arg Glu His Tyr Asp His Gln Arg Met Arg Ala Ala Arg
                260                 265                 270

Gln Glu Ala Ile Ala Thr Ala Arg Ser Ala Lys Ser Trp Gly Leu Ile
                275                 280                 285

Leu Gly Thr Leu Gly Arg Gln Gly Ser Pro Lys Ile Leu Glu His Leu
    290                 295                 300

Glu Ser Arg Leu Arg Ala Leu Gly Leu Ser Phe Val Arg Leu Leu Leu
305                 310                 315                 320

Ser Glu Ile Phe Pro Ser Lys Leu Gly Leu Leu Pro Glu Val Asp Val
                325                 330                 335

Trp Val Gln Val Ala Cys Pro Arg Leu Ser Ile Asp Trp Gly Thr Ala
                340                 345                 350

Phe Pro Lys Pro Leu Leu Thr Pro Tyr Glu Ala Ala Val Ala Leu Arg
                355                 360                 365

Asp Ile Ser Trp Gln Gln Pro Tyr Pro Met Asp Phe Tyr Ala Gly Ser
    370                 375                 380

Ser Leu Gly Pro Trp Thr Val Asn His Gly Leu Asp Arg Arg Pro Gln
385                 390                 395                 400

Thr Pro Gly Arg Pro Thr Arg Gly Lys Val Gln Glu Gly Ser Thr His
                405                 410                 415

Pro Pro Ser Ala Val Ala Cys Glu Asp Cys Ser Cys Arg Asp Lys Lys
                420                 425                 430

Val Ala Pro Leu Ala Pro
        435

<210> SEQ ID NO 15
<211> LENGTH: 1317
<212> TYPE: DNA
<213> ORGANISM: Bos taurus

<400> SEQUENCE: 15
```

```
atggcggcgc tggtggcggc cgaggccgca gagtcttgca gccgaaacgg cccgggcaga    60
ggtcgagccc ctcggggccg cttggccaat cagatcccgg ctgagatcct gaacaatccc   120
cagctgcagg cggccatcca agtcctgcct tccaactata actttgaggt tcccaagacc   180
atctggagga tccaacaggc ccaggccaag aaggtggcct acaaatgccc gaaggcctc    240 ctcctcttcg cctgtaccat tgtggatatc ttggaaaggt tcacggaggc cgaagtgatg   300
gtgatgggag acgtgaccta cggggcttgc tgtgtggacg acttcactgc aagagccttg   360
ggagctgact tcctggtcca ctatggccac agctgcctgg ttcccatgga cacctcggcc   420
caagacttcc gggtgctgta tgtctttgtg gacatccgga tagacactgc ccacctcctg   480
gactctatcc gcctcacctt tcccccagcc agtgcccttg cgctggtcag caccattcag   540
ttcgtgtcaa ccttgcaggc agctgcccaa gagctgaaag ctgagtatcg tgtgagtgtc   600
ccacagtgca agcccctgtc tcctggggag attctgggct gcacgtctcc ctgcctaccc   660
aaggaggtgg aggctgtggt gtatcttgga tggccgct tccacctgga gtctgtcatg    720
atcgccaacc ctaacatctc cgcttaccga tacgacccctt acagcaaggt cctgtccaga   780
gagcactatg accaccagcg catgcaggcc aaccgccagg aagccatagc cactgcccgg   840
tcagctaaat cctggggtct catcctgggc actttgggcc gccaaggcag tcccaagatc   900
ctggagcacc tggaatctcg gctccaagcc ttgggacttc ccttcgtgag ctgctgctc    960 tctgagatct tccccagcaa gctcagcctc cttcccgagg tggatgtgtg ggtgcaggtg  1020
gcatgtccac gcctgtccat cgactggggt acagccttcc ccaagccgct gctcacaccc  1080
tatgaggcgg cggtggcctt gagggacatt tcctggcagc agccctaccc tatggacttc  1140
tacgccagca gctccttggg gccgtggacg gtgaaccacg gcgggatcg gctgctccag  1200 gtcccaggcc ggctggccct ggggaaggtt caggggggc ccgcgcgccc ctctccagcc  1260
gcggcttgcg aggcttgcag ctgcagagac gaggaggtgt cgccgatcgc tctctga     1317
```

<210> SEQ ID NO 16
<211> LENGTH: 438
<212> TYPE: PRT
<213> ORGANISM: Bos taurus

<400> SEQUENCE: 16

```
Met Ala Ala Leu Val Ala Ala Glu Ala Ala Glu Ser Cys Ser Arg Asn
1               5                   10                  15

Gly Pro Gly Arg Gly Arg Ala Pro Arg Gly Arg Leu Ala Asn Gln Ile
            20                  25                  30

Pro Ala Glu Ile Leu Asn Asn Pro Gln Leu Gln Ala Ala Ile Gln Val
        35                  40                  45

Leu Pro Ser Asn Tyr Asn Phe Glu Val Pro Lys Thr Ile Trp Arg Ile
    50                  55                  60

Gln Gln Ala Gln Ala Lys Lys Val Ala Leu Gln Met Pro Glu Gly Leu
65                  70                  75                  80

Leu Leu Phe Ala Cys Thr Ile Val Asp Ile Leu Glu Arg Phe Thr Glu
                85                  90                  95

Ala Glu Val Met Val Met Gly Asp Val Thr Tyr Gly Ala Cys Cys Val
            100                 105                 110

Asp Asp Phe Thr Ala Arg Ala Leu Gly Ala Asp Phe Leu Val His Tyr
        115                 120                 125

Gly His Ser Cys Leu Val Pro Met Asp Thr Ser Ala Gln Asp Phe Arg
    130                 135                 140
```

```
Val Leu Tyr Val Phe Val Asp Ile Arg Ile Asp Thr Ala His Leu Leu
145                 150                 155                 160

Asp Ser Ile Arg Leu Thr Phe Pro Pro Ala Ser Ala Leu Ala Leu Val
            165                 170                 175

Ser Thr Ile Gln Phe Val Ser Thr Leu Gln Ala Ala Gln Glu Leu
        180                 185                 190

Lys Ala Glu Tyr Arg Val Ser Val Pro Gln Cys Lys Pro Leu Ser Pro
        195                 200                 205

Gly Glu Ile Leu Gly Cys Thr Ser Pro Cys Leu Pro Lys Glu Val Glu
        210                 215                 220

Ala Val Val Tyr Leu Gly Asp Gly Arg Phe His Leu Glu Ser Val Met
225                 230                 235                 240

Ile Ala Asn Pro Asn Ile Ser Ala Tyr Arg Tyr Asp Pro Tyr Ser Lys
            245                 250                 255

Val Leu Ser Arg Glu His Tyr Asp His Gln Arg Met Gln Ala Asn Arg
            260                 265                 270

Gln Glu Ala Ile Ala Thr Ala Arg Ser Ala Lys Ser Trp Gly Leu Ile
        275                 280                 285

Leu Gly Thr Leu Gly Arg Gln Gly Ser Pro Lys Ile Leu Glu His Leu
        290                 295                 300

Glu Ser Arg Leu Gln Ala Leu Gly Leu Pro Phe Val Arg Leu Leu Leu
305                 310                 315                 320

Ser Glu Ile Phe Pro Ser Lys Leu Ser Leu Leu Pro Glu Val Asp Val
            325                 330                 335

Trp Val Gln Val Ala Cys Pro Arg Leu Ser Ile Asp Trp Gly Thr Ala
            340                 345                 350

Phe Pro Lys Pro Leu Leu Thr Pro Tyr Glu Ala Ala Val Ala Leu Arg
            355                 360                 365

Asp Ile Ser Trp Gln Gln Pro Tyr Pro Met Asp Phe Tyr Ala Ser Ser
            370                 375                 380

Ser Leu Gly Pro Trp Thr Val Asn His Gly Arg Asp Arg Leu Leu Gln
385                 390                 395                 400

Val Pro Gly Arg Leu Ala Leu Gly Lys Val Gln Gly Gly Pro Ala Arg
            405                 410                 415

Pro Ser Pro Ala Ala Ala Cys Glu Ala Cys Ser Cys Arg Asp Glu Glu
            420                 425                 430

Val Ser Pro Ile Ala Leu
        435
```

<210> SEQ ID NO 17
<211> LENGTH: 1317
<212> TYPE: DNA
<213> ORGANISM: Rattus norvegicus

<400> SEQUENCE: 17

```
atggcggcgc tggttgtgcc cgagacttcc gagccaggaa gccgagtcgg ccctggcaga      60
ggtcgcatct ctcggggccg actggccaat cagatccccc ctgagatcct gaacagtccc     120
cagctacagg ccgctgtcca tgccctgcct tctaactaca actttgagat ccccaagacc     180
atctggagga tccagcaagc ccaggccaag aaggtggcct acaaatgcc agaaggcctc      240 ctgctctttg cctgcaccat tgtggatatc ttggaaaggt tcacaaaggc tgaggtgatg     300
gtgatgggcg atgtgaccta cggagcatgc tgtgtgacg acttcactgc aagggccttg      360
ggagttgact tcctggtgca ctatggccac agctgcctag tccccatgga cacctcagtc     420
```

-continued

```
caagacttcc gtgtgctgta tgtctttgtg gatatccgga tagacactgc ccaccttctg        480
gactcggtcc gcctcacctt caccccaggc agctcgcttg ctctggtcag caccattcag        540
tttgtgtcaa ctttacaggc agctgcccag gagctgaaag ctgattatca catcagtgtc        600
ccacagtgca agcccttgtc ccctggggag atcctaggct gcacgtcccc tcgactaccc        660
aaggaagtgg aagctgttgt gtatcttgga gatggccgct ccatctgga gtctgtcatg         720 atcgccaacc ctaatatacc tagttaccgg tacgacccat atagcaaagt cctatccaga        780
gaatactatg accatcagcg catgcaggcc actcgtcagg aagccatcgc tgctcacgc         840 tcagccaagt tctggggcct tattctggga actttgggcc gccagggaag tcccaaggtc        900
ctggagcact ggaatctca gctcagaaac ttgggacttc ctttcctgag gctgcttctc         960
tctgagatct cccccagcaa gctcagtcta cttccttcgg tggacgtgtg ggtgcaggtg       1020
gcatgtccac gcctctccat tgactggggc tcagcctttc ccaagccact gctgacaccc       1080
tacgaggcag ctgtggccct gaaagagatt tcttggcagc aaccctaccc tatggacttc       1140
tacgctggca gctccttagg gccatggaca gtgaaccatg gtcgggaccg agcacccagg       1200
ggtctctgcc agcctgcatc cgacaaggtg cagcaggggt ccagaggcca ctctccagtc       1260
ccggcctgtg agggctgcag ctgcgcagac cagaaagcta caccgccagc tccctga         1317
```

<210> SEQ ID NO 18
<211> LENGTH: 438
<212> TYPE: PRT
<213> ORGANISM: Rattus norvegicus

<400> SEQUENCE: 18

```
Met Ala Ala Leu Val Val Pro Glu Thr Ser Glu Pro Gly Ser Arg Val
1               5                   10                  15

Gly Pro Gly Arg Gly Arg Ile Ser Arg Gly Arg Leu Ala Asn Gln Ile
            20                  25                  30

Pro Pro Glu Ile Leu Asn Ser Pro Gln Leu Gln Ala Ala Val His Ala
        35                  40                  45

Leu Pro Ser Asn Tyr Asn Phe Glu Ile Pro Lys Thr Ile Trp Arg Ile
50                  55                  60

Gln Gln Ala Gln Ala Lys Lys Val Ala Leu Gln Met Pro Glu Gly Leu
65                  70                  75                  80

Leu Leu Phe Ala Cys Thr Ile Val Asp Ile Leu Glu Arg Phe Thr Lys
                85                  90                  95

Ala Glu Val Met Val Met Gly Asp Val Thr Tyr Gly Ala Cys Cys Val
            100                 105                 110

Asp Asp Phe Thr Ala Arg Ala Leu Gly Val Asp Phe Leu Val His Tyr
        115                 120                 125

Gly His Ser Cys Leu Val Pro Met Asp Thr Ser Val Gln Asp Phe Arg
    130                 135                 140

Val Leu Tyr Val Phe Val Asp Ile Arg Ile Asp Thr Ala His Leu Leu
145                 150                 155                 160

Asp Ser Val Arg Leu Thr Phe Thr Pro Gly Ser Ser Leu Ala Leu Val
                165                 170                 175

Ser Thr Ile Gln Phe Val Ser Thr Leu Gln Ala Ala Gln Glu Leu
            180                 185                 190

Lys Ala Asp Tyr His Ile Ser Val Pro Gln Cys Lys Pro Leu Ser Pro
        195                 200                 205

Gly Glu Ile Leu Gly Cys Thr Ser Pro Arg Leu Pro Lys Glu Val Glu
```

```
            210                 215                 220
Ala Val Val Tyr Leu Gly Asp Gly Arg Phe His Leu Glu Ser Val Met
225                 230                 235                 240

Ile Ala Asn Pro Asn Ile Pro Ser Tyr Arg Tyr Asp Pro Tyr Ser Lys
            245                 250                 255

Val Leu Ser Arg Glu Tyr Tyr Asp His Gln Arg Met Gln Ala Thr Arg
            260                 265                 270

Gln Glu Ala Ile Ala Ala Arg Ser Ala Lys Phe Trp Gly Leu Ile
        275                 280                 285

Leu Gly Thr Leu Gly Arg Gln Gly Ser Pro Lys Val Leu Glu His Leu
        290                 295                 300

Glu Ser Gln Leu Arg Asn Leu Gly Leu Pro Phe Leu Arg Leu Leu Leu
305                 310                 315                 320

Ser Glu Ile Phe Pro Ser Lys Leu Ser Leu Leu Pro Ser Val Asp Val
                325                 330                 335

Trp Val Gln Val Ala Cys Pro Arg Leu Ser Ile Asp Trp Gly Ser Ala
                340                 345                 350

Phe Pro Lys Pro Leu Leu Thr Pro Tyr Glu Ala Val Ala Leu Lys
            355                 360                 365

Glu Ile Ser Trp Gln Gln Pro Tyr Pro Met Asp Phe Tyr Ala Gly Ser
370                 375                 380

Ser Leu Gly Pro Trp Thr Val Asn His Gly Arg Asp Arg Ala Pro Arg
385                 390                 395                 400

Gly Leu Cys Gln Pro Ala Ser Asp Lys Val Gln Gln Gly Ser Arg Gly
            405                 410                 415

His Ser Pro Val Pro Ala Cys Glu Gly Cys Ser Cys Ala Asp Gln Lys
                420                 425                 430

Ala Thr Pro Pro Ala Pro
            435

<210> SEQ ID NO 19
<211> LENGTH: 1275
<212> TYPE: DNA
<213> ORGANISM: Gallus gallus

<400> SEQUENCE: 19
atggccgcac cgcagcgttc cggcagcgcg gctcttctgc cctccgccaa cggcgcaggc    60
cgagccccac gtcgcactgc ccgccaggtc cccgaggagc tgctgaacaa tgtggagctg   120
cgggaggcga tggggctct gccctccaac tacaacttcg agatccccaa aaccatctgg   180
cggatccagc aggcgggagc caaaaaggtg gccctgcaga tgccggaggg gctgctcatg   240
tttgcctgca ccatcgcaga tatcattgag cggttcacgg acgccaaggc ggtggtgatg   300
ggcgatgtga cctacggcgc gtgctgcgtg acgactaca cagcgcgggc tctgggtgct   360
gacttcttgg tgcactatgg acacagctgc ctgatcccca tcgatgccac gcgtgggctg   420
aagatgctct acgtcttcgt ggacatcaag attgacacat cccatttcct cgacaccatc   480
cgcttcaact tcgccgtggg ctcttccctg gccctggtca gcaccatcca gttcgtggca   540
gcagtgcagg cggcctcaca ggagctgcag tcacagtaca aggtgtgcgt gcccagtgc   600 aagccgctgt ccctggtga tactgggc tgcacatcgc cccggctcgc acgggacacc   660
gatgccattg tctatttggg ggatggccgt ttccacctgg agtccatcat gatcgccaac   720
ccggggatac cgcctacag gtatgatccc tacagcaagg tcttctcgca ggagcattat   780
gcccatgacc gcatgcgtga agcccggcag ctgccatcc gctccgccgc cgcgcccgg   840
```

```
tgctgggggc tgctgctggg caccctgggg cgacagggat cccccgccat cctacagcac    900
ctggagtcac ggctgcgtgc cctgggccgg ccctttgtgc gggtgctgct gtctgagatc    960
ttccccagca agctgcagct ctttgacagc gtggatgcgt gggtgcagat cgcctgtccc   1020
cggctctcca tcgactgggg ggaggcattc agcaaaccac tgctgacacc ctatgaggca   1080
gcggtggctc ttggggacat cgagtggcaa cagccgtacc ccatggactt ctatgccagt   1140
caatccctgg ggccgtggac ggccaaccac acagcgcggc ccgcccagga agccaccc    1200 gcaaccccca gcctgaagaa tggcactgag gggtcccgca gtgcccaccc gcctgaggac   1260
acggccacct cctga                                                    1275
```

<210> SEQ ID NO 20
<211> LENGTH: 424
<212> TYPE: PRT
<213> ORGANISM: Gallus gallus

<400> SEQUENCE: 20

```
Met Ala Ala Pro Gln Arg Ser Gly Ser Ala Ala Leu Leu Pro Ser Ala
 1               5                  10                  15

Asn Gly Ala Gly Arg Ala Pro Arg Arg Thr Ala Arg Gln Val Pro Glu
            20                  25                  30

Glu Leu Leu Asn Asn Val Glu Leu Arg Glu Ala Met Gly Ala Leu Pro
        35                  40                  45

Ser Asn Tyr Asn Phe Glu Ile Pro Lys Thr Ile Trp Arg Ile Gln Gln
    50                  55                  60

Ala Gly Ala Lys Lys Val Ala Leu Gln Met Pro Glu Gly Leu Leu Met
65                  70                  75                  80

Phe Ala Cys Thr Ile Ala Asp Ile Ile Glu Arg Phe Thr Asp Ala Lys
                85                  90                  95

Ala Val Val Met Gly Asp Val Thr Tyr Gly Ala Cys Cys Val Asp Asp
            100                 105                 110

Tyr Thr Ala Arg Ala Leu Gly Ala Asp Phe Leu Val His Tyr Gly His
        115                 120                 125

Ser Cys Leu Ile Pro Ile Asp Ala Thr Arg Gly Leu Lys Met Leu Tyr
    130                 135                 140

Val Phe Val Asp Ile Lys Ile Asp Thr Ser His Phe Leu Asp Thr Ile
145                 150                 155                 160

Arg Phe Asn Phe Ala Val Gly Ser Ser Leu Ala Leu Val Ser Thr Ile
                165                 170                 175

Gln Phe Val Ala Ala Val Gln Ala Ala Ser Gln Glu Leu Gln Ser Gln
            180                 185                 190

Tyr Lys Val Cys Val Pro Gln Cys Lys Pro Leu Ser Pro Gly Glu Ile
        195                 200                 205

Leu Gly Cys Thr Ser Pro Arg Leu Ala Arg Asp Thr Asp Ala Ile Val
    210                 215                 220

Tyr Leu Gly Asp Gly Arg Phe His Leu Glu Ser Ile Met Ile Ala Asn
225                 230                 235                 240

Pro Gly Ile Pro Ala Tyr Arg Tyr Asp Pro Tyr Ser Lys Val Phe Ser
                245                 250                 255

Gln Glu His Tyr Ala His Asp Arg Met Arg Glu Ala Arg Gln Ala Ala
            260                 265                 270

Ile Arg Ser Ala Ala Arg Ala Arg Cys Trp Gly Leu Leu Leu Gly Thr
        275                 280                 285
```

```
Leu Gly Arg Gln Gly Ser Pro Ala Ile Leu Gln His Leu Glu Ser Arg
            290                 295                 300

Leu Arg Ala Leu Gly Arg Pro Phe Val Arg Val Leu Leu Ser Glu Ile
305                 310                 315                 320

Phe Pro Ser Lys Leu Gln Leu Phe Asp Ser Val Asp Ala Trp Val Gln
                325                 330                 335

Ile Ala Cys Pro Arg Leu Ser Ile Asp Trp Gly Glu Ala Phe Ser Lys
            340                 345                 350

Pro Leu Leu Thr Pro Tyr Glu Ala Val Ala Leu Gly Asp Ile Glu
        355                 360                 365

Trp Gln Gln Pro Tyr Pro Met Asp Phe Tyr Ala Ser Gln Ser Leu Gly
370                 375                 380

Pro Trp Thr Ala Asn His Thr Ala Arg Pro Ala Gln Glu Lys Pro Pro
385                 390                 395                 400

Ala Thr Pro Ser Leu Lys Asn Gly Thr Glu Gly Ser Arg Ser Ala His
                405                 410                 415

Pro Pro Glu Asp Thr Ala Thr Ser
            420

<210> SEQ ID NO 21
<211> LENGTH: 1434
<212> TYPE: DNA
<213> ORGANISM: Gallus gallus

<400> SEQUENCE: 21
atgttcgacg gggcggcggt gaataacgga gcgctgcccc ccttcccacc ccccgccgg      60 ctgtggggga gaacgctgct gagtgcccgc tggtgggaag gggccgagc cccacgtcgc    120 actgcccgcc aggtccccga ggagctgctg aacaatgtgg agctgcggga ggcgatgggg    180
gctctgccct ccaactacaa cttcgagatc cccaaaacca tctggcggat ccagcaggcg    240
ggagccaaaa aggtggccct gcagatgccg gaggggctgc tcatgtttgc ctgcaccatc    300
gcagatatca ttgagcggtt cacggacgcc aaggcggtgg tgatgggcga tgtgacctac    360
ggcgcgtgct cgtggacga ctacacagcg cgggctctgg gtgctgactt cttggtgcac    420
tatggacaca gctgcctgat ccccatcgat gccacgcgtg ggctgaagat gctctacgtc    480
ttcgtggaca tcaagattga cacatcccat ttcctcgaca ccatccgctt caacttcgcc    540
gtgggctctt ccctggccct ggtcagcacc atccagttcg tggcagcagt gcaggcggcc    600
tcacaggagc tgcagtcaca gtacaaggtg tgcgtgcccc agtgcaagcc gctgtcccct    660
ggtgagatac tgggctgcac atcgccccgg ctcgcacggg acaccgatgc cattgtctat    720
ttgggggatg gccgtttcca cctggagtcc atcatgatcg ccaacccggg atacccgcc    780 tacaggtatg atccctacag caaggtcttc tcgcaggagc attatgccca tgaccgcatg    840
cgtgaagccc ggcaggctgc catccgctcc gccgcccgcg cccggtgctg ggggctgctg    900
ctgggcaccc tggggcgaca gggatccccc gccatcctac agcacctgga gtcacggctg    960
cgtgccctgg gcggcccctt tgtgcgggtg ctgctgtctg agatcttccc cagcaagctg   1020
cagctctttg acagcgtgga tgcgtgggtg cagatcgcct gtccccggct ctccatcgac   1080 tgggggggagg cattcagcaa accactgctg acacccatg aggcagcggt ggctcttggg   1140
gacatcgagt ggcaacagcc gtaccccatg gacttctatg ccagtcaatc cctggggccg   1200
tggacggcca accacacagc gcggcccgcc caggtaggct ctgggggtg ggggggcc      1260 ccctgtgtcc cctggtgctc gctgccatgt ggcacaagcg ccacccagtg gctcgctccc   1320
```
tggagagcag ggctggcgcc cacccggtgc cctccatcgg ggcacacatg gccccatctt    1380
tgcttacccc atgtctgtcc ctacaggaga agccacccgc aacccccagc ctga          1434

<210> SEQ ID NO 22
<211> LENGTH: 477
<212> TYPE: PRT
<213> ORGANISM: Gallus gallus

<400> SEQUENCE: 22

```
Met Phe Asp Gly Ala Ala Val Asn Asn Gly Ala Leu Pro Pro Phe Pro
1               5                   10                  15

Pro Pro Arg Arg Leu Trp Gly Arg Thr Leu Leu Ser Ala Arg Trp Trp
            20                  25                  30

Glu Gly Gly Arg Ala Pro Arg Arg Thr Ala Arg Gln Val Pro Glu Glu
        35                  40                  45

Leu Leu Asn Asn Val Glu Leu Arg Glu Ala Met Gly Ala Leu Pro Ser
    50                  55                  60

Asn Tyr Asn Phe Glu Ile Pro Lys Thr Ile Trp Arg Ile Gln Gln Ala
65                  70                  75                  80

Gly Ala Lys Lys Val Ala Leu Gln Met Pro Glu Gly Leu Leu Met Phe
                85                  90                  95

Ala Cys Thr Ile Ala Asp Ile Ile Glu Arg Phe Thr Asp Ala Lys Ala
            100                 105                 110

Val Val Met Gly Asp Val Thr Tyr Gly Ala Cys Cys Val Asp Asp Tyr
        115                 120                 125

Thr Ala Arg Ala Leu Gly Ala Asp Phe Leu Val His Tyr Gly His Ser
    130                 135                 140

Cys Leu Ile Pro Ile Asp Ala Thr Arg Gly Leu Lys Met Leu Tyr Val
145                 150                 155                 160

Phe Val Asp Ile Lys Ile Asp Thr Ser His Phe Leu Asp Thr Ile Arg
                165                 170                 175

Phe Asn Phe Ala Val Gly Ser Ser Leu Ala Leu Val Ser Thr Ile Gln
            180                 185                 190

Phe Val Ala Ala Val Gln Ala Ser Gln Glu Leu Gln Ser Gln Tyr
        195                 200                 205

Lys Val Cys Val Pro Gln Cys Lys Pro Leu Ser Pro Gly Glu Ile Leu
    210                 215                 220

Gly Cys Thr Ser Pro Arg Leu Ala Arg Asp Thr Asp Ala Ile Val Tyr
225                 230                 235                 240

Leu Gly Asp Gly Arg Phe His Leu Glu Ser Ile Met Ile Ala Asn Pro
                245                 250                 255

Gly Ile Pro Ala Tyr Arg Tyr Asp Pro Tyr Ser Lys Val Phe Ser Gln
            260                 265                 270

Glu His Tyr Ala His Asp Arg Met Arg Glu Ala Arg Gln Ala Ala Ile
        275                 280                 285

Arg Ser Ala Ala Arg Ala Arg Cys Trp Gly Leu Leu Leu Gly Thr Leu
    290                 295                 300

Gly Arg Gln Gly Ser Pro Ala Ile Leu Gln His Leu Glu Ser Arg Leu
305                 310                 315                 320

Arg Ala Leu Gly Arg Pro Phe Val Arg Val Leu Leu Ser Glu Ile Phe
                325                 330                 335

Pro Ser Lys Leu Gln Leu Phe Asp Ser Val Asp Ala Trp Val Gln Ile
            340                 345                 350

Ala Cys Pro Arg Leu Ser Ile Asp Trp Gly Glu Ala Phe Ser Lys Pro
```

|  |  | 355 |  |  | 360 |  |  | 365 |  |  |  |
|---|---|---|---|---|---|---|---|---|---|---|---|

Leu Leu Thr Pro Tyr Glu Ala Ala Val Ala Leu Gly Asp Ile Glu Trp
370 375 380

Gln Gln Pro Tyr Pro Met Asp Phe Tyr Ala Ser Gln Ser Leu Gly Pro
385 390 395 400

Trp Thr Ala Asn His Thr Ala Arg Pro Ala Gln Val Gly Ser Gly Gly
405 410 415

Trp Gly Gly Pro Pro Cys Val Pro Trp Cys Ser Leu Pro Cys Gly Thr
420 425 430

Ser Ala Thr Gln Trp Leu Ala Pro Trp Arg Ala Gly Leu Ala Pro Thr
435 440 445

Arg Cys Pro Pro Ser Gly His Thr Trp Pro His Leu Cys Leu Pro His
450 455 460

Val Cys Pro Tyr Arg Arg Ser His Pro Gln Pro Pro Ala
465 470 475

<210> SEQ ID NO 23
<211> LENGTH: 1389
<212> TYPE: DNA
<213> ORGANISM: Gallus gallus

<400> SEQUENCE: 23

```
atggccgcac cgcagcgttc cggcagcgcg gctcttctgc cctccgccaa cggcgcaggc      60
cgagccccac gtcgcactgc ccgccaggtc cccgaggagc tgctgaacaa tgtggagctg     120
cgggaggcga tgggggctct gccctccaac tacaacttcg agatccccaa aaccatctgg     180
cggatccagc aggcgggagc caaaaaggtg gccctgcaga tgccggaggg gctgctcatg     240
tttgcctgca ccatcgcaga tatcattgag cggttcacgg acgccaaggc ggtggtgatg     300
ggcgatgtga cctacggcgc gtgctgcgtg gacgactaca cagcgcgggc tctgggtgct     360
gacttcttgg tgcactatgg acacagctgc ctgatcccca tcgatgccac cgtgggctg      420
aagatgctct acgtcttcgt ggacatcaag attgacacat cccatttcct cgacaccatc     480
cgcttcaact cgccgtgggg ctcttccctg gccctggtca gcaccatcca gttcgtggca     540
gcagtgcagg cggcctcaca ggagctgcag tcacagtaca aggtgtgcgt gcccagtgc      600
aagccgctgt ccctggtga  gatactgggc tgcacatcgc cccggctcgc acgggacacc     660
gatgccattg tctatttggg ggatggccgt ttccacctgg agtccatcat gatcgccaac     720
ccggggatac ccgcctacag gtatgatccc tacagcaagg tcttctcgca ggagcattat     780
gcccatgacc gcatgcgtga agcccggcag gctgccatcc gctccgccgc ccgcgcccgg     840
tgctggggc tgctgctggg caccctgggg cgacagggat ccccgccat cctacagcac       900
ctggagtcac ggctgcgtgc cctggccgg  ccctttgtgc gggtgctgct gtctgagatc     960
ttccccagca agctgcagct ctttgacagc gtggatgcgt gggtgcagat cgcctgtccc    1020
cggctctcca tcgactgggg ggaggcattc agcaaaccac tgctgacacc ctatgaggca    1080
gcggtggctc ttggggacat cgagtggcaa cagccgtacc ccatggactt ctatgccagt    1140
caatccctgg gccgtggac  ggccaaccac acagcgcggc ccgcccaggt aggctctggg    1200
gggtgggggg ggcccccctg tgtccctgg tgctcgctgc catgtggcac aagcgccacc      1260
cagtggctcg ctccctggag agcagggctg gcgcccaccc ggtgccctcc atcggggcac    1320
acatggcccc atctttgctt accccatgtc tgtccctaca ggagaagcca cccgcaaccc    1380
ccagcctga                                                            1389
```

<210> SEQ ID NO 24
<211> LENGTH: 462
<212> TYPE: PRT
<213> ORGANISM: Gallus gallus

<400> SEQUENCE: 24

Met Ala Ala Pro Gln Arg Ser Gly Ser Ala Ala Leu Leu Pro Ser Ala
1               5                   10                  15

Asn Gly Ala Gly Arg Ala Pro Arg Arg Thr Ala Arg Gln Val Pro Glu
            20                  25                  30

Glu Leu Leu Asn Asn Val Glu Leu Arg Glu Ala Met Gly Ala Leu Pro
        35                  40                  45

Ser Asn Tyr Asn Phe Glu Ile Pro Lys Thr Ile Trp Arg Ile Gln Gln
    50                  55                  60

Ala Gly Ala Lys Lys Val Ala Leu Gln Met Pro Glu Gly Leu Leu Met
65                  70                  75                  80

Phe Ala Cys Thr Ile Ala Asp Ile Ile Glu Arg Phe Thr Asp Ala Lys
                85                  90                  95

Ala Val Val Met Gly Asp Val Thr Tyr Gly Ala Cys Cys Val Asp Asp
            100                 105                 110

Tyr Thr Ala Arg Ala Leu Gly Ala Asp Phe Leu Val His Tyr Gly His
        115                 120                 125

Ser Cys Leu Ile Pro Ile Asp Ala Thr Arg Gly Leu Lys Met Leu Tyr
    130                 135                 140

Val Phe Val Asp Ile Lys Ile Asp Thr Ser His Phe Leu Asp Thr Ile
145                 150                 155                 160

Arg Phe Asn Phe Ala Val Gly Ser Ser Leu Ala Leu Val Ser Thr Ile
                165                 170                 175

Gln Phe Val Ala Ala Val Ala Ala Ser Gln Glu Leu Gln Ser Gln
            180                 185                 190

Tyr Lys Val Cys Val Pro Gln Cys Lys Pro Leu Ser Pro Gly Glu Ile
        195                 200                 205

Leu Gly Cys Thr Ser Pro Arg Leu Ala Arg Asp Thr Asp Ala Ile Val
    210                 215                 220

Tyr Leu Gly Asp Gly Arg Phe His Leu Glu Ser Ile Met Ile Ala Asn
225                 230                 235                 240

Pro Gly Ile Pro Ala Tyr Arg Tyr Asp Pro Tyr Ser Lys Val Phe Ser
                245                 250                 255

Gln Glu His Tyr Ala His Asp Arg Met Arg Glu Ala Arg Gln Ala Ala
            260                 265                 270

Ile Arg Ser Ala Ala Arg Ala Arg Cys Trp Gly Leu Leu Leu Gly Thr
        275                 280                 285

Leu Gly Arg Gln Gly Ser Pro Ala Ile Leu Gln His Leu Glu Ser Arg
    290                 295                 300

Leu Arg Ala Leu Gly Arg Pro Phe Val Arg Val Leu Leu Ser Glu Ile
305                 310                 315                 320

Phe Pro Ser Lys Leu Gln Leu Phe Asp Ser Val Asp Ala Trp Val Gln
                325                 330                 335

Ile Ala Cys Pro Arg Leu Ser Ile Asp Trp Gly Glu Ala Phe Ser Lys
            340                 345                 350

Pro Leu Leu Thr Pro Tyr Glu Ala Ala Val Ala Leu Gly Asp Ile Glu
        355                 360                 365

Trp Gln Gln Pro Tyr Pro Met Asp Phe Tyr Ala Ser Gln Ser Leu Gly
    370                 375                 380

Pro Trp Thr Ala Asn His Thr Ala Arg Pro Ala Gln Val Gly Ser Gly
385                 390                 395                 400

Gly Trp Gly Gly Pro Pro Cys Val Pro Trp Cys Ser Leu Pro Cys Gly
            405                 410                 415

Thr Ser Ala Thr Gln Trp Leu Ala Pro Trp Arg Ala Gly Leu Ala Pro
        420                 425                 430

Thr Arg Cys Pro Pro Ser Gly His Thr Trp Pro His Leu Cys Leu Pro
        435                 440                 445

His Val Cys Pro Tyr Arg Arg Ser His Pro Gln Pro Pro Ala
    450                 455                 460

<210> SEQ ID NO 25
<211> LENGTH: 1341
<212> TYPE: DNA
<213> ORGANISM: Gallus gallus

<400> SEQUENCE: 25
atgttcgacg gggcggcggt gaataacgga gcgctgcccc ccttcccacc ccccgccgg      60 ctgtggggga gaacgctgct gagtgcccgc tggtgggaag gggccgagc cccacgtcgc     120 actgcccgcc aggtccccga ggagctgctg aacaatgtgg agctgcggga ggcgatgggg     180
gctctgccct ccaactacaa cttcgagatc cccaaaacca tctggcggat ccagcaggcg     240
ggagccaaaa aggtggccct gcagatgccg gaggggctgc tcatgtttgc ctgcaccatc     300
gcagatatca ttgagcggtt cacggacgcc aaggcggtgg tgatgggcga tgtgacctac     360
ggcgcgtgct cgtggacga ctacacagcg cgggctctgg tgctgacttc cttggtgcac     420
tatggacaca gctgcctgat ccccatcgat gccacgcgtg ggctgaagat gctctacgtc     480
ttcgtggaca tcaagattga cacatcccat ttcctcgaca ccatccgctt caacttcgcc     540
gtgggctctt ccctggccct ggtcagcacc atccagttcg tggcagcagt gcaggcggcc     600
tcacaggagc tgcagtcaca gtacaaggtg tgcgtgcccc agtgcaagcc gctgtccccct    660 ggtgagatac tgggctgcac atcgccccgg ctcgcacggg acaccgatgc cattgtctat     720 ttggggggatg ccgtttcca cctggagtcc atcatgatcg ccaacccggg gatacccgcc     780
tacaggtatg atccctacag caaggtcttc tcgcaggagc attatgccca tgaccgcatg     840
cgtgaagccc gcaggctgc catccgctcc gccgccgcg cccggtgctg ggggctgctg      900
ctgggcaccc tggggcgaca gggatccccc gccatcctac agcacctgga gtcacggctg     960
cgtgccctgg gccggccctt tgtgcggggtc ctgctgtctg agatcttccc cagcaagctg    1020
cagctctttg acagcgtgga tgcgtgggtg cagatcgcct gtccccggct ctccatcgac    1080
tggggggagg cattcagcaa accactgctg acaccctatg aggtgagcag tccccggtgg     1140
gtttcgggag accccttccc agccctgcgc gtggcactca gccccttatc ccctcctcac    1200
aggcagcggt ggctcttggg gacatcgagt ggcaacagcc gtaccccatg gacttctatg    1260
ccagtcaatc cctggggccg tggacggcca accacacagc gcggcccgcc caggagaagc    1320
cacccgcaac ccccagcctg a                                               1341

<210> SEQ ID NO 26
<211> LENGTH: 446
<212> TYPE: PRT
<213> ORGANISM: Gallus gallus

<400> SEQUENCE: 26

Met Phe Asp Gly Ala Ala Val Asn Asn Gly Ala Leu Pro Pro Phe Pro

-continued

```
1               5                   10                  15
Pro Pro Arg Arg Leu Trp Gly Arg Thr Leu Leu Ser Ala Arg Trp Trp
                20                  25                  30
Glu Gly Gly Arg Ala Pro Arg Arg Thr Ala Arg Gln Val Pro Glu Glu
                35                  40                  45
Leu Leu Asn Asn Val Glu Leu Arg Glu Ala Met Gly Ala Leu Pro Ser
 50                  55                  60
Asn Tyr Asn Phe Glu Ile Pro Lys Thr Ile Trp Arg Ile Gln Gln Ala
 65                  70                  75                  80
Gly Ala Lys Lys Val Ala Leu Gln Met Pro Glu Gly Leu Leu Met Phe
                85                  90                  95
Ala Cys Thr Ile Ala Asp Ile Ile Glu Arg Phe Thr Asp Ala Lys Ala
                100                 105                 110
Val Val Met Gly Asp Val Thr Tyr Gly Ala Cys Cys Val Asp Asp Tyr
                115                 120                 125
Thr Ala Arg Ala Leu Gly Ala Asp Phe Leu Val His Tyr Gly His Ser
 130                 135                 140
Cys Leu Ile Pro Ile Asp Ala Thr Arg Gly Leu Lys Met Leu Tyr Val
145                 150                 155                 160
Phe Val Asp Ile Lys Ile Asp Thr Ser His Phe Leu Asp Thr Ile Arg
                165                 170                 175
Phe Asn Phe Ala Val Gly Ser Ser Leu Ala Leu Val Ser Thr Ile Gln
                180                 185                 190
Phe Val Ala Ala Val Gln Ala Ser Gln Glu Leu Gln Ser Gln Tyr
                195                 200                 205
Lys Val Cys Val Pro Gln Cys Lys Pro Leu Ser Pro Gly Glu Ile Leu
 210                 215                 220
Gly Cys Thr Ser Pro Arg Leu Ala Arg Asp Thr Asp Ala Ile Val Tyr
225                 230                 235                 240
Leu Gly Asp Gly Arg Phe His Leu Glu Ser Ile Met Ile Ala Asn Pro
                245                 250                 255
Gly Ile Pro Ala Tyr Arg Tyr Asp Pro Tyr Ser Lys Val Phe Ser Gln
                260                 265                 270
Glu His Tyr Ala His Asp Arg Met Arg Glu Ala Arg Gln Ala Ala Ile
                275                 280                 285
Arg Ser Ala Ala Arg Ala Arg Cys Trp Gly Leu Leu Leu Gly Thr Leu
 290                 295                 300
Gly Arg Gln Gly Ser Pro Ala Ile Leu Gln His Leu Glu Ser Arg Leu
305                 310                 315                 320
Arg Ala Leu Gly Arg Pro Phe Val Arg Val Leu Leu Ser Glu Ile Phe
                325                 330                 335
Pro Ser Lys Leu Gln Leu Phe Asp Ser Val Asp Ala Trp Val Gln Ile
                340                 345                 350
Ala Cys Pro Arg Leu Ser Ile Asp Trp Gly Glu Ala Phe Ser Lys Pro
                355                 360                 365
Leu Leu Thr Pro Tyr Glu Val Ser Ser Pro Arg Trp Val Ser Gly Gly
 370                 375                 380
Pro Leu Pro Ala Leu Arg Val Ala Leu Ser Pro Leu Ser Pro His
385                 390                 395                 400
Arg Gln Arg Trp Leu Leu Gly Thr Ser Ser Gly Asn Ser Arg Thr Pro
                405                 410                 415
Trp Thr Ser Met Pro Val Asn Pro Trp Gly Arg Gly Arg Pro Thr Thr
                420                 425                 430
```

Gln Arg Gly Pro Pro Arg Arg Ser His Pro Gln Pro Pro Ala
        435                 440                 445

<210> SEQ ID NO 27
<211> LENGTH: 1319
<212> TYPE: DNA
<213> ORGANISM: Gallus gallus

<400> SEQUENCE: 27

| | | |
|---|---|---|
| atgttcgacg gggcggcggt gaataacgga gcgctgcccc ccttcccacc ccccgccgg | 60 |
| ctgtggggga gaacgctgct gagtgcccgc tggtgggaag ggggccgagc ccacgtcgc | 120 |
| actgcccgcc aggtccccga ggagctgctg aacaatgtgg agctgcggga ggcgatgggg | 180 |
| gctctgccct ccaactacaa cttcgagatc cccaaaacca tctggcggat ccagcaggcg | 240 |
| ggagccaaaa aggtggccct gcagatgccg gaggggctgc tcatgtttgc ctgcaccatc | 300 |
| gcagatatca ttgagcggtt cacggacgcc aaggcggtgg tgatgggcga tgtgacctac | 360 |
| ggcgcgtgct gcgtggacga ctacacagcg cgggctctgg gtgctgactt cttggtgcac | 420 |
| tatggacaca gctgcctgat ccccatcgat gccacgcgtg ggctgaagat gctctacgtc | 480 |
| ttcgtggaca tcaagattga cacatcccat ttcctcgaca ccatccgctt caacttcgcc | 540 |
| gtgggctctt ccctggccct ggtcagcacc atccagttcg tggcagcagt gcaggcggcc | 600 |
| tcacaggagc tgcagtcaca gtacaaggtg tgcgtgcccc agtgcaagcc gctgtccccct | 660 |
| ggtgagatac tgggctgcac atcgccccgg ctcgcacggg acaccgatgc cattgtctat | 720 |
| ttgggggatg ccgttttcca cctggagtcc atcatgatcg ccaacccggg ataccccgcc | 780 |
| tacaggtatg atccctacag caaggtcttc tcgcaggagc attatgccca tgaccgcatg | 840 |
| cgtgaagccc ggcaggctgc catccgctcc gccgccgcg cccggtgctg ggggctgctg | 900 |
| ctgggcaccc tggggcgaca gggatccccc gccatcctac agcacctgga gtcacggctg | 960 |
| cgtgccctgg gccggccctt gtgcggggtg ctgctgtctg agatcttccc cagcaagctg | 1020 |
| cagctctttg acagcgtgga tgcgtgggtg cagatcgcct gtccccggct ctccatcgac | 1080 |
| tggggggagg cattcagcaa accactgctg acaccctatg aggcagcggt ggctcttggg | 1140 |
| gacatcgagt ggcaacagcc gtaccccatg gacttctatg ccagtcaatc cctggggccg | 1200 |
| tggacggcca accacacagc gcggcccgcc caggagaagc cacccgcaac ccccagcctg | 1260 |
| aagaatggca ctgaggggtc ccgcagtgcc cacccgcctg aggacacggc cacctcctg | 1319 |

<210> SEQ ID NO 28
<211> LENGTH: 439
<212> TYPE: PRT
<213> ORGANISM: Gallus gallus

<400> SEQUENCE: 28

Met Phe Asp Gly Ala Ala Val Asn Asn Gly Ala Leu Pro Pro Phe Pro
1               5                   10                  15

Pro Pro Arg Arg Leu Trp Gly Arg Thr Leu Leu Ser Ala Arg Trp Trp
            20                  25                  30

Glu Gly Gly Arg Ala Pro Arg Arg Thr Ala Arg Gln Val Pro Glu Glu
        35                  40                  45

Leu Leu Asn Asn Val Glu Leu Arg Glu Ala Met Gly Ala Leu Pro Ser
    50                  55                  60

Asn Tyr Asn Phe Glu Ile Pro Lys Thr Ile Trp Arg Ile Gln Gln Ala
65                  70                  75                  80

Gly Ala Lys Lys Val Ala Leu Gln Met Pro Glu Gly Leu Leu Met Phe
            85                  90                  95

Ala Cys Thr Ile Ala Asp Ile Ile Glu Arg Phe Thr Asp Ala Lys Ala
           100                 105                 110

Val Val Met Gly Asp Val Thr Tyr Gly Ala Cys Cys Val Asp Asp Tyr
           115                 120                 125

Thr Ala Arg Ala Leu Gly Ala Asp Phe Leu Val His Tyr Gly His Ser
130                 135                 140

Cys Leu Ile Pro Ile Asp Ala Thr Arg Gly Leu Lys Met Leu Tyr Val
145                 150                 155                 160

Phe Val Asp Ile Lys Ile Asp Thr Ser His Phe Leu Asp Thr Ile Arg
                165                 170                 175

Phe Asn Phe Ala Val Gly Ser Ser Leu Ala Leu Val Ser Thr Ile Gln
            180                 185                 190

Phe Val Ala Ala Val Gln Ala Ala Ser Gln Glu Leu Gln Ser Gln Tyr
        195                 200                 205

Lys Val Cys Val Pro Gln Cys Lys Pro Leu Ser Pro Gly Glu Ile Leu
210                 215                 220

Gly Cys Thr Ser Pro Arg Leu Ala Arg Asp Thr Asp Ala Ile Val Tyr
225                 230                 235                 240

Leu Gly Asp Gly Arg Phe His Leu Glu Ser Ile Met Ile Ala Asn Pro
                245                 250                 255

Gly Ile Pro Ala Tyr Arg Tyr Asp Pro Tyr Ser Lys Val Phe Ser Gln
            260                 265                 270

Glu His Tyr Ala His Asp Arg Met Arg Glu Ala Arg Gln Ala Ala Ile
        275                 280                 285

Arg Ser Ala Ala Arg Ala Arg Cys Trp Gly Leu Leu Leu Gly Thr Leu
290                 295                 300

Gly Arg Gln Gly Ser Pro Ala Ile Leu Gln His Leu Glu Ser Arg Leu
305                 310                 315                 320

Arg Ala Leu Gly Arg Pro Phe Val Arg Val Leu Leu Ser Glu Ile Phe
                325                 330                 335

Pro Ser Lys Leu Gln Leu Phe Asp Ser Val Asp Ala Trp Val Gln Ile
            340                 345                 350

Ala Cys Pro Arg Leu Ser Ile Asp Trp Gly Glu Ala Phe Ser Lys Pro
        355                 360                 365

Leu Leu Thr Pro Tyr Glu Ala Val Ala Leu Gly Asp Ile Glu Trp
370                 375                 380

Gln Gln Pro Tyr Pro Met Asp Phe Tyr Ala Ser Gln Ser Leu Gly Pro
385                 390                 395                 400

Trp Thr Ala Asn His Thr Ala Arg Pro Ala Gln Glu Lys Pro Pro Ala
                405                 410                 415

Thr Pro Ser Leu Lys Asn Gly Thr Glu Gly Ser Arg Ser Ala His Pro
            420                 425                 430

Pro Glu Asp Thr Ala Thr Ser
        435

<210> SEQ ID NO 29
<211> LENGTH: 1377
<212> TYPE: DNA
<213> ORGANISM: Xenopus tropicalis

<400> SEQUENCE: 29
atgtcagaga tggcggaaga gccggttggg ttggagactg cgactgggac ggatcctcag      60

-continued

| | |
|---|---|
| ctgggaatga tggctccggc gagaagccag tcagtagcac tgacacctgc ggctcccagt | 120 |
| aatgcaggcc gtgcacccat ccgtcgcgtg gctaaccaga tccctgatga aatctcccac | 180 |
| aatcctcttc tgctggaagc catgaaagtg ctgcccgaaa actacaattt tgaaataccc | 240 |
| aagacaatat ggagaattca gcaagcctca gccaaaagag ttgctttgca gatgccagaa | 300 |
| gggcttctca tgtttgcctg tactattgct gatatcatag aaaggttcac atcagcagag | 360 |
| acagtagtga tgggcgatgt gacgtatgga gcatgctgtg tggatgatta cactgcacaa | 420 |
| gcgctaggag ctgactttat ggtacattat ggacacagct gcctcatccc gattgatgcc | 480 |
| acgcatgggg tgcgtatgtt atatgttttt gtcgacataa agattgacac gtctcatttt | 540 |
| gtggacacca ttcgcttcaa ctttcaaccg ggagcatcac tagcgcttgt cagcacggtg | 600 |
| cagtttgtgt cagcacttca ggcagctcac caagccttac gtatggacta caaagtgact | 660 |
| gttccacagt gcaagccgct gtcacctgga gaaatcttag gttgcacctc tccaaagctg | 720 |
| gacaagtctg tggatgccgt agtgtatctg ggagatggac gctttcacct ggagtctgtt | 780 |
| atgatttcca accctgatac aaaagcttac aggtatgatc catacagcaa ggtattctct | 840 |
| cgggaatatt atgaccacag tgccatgctt aaacacagag gggaggccat ctcagctgct | 900 |
| gccggtgcaa aaacatgggg gcttatcctg gtactctggg tcgtcaggg atctcccaaa | 960 |
| atcctggagc acctggagtc acgtctgcag gcactcggct gtcgttacgt gcggctgctg | 1020 |
| ctgtcggaaa tcttccctaa taaactcaag ctgttcccag aggtggaagt gtgggtgcag | 1080 |
| gttgcctgcc aagactatc cattgattgg gggacagcat tctccaggcc tttgcttact | 1140 |
| ccatatgagg cctcagtggc tctgaaagaa gcagaatggc agcatactta tccaatggat | 1200 |
| ttctacgcca atgagtccct tggtccgtgg accgtgaacc atgaatccca ccgccccacc | 1260 |
| cgtgcaacag tccagcgcac acagaaatca gagcagagaa agcttcggag cacagacata | 1320 |
| agtgcaaagg ttgaagaatg cccctgtcag gataaaggag agaccaagac tgagtga | 1377 |

<210> SEQ ID NO 30
<211> LENGTH: 458
<212> TYPE: PRT
<213> ORGANISM: Xenopus tropicalis

<400> SEQUENCE: 30

Met Ser Glu Met Ala Glu Glu Pro Val Gly Leu Glu Thr Ala Thr Gly
1               5                   10                  15

Thr Asp Pro Gln Leu Gly Met Met Ala Pro Ala Arg Ser Gln Ser Val
            20                  25                  30

Ala Leu Thr Pro Ala Ala Pro Ser Asn Ala Gly Arg Ala Pro Ile Arg
        35                  40                  45

Arg Val Ala Asn Gln Ile Pro Asp Glu Ile Ser His Asn Pro Leu Leu
    50                  55                  60

Leu Glu Ala Met Lys Val Leu Pro Glu Asn Tyr Asn Phe Glu Ile Pro
65                  70                  75                  80

Lys Thr Ile Trp Arg Ile Gln Gln Ala Ser Ala Lys Arg Val Ala Leu
                85                  90                  95

Gln Met Pro Glu Gly Leu Leu Met Phe Ala Cys Thr Ile Ala Asp Ile
            100                 105                 110

Ile Glu Arg Phe Thr Ser Ala Glu Thr Val Val Met Gly Asp Val Thr
        115                 120                 125

Tyr Gly Ala Cys Cys Val Asp Asp Tyr Thr Ala Gln Ala Leu Gly Ala
    130                 135                 140

Asp Phe Met Val His Tyr Gly His Ser Cys Leu Ile Pro Ile Asp Ala
145                 150                 155                 160

Thr His Gly Val Arg Met Leu Tyr Val Phe Val Asp Ile Lys Ile Asp
            165                 170                 175

Thr Ser His Phe Val Asp Thr Ile Arg Phe Asn Phe Gln Pro Gly Ala
        180                 185                 190

Ser Leu Ala Leu Val Ser Thr Val Gln Phe Val Ser Ala Leu Gln Ala
    195                 200                 205

Ala His Gln Ala Leu Arg Met Asp Tyr Lys Val Thr Val Pro Gln Cys
210                 215                 220

Lys Pro Leu Ser Pro Gly Glu Ile Leu Gly Cys Thr Ser Pro Lys Leu
225                 230                 235                 240

Asp Lys Ser Val Asp Ala Val Val Tyr Leu Gly Asp Gly Arg Phe His
            245                 250                 255

Leu Glu Ser Val Met Ile Ser Asn Pro Asp Thr Lys Ala Tyr Arg Tyr
        260                 265                 270

Asp Pro Tyr Ser Lys Val Phe Ser Arg Glu Tyr Tyr Asp His Ser Ala
    275                 280                 285

Met Leu Lys His Arg Gly Glu Ala Ile Ser Ala Ala Gly Ala Lys
290                 295                 300

Thr Trp Gly Leu Ile Leu Gly Thr Leu Gly Arg Gln Gly Ser Pro Lys
305                 310                 315                 320

Ile Leu Glu His Leu Glu Ser Arg Leu Gln Ala Leu Gly Cys Arg Tyr
            325                 330                 335

Val Arg Leu Leu Leu Ser Glu Ile Phe Pro Asn Lys Leu Lys Leu Phe
        340                 345                 350

Pro Glu Val Glu Val Trp Val Gln Val Ala Cys Pro Arg Leu Ser Ile
    355                 360                 365

Asp Trp Gly Thr Ala Phe Ser Arg Pro Leu Leu Thr Pro Tyr Glu Ala
370                 375                 380

Ser Val Ala Leu Lys Glu Ala Glu Trp Gln His Thr Tyr Pro Met Asp
385                 390                 395                 400

Phe Tyr Ala Asn Glu Ser Leu Gly Pro Trp Thr Val Asn His Glu Ser
            405                 410                 415

His Arg Pro Thr Arg Ala Thr Val Gln Arg Thr Gln Lys Ser Glu Gln
        420                 425                 430

Arg Lys Leu Arg Ser Thr Asp Ile Ser Ala Lys Val Glu Glu Cys Pro
    435                 440                 445

Cys Gln Asp Lys Gly Thr Lys Thr Glu
450                 455

<210> SEQ ID NO 31
<211> LENGTH: 1470
<212> TYPE: DNA
<213> ORGANISM: Homo sapiens

<400> SEQUENCE: 31
atggagtcga tgtttagcag ccctgccgag gcggcgctgc agcgagagac cggggtgcca      60
ggactgctta ctcctcttcc ggacctggac ggagtgtacg agctggagcg agtcgctgga     120
tttgtccgcg acctggggtg tgaacgagtt gccttgcagt tccctgacca gctattggga     180
gatgctgtgg ctgtggctgc acgactggag gagacgacag ggtcaaagat gttcattctg     240
ggtgacacag cctacggcag ctgctgcgtg gatgtgctgg gtgctgagca agctggagct     300
caggctctca tacattttgg ccctgcctgc ttaagccctc agcccgccc actgcccgtt      360

```
gccttcgtgc ttcgtcaacg ttctgtggcc ttggagctct gtgtcaaggc ctttgaggcc      420
cagaacccag accccaaagc gcctgtggtg ctgctgagtg agccggcctg tgcccatgcc      480
ctggaggctt tggctactct cctgcgccca cggtacctgg acctgctagt ctccagccca      540
gcttttcccc aaccagtggg ttccctgagt ccagagccta tgcccctaga gcgttttggg      600
cgccgcttcc cccttgcccc agggaggcgt ctagaagagt atggtgcctt ctatgtaggg      660
ggctctaagg ccagccctga cccagacctt gacccagacc tgagtcggct gctcttgggg      720
tgggcaccag gtcaacccct tcctcctgc tgtccagata cagggaagac tcaggatgag       780
ggtgcccggg ctggacggct aagggcacga agacgatatc tggtagagag ggccagagat      840
gcccgcgtgg tagggctgct ggcaggcaca ctgggtgtag cccaacaccg tgaggcactg      900
gcccacttgc ggaacctgac tcaggctgct ggcaagcgta gctatgtgtt ggccctgggg      960
cggcccaccc ctgccaagct tgccaacttc cctgaggtgg atgtctttgt gctattagcc     1020
tgtcctctgg gtgctctagc cccccagctt tctggtagct tcttccagcc tatactggca     1080
ccatgtgagc tggaagctgc ctgcaaccct gcctggccac ctccaggcct ggctccccac     1140
ctcacacatt atgcggactt attgcctggc tctcccttcc acgtggctct cccaccacct     1200
gagtcagagc tgtgggaaac cccagacgtg tcactcatta ctggagatct ccgaccccca     1260
cctgcctgga agtcatcaaa tgatcatgga agcttggctc tgaccccacg gcccagctg      1320 gagctggctg agagcagtcc tgcagcctca ttccttagtt cccggagctg caagggctg      1380 gagccccgcc tgggtcagac gccagtgaca gaagctgtga gtggaagacg agggattgcc     1440
atcgcctatg aggatgaggg aagcggctga                                      1470
```

<210> SEQ ID NO 32
<211> LENGTH: 786
<212> TYPE: DNA
<213> ORGANISM: Homo sapiens

<400> SEQUENCE: 32

```
atggagtcga tgtttagcag ccctgccgag gcggcgctgc agcgagagac cggggtgcca       60
ggactgctta ctcctcttcc ggacctggac ggagtgtacg agctggagcg agtcgctgga      120
tttgtccgcg acctggggtg tgaacgagtt gccttgcagt tccctgacca gctattggga      180
gatgctgtgg ctgtggctgc acgactggag agacgacag ggtcaaagat gttcattctg       240
ggtgacacag cctacggcag ctgctgcgtg gatgtgctgg gtgctgagca agctggagct      300
caggctctca tacattttgg ccctgcctgc ttaagccctc cagcccgccc actgcccgtt      360
gccttcgtgc ttcgtcaacg ttctgtggcc ttggagctct gtgtcaaggc ctttgaggcc      420
cagaacccag accccaaagc gcctgtggtg ctgctgagtg agccggcctg tgcccatgcc      480
ctgggctctc ccttccacgt ggctctccca ccacctgagt cagagctgtg ggaaacccca      540
gacgtgtcac tcattactgg agatctccga ccccacctg cctggaagtc atcaaatgat       600
catggaagct ggctctgac cccacggccc agctggagc tggctgagag cagtcctgca        660
gcctcattcc ttagttcccg gagctggcaa gggctggagc ccgcctgggt cagacgcca      720 gtgacagaag ctgtgagtgg aagacgaggg attgccatcg cctatgagga tgagggaagc     780
ggctga                                                                 786
```

<210> SEQ ID NO 33
<211> LENGTH: 1242
<212> TYPE: DNA

<213> ORGANISM: Homo sapiens

<400> SEQUENCE: 33

```
atgttcattc tgggtgacac agcctacggc agctgctgcg tggatgtgct gggtgctgag      60
caagctggag ctcaggctct catacatttt ggccctgcct gcttaagccc tccagcccgc     120
ccactgcccg ttgccttcgt gcttcgtcaa cgttctgtgg ccttggagct ctgtgtcaag     180
gcctttgagg cccagaaccc agaccccaaa gcgcctgtgg tgctgctgag tgagccggcc     240
tgtgcccatg ccctggaggc tttggctact ctcctgcgcc acggtacct  ggacctgcta     300
gtctccagcc cagcttttcc caaccagtg  ggttccctga gtccagagcc tatgccccta     360
gagcgttttg ggcgccgctt ccccttgcc  ccagggaggc gtctagaaga gtatggtgcc     420
ttctatgtag ggggctctaa ggccagccct gacccagacc ttgacccaga cctgagtcgg     480
ctgctcttgg ggtgggcacc aggtcaaccc ttctcctcct gctgtccaga tacagggaag     540
actcaggatg agggtgcccg ggctggacgg ctaagggcac gaagacgata tctggtagag     600
agggccagag atgcccgcgt ggtagggctg ctggcaggca cactgggtgt agcccaacac     660
cgtgaggcac tggcccactt gcggaacctg actcaggctg ctggcaagcg tagctatgtg     720
ttggccctgg ggcggcccac ccctgccaag cttgccaact ccctgaggt  ggatgtctttt    780
gtgctattag cctgtcctct gggtgctcta gcccccagc  tttctggtag cttcttccag     840
cctatactgg caccatgtga gctggaagct gcctgcaacc ctgcctggcc acctccaggc     900
ctggctcccc acctcacaca ttatgcggac ttattgcctg gctctccctt ccacgtggct     960
ctcccaccac ctgagtcaga gctgtgggaa accccagacg tgtcactcat tactgggagat   1020
ctccgacccc cacctgcctg gaagtcatca aatgatcatg gaagcttggc tctgaccccca   1080
cggccccagc tggagctggc tgagagcagt cctgcagcct cattccttag ttcccggagc    1140
tggcaagggc tggagccccg cctgggtcag acgccagtga cagaagctgt gagtggaaga    1200
cgagggattg ccatcgccta tgaggatgag ggaagcggct ga                       1242
```

<210> SEQ ID NO 34
<211> LENGTH: 1197
<212> TYPE: DNA
<213> ORGANISM: Homo sapiens

<400> SEQUENCE: 34

```
atggagtcga tgtttagcag ccctgccgag gcggcgctgc agcgagagac cggggtgcca    60
ggactgctta ctcctcttcc ggacctggac ggagtgtacg agctggagcg agtcgctgga   120
tttgtccgcg acctggggtg tgaacgagtt gccttgcagt ccctgaccca gctattggga   180
gatgctgtgg ctgtggctgc acgactggag gagacgacag ggtcaaagat gttcattctg   240
ggtgacacag cctacggcag ctgctgcgtg gatgtgctgg tgctgagca  agctggagct   300
caggctctca tacattttgg ccctgcctgc ttaagccctc agcccgccc  actgccgtt    360
gccttcgtgc ttcgtcaacg ttctgtgcc  ttggagctct gtgtcaaggc ctttgaggcc   420
cagaacccag accccaaagc gcctgtggtg ctgctgagtg agccggcctg tgcccatgcc   480
ctggatacag ggaagactca ggatgagggt gcccggctg  acggctaag  ggcacgaaga   540
cgatatctgg tagagagggc cagagatgcc cgcgtggtag ggctgctggc aggcacactg   600
ggtgtagccc aacaccgtga ggcactggcc cacttgcgga acctgactca ggctgctggc   660
aagcgtagct atgtgttggc cctggggcgg cccaccctg  ccaagcttgc caacttccct   720
gaggtggatg tctttgtgct attagcctgt cctctgggtg ctctagcccc ccagctttct    780
```

```
ggtagcttct tccagcctat actggcacca tgtgagctgg aagctgcctg caaccctgcc      840
tggccacctc caggcctggc tccccacctc acacattatg cggacttatt gcctggctct      900
cccttccacg tggctctccc accacctgag tcagagctgt gggaaacccc agacgtgtca      960
ctcattactg gagatctccg accccacct gcctggaagt catcaaatga tcatggaagc     1020
ttggctctga ccccacggcc ccagctggag ctggctgaga gcagtcctgc agcctcattc     1080
cttagttccc ggagctggca agggctggag ccccgcctgg gtcagacgcc agtgacagaa     1140
gctgtgagtg aagacgagg gattgccatc gcctatgagg atgagggaag cggctga         1197
```

<210> SEQ ID NO 35
<211> LENGTH: 891
<212> TYPE: DNA
<213> ORGANISM: Homo sapiens

<400> SEQUENCE: 35

```
atgcccctag agcgttttgg gcgccgcttc ccccttgccc cagggaggcg tctagaagag       60
tatggtgcct tctatgtagg gggctctaag gccagccctg acccagacct tgacccagac      120
ctgagtcggc tgctcttggg gtgggcacca ggtcaaccct tctcctcctg ctgtccagat      180
acagggaaga ctcaggatga gggtgcccgg gctggacggc taagggcacg aagacgatat      240
ctggtagaga gggccagaga tgcccgcgtg gtagggctgc tggcaggcac actgggtgta      300
gcccaacacc gtgaggcact ggcccacttg cggaacctga ctcaggctgc tggcaagcgt      360
agctatgtgt tggccctggg gcggccacc cctgccaagc ttgccaactt ccctgaggtg      420
gatgtctttg tgctattagc ctgtcctctg ggtgctctag ccccccagct ttctggtagc      480
ttcttccagc ctatactggc accatgtgag ctggaagctg cctgcaaccc tgcctggcca      540
cctccaggcc tggctcccca cctcacacat tatgcggact tattgcctgg ctctcccttc      600
cacgtggctc tcccaccacc tgagtcagag ctgtgggaaa ccccagacgt gtcactcatt      660
actggagatc tccgaccccc acctgcctgg aagtcatcaa atgatcatgg aagcttggct      720
ctgaccccac ggccccagct ggagctggct gagagcagtc ctgcagcctc attccttagt      780
tcccggagct ggcaagggct ggagcccgc ctgggtcaga cgccagtgac agaagctgtg      840
agtggaagac gagggattgc catcgcctat gaggatgagg aagcggctg a                891
```

<210> SEQ ID NO 36
<211> LENGTH: 1242
<212> TYPE: DNA
<213> ORGANISM: Homo sapiens

<400> SEQUENCE: 36

```
atgttcattc tgggtgacac agcctacggc agctgctgcg tggatgtgct gggtgctgag       60
caagctggag ctcaggctct catacatttt ggccctgcct gcttaagccc tccagcccgc      120
ccactgcccg ttgccttcgt gcttcgtcaa cgttctgtgg ccttggagct ctgtgtcaag      180
gcctttgagg cccagaaccc agaccccaaa gcgcctgtgg tgctgctgag tgagccggcc      240
tgtgcccatg ccctggaggc tttggctact ctcctgcgcc cacggtacct ggacctgcta      300
gtctccagcc cagcttttcc ccaaccagtg ggttccctga gtccagagcc tatgccccta      360
gagcgttttg ggcgccgctt ccccctgcc ccagggaggc gtctagaaga gtatggtgcc      420
ttctatgtag ggggctctaa ggccagccct gacccagacc ttgacccaga cctgagtcgg      480
ctgctcttgg ggtgggcacc aggtcaaccc ttctcctcct gctgtccaga tacagggaag      540
```

| | |
|---|---|
| actcaggatg agggtgcccg ggctggacgg ctaagggcac gaagacgata tctggtagag | 600 |
| agggccagag atgcccgcgt ggtagggctg ctggcaggca cactgggtgt agcccaacac | 660 |
| cgtgaggcac tggcccactt gcggaacctg actcaggctg ctggcaagcg tagctatgtg | 720 |
| ttggccctgg ggcggcccac ccctgccaag cttgccaact tccctgaggt ggatgtcttt | 780 |
| gtgctattag cctgtcctct gggtgctcta gccccccagc tttctggtag cttcttccag | 840 |
| cctatactgg caccatgtga gctggaagct gcctgcaacc ctgcctggcc acctccaggc | 900 |
| ctggctcccc acctcacaca ttatgcggac ttattgcctg gctctccctt ccacgtggct | 960 |
| ctcccaccac ctgagtcaga gctgtgggaa accccagacg tgtcactcat tactggagat | 1020 |
| ctccgacccc cacctgcctg gaagtcatca aatgatcatg gaagcttggc tctgacccca | 1080 |
| cggccccagc tggagctggc tgagagcagt cctgcagcct cattccttag ttcccggagc | 1140 |
| tggcaagggc tggagcccg cctgggtcag acgccagtga cagaagctgt gagtggaaga | 1200 |
| cgagggattg ccatcgccta tgaggatgag ggaagcggct ga | 1242 |

<210> SEQ ID NO 37
<211> LENGTH: 1065
<212> TYPE: DNA
<213> ORGANISM: Homo sapiens

<400> SEQUENCE: 37

| | |
|---|---|
| atgctgtggc tgtggctgca cgactggagg agacgacagg gtcaaagatg ttcattctgg | 60 |
| gtgacacagc ctacggcaga ggctttggct actctcctgc gcccacggta cctggacctg | 120 |
| ctagtctcca gccagctttt tcccaaccca gtgggttccc tgagtccaga gcctatgccc | 180 |
| ctagagcgtt ttgggcgccg cttccccctt gccccaggga ggcgtctaga agagtatggt | 240 |
| gccttctatg taggggggctc taaggccagc cctgacccag accttgaccc agacctgagt | 300 |
| cggctgctct tggggtgggc accaggtcaa cccttctcct cctgctgtcc agatacaggg | 360 |
| aagactcagg atgagggtgc ccgggctgga cggctaaggg cacgaagacg atatctggta | 420 |
| gagagggcca gagatgcccg cgtggtaggg ctgctggcag gcacactggg tgtagcccaa | 480 |
| caccgtgagg cactggccca cttgcggaac ctgactcagg ctgctggcaa gcgtagctat | 540 |
| gtgttggccc tggggcggcc caccctgcc aagcttgcca acttccctga ggtggatgtc | 600 |
| tttgtgctat agcctgtcc tctgggtgct ctagcccccc agctttctgg tagcttcttc | 660 |
| cagcctatac tggcaccatg tgagctggaa gctgcctgca accctgcctg gccacctcca | 720 |
| ggcctggctc cccacctcac acattatgcg gacttattgc ctggctctcc cttccacgtg | 780 |
| gctctcccac cacctgagtc agagctgtgg gaaacccag acgtgtcact cattactgga | 840 |
| gatctccgac ccccacctgc ctggaagtca tcaaatgatc atggaagctt ggctctgacc | 900 |
| ccacggcccc agctggagct ggctgagagc agtcctgcag cctcattcct tagttcccgg | 960 |
| agctggcaag gctggagcc ccgcctgggt cagacgccag tgacagaagc tgtgagtgga | 1020 |
| agacgaggga ttgccatcgc ctatgaggat gagggaagcg gctga | 1065 |

<210> SEQ ID NO 38
<211> LENGTH: 891
<212> TYPE: DNA
<213> ORGANISM: Homo sapiens

<400> SEQUENCE: 38

| | |
|---|---|
| atgcccctag agcgttttgg gcgccgcttc ccccttgccc cagggaggcg tctagaagag | 60 |
| tatggtgcct tctatgtagg gggctctaag gccagccctg acccagacct tgacccagac | 120 |

```
ctgagtcggc tgctcttggg gtgggcacca ggtcaaccct tctcctcctg ctgtccagat      180
acagggaaga ctcaggatga gggtgcccgg gctggacggc taagggcacg aagacgatat      240
ctggtagaga gggccagaga tgcccgcgtg gtagggctgc tggcaggcac actgggtgta      300
gcccaacacc gtgaggcact ggcccacttg cggaacctga ctcaggctgc tggcaagcgt      360
agctatgtgt tggccctggg gcggcccacc cctgccaagc ttgccaactt ccctgaggtg      420
gatgtctttg tgctattagc ctgtcctctg ggtgctctag ccccccagct ttctggtagc      480
ttcttccagc ctatactggc accatgtgag ctggaagctg cctgcaaccc tgcctggcca      540
cctccaggcc tggctcccca cctcacacat tatgcggact tattgcctgg ctctcccttc      600
cacgtggctc tcccaccacc tgagtcagag ctgtgggaaa ccccagacgt gtcactcatt      660 actgagagatc tccgaccccc acctgcctgg aagtcatcaa atgatcatgg aagcttggct      720
ctgaccccac ggcccagct ggagctggct gagagcagtc ctgcagcctc attccttagt      780
tcccggagct ggcaagggct ggagccccgc ctgggtcaga cgccagtgac agaagctgtg      840
agtggaagac gagggattgc catcgcctat gaggatgagg aagcggctg a                891
```

`<210>` SEQ ID NO 39
`<211>` LENGTH: 1026
`<212>` TYPE: DNA
`<213>` ORGANISM: Homo sapiens

`<400>` SEQUENCE: 39

```
atgccctggg taaggggttt tgcctgtgta tgcacaaagg aggctttggc tactctcctg       60
cgcccacggt acctggacct gctagtctcc agcccagctt ttccccaacc agtgggttcc      120
ctgagtccag agcctatgcc cctagagcgt tttgggcgcc gcttcccct tgccccaggg       180 aggcgtctag aagagtatgg tgccttctat gtaggggct ctaaggccag ccctgaccca      240
gaccttgacc cagacctgag tcggctgctc ttggggtggg caccaggtca acccttctcc      300
tcctgctgtc cagatacagg gaagactcag gatgaggtg cccgggctgg acggctaagg      360
gcacgaagac gatatctggt agagagggcc agagatgccc gcgtggtagg gctgctggca      420
ggcacactgg gtgtagccca acaccgtgag gcactggccc acttgcggaa cctgactcag      480
gctgctggca agcgtagcta tgtgttggcc ctggggcggc ccaccctgc caagcttgcc      540 aacttccctg aggtggatgt ctttgtgcta ttagcctgtc ctctgggtgc tctagccccc      600
cagctttctg gtagcttctt ccagcctata ctggcaccat gtgagctgga agctgcctgc      660
aaccctgcct ggccacctcc aggcctggct ccccacctca cacattatgc ggacttattg      720
cctggctctc ccttccacgt ggctctccca ccacctgagt cagagctgtg ggaaacccca      780
gacgtgtcac tcattactgg agatctccga ccccacctg cctggaagtc atcaaatgat      840
catggaagct tggctctgac cccacggccc cagctggagc tggctgagag cagtcctgca      900
gcctcattcc ttagttcccg gagctggcaa gggctggagc ccgcctggg tcagacgcca      960 gtgacagaag ctgtgagtgg aagacgaggg attgccatcg cctatgagga tgagggaagc     1020
ggctga                                                               1026
```

`<210>` SEQ ID NO 40
`<211>` LENGTH: 489
`<212>` TYPE: PRT
`<213>` ORGANISM: Homo sapiens

`<400>` SEQUENCE: 40

```
Met Glu Ser Met Phe Ser Ser Pro Ala Glu Ala Ala Leu Gln Arg Glu
1               5                   10                  15

Thr Gly Val Pro Gly Leu Leu Thr Pro Leu Pro Asp Leu Asp Gly Val
            20                  25                  30

Tyr Glu Leu Glu Arg Val Ala Gly Phe Val Arg Asp Leu Gly Cys Glu
                35                  40                  45

Arg Val Ala Leu Gln Phe Pro Asp Gln Leu Leu Gly Asp Ala Val Ala
        50                  55                  60

Val Ala Ala Arg Leu Glu Thr Thr Gly Ser Lys Met Phe Ile Leu
65                  70                  75                  80

Gly Asp Thr Ala Tyr Gly Ser Cys Cys Val Asp Val Leu Gly Ala Glu
                85                  90                  95

Gln Ala Gly Ala Gln Ala Leu Ile His Phe Gly Pro Ala Cys Leu Ser
            100                 105                 110

Pro Pro Ala Arg Pro Leu Pro Val Ala Phe Val Leu Arg Gln Arg Ser
        115                 120                 125

Val Ala Leu Glu Leu Cys Val Lys Ala Phe Glu Ala Gln Asn Pro Asp
        130                 135                 140

Pro Lys Ala Pro Val Val Leu Leu Ser Glu Pro Ala Cys Ala His Ala
145                 150                 155                 160

Leu Glu Ala Leu Ala Thr Leu Leu Arg Pro Arg Tyr Leu Asp Leu Leu
                165                 170                 175

Val Ser Ser Pro Ala Phe Pro Gln Pro Val Gly Ser Leu Ser Pro Glu
            180                 185                 190

Pro Met Pro Leu Glu Arg Phe Gly Arg Arg Phe Pro Leu Ala Pro Gly
        195                 200                 205

Arg Arg Leu Glu Glu Tyr Gly Ala Phe Tyr Val Gly Gly Ser Lys Ala
        210                 215                 220

Ser Pro Asp Pro Asp Leu Asp Pro Asp Leu Ser Arg Leu Leu Leu Gly
225                 230                 235                 240

Trp Ala Pro Gly Gln Pro Phe Ser Ser Cys Cys Pro Asp Thr Gly Lys
            245                 250                 255

Thr Gln Asp Glu Gly Ala Arg Ala Gly Arg Leu Arg Ala Arg Arg Arg
        260                 265                 270

Tyr Leu Val Glu Arg Ala Arg Asp Ala Arg Val Val Gly Leu Leu Ala
        275                 280                 285

Gly Thr Leu Gly Val Ala Gln His Arg Glu Ala Leu Ala His Leu Arg
        290                 295                 300

Asn Leu Thr Gln Ala Ala Gly Lys Arg Ser Tyr Val Leu Ala Leu Gly
305                 310                 315                 320

Arg Pro Thr Pro Ala Lys Leu Ala Asn Phe Pro Glu Val Asp Val Phe
            325                 330                 335

Val Leu Leu Ala Cys Pro Leu Gly Ala Leu Ala Pro Gln Leu Ser Gly
            340                 345                 350

Ser Phe Phe Gln Pro Ile Leu Ala Pro Cys Glu Leu Glu Ala Ala Cys
        355                 360                 365

Asn Pro Ala Trp Pro Pro Gly Leu Ala Pro His Leu Thr His Tyr
370                 375                 380

Ala Asp Leu Leu Pro Gly Ser Pro Phe His Val Ala Leu Pro Pro Pro
385                 390                 395                 400

Glu Ser Glu Leu Trp Glu Thr Pro Asp Val Ser Leu Ile Thr Gly Asp
            405                 410                 415

Leu Arg Pro Pro Pro Ala Trp Lys Ser Ser Asn Asp His Gly Ser Leu
```

```
                  420                 425                 430
Ala Leu Thr Pro Arg Pro Gln Leu Glu Leu Ala Glu Ser Ser Pro Ala
            435                 440                 445

Ala Ser Phe Leu Ser Ser Arg Ser Trp Gln Gly Leu Glu Pro Arg Leu
    450                 455                 460

Gly Gln Thr Pro Val Thr Glu Ala Val Ser Gly Arg Arg Gly Ile Ala
465                 470                 475                 480

Ile Ala Tyr Glu Asp Glu Gly Ser Gly
            485

<210> SEQ ID NO 41
<211> LENGTH: 261
<212> TYPE: PRT
<213> ORGANISM: Homo sapiens

<400> SEQUENCE: 41

Met Glu Ser Met Phe Ser Ser Pro Ala Glu Ala Ala Leu Gln Arg Glu
1               5                   10                  15

Thr Gly Val Pro Gly Leu Leu Thr Pro Leu Pro Asp Leu Asp Gly Val
            20                  25                  30

Tyr Glu Leu Glu Arg Val Ala Gly Phe Val Arg Asp Leu Gly Cys Glu
        35                  40                  45

Arg Val Ala Leu Gln Phe Pro Asp Gln Leu Leu Gly Asp Ala Val Ala
    50                  55                  60

Val Ala Ala Arg Leu Glu Glu Thr Thr Gly Ser Lys Met Phe Ile Leu
65                  70                  75                  80

Gly Asp Thr Ala Tyr Gly Ser Cys Cys Val Asp Val Leu Gly Ala Glu
                85                  90                  95

Gln Ala Gly Ala Gln Ala Leu Ile His Phe Gly Pro Ala Cys Leu Ser
            100                 105                 110

Pro Pro Ala Arg Pro Leu Pro Val Ala Phe Val Leu Arg Gln Arg Ser
        115                 120                 125

Val Ala Leu Glu Leu Cys Val Lys Ala Phe Glu Ala Gln Asn Pro Asp
    130                 135                 140

Pro Lys Ala Pro Val Val Leu Ser Glu Pro Ala Cys Ala His Ala
145                 150                 155                 160

Leu Gly Ser Pro Phe His Val Ala Leu Pro Pro Glu Ser Glu Leu
                165                 170                 175

Trp Glu Thr Pro Asp Val Ser Leu Ile Thr Gly Asp Leu Arg Pro Pro
            180                 185                 190

Pro Ala Trp Lys Ser Ser Asn Asp His Gly Ser Leu Ala Leu Thr Pro
        195                 200                 205

Arg Pro Gln Leu Glu Leu Ala Glu Ser Ser Pro Ala Ala Ser Phe Leu
    210                 215                 220

Ser Ser Arg Ser Trp Gln Gly Leu Glu Pro Arg Leu Gly Gln Thr Pro
225                 230                 235                 240

Val Thr Glu Ala Val Ser Gly Arg Arg Gly Ile Ala Ile Ala Tyr Glu
                245                 250                 255

Asp Glu Gly Ser Gly
            260

<210> SEQ ID NO 42
<211> LENGTH: 413
<212> TYPE: PRT
<213> ORGANISM: Homo sapiens
```

```
<400> SEQUENCE: 42

Met Phe Ile Leu Gly Asp Thr Ala Tyr Gly Ser Cys Cys Val Asp Val
1               5                   10                  15

Leu Gly Ala Glu Gln Ala Gly Ala Gln Ala Leu Ile His Phe Gly Pro
            20                  25                  30

Ala Cys Leu Ser Pro Pro Ala Arg Pro Leu Pro Val Ala Phe Val Leu
        35                  40                  45

Arg Gln Arg Ser Val Ala Leu Glu Leu Cys Val Lys Ala Phe Glu Ala
    50                  55                  60

Gln Asn Pro Asp Pro Lys Ala Pro Val Val Leu Leu Ser Glu Pro Ala
65                  70                  75                  80

Cys Ala His Ala Leu Glu Ala Leu Ala Thr Leu Leu Arg Pro Arg Tyr
                85                  90                  95

Leu Asp Leu Leu Val Ser Ser Pro Ala Phe Pro Gln Pro Val Gly Ser
                100                 105                 110

Leu Ser Pro Glu Pro Met Pro Leu Glu Arg Phe Gly Arg Arg Phe Pro
                115                 120                 125

Leu Ala Pro Gly Arg Arg Leu Glu Glu Tyr Gly Ala Phe Tyr Val Gly
                130                 135                 140

Gly Ser Lys Ala Ser Pro Asp Pro Asp Leu Asp Pro Asp Leu Ser Arg
145                 150                 155                 160

Leu Leu Leu Gly Trp Ala Pro Gly Gln Pro Phe Ser Ser Cys Cys Pro
                165                 170                 175

Asp Thr Gly Lys Thr Gln Asp Glu Gly Ala Arg Ala Gly Arg Leu Arg
                180                 185                 190

Ala Arg Arg Arg Tyr Leu Val Glu Arg Ala Arg Asp Ala Arg Val Val
                195                 200                 205

Gly Leu Leu Ala Gly Thr Leu Gly Val Ala Gln His Arg Glu Ala Leu
                210                 215                 220

Ala His Leu Arg Asn Leu Thr Gln Ala Ala Gly Lys Arg Ser Tyr Val
225                 230                 235                 240

Leu Ala Leu Gly Arg Pro Thr Pro Ala Lys Leu Ala Asn Phe Pro Glu
                245                 250                 255

Val Asp Val Phe Val Leu Leu Ala Cys Pro Leu Gly Ala Leu Ala Pro
                260                 265                 270

Gln Leu Ser Gly Ser Phe Phe Gln Pro Ile Leu Ala Pro Cys Glu Leu
                275                 280                 285

Glu Ala Ala Cys Asn Pro Ala Trp Pro Pro Gly Leu Ala Pro His
                290                 295                 300

Leu Thr His Tyr Ala Asp Leu Leu Pro Gly Ser Pro Phe His Val Ala
305                 310                 315                 320

Leu Pro Pro Pro Glu Ser Glu Leu Trp Glu Thr Pro Asp Val Ser Leu
                325                 330                 335

Ile Thr Gly Asp Leu Arg Pro Pro Ala Trp Lys Ser Ser Asn Asp
                340                 345                 350

His Gly Ser Leu Ala Leu Thr Pro Arg Pro Gln Leu Glu Leu Ala Glu
                355                 360                 365

Ser Ser Pro Ala Ala Ser Phe Leu Ser Ser Arg Ser Trp Gln Gly Leu
                370                 375                 380

Glu Pro Arg Leu Gly Gln Thr Pro Val Thr Glu Ala Val Ser Gly Arg
385                 390                 395                 400

Arg Gly Ile Ala Ile Ala Tyr Glu Asp Glu Gly Ser Gly
                405                 410
```

<210> SEQ ID NO 43
<211> LENGTH: 398
<212> TYPE: PRT
<213> ORGANISM: Homo sapiens

<400> SEQUENCE: 43

```
Met Glu Ser Met Phe Ser Ser Pro Ala Glu Ala Leu Gln Arg Glu
1               5                   10                  15

Thr Gly Val Pro Gly Leu Leu Thr Leu Pro Asp Leu Asp Gly Val
            20                  25                  30

Tyr Glu Leu Glu Arg Val Ala Gly Phe Val Arg Asp Leu Gly Cys Glu
        35                  40                  45

Arg Val Ala Leu Gln Phe Pro Asp Gln Leu Leu Gly Asp Ala Val Ala
    50                  55                  60

Val Ala Ala Arg Leu Glu Glu Thr Thr Gly Ser Lys Met Phe Ile Leu
65                  70                  75                  80

Gly Asp Thr Ala Tyr Gly Ser Cys Cys Val Asp Val Leu Gly Ala Glu
                85                  90                  95

Gln Ala Gly Ala Gln Ala Leu Ile His Phe Gly Pro Ala Cys Leu Ser
            100                 105                 110

Pro Pro Ala Arg Pro Leu Pro Val Ala Phe Val Leu Arg Gln Arg Ser
        115                 120                 125

Val Ala Leu Glu Leu Cys Val Lys Ala Phe Glu Ala Gln Asn Pro Asp
    130                 135                 140

Pro Lys Ala Pro Val Val Leu Leu Ser Glu Pro Ala Cys Ala His Ala
145                 150                 155                 160

Leu Asp Thr Gly Lys Thr Gln Asp Glu Gly Ala Arg Ala Gly Arg Leu
                165                 170                 175

Arg Ala Arg Arg Arg Tyr Leu Val Glu Arg Ala Arg Asp Ala Arg Val
            180                 185                 190

Val Gly Leu Leu Ala Gly Thr Leu Gly Val Ala Gln His Arg Glu Ala
        195                 200                 205

Leu Ala His Leu Arg Asn Leu Thr Gln Ala Ala Gly Lys Arg Ser Tyr
    210                 215                 220

Val Leu Ala Leu Gly Arg Pro Thr Pro Ala Lys Leu Ala Asn Phe Pro
225                 230                 235                 240

Glu Val Asp Val Phe Val Leu Leu Ala Cys Pro Leu Gly Ala Leu Ala
                245                 250                 255

Pro Gln Leu Ser Gly Ser Phe Phe Gln Pro Ile Leu Ala Pro Cys Glu
            260                 265                 270

Leu Glu Ala Ala Cys Asn Pro Ala Trp Pro Pro Gly Leu Ala Pro
        275                 280                 285

His Leu Thr His Tyr Ala Asp Leu Leu Pro Gly Ser Pro Phe His Val
    290                 295                 300

Ala Leu Pro Pro Pro Glu Ser Glu Leu Trp Thr Pro Asp Val Ser
305                 310                 315                 320

Leu Ile Thr Gly Asp Leu Arg Pro Pro Ala Trp Lys Ser Ser Asn
                325                 330                 335

Asp His Gly Ser Leu Ala Leu Thr Arg Pro Gln Leu Glu Leu Ala
            340                 345                 350

Glu Ser Ser Pro Ala Ala Ser Phe Leu Ser Ser Arg Ser Trp Gln Gly
        355                 360                 365

Leu Glu Pro Arg Leu Gly Gln Thr Pro Val Thr Glu Ala Val Ser Gly
```

<210> SEQ ID NO 44
<211> LENGTH: 296
<212> TYPE: PRT
<213> ORGANISM: Homo sapiens

<400> SEQUENCE: 44

Met Pro Leu Glu Arg Phe Gly Arg Arg Phe Pro Leu Ala Pro Gly Arg
1               5                   10                  15
Arg Leu Glu Glu Tyr Gly Ala Phe Tyr Val Gly Gly Ser Lys Ala Ser
            20                  25                  30
Pro Asp Pro Asp Leu Asp Pro Asp Leu Ser Arg Leu Leu Leu Gly Trp
        35                  40                  45
Ala Pro Gly Gln Pro Phe Ser Ser Cys Cys Pro Asp Thr Gly Lys Thr
    50                  55                  60
Gln Asp Glu Gly Ala Arg Ala Gly Arg Leu Arg Ala Arg Arg Arg Tyr
65                  70                  75                  80
Leu Val Glu Arg Ala Arg Asp Ala Arg Val Val Gly Leu Leu Ala Gly
                85                  90                  95
Thr Leu Gly Val Ala Gln His Arg Glu Ala Leu Ala His Leu Arg Asn
            100                 105                 110
Leu Thr Gln Ala Ala Gly Lys Arg Ser Tyr Val Leu Ala Leu Gly Arg
        115                 120                 125
Pro Thr Pro Ala Lys Leu Ala Asn Phe Pro Glu Val Asp Val Phe Val
    130                 135                 140
Leu Leu Ala Cys Pro Leu Gly Ala Leu Ala Pro Gln Leu Ser Gly Ser
145                 150                 155                 160
Phe Phe Gln Pro Ile Leu Ala Pro Cys Glu Leu Glu Ala Ala Cys Asn
                165                 170                 175
Pro Ala Trp Pro Pro Gly Leu Ala Pro His Leu Thr His Tyr Ala
            180                 185                 190
Asp Leu Leu Pro Gly Ser Pro Phe His Val Ala Leu Pro Pro Glu
        195                 200                 205
Ser Glu Leu Trp Glu Thr Pro Asp Val Ser Leu Ile Thr Gly Asp Leu
    210                 215                 220
Arg Pro Pro Ala Trp Lys Ser Ser Asn Asp His Gly Ser Leu Ala
225                 230                 235                 240
Leu Thr Pro Arg Pro Gln Leu Glu Leu Ala Glu Ser Ser Pro Ala Ala
                245                 250                 255
Ser Phe Leu Ser Ser Arg Ser Trp Gln Gly Leu Glu Pro Arg Leu Gly
            260                 265                 270
Gln Thr Pro Val Thr Glu Ala Val Ser Gly Arg Arg Gly Ile Ala Ile
        275                 280                 285
Ala Tyr Glu Asp Glu Gly Ser Gly
    290                 295

<210> SEQ ID NO 45
<211> LENGTH: 354
<212> TYPE: PRT
<213> ORGANISM: Homo sapiens

<400> SEQUENCE: 45

Met Leu Trp Leu Trp Leu His Asp Trp Arg Arg Arg Gln Gly Gln Arg

```
1               5                   10                  15
Cys Ser Phe Trp Val Thr Gln Pro Thr Ala Glu Ala Leu Ala Thr Leu
            20                  25                  30

Leu Arg Pro Arg Tyr Leu Asp Leu Leu Val Ser Ser Pro Ala Phe Pro
            35                  40                  45

Gln Pro Val Gly Ser Leu Ser Pro Glu Pro Met Pro Leu Glu Arg Phe
            50                  55                  60

Gly Arg Arg Phe Pro Leu Ala Pro Gly Arg Arg Leu Glu Glu Tyr Gly
65                      70                  75                  80

Ala Phe Tyr Val Gly Gly Ser Lys Ala Ser Pro Asp Pro Asp Leu Asp
                        85                  90                  95

Pro Asp Leu Ser Arg Leu Leu Leu Gly Trp Ala Pro Gly Gln Pro Phe
                100                 105                 110

Ser Ser Cys Cys Pro Asp Thr Gly Lys Thr Gln Asp Glu Gly Ala Arg
                115                 120                 125

Ala Gly Arg Leu Arg Ala Arg Arg Tyr Leu Val Glu Arg Ala Arg
                130                 135                 140

Asp Ala Arg Val Val Gly Leu Leu Ala Gly Thr Leu Gly Val Ala Gln
145                 150                 155                 160

His Arg Glu Ala Leu Ala His Leu Arg Asn Leu Thr Gln Ala Ala Gly
                165                 170                 175

Lys Arg Ser Tyr Val Leu Ala Leu Gly Arg Pro Thr Pro Ala Lys Leu
                180                 185                 190

Ala Asn Phe Pro Glu Val Asp Val Phe Val Leu Leu Ala Cys Pro Leu
                195                 200                 205

Gly Ala Leu Ala Pro Gln Leu Ser Gly Ser Phe Phe Gln Pro Ile Leu
                210                 215                 220

Ala Pro Cys Glu Leu Glu Ala Ala Cys Asn Pro Ala Trp Pro Pro Pro
225                 230                 235                 240

Gly Leu Ala Pro His Leu Thr His Tyr Ala Asp Leu Leu Pro Gly Ser
                245                 250                 255

Pro Phe His Val Ala Leu Pro Pro Glu Ser Glu Leu Trp Glu Thr
                260                 265                 270

Pro Asp Val Ser Leu Ile Thr Gly Asp Leu Arg Pro Pro Ala Trp
                275                 280                 285

Lys Ser Ser Asn Asp His Gly Ser Leu Ala Leu Thr Pro Arg Pro Gln
290                 295                 300

Leu Glu Leu Ala Glu Ser Ser Pro Ala Ala Ser Phe Leu Ser Ser Arg
305                 310                 315                 320

Ser Trp Gln Gly Leu Glu Pro Arg Leu Gly Gln Thr Pro Val Thr Glu
                325                 330                 335

Ala Val Ser Gly Arg Arg Gly Ile Ala Ile Ala Tyr Glu Asp Glu Gly
                340                 345                 350

Ser Gly

<210> SEQ ID NO 46
<211> LENGTH: 341
<212> TYPE: PRT
<213> ORGANISM: Homo sapiens

<400> SEQUENCE: 46

Met Pro Trp Val Arg Gly Phe Ala Cys Val Cys Thr Lys Glu Ala Leu
1               5                   10                  15

Ala Thr Leu Leu Arg Pro Arg Tyr Leu Asp Leu Leu Val Ser Ser Pro
```

```
                20                  25                  30
Ala Phe Pro Gln Pro Val Gly Ser Leu Ser Pro Glu Pro Met Pro Leu
            35                  40                  45

Glu Arg Phe Gly Arg Arg Phe Pro Leu Ala Pro Gly Arg Arg Leu Glu
        50                  55                  60

Glu Tyr Gly Ala Phe Tyr Val Gly Gly Ser Lys Ala Ser Pro Asp Pro
65                  70                  75                  80

Asp Leu Asp Pro Asp Leu Ser Arg Leu Leu Gly Trp Ala Pro Gly
                85                  90                  95

Gln Pro Phe Ser Ser Cys Cys Pro Asp Thr Gly Lys Thr Gln Asp Glu
            100                 105                 110

Gly Ala Arg Ala Gly Arg Leu Arg Ala Arg Arg Tyr Leu Val Glu
        115                 120                 125

Arg Ala Arg Asp Ala Arg Val Val Gly Leu Leu Ala Gly Thr Leu Gly
        130                 135                 140

Val Ala Gln His Arg Glu Ala Leu Ala His Leu Arg Asn Leu Thr Gln
145                 150                 155                 160

Ala Ala Gly Lys Arg Ser Tyr Val Leu Ala Leu Gly Arg Pro Thr Pro
                165                 170                 175

Ala Lys Leu Ala Asn Phe Pro Glu Val Asp Val Phe Val Leu Leu Ala
            180                 185                 190

Cys Pro Leu Gly Ala Leu Ala Pro Gln Leu Ser Gly Ser Phe Phe Gln
        195                 200                 205

Pro Ile Leu Ala Pro Cys Glu Leu Glu Ala Ala Cys Asn Pro Ala Trp
        210                 215                 220

Pro Pro Pro Gly Leu Ala Pro His Leu Thr His Tyr Ala Asp Leu Leu
225                 230                 235                 240

Pro Gly Ser Pro Phe His Val Ala Leu Pro Pro Glu Ser Glu Leu
                245                 250                 255

Trp Glu Thr Pro Asp Val Ser Leu Ile Thr Gly Asp Leu Arg Pro Pro
            260                 265                 270

Pro Ala Trp Lys Ser Ser Asn Asp His Gly Ser Leu Ala Leu Thr Pro
        275                 280                 285

Arg Pro Gln Leu Glu Leu Ala Glu Ser Ser Pro Ala Ala Ser Phe Leu
        290                 295                 300

Ser Ser Arg Ser Trp Gln Gly Leu Glu Pro Arg Leu Gly Gln Thr Pro
305                 310                 315                 320

Val Thr Glu Ala Val Ser Gly Arg Arg Gly Ile Ala Ile Ala Tyr Glu
                325                 330                 335

Asp Glu Gly Ser Gly
            340

<210> SEQ ID NO 47
<211> LENGTH: 1470
<212> TYPE: DNA
<213> ORGANISM: Mus musculus

<400> SEQUENCE: 47
atggagtcta cgttcagcag ccctgcggag gcagccctgc aacgggaggc gggcgttcca      60
ggacagttca ctcctcctga agacctggac cgcgtgtatg agctggagcg agttacgaaa     120
tttgtctgcg atttaggttg tcagcgggtg actttgcagt tccctgacca gttactagga     180
gatgcgggag cggtggctgc ccggctggag gaagtcacag gagctaagat gttcatttta     240
ggggacacag cttatggcag ctgctgtgtg gatgtgctgg gcgccgagca ggctggagct     300
```

```
caagcccttg tgcacttcgg tcctgcctgc ttaagccccc cagcctcgca gctgcccatc     360
acctttgtcc ttggtcagcg acccgttgct ttagagctct gtgcaaaggc ctttgaagcc     420
cagaacccag atccgacagc cccggtggta ctgctgagtg agccagcttg tgcccatgcc     480
ctagagcctt tggccatgct cctgctccca aagtaccaag atctgctcat ctcccgccca     540
gctcttcccc tgccagtggg atccccgagc tcacagcctg agtccctgga gcgttttggg     600
cgctgcttcc ccctgaatcc agggagacgt ctggaagaat atggtgcctt ctatgtaggg     660
gcttctcaag caagctcgga ctccagcctt gatcccgacc tgagcagact gctcttgggt     720
tggacaccag gcggcccctt cttttcctgt tgtccagata caggacagac acaagaccag     780
ggtgccaagg ctgggagact aagagcacga agactgtatc tcatagagag gccagagat      840 gcccgtgtgg ttgggctgct ggcaggcaca ttaggtgtgg ctcgacaccg tgaggcactg     900
gcacacttgc ggaaactgac ggaagctgct ggaaaacgta gctatgtgtt agccgtgggg     960
aagcccacac ccgccaagct tgccaacttc cctgagatgg acgtctttgt gctgttagcc    1020
tgtcccctgg gggcactagc cccccagcct tcgggtggct tctttcggcc tgtattgacg    1080
ccatgtgaat tggaggctgc ctgcaaccct gcctggcccc cgccaggcct ggctccccac    1140
ctcacacatt atgcagagct gttgcctggt tctcccttcc atgtgccact ccctccacct    1200
gagtcagagt tgtgggatac cccagatgtg tcactcattt ctggggagct ccgaccacca    1260
cctccttgga agtcatcaga tgacactaga tgttcggcct taattccgag gccccaactg    1320
gagctggcgg agagcagccc tgcagcttca ttccttagtt ctcggaactg cagggggctg    1380
gagccacgct tgggccagac accagtgaaa gaagccgtca gaggaagacg aggtatcgcc    1440
atcgcctacg aggatgaggg gagcagctga                                     1470
```

<210> SEQ ID NO 48
<211> LENGTH: 489
<212> TYPE: PRT
<213> ORGANISM: Mus musculus

<400> SEQUENCE: 48

```
Met Glu Ser Thr Phe Ser Ser Pro Ala Glu Ala Leu Gln Arg Glu
1               5                   10                  15

Ala Gly Val Pro Gly Gln Phe Thr Pro Pro Glu Asp Leu Asp Arg Val
            20                  25                  30

Tyr Glu Leu Glu Arg Val Thr Lys Phe Val Cys Asp Leu Gly Cys Gln
        35                  40                  45

Arg Val Thr Leu Gln Phe Pro Asp Gln Leu Leu Gly Asp Ala Gly Ala
    50                  55                  60

Val Ala Ala Arg Leu Glu Glu Val Thr Gly Ala Lys Met Phe Ile Leu
65                  70                  75                  80

Gly Asp Thr Ala Tyr Gly Ser Cys Cys Val Asp Val Leu Gly Ala Glu
                85                  90                  95

Gln Ala Gly Ala Gln Ala Leu Val His Phe Gly Pro Ala Cys Leu Ser
            100                 105                 110

Pro Pro Ala Ser Gln Leu Pro Ile Thr Phe Val Leu Gly Gln Arg Pro
        115                 120                 125

Val Ala Leu Glu Leu Cys Ala Lys Ala Phe Glu Ala Gln Asn Pro Asp
    130                 135                 140

Pro Thr Ala Pro Val Val Leu Leu Ser Glu Pro Ala Cys Ala His Ala
145                 150                 155                 160
```

Leu Glu Pro Leu Ala Met Leu Leu Pro Lys Tyr Gln Asp Leu Leu
            165                 170                 175

Ile Ser Arg Pro Ala Leu Pro Leu Pro Val Gly Ser Pro Ser Gln
        180                 185                 190

Pro Glu Ser Leu Glu Arg Phe Gly Arg Cys Phe Pro Leu Asn Pro Gly
            195                 200                 205

Arg Arg Leu Glu Glu Tyr Gly Ala Phe Tyr Val Gly Ala Ser Gln Ala
    210                 215                 220

Ser Ser Asp Ser Ser Leu Asp Pro Asp Leu Ser Arg Leu Leu Leu Gly
225                 230                 235                 240

Trp Thr Pro Gly Arg Pro Phe Phe Ser Cys Cys Pro Asp Thr Gly Gln
                245                 250                 255

Thr Gln Asp Gln Gly Ala Lys Ala Gly Arg Leu Arg Ala Arg Arg Leu
            260                 265                 270

Tyr Leu Ile Glu Arg Ala Arg Asp Ala Arg Val Val Gly Leu Leu Ala
        275                 280                 285

Gly Thr Leu Gly Val Ala Arg His Arg Glu Ala Leu Ala His Leu Arg
    290                 295                 300

Lys Leu Thr Glu Ala Ala Gly Lys Arg Ser Tyr Val Leu Ala Val Gly
305                 310                 315                 320

Lys Pro Thr Pro Ala Lys Leu Ala Asn Phe Pro Glu Met Asp Val Phe
                325                 330                 335

Val Leu Leu Ala Cys Pro Leu Gly Ala Leu Ala Pro Gln Pro Ser Gly
            340                 345                 350

Gly Phe Phe Arg Pro Val Leu Thr Pro Cys Glu Leu Glu Ala Ala Cys
        355                 360                 365

Asn Pro Ala Trp Pro Pro Gly Leu Ala Pro His Leu Thr His Tyr
    370                 375                 380

Ala Glu Leu Leu Pro Gly Ser Pro Phe His Val Pro Leu Pro Pro
385                 390                 395                 400

Glu Ser Glu Leu Trp Asp Thr Pro Asp Val Ser Leu Ile Ser Gly Glu
                405                 410                 415

Leu Arg Pro Pro Pro Trp Lys Ser Ser Asp Asp Thr Arg Cys Ser
            420                 425                 430

Ala Leu Ile Pro Arg Pro Gln Leu Glu Leu Ala Glu Ser Ser Pro Ala
        435                 440                 445

Ala Ser Phe Leu Ser Ser Arg Asn Trp Gln Gly Leu Glu Pro Arg Leu
    450                 455                 460

Gly Gln Thr Pro Val Lys Glu Ala Val Arg Gly Arg Gly Ile Ala
465                 470                 475                 480

Ile Ala Tyr Glu Asp Glu Gly Ser Ser
                485

<210> SEQ ID NO 49
<211> LENGTH: 249
<212> TYPE: DNA
<213> ORGANISM: Homo sapiens

<400> SEQUENCE: 49
atggcagtgt tcatgacga ggtggaaatc gaggacttcc aatatgacga ggactcggag      60
acgtatttct atccctgccc atgtggagat aacttctcca tcaccaagga agatttggag     120
aatggggaag acgtggcaac gtgtcctagc tgctctctca ttataaaagt gatttatgac     180
aaagatcagt ttgtgtgtgg agaaacagtc ccagccccct tcagccaaca agaattagtt     240

```
aaatgctga                                                                  249
```

<210> SEQ ID NO 50
<211> LENGTH: 174
<212> TYPE: DNA
<213> ORGANISM: Homo sapiens

<400> SEQUENCE: 50

```
atggcagtgt tcatgacga ggtggaaatc gaggacttcc aatatgacga ggactcggag    60
acgtatttct atccctgccc atgtggagat aacttctcca tcaccaagga tcagtttgtg   120
tgtggagaaa cagtcccagc cccttcagcc aacaaagaat tagttaaatg ctga         174
```

<210> SEQ ID NO 51
<211> LENGTH: 82
<212> TYPE: PRT
<213> ORGANISM: Homo sapiens

<400> SEQUENCE: 51

```
Met Ala Val Phe His Asp Glu Val Glu Ile Glu Asp Phe Gln Tyr Asp
1               5                   10                  15

Glu Asp Ser Glu Thr Tyr Phe Tyr Pro Cys Pro Cys Gly Asp Asn Phe
            20                  25                  30

Ser Ile Thr Lys Glu Asp Leu Glu Asn Gly Glu Asp Val Ala Thr Cys
        35                  40                  45

Pro Ser Cys Ser Leu Ile Ile Lys Val Ile Tyr Asp Lys Asp Gln Phe
    50                  55                  60

Val Cys Gly Glu Thr Val Pro Ala Pro Ser Ala Asn Lys Glu Leu Val
65                  70                  75                  80

Lys Cys
```

<210> SEQ ID NO 52
<211> LENGTH: 57
<212> TYPE: PRT
<213> ORGANISM: Homo sapiens

<400> SEQUENCE: 52

```
Met Ala Val Phe His Asp Glu Val Glu Ile Glu Asp Phe Gln Tyr Asp
1               5                   10                  15

Glu Asp Ser Glu Thr Tyr Phe Tyr Pro Cys Pro Cys Gly Asp Asn Phe
            20                  25                  30

Ser Ile Thr Lys Asp Gln Phe Val Cys Gly Glu Thr Val Pro Ala Pro
        35                  40                  45

Ser Ala Asn Lys Glu Leu Val Lys Cys
    50                  55
```

<210> SEQ ID NO 53
<211> LENGTH: 249
<212> TYPE: DNA
<213> ORGANISM: Mus musculus

<400> SEQUENCE: 53

```
atggcggtgt tcacgacga ggtggagatc gaggactttc aatatgacga ggactcggag    60
acatatttct acccttgccc ctgtggggat aactttgcca tcaccaagga agatttggaa   120
aatggagaag atgtggccac gtgtcctagc tgctcactca ttataaaagt gatttatgac   180
aaagatcagt tcatgtgtgg agaaacagtc ccagcacctt caaccaacaa ggagttagtt   240
aaatgctga                                                           249
```

<210> SEQ ID NO 54
<211> LENGTH: 174
<212> TYPE: DNA
<213> ORGANISM: Mus musculus

<400> SEQUENCE: 54
atggcggtgt tcacgacga ggtggagatc gaggactttc aatatgacga ggactcggag    60
acatatttct acccttgccc ctgtggggat aactttgcca tcaccaagga tcagttcatg   120
tgtggagaaa cagtcccagc accttcaacc aacaaggagt tagttaaatg ctga         174

<210> SEQ ID NO 55
<211> LENGTH: 249
<212> TYPE: DNA
<213> ORGANISM: Mus musculus

<400> SEQUENCE: 55
atggcggtgt tcacgacga ggtggagatc gaggactttc aatatgacga ggactcggag    60
acatatttct acccttgccc ctgtggggat aactttgcca tcaccaagga agatttggaa   120
aatggagaag atgtggccac gtgtcctagc tgctcactca ttataaaagt gatttatgac   180
aaagatcagt tcatgtgtgg agaaacagtc ccagcacctt caaccaacaa ggagttagtt   240
aaatgctga                                                           249

<210> SEQ ID NO 56
<211> LENGTH: 82
<212> TYPE: PRT
<213> ORGANISM: Mus musculus

<400> SEQUENCE: 56

Met Ala Val Phe His Asp Glu Val Glu Ile Glu Asp Phe Gln Tyr Asp
1               5                   10                  15

Glu Asp Ser Glu Thr Tyr Phe Tyr Pro Cys Pro Cys Gly Asp Asn Phe
            20                  25                  30

Ala Ile Thr Lys Glu Asp Leu Glu Asn Gly Glu Asp Val Ala Thr Cys
        35                  40                  45

Pro Ser Cys Ser Leu Ile Ile Lys Val Ile Tyr Asp Lys Asp Gln Phe
    50                  55                  60

Met Cys Gly Glu Thr Val Pro Ala Pro Ser Thr Asn Lys Glu Leu Val
65                  70                  75                  80

Lys Cys

<210> SEQ ID NO 57
<211> LENGTH: 57
<212> TYPE: PRT
<213> ORGANISM: Mus musculus

<400> SEQUENCE: 57

Met Ala Val Phe His Asp Glu Val Glu Ile Glu Asp Phe Gln Tyr Asp
1               5                   10                  15

Glu Asp Ser Glu Thr Tyr Phe Tyr Pro Cys Pro Cys Gly Asp Asn Phe
            20                  25                  30

Ala Ile Thr Lys Asp Gln Phe Met Cys Gly Glu Thr Val Pro Ala Pro
        35                  40                  45

Ser Thr Asn Lys Glu Leu Val Lys Cys
    50                  55

<210> SEQ ID NO 58

<211> LENGTH: 450
<212> TYPE: DNA
<213> ORGANISM: Homo sapiens

<400> SEQUENCE: 58

| | | | | | |
|---|---|---|---|---|---|
| atgatggcgg | ttgagcagat | gccaaaaaag | gattggtaca | gcatcctggg | agcagaccca | 60 |
| tctgcaaata | tatcagacct | aaaacaaaaa | tatcaaaaac | tcatattaat | gtatcatcca | 120 |
| gataaacaaa | gtacagatgt | accagcagga | acagtggagg | aatgtgtaca | gaagttcatc | 180 |
| gaaattgatc | aagcatggaa | aattctagga | aatgaagaga | caaaagaga | gtatgacctg | 240 |
| cagcggtgtg | aagatgatct | aagaaatgta | ggaccagtag | atgctcaagt | atatcttgaa | 300 |
| gaaatgtctt | ggaatgaagg | tgatcactct | ttttatctga | gttgcagatg | tggtggaaaa | 360 |
| tacagtgttt | ccaaggatga | agcggaagaa | gttagcctga | tttcttgtga | tacatgttca | 420 |
| ctaattatag | aactccttca | ttataactaa | | | | 450 |

<210> SEQ ID NO 59
<211> LENGTH: 149
<212> TYPE: PRT
<213> ORGANISM: Homo sapiens

<400> SEQUENCE: 59

```
Met Met Ala Val Glu Gln Met Pro Lys Lys Asp Trp Tyr Ser Ile Leu
1               5                   10                  15
Gly Ala Asp Pro Ser Ala Asn Ile Ser Asp Leu Lys Gln Lys Tyr Gln
            20                  25                  30
Lys Leu Ile Leu Met Tyr His Pro Asp Lys Gln Ser Thr Asp Val Pro
        35                  40                  45
Ala Gly Thr Val Glu Glu Cys Val Gln Lys Phe Ile Glu Ile Asp Gln
    50                  55                  60
Ala Trp Lys Ile Leu Gly Asn Glu Glu Thr Lys Arg Glu Tyr Asp Leu
65                  70                  75                  80
Gln Arg Cys Glu Asp Asp Leu Arg Asn Val Gly Pro Val Asp Ala Gln
                85                  90                  95
Val Tyr Leu Glu Glu Met Ser Trp Asn Glu Gly Asp His Ser Phe Tyr
            100                 105                 110
Leu Ser Cys Arg Cys Gly Gly Lys Tyr Ser Val Ser Lys Asp Glu Ala
        115                 120                 125
Glu Glu Val Ser Leu Ile Ser Cys Asp Thr Cys Ser Leu Ile Ile Glu
    130                 135                 140
Leu Leu His Tyr Asn
145
```

<210> SEQ ID NO 60
<211> LENGTH: 447
<212> TYPE: DNA
<213> ORGANISM: Mus musculus

<400> SEQUENCE: 60

| | | | | | |
|---|---|---|---|---|---|
| atggctttgg | agcagacact | caaaaaggat | tggtacagca | ttctgggtgc | agacccatct | 60 |
| gcaaatatgt | cagacctaaa | acaaaaatat | cagaaactca | tattactgta | tcatccagat | 120 |
| aaacaaagtg | cagatgtgcc | agctggaacc | atggaggagt | gtatgcagaa | gtttattgaa | 180 |
| attgatcagg | catggaaaat | tctagggaat | gaagaaacca | agaaaaagta | tgacctgcag | 240 |
| cggcatgaag | atgagctaag | aaatgtgggg | ccagtagatg | cacaggtgcg | ccttgaagag | 300 |
| atgtcctgga | accaaggtga | tgaatctttc | tttctgagct | gtcgatgtgg | tgggaaatac | 360 |

```
actgtctcca aggatgaagc acaagaagcc accctcatct cctgtgacgc gtgctcgctg    420
attgtggagc tcctccatca gagctga                                        447
```

<210> SEQ ID NO 61
<211> LENGTH: 148
<212> TYPE: PRT
<213> ORGANISM: Mus musculus

<400> SEQUENCE: 61

```
Met Ala Leu Glu Gln Thr Leu Lys Lys Asp Trp Tyr Ser Ile Leu Gly
1               5                   10                  15

Ala Asp Pro Ser Ala Asn Met Ser Asp Leu Lys Gln Lys Tyr Gln Lys
            20                  25                  30

Leu Ile Leu Leu Tyr His Pro Asp Lys Gln Ser Ala Asp Val Pro Ala
        35                  40                  45

Gly Thr Met Glu Glu Cys Met Gln Lys Phe Ile Glu Ile Asp Gln Ala
    50                  55                  60

Trp Lys Ile Leu Gly Asn Glu Glu Thr Lys Lys Tyr Asp Leu Gln
65                  70                  75                  80

Arg His Glu Asp Glu Leu Arg Asn Val Gly Pro Val Asp Ala Gln Val
                85                  90                  95

Arg Leu Glu Glu Met Ser Trp Asn Gln Gly Asp Glu Ser Phe Phe Leu
            100                 105                 110

Ser Cys Arg Cys Gly Gly Lys Tyr Thr Val Ser Lys Asp Glu Ala Gln
        115                 120                 125

Glu Ala Thr Leu Ile Ser Cys Asp Ala Cys Ser Leu Ile Val Glu Leu
    130                 135                 140

Leu His Gln Ser
145
```

<210> SEQ ID NO 62
<211> LENGTH: 858
<212> TYPE: DNA
<213> ORGANISM: Homo sapiens

<400> SEQUENCE: 62

```
atgctttatc tcatcgggtt gggcctggga gatgccaagg acatcacagt caagggcctg    60
gaagttgtta gacgctgcag tcgagtgtat ctggaagcct acacctcagt cctaactgta   120
gggaaggaag ccttggaaga gttttatgga agaaaattgg ttgttgctga tagaagaa    180 gtggaacaag aagcagataa tattttaaag gatgctgata tcagtgatgt tgcattcctt   240
gtggttggtg atccatttgg ggccacaaca cacagtgatc ttgttctaag agcaacaaag   300
ctgggaattc cttatagagt tattcacaat gcctccataa tgaatgctgt aggctgctgt   360
ggtttacagt tatataagtt tggagagaca gtttctattg ttttttggac agacacttgg   420
agaccagaaa gcttctttga caaagtgaag aagaacagac aaaatggcat gcacacatta   480
tgtttactag acatcaaagt aaaggagcag tctttggaaa atctaatcaa gggaaggaag   540
atctatgaac ctccacggta tatgagtgta aaccaagcag cccagcagct tctggagatt   600
gttcaaaatc aaagaatacg aggagaagaa ccagcagtta ccgaggagac actttgtgtt   660
ggcttagcca gggttggagc cgacgaccag aaaattgcag caggcacttt aaggcaaatg   720
tgcactgtgg acttgggaga accattgcat tccttgatca tcacaggagg cagcatacat   780
ccaatggaga tggagatgct aagtctgttt tccataccag aaaatagctc agaatctcaa   840
```

```
agcatcaatg gactttga                                                 858

<210> SEQ ID NO 63
<211> LENGTH: 858
<212> TYPE: DNA
<213> ORGANISM: Homo sapiens

<400> SEQUENCE: 63
atgctttatc tcatcgggtt gggcctggga gatgccaagg acatcacagt caagggcctg    60
gaagttgtta gacgctgcag tcgagtgtat ctggaagcct acacctcagt cctaactgta   120
gggaaggaag ccttggaaga gttttatgga agaaaattgg ttgttgctga tagagaagaa   180
gtggaacaag aagcagataa tattttaaag gatgctgata tcagtgatgt tgcattcctt   240
gtggttggtg atccatttgg ggccacaaca cacagtgatc ttgttctaag agcaacaaag   300
ctgggaattc cttatagagt tattcacaat gcctccataa tgaatgctgt aggctgctgt   360
ggtttacagt tatataagtt tggagagaca gtttctattg ttttttggac agacacttgg   420
agaccagaaa gcttctttga caaagtgaag aagaacagac aaaatggcat gcacacatta   480
tgtttactag acatcaaagt aaaggagcag tctttggaaa atctaatcaa gggaaggaag   540
atctatgaac ctccacggta tatgagtgta aaccaagcag cccagcagct tctggagatt   600
gttcaaaatc aaagaatacg aggagaagaa ccagcagtta ccgaggagac actttgtgtt   660
ggcttagcca gggttggagc cgacgaccag aaaattgcag caggcacttt aaggcaaatg   720
tgcactgtgg acttgggaga accattgcat tccttgatca tcacaggagg cagcatacat   780
ccaatggaga tggagatgct aagtctgttt tccataccag aaaatagctc agaatctcaa   840
agcatcaatg gactttga                                                 858

<210> SEQ ID NO 64
<211> LENGTH: 855
<212> TYPE: DNA
<213> ORGANISM: Homo sapiens

<400> SEQUENCE: 64
atgctttatc tcatcgggtt gggcctggga gatgccaagg acatcacagt caagggcctg    60
gaagttgtta gacgctgcag tcgagtgtat ctggaagcct acacctcagt cctaactgta   120
gggaaggaag ccttggaaga gttttatgga agaaaattgg ttgttgctga tagagaagaa   180
gtggaacaag aagcagataa tattttaaag gatgctgata tcagtgatgt tgcattcctt   240
gtggttggtg atccatttgg ggccacaaca cacagtgatc ttgttctaag agcaacaaag   300
ctgggaattc cttatagagt tattcacaat gcctccataa tgaatgctgt aggctgctgt   360
ggtttacagt tatataagtt tggagagaca gtttctattg ttttttggac agacacttgg   420
agaccagaaa gcttctttga caaagtgaag aagaacagac aaaatggcat gcacacatta   480
tgtttactag acatcaaagt aaaggagcag tctttggaaa atctaatcaa gggaaggaag   540
atctatgaac ctccacggta tatgagtgta aaccaagcag cccagcagct tctggagatt   600
gttcaaaatc aaagaatacg aggagaagaa ccagttaccg aggagacact tgtgttggc    660 ttagccaggg ttggagccga cgaccagaaa attgcagcag cactttaag gcaaatgtgc    720 actgtggact tgggagaacc attgcattcc ttgatcatca caggaggcag catacatcca   780
atggagatgg agatgctaag tctgttttcc ataccagaaa atagctcaga atctcaaagc   840
atcaatggac tttga                                                    855
```

<210> SEQ ID NO 65
<211> LENGTH: 285
<212> TYPE: PRT
<213> ORGANISM: Homo sapiens

<400> SEQUENCE: 65

Met Leu Tyr Leu Ile Gly Leu Gly Leu Gly Asp Ala Lys Asp Ile Thr
1               5                   10                  15

Val Lys Gly Leu Glu Val Val Arg Arg Cys Ser Arg Val Tyr Leu Glu
            20                  25                  30

Ala Tyr Thr Ser Val Leu Thr Val Gly Lys Glu Ala Leu Glu Glu Phe
        35                  40                  45

Tyr Gly Arg Lys Leu Val Val Ala Asp Arg Glu Glu Val Glu Gln Glu
    50                  55                  60

Ala Asp Asn Ile Leu Lys Asp Ala Asp Ile Ser Asp Val Ala Phe Leu
65                  70                  75                  80

Val Val Gly Asp Pro Phe Gly Ala Thr Thr His Ser Asp Leu Val Leu
                85                  90                  95

Arg Ala Thr Lys Leu Gly Ile Pro Tyr Arg Val Ile His Asn Ala Ser
            100                 105                 110

Ile Met Asn Ala Val Gly Cys Cys Gly Leu Gln Leu Tyr Lys Phe Gly
        115                 120                 125

Glu Thr Val Ser Ile Val Phe Trp Thr Asp Thr Trp Arg Pro Glu Ser
    130                 135                 140

Phe Phe Asp Lys Val Lys Lys Asn Arg Gln Asn Gly Met His Thr Leu
145                 150                 155                 160

Cys Leu Leu Asp Ile Lys Val Lys Glu Gln Ser Leu Glu Asn Leu Ile
                165                 170                 175

Lys Gly Arg Lys Ile Tyr Glu Pro Pro Arg Tyr Met Ser Val Asn Gln
            180                 185                 190

Ala Ala Gln Gln Leu Leu Glu Ile Val Gln Asn Gln Arg Ile Arg Gly
        195                 200                 205

Glu Glu Pro Ala Val Thr Glu Thr Leu Cys Val Gly Leu Ala Arg
    210                 215                 220

Val Gly Ala Asp Asp Gln Lys Ile Ala Ala Gly Thr Leu Arg Gln Met
225                 230                 235                 240

Cys Thr Val Asp Leu Gly Glu Pro Leu His Ser Leu Ile Ile Thr Gly
                245                 250                 255

Gly Ser Ile His Pro Met Glu Met Glu Met Leu Ser Leu Phe Ser Ile
            260                 265                 270

Pro Glu Asn Ser Ser Glu Ser Gln Ser Ile Asn Gly Leu
        275                 280                 285

<210> SEQ ID NO 66
<211> LENGTH: 284
<212> TYPE: PRT
<213> ORGANISM: Homo sapiens

<400> SEQUENCE: 66

Met Leu Tyr Leu Ile Gly Leu Gly Leu Gly Asp Ala Lys Asp Ile Thr
1               5                   10                  15

Val Lys Gly Leu Glu Val Val Arg Arg Cys Ser Arg Val Tyr Leu Glu
            20                  25                  30

Ala Tyr Thr Ser Val Leu Thr Val Gly Lys Glu Ala Leu Glu Glu Phe
        35                  40                  45

Tyr Gly Arg Lys Leu Val Val Ala Asp Arg Glu Glu Val Glu Gln Glu

| | | | | 50 | | | | | 55 | | | | | 60 | | | |
|---|---|---|---|---|---|---|---|---|---|---|---|---|---|---|---|---|---|

Ala Asp Asn Ile Leu Lys Asp Ala Asp Ile Ser Asp Val Ala Phe Leu
65                  70                  75                  80

Val Val Gly Asp Pro Phe Gly Ala Thr Thr His Ser Asp Leu Val Leu
                85                  90                  95

Arg Ala Thr Lys Leu Gly Ile Pro Tyr Arg Val Ile His Asn Ala Ser
            100                 105                 110

Ile Met Asn Ala Val Gly Cys Cys Gly Leu Gln Leu Tyr Lys Phe Gly
        115                 120                 125

Glu Thr Val Ser Ile Val Phe Trp Thr Asp Thr Trp Arg Pro Glu Ser
    130                 135                 140

Phe Phe Asp Lys Val Lys Lys Asn Arg Gln Asn Gly Met His Thr Leu
145                 150                 155                 160

Cys Leu Leu Asp Ile Lys Val Lys Glu Gln Ser Leu Glu Asn Leu Ile
                165                 170                 175

Lys Gly Arg Lys Ile Tyr Glu Pro Pro Arg Tyr Met Ser Val Asn Gln
            180                 185                 190

Ala Ala Gln Gln Leu Leu Glu Ile Val Gln Asn Gln Arg Ile Arg Gly
        195                 200                 205

Glu Glu Pro Val Thr Glu Glu Thr Leu Cys Val Gly Leu Ala Arg Val
    210                 215                 220

Gly Ala Asp Asp Gln Lys Ile Ala Ala Gly Thr Leu Arg Gln Met Cys
225                 230                 235                 240

Thr Val Asp Leu Gly Glu Pro Leu His Ser Leu Ile Ile Thr Gly Gly
                245                 250                 255

Ser Ile His Pro Met Glu Met Glu Met Leu Ser Leu Phe Ser Ile Pro
            260                 265                 270

Glu Asn Ser Ser Glu Ser Gln Ser Ile Asn Gly Leu
        275                 280

<210> SEQ ID NO 67
<211> LENGTH: 846
<212> TYPE: DNA
<213> ORGANISM: Mus musculus

<400> SEQUENCE: 67

| | | |
|---|---|---|
| atgctttact tgatcggctt gggcctggga gatgccaagg acatcacagt caagggcctg | 60 |
| gaagttgtga dacgatgcag tcgcgtgtat ctggaagcct acacctcagt cctgactgta | 120 |
| gggaaggaag ccctggaaga gttttatgga agaaaattga ttcttgctga cagagaagaa | 180 |
| gtagaacaag aagcagataa tatttttaag gatgcagatg tcagtgatgt tgcgttcctt | 240 |
| gtggttggtg atccatttgg ggctacaaca cacagtgatc ttattctgag agcaacaaag | 300 |
| ttgggcatcc cttatcaagt tattcacaat gcctccataa tgaacgctgt aggctgctgt | 360 |
| ggtttgcagt tgtacaggtt tggagaaaca gtttctattg tgttttggac ggacacttgg | 420 |
| cgaccagaga gcttctttga caaggtgaag aggaaccggg ccaatggcat gcacacgctg | 480 |
| tgcttactcg atatcaaagt gaaggagcag tctctggaga acctcatcag aggaagaaag | 540 |
| atctatgaac cccctcggta catgagtgtg aaccaggcgg cccagcagct tctagagatt | 600 |
| gttcagaatc acagagcacg cggggaggaa ccagcaatca ctgaggagac actctgtgtc | 660 |
| ggcttagcca gagtgggagc tgaagatcag aaaattgcag caggcacgtt acagcagatg | 720 |
| tgcacagtga gcttgggaga accactgcat tctttggtca ttacaggggg caacctgcac | 780 |
| ccactggaga tggagatgct aagtctcttc tctataccgg aatcccagag tactgatgga | 840 | ctctga 846

<210> SEQ ID NO 68
<211> LENGTH: 281
<212> TYPE: PRT
<213> ORGANISM: Mus musculus

<400> SEQUENCE: 68

Met Leu Tyr Leu Ile Gly Leu Gly Leu Gly Asp Ala Lys Asp Ile Thr
1               5                   10                  15

Val Lys Gly Leu Glu Val Val Arg Arg Cys Ser Arg Val Tyr Leu Glu
            20                  25                  30

Ala Tyr Thr Ser Val Leu Thr Val Gly Lys Glu Ala Leu Glu Glu Phe
        35                  40                  45

Tyr Gly Arg Lys Leu Ile Leu Ala Asp Arg Glu Val Glu Gln Glu
    50                  55                  60

Ala Asp Asn Ile Phe Lys Asp Ala Asp Val Ser Asp Val Ala Phe Leu
65                  70                  75                  80

Val Val Gly Asp Pro Phe Gly Ala Thr Thr His Ser Asp Leu Ile Leu
                85                  90                  95

Arg Ala Thr Lys Leu Gly Ile Pro Tyr Gln Val Ile His Asn Ala Ser
            100                 105                 110

Ile Met Asn Ala Val Gly Cys Cys Gly Leu Gln Leu Tyr Arg Phe Gly
        115                 120                 125

Glu Thr Val Ser Ile Val Phe Trp Thr Asp Thr Trp Arg Pro Glu Ser
130                 135                 140

Phe Phe Asp Lys Val Lys Arg Asn Arg Ala Asn Gly Met His Thr Leu
145                 150                 155                 160

Cys Leu Leu Asp Ile Lys Val Lys Glu Gln Ser Leu Glu Asn Leu Ile
                165                 170                 175

Arg Gly Arg Lys Ile Tyr Glu Pro Pro Arg Tyr Met Ser Val Asn Gln
            180                 185                 190

Ala Ala Gln Gln Leu Leu Glu Ile Val Gln Asn His Arg Ala Arg Gly
        195                 200                 205

Glu Glu Pro Ala Ile Thr Glu Glu Thr Leu Cys Val Gly Leu Ala Arg
    210                 215                 220

Val Gly Ala Glu Asp Gln Lys Ile Ala Ala Gly Thr Leu Gln Gln Met
225                 230                 235                 240

Cys Thr Val Ser Leu Gly Glu Pro Leu His Ser Leu Val Ile Thr Gly
                245                 250                 255

Gly Asn Leu His Pro Leu Glu Met Glu Met Leu Ser Leu Phe Ser Ile
            260                 265                 270

Pro Glu Ser Gln Ser Thr Asp Gly Leu
        275                 280

<210> SEQ ID NO 69
<211> LENGTH: 804
<212> TYPE: DNA
<213> ORGANISM: Homo sapiens

<400> SEQUENCE: 69
atgagggtcg cggctctgat cagtggtggg aaggacagct gctataatat gatgcagtgc      60
attgctgctg ggcatcagat cgttgctttta gcaaatctaa gaccagctga aaaccaagtg    120
gggtctgatg aactggatag ctacatgtat cagacagtgg ggcaccatgc cattgacttg    180

```
tatgcagaag caatggctct tcccctctat cgccgaacca taagaggaag gagcttggat    240
acaagacaag tgtacaccaa atgtgaaggt gatgaggttg aagatctcta tgagcttttg    300
aaacttgtta aggaaaaaga agaagtagag gggatatcag taggtgctat actttctgac    360
tatcagcgta ttcgagtgga aaatgtgtgt aaaaggctta atctccagcc tttagcttat    420
ctttggcaga gaaaccagga agatttgctc agagagatga tatcatctaa cattcaagca    480
atgatcatca aagtagcagc tttgggttta gatcctgata agcatcttgg gaaaaccctg    540
gatcaaatgg agccttatct catagagctt tctaagaagt atggagtaca tgtttgtgga    600
gaaggtggag agtatgaaac tttcactttg gattgccctc tatttaagaa gaaaataatt    660
gtggattcat cagaagtagt catacattca gctgatgcat ttgcacctgt ggcttatcta    720
cgctttttag aattgcactt ggaggacaag gtgtcctcag tgcctgacaa ctacagaaca    780
tctaattata tatataattt ttga                                            804

<210> SEQ ID NO 70
<211> LENGTH: 498
<212> TYPE: DNA
<213> ORGANISM: Homo sapiens

<400> SEQUENCE: 70
atgagggtcg cggctctgat cagtggtggg aaggacagct gctataatat gatgcagtgc     60
attgctgctg gcatcagat cgttgcttta gcaaatctaa gaccagctga aaaccaagtg    120
gggtctgatg aactggatag ctacatgtat cagacagtgg ggcaccatgc cattgacttg    180
tatgcagaag caatggctct tcccctctat cgccgaacca taagaggaag gagcttggat    240
acaagacaag tgtacaccaa atgtgaaggt gatgaggttg aagatctcta tgagcttttg    300
aaacttgtta aggcatcac tagaatgacc ttgcttgctg aatatgatgc tctgaatctc    360
caagattttc acatgcattt gaaagtgggc agccaggcga ttgtttacag gactccaaat    420
gaactgtgca ctcacagcaa gtttgataaa cacacatttc ctccttttat cagtgagatt    480
gcaaaatgtg aagtatga                                                  498

<210> SEQ ID NO 71
<211> LENGTH: 267
<212> TYPE: PRT
<213> ORGANISM: Homo sapiens

<400> SEQUENCE: 71

Met Arg Val Ala Ala Leu Ile Ser Gly Gly Lys Asp Ser Cys Tyr Asn
1               5                   10                  15

Met Met Gln Cys Ile Ala Ala Gly His Gln Ile Val Ala Leu Ala Asn
            20                  25                  30

Leu Arg Pro Ala Glu Asn Gln Val Gly Ser Asp Glu Leu Asp Ser Tyr
        35                  40                  45

Met Tyr Gln Thr Val Gly His His Ala Ile Asp Leu Tyr Ala Glu Ala
    50                  55                  60

Met Ala Leu Pro Leu Tyr Arg Arg Thr Ile Arg Gly Arg Ser Leu Asp
65                  70                  75                  80

Thr Arg Gln Val Tyr Thr Lys Cys Glu Gly Asp Glu Val Glu Asp Leu
                85                  90                  95

Tyr Glu Leu Leu Lys Leu Val Lys Glu Lys Glu Val Glu Gly Ile
            100                 105                 110

Ser Val Gly Ala Ile Leu Ser Asp Tyr Gln Arg Ile Arg Val Glu Asn
        115                 120                 125
```

```
Val Cys Lys Arg Leu Asn Leu Gln Pro Leu Ala Tyr Leu Trp Gln Arg
    130                 135                 140

Asn Gln Glu Asp Leu Leu Arg Glu Met Ile Ser Asn Ile Gln Ala
145                 150                 155                 160

Met Ile Ile Lys Val Ala Ala Leu Gly Leu Asp Pro Asp Lys His Leu
                165                 170                 175

Gly Lys Thr Leu Asp Gln Met Glu Pro Tyr Leu Ile Glu Leu Ser Lys
                180                 185                 190

Lys Tyr Gly Val His Val Cys Gly Glu Gly Glu Tyr Glu Thr Phe
                195                 200                 205

Thr Leu Asp Cys Pro Leu Phe Lys Lys Ile Ile Val Asp Ser Ser
                210                 215                 220

Glu Val Val Ile His Ser Ala Asp Ala Phe Ala Pro Val Ala Tyr Leu
225                 230                 235                 240

Arg Phe Leu Glu Leu His Leu Glu Asp Lys Val Ser Ser Val Pro Asp
                245                 250                 255

Asn Tyr Arg Thr Ser Asn Tyr Ile Tyr Asn Phe
                260                 265

<210> SEQ ID NO 72
<211> LENGTH: 165
<212> TYPE: PRT
<213> ORGANISM: Homo sapiens

<400> SEQUENCE: 72

Met Arg Val Ala Ala Leu Ile Ser Gly Gly Lys Asp Ser Cys Tyr Asn
1               5                   10                  15

Met Met Gln Cys Ile Ala Ala Gly His Gln Ile Val Ala Leu Ala Asn
                20                  25                  30

Leu Arg Pro Ala Glu Asn Gln Val Gly Ser Asp Glu Leu Asp Ser Tyr
            35                  40                  45

Met Tyr Gln Thr Val Gly His His Ala Ile Asp Leu Tyr Ala Glu Ala
    50                  55                  60

Met Ala Leu Pro Leu Tyr Arg Arg Thr Ile Arg Gly Arg Ser Leu Asp
65                  70                  75                  80

Thr Arg Gln Val Tyr Thr Lys Cys Glu Gly Asp Glu Val Glu Asp Leu
                85                  90                  95

Tyr Glu Leu Leu Lys Leu Val Lys Gly Ile Thr Arg Met Thr Leu Leu
                100                 105                 110

Ala Glu Tyr Asp Ala Leu Asn Leu Gln Asp Phe His Met His Leu Lys
            115                 120                 125

Val Gly Ser Gln Ala Ile Val Tyr Arg Thr Pro Asn Glu Leu Cys Thr
    130                 135                 140

His Ser Lys Phe Asp Lys His Thr Phe Pro Pro Phe Ile Ser Glu Ile
145                 150                 155                 160

Ala Lys Cys Glu Val
                165

<210> SEQ ID NO 73
<211> LENGTH: 816
<212> TYPE: DNA
<213> ORGANISM: Mus musculus

<400> SEQUENCE: 73
atgagggtcg cggccctgat cagtggtggg aaggacagct gttacaacat gatgcagtgc     60
```

| | |
|---|---|
| attgctgagg ggcatcaaat tgttgcatta gcaaatctaa gaccagatga aaaccaagtg | 120 |
| gagtcagatg aactggatag ctatatgtat cagacagtgg gtcaccatgc cattgacttg | 180 |
| tatgctgaag caatggcgct gcccctgtat cgcagagcca tcagaggaag gagcttggag | 240 |
| acaggaagag tttatacgca atgtgaaggt gacgaggttg aagatctcta tgaactgttg | 300 |
| aaacttgtta aggaaaaaga agaaatcgaa ggggtatcag taggtgctat actctctgac | 360 |
| tatcaacgtg gacgagtaga aaatgtatgt aaacgactca atctccagcc tttagcttat | 420 |
| ctttggcaaa gaaaccagga agatttgctc cgagagatga tagcttctaa tatcaaggcc | 480 |
| attatcatca aagtagcagc tttgggctta gatcctgata agcatcttgg gaaaaccctg | 540 |
| gttgaaatgg agccttatct tttagagctt tctaagaagt acggtgtcca cgtgtgtgga | 600 |
| gaaggtggag agtatgagac attcacgttg gactgccctc tattcaagaa gaagattgtt | 660 |
| gtggactctt cagaagcagt catgcactca gcggatgcat tcgcacctgt ggcttatctg | 720 |
| cggctctccc ggctgcactt ggaagagaaa gtgagtaaag ctcagatggc agagattcca | 780 |
| aggcgagtga gaggtgtcgt cagtacctgc ggatga | 816 |

<210> SEQ ID NO 74
<211> LENGTH: 804
<212> TYPE: DNA
<213> ORGANISM: Mus musculus

<400> SEQUENCE: 74

| | |
|---|---|
| atgagggtcg cggccctgat cagtggtggg aaggacagct gttacaacat gatgcagtgc | 60 |
| attgctgagg ggcatcaaat tgttgcatta gcaaatctaa gaccagatga aaaccaagtg | 120 |
| gagtcagatg aactggatag ctatatgtat cagacagtgg gtcaccatgc cattgacttg | 180 |
| tatgctgaag caatggcgct gcccctgtat cgcagagcca tcagaggaag gagcttggag | 240 |
| acaggaagag tttatacgca atgtgaaggt gacgaggttg aagatctcta tgaactgttg | 300 |
| aaacttgtta aggaaaaaga agaaatcgaa ggggtatcag taggtgctat actctctgac | 360 |
| tatcaacgtg gacgagtaga aaatgtatgt aaacgactca atctccagcc tttagcttat | 420 |
| ctttggcaaa gaaaccagga agatttgctc cgagagatga tagcttctaa tatcaaggcc | 480 |
| attatcatca aagtagcagc tttgggctta gatcctgata agcatcttgg gaaaaccctg | 540 |
| gttgaaatgg agccttatct tttagagctt tctaagaagt acggtgtcca cgtgtgtgga | 600 |
| gaaggtggag agtatgagac attcacgttg gactgccctc tattcaagaa gaagattgtt | 660 |
| gtggactctt cagaagcagt catgcactca gcggatgcat tcgcacctgt ggcttatctg | 720 |
| cggctctccc ggctgcactt ggaagagaaa gtgtcgtcag tacctgcgga tgatgaaaca | 780 |
| gctaactcta tacacagctc ttaa | 804 |

<210> SEQ ID NO 75
<211> LENGTH: 678
<212> TYPE: DNA
<213> ORGANISM: Mus musculus

<400> SEQUENCE: 75

| | |
|---|---|
| atgagggtcg cggccctgat cagtggtggg aaggacagct gttacaacat gatgcagtgc | 60 |
| attgctgagg ggcatcaaat tgttgcatta gcaaatctaa gaccagatga aaaccaagtg | 120 |
| gagtcagatg aactggatag ctatatgtat cagacagtgg gtcaccatgc cattgacttg | 180 |
| tatgctgaag caatggcgct gcccctgtat cgcagagcca tcagaggaag gagcttggag | 240 |
| acaggaagag tttatacgca atgtgaaggt gacgaggttg aagatctcta tgaactgttg | 300 |

```
aaacttgtta aggaaaaaga agaaatcgaa ggggtatcag taggtgctat actctctgac    360
tatcaacgtg acgagtaga aaatgtatgt aaacgactca atctccagcc tttagcttat    420
ctttggcaaa gaaccagga agatttgctc cgagagatga tagcttctaa tatcaaggcc    480
attatcatca aagtagcagc tttgggctta gatcctgata agcatcttgg gaaaaccctg    540
gttgaaatgg agccttatct tttagaggga ctcttcagaa gcagtcatgc actcagcgga    600
tgcattcgca cctgtggctt atctgcggct ctcccggctg cacttggaag agaaagtgtc    660
gtcagtacct gcggatga                                                 678
```

```
<210> SEQ ID NO 76
<211> LENGTH: 271
<212> TYPE: PRT
<213> ORGANISM: Mus musculus

<400> SEQUENCE: 76

Met Arg Val Ala Ala Leu Ile Ser Gly Gly Lys Asp Ser Cys Tyr Asn
1               5                   10                  15

Met Met Gln Cys Ile Ala Glu Gly His Gln Ile Val Ala Leu Ala Asn
            20                  25                  30

Leu Arg Pro Asp Glu Asn Gln Val Glu Ser Asp Glu Leu Asp Ser Tyr
        35                  40                  45

Met Tyr Gln Thr Val Gly His His Ala Ile Asp Leu Tyr Ala Glu Ala
    50                  55                  60

Met Ala Leu Pro Leu Tyr Arg Arg Ala Ile Arg Gly Arg Ser Leu Glu
65                  70                  75                  80

Thr Gly Arg Val Tyr Thr Gln Cys Glu Gly Asp Glu Val Glu Asp Leu
                85                  90                  95

Tyr Glu Leu Leu Lys Leu Val Lys Glu Lys Glu Ile Glu Gly Val
            100                 105                 110

Ser Val Gly Ala Ile Leu Ser Asp Tyr Gln Arg Gly Arg Val Glu Asn
        115                 120                 125

Val Cys Lys Arg Leu Asn Leu Gln Pro Leu Ala Tyr Leu Trp Gln Arg
    130                 135                 140

Asn Gln Glu Asp Leu Leu Arg Glu Met Ile Ala Ser Asn Ile Lys Ala
145                 150                 155                 160

Ile Ile Ile Lys Val Ala Ala Leu Gly Leu Asp Pro Asp Lys His Leu
                165                 170                 175

Gly Lys Thr Leu Val Glu Met Glu Pro Tyr Leu Leu Glu Leu Ser Lys
            180                 185                 190

Lys Tyr Gly Val His Val Cys Gly Glu Gly Gly Glu Tyr Glu Thr Phe
        195                 200                 205

Thr Leu Asp Cys Pro Leu Phe Lys Lys Ile Val Val Asp Ser Ser
    210                 215                 220

Glu Ala Val Met His Ser Ala Asp Ala Phe Ala Pro Val Ala Tyr Leu
225                 230                 235                 240

Arg Leu Ser Arg Leu His Leu Glu Glu Lys Val Ser Lys Ala Gln Met
                245                 250                 255

Ala Glu Ile Pro Arg Arg Val Arg Gly Val Val Ser Thr Cys Gly
            260                 265                 270

<210> SEQ ID NO 77
<211> LENGTH: 267
<212> TYPE: PRT
<213> ORGANISM: Mus musculus
```

<400> SEQUENCE: 77

Met Arg Val Ala Ala Leu Ile Ser Gly Gly Lys Asp Ser Cys Tyr Asn
1               5                   10                  15

Met Met Gln Cys Ile Ala Glu Gly His Gln Ile Val Ala Leu Ala Asn
            20                  25                  30

Leu Arg Pro Asp Glu Asn Gln Val Glu Ser Asp Glu Leu Asp Ser Tyr
        35                  40                  45

Met Tyr Gln Thr Val Gly His His Ala Ile Asp Leu Tyr Ala Glu Ala
50                  55                  60

Met Ala Leu Pro Leu Tyr Arg Arg Ala Ile Arg Gly Arg Ser Leu Glu
65                  70                  75                  80

Thr Gly Arg Val Tyr Thr Gln Cys Glu Gly Asp Glu Val Glu Asp Leu
                85                  90                  95

Tyr Glu Leu Leu Lys Leu Val Lys Glu Lys Glu Ile Glu Gly Val
                100                 105                 110

Ser Val Gly Ala Ile Leu Ser Asp Tyr Gln Arg Gly Arg Val Glu Asn
            115                 120                 125

Val Cys Lys Arg Leu Asn Leu Gln Pro Leu Ala Tyr Leu Trp Gln Arg
130                 135                 140

Asn Gln Glu Asp Leu Leu Arg Glu Met Ile Ala Ser Asn Ile Lys Ala
145                 150                 155                 160

Ile Ile Ile Lys Val Ala Ala Leu Gly Leu Asp Pro Asp Lys His Leu
                165                 170                 175

Gly Lys Thr Leu Val Glu Met Glu Pro Tyr Leu Leu Glu Leu Ser Lys
            180                 185                 190

Lys Tyr Gly Val His Val Cys Gly Glu Gly Gly Glu Tyr Glu Thr Phe
        195                 200                 205

Thr Leu Asp Cys Pro Leu Phe Lys Lys Lys Ile Val Val Asp Ser Ser
210                 215                 220

Glu Ala Val Met His Ser Ala Asp Ala Phe Ala Pro Val Ala Tyr Leu
225                 230                 235                 240

Arg Leu Ser Arg Leu His Leu Glu Glu Lys Val Ser Ser Val Pro Ala
                245                 250                 255

Asp Asp Glu Thr Ala Asn Ser Ile His Ser Ser
            260                 265

<210> SEQ ID NO 78
<211> LENGTH: 225
<212> TYPE: PRT
<213> ORGANISM: Mus musculus

<400> SEQUENCE: 78

Met Arg Val Ala Ala Leu Ile Ser Gly Gly Lys Asp Ser Cys Tyr Asn
1               5                   10                  15

Met Met Gln Cys Ile Ala Glu Gly His Gln Ile Val Ala Leu Ala Asn
            20                  25                  30

Leu Arg Pro Asp Glu Asn Gln Val Glu Ser Asp Glu Leu Asp Ser Tyr
        35                  40                  45

Met Tyr Gln Thr Val Gly His His Ala Ile Asp Leu Tyr Ala Glu Ala
50                  55                  60

Met Ala Leu Pro Leu Tyr Arg Arg Ala Ile Arg Gly Arg Ser Leu Glu
65                  70                  75                  80

Thr Gly Arg Val Tyr Thr Gln Cys Glu Gly Asp Glu Val Glu Asp Leu
                85                  90                  95

Tyr Glu Leu Leu Lys Leu Val Lys Glu Lys Glu Ile Glu Gly Val
            100                 105                 110

Ser Val Gly Ala Ile Leu Ser Asp Tyr Gln Arg Gly Arg Val Glu Asn
            115                 120                 125

Val Cys Lys Arg Leu Asn Leu Gln Pro Leu Ala Tyr Leu Trp Gln Arg
130                 135                 140

Asn Gln Glu Asp Leu Leu Arg Glu Met Ile Ala Ser Asn Ile Lys Ala
145                 150                 155                 160

Ile Ile Ile Lys Val Ala Ala Leu Gly Leu Asp Pro Asp Lys His Leu
                165                 170                 175

Gly Lys Thr Leu Val Glu Met Glu Pro Tyr Leu Leu Glu Gly Leu Phe
            180                 185                 190

Arg Ser Ser His Ala Leu Ser Gly Cys Ile Arg Thr Cys Gly Leu Ser
            195                 200                 205

Ala Ala Leu Pro Ala Ala Leu Gly Arg Glu Ser Val Val Ser Thr Cys
            210                 215                 220

Gly
225

<210> SEQ ID NO 79
<211> LENGTH: 1359
<212> TYPE: DNA
<213> ORGANISM: Homo sapiens

<400> SEQUENCE: 79

```
atgatgggct gtttcgccct gcaaacggtg gacaccgagc tgaccgcgga ctcggtggag     60
tggtgcccgc tgcaaggctg caggcacctg ctggcgtgcg ggacctacca gctgcggcgg    120
ccggaggacc ggcctgccgg ccccagaac aagggtggaa tggaagttaa ggagcctcag    180
gtccgtttag ccgtctctt cctgtacagt ttcaatgaca caactctat tcaccctctg    240
gtcgaggtcc aaagaaaaga tacttctgca atcctggaca tgaaatggtg tcacatcccg    300
gtggctggac atgccctctt gggcttggca gatgccagtg gatccataca actgctccgc    360
ctggtggaat ctgagaagag ccacgtgctg agccattgt ccagccttgc cctggaggag    420
cagtgtctgg ctttgtccct agattggtcc actgggaaaa ctggaagggc cggggaccag    480
cccttgaaga tcatcagcag tgactccaca gggcagctcc acctcctgat ggtgaatgag    540
acgaggccca ggctgcagaa agtggcctca tggcaggcac atcaattcga ggcctggatt    600
gctgctttca attactggca tccagaaatt gtgtattcag ggggcgacga tggccttctg    660
aggggctggg acaccagggt acccggcaaa tttctcttca ccagcaaaag acacaccatg    720
ggtgtgtgca gcatccagag cagccctcat cgggagcaca tcctggccac gggaagctat    780
gatgaacaca tcctactgtg ggacacacga aacatgaagc agccgttggc agatacgcct    840
gtgcagggtg gggtatggag aatcaagtgg cacccttttcc accaccacct gctcctggcc    900
gcctgcatgc acagtggctt taagatcctc aactgccaaa aggcaatgga ggagaggcag    960
gaggcgacgg tcctgacatc tcacacattg cccgactcgc tggtgtatgg agccgactgg   1020
tcctggctgc tcttccgttc tctgcagcgg gccccctcgt ggtccttttcc tagcaaccta   1080
ggaaccaaga cggcagacct gaagggtgca agcgagttgc caacaccctg tcatgaatgc   1140
agagaggata cgatgggga gggccatgcc agacccagaa gtggaatgaa gccactcaca   1200
gagggcatga ggaagaatgg cacctggctg caggctacag cagccaccac acgtgactgt   1260
ggcgtgaacc cagaagaagc agactcagcc ttcagcctcc tggccacctg ctccttctat   1320
```

-continued

```
gaccatgcgc tccacctctg ggagtgggag gggaactga                                 1359
```

<210> SEQ ID NO 80
<211> LENGTH: 1293
<212> TYPE: DNA
<213> ORGANISM: Homo sapiens

<400> SEQUENCE: 80

```
atgatgggct gtttcgccct gcaaacggtg gacaccgagc tgaccgcgga ctcggtggag    60
tggtgcccgc tgcaaggctg caggcacctg ctggcgtgcg ggacctacca gctgcggcgg   120
ccggaggacc ggcctgccgg cccccagaac aagggtggaa tggaagttaa ggagcctcag   180
gtccgtttag gccgtctctt cctgtacagt ttcaatgaca caactctat tcaccctctg    240
gtcgaggtcc aaagaaaaga tacttctgca atcctggaca tgaaatggtg tcacatcccg   300
gtggctggac atgccctctt gggcttggca gatgccagtg gatccataca actgctccgc   360
ctggtggaat ctgagaagag ccacgtgctg gagccattgt ccagccttgc cctggaggag   420
cagtgtctgg ctttgtccct agattggtcc actgggaaaa ctggaagggc cggggaccag   480
cccttgaaga tcatcagcag tgactccaca gggcagctcc acctcctgat ggtgaatgag   540
acgaggccca ggctgcagaa agtggcctca tggcaggcac atcaattcga ggcctggatt   600
gctgctttca attactggca tccagaaatt gtgtattcag gggcgacga tggccttctg    660
aggggctggg acaccagggt acccggcaaa tttctcttca ccagcaaaag ctatgatgaa   720
cacatcctac tgtgggacac acgaaacatg aagcagccgt tggcagatac gcctgtgcag   780
ggtggggtat ggagaatcaa gtggcaccct ttccaccacc cctgctcct ggccgcctgc    840
atgcacagtg gctttaagat cctcaactgc caaaaggcaa tggaggagag caggaggcg    900
acggtcctga catctcacac attgcccgac tcgctggtgt atggagccga ctggtcctgg   960
ctgctcttcc gttctctgca gcgggccccc tcgtggtcct ttcctagcaa cctaggaacc  1020
aagacggcag acctgaaggg tgcaagcgag ttgccaacac cctgtcatga atgcagagag  1080
gataacgatg gggagggcca tgccagaccc cagagtggaa tgaagccact cacagagggc  1140
atgaggaaga atggcacctg gctgcaggct acagcagcca ccacacgtga ctgtggcgtg  1200
aacccagaag aagcagactc agccttcagc ctcctggcca cctgctcctt ctatgaccat  1260
gcgctccacc tctgggagtg ggaggggaac tga                               1293
```

<210> SEQ ID NO 81
<211> LENGTH: 1011
<212> TYPE: DNA
<213> ORGANISM: Homo sapiens

<400> SEQUENCE: 81

```
atgatgggct gtttcgccct gcaaacggtg gacaccgagc tgaccgcgga ctcggtggag    60
tggtgcccgc tgcaaggctg caggcacctg ctggcgtgcg ggacctacca gctgcggcgg   120
ccggaggacc ggcctgccgg cccccagaac aagggtggaa tggaagttaa ggagcctcag   180
gtccgtttag gccgtctctt cctgtacagt ttcaatgaca caactctat tcaccctctg    240
gtcgaggtcc aaagaaaaga tacttctgca atcctggaca tgaaatggtg tcacatcccg   300
gtggctggac atgccctctt gggcttggca gatgccagtg gatccataca actgctccgc   360
ctggtggaat ctgagaagag ccacgtgctg gagccattgt ccagccttgc cctggaggag   420
cagtgtctgg ctttgtccct agattggtcc actgggaaaa ctggaagggc cggggaccag   480
```

| | |
|---|---|
| cccttgaaga tcatcagcag tgactccaca gggcagctcc acctcctgat ggtgaatgag | 540 |
| acgaggccca ggctgcagaa agtggcctca tggcaggcac atcaattcga ggcctggatt | 600 |
| gctgctttca attactggca tccagaaatt gtgtattcag ggggcgacga tggccttctg | 660 |
| aggggctggg acaccagggt acccggcaaa tttctcttca ccagcaaaag acacaccatg | 720 |
| ggtgtgtgca gcatccagag cagccctcat cgggagcaca tcctggccac gggaagctat | 780 |
| gatgaacaca tcctactgtg gacacacgaa acatgaagc agccgttggc agatacgcct | 840 |
| gtgcagggtg gggtatggag aatcaagtgg cacccttttcc accaccacct gctcctggcc | 900 |
| gcctgcatgc acagtggctt taagatcctc aactgccaaa aggcaatggc tgtagaagag | 960 |
| gtcctgctgg cccgagtgga cgtgttgagc gattgctgga tgaaagacta g | 1011 |

<210> SEQ ID NO 82
<211> LENGTH: 972
<212> TYPE: DNA
<213> ORGANISM: Homo sapiens

<400> SEQUENCE: 82

| | |
|---|---|
| atgatgggct gtttcgccct gcaaacggtg acaccgagc tgaccgcgga ctcggtggag | 60 |
| tggtgcccgc tgcaaggctg caggcacctg ctggcgtgcg ggacctacca gctgcggcgg | 120 |
| ccggaggacc ggcctgccgg cccccagaac aagggtggaa tggaagttaa ggagcctcag | 180 |
| gtccgtttag gccgtctctt cctgtacagt ttcaatgaca caactctat tcaccctctg | 240 |
| gtcgaggtcc aaagaaaaga tacttctgca atcctggaca tgaaatggtg tcacatcccg | 300 |
| gtggctggac atgccctctt gggcttggca gatgccagtg gatccataca actgctccgc | 360 |
| ctggtggaat ctgagaagag ccacgtgctg gagccattgt ccagccttgc cctggaggag | 420 |
| cagtgtctgg ctttgtccct agattggtcc actgggaaaa ctggaagggc cggggaccag | 480 |
| cccttgaaga tcatcagcag tgactccaca gggcagctcc acctcctgat ggtgaatgag | 540 |
| acgaggccca ggctgcagaa agtggcctca tggcaggcac atcaattcga ggcctggatt | 600 |
| gctgctttca attactggca tccagaaatt gtgtattcag ggggcgacga tggccttctg | 660 |
| aggggctggg acaccagggt acccggcaaa tttctcttca ccagcaaaag acacaccatg | 720 |
| ggtgtgtgca gcatccagag cagccctcat cgggagcaca tcctggccac gggaagctat | 780 |
| gatgaacaca tcctactgtg gacacacgaa acatgaagc agccgttggc agatacgcct | 840 |
| gtgcagggtg gggtatggag aatcaagtgg cacccttttcc accaccacct gctcctggcc | 900 |
| gcctgcatgc acagtggctt taagatcctc aactgccaaa aggcaatggg ctgtggctct | 960 |
| ctgagggctt ag | 972 |

<210> SEQ ID NO 83
<211> LENGTH: 957
<212> TYPE: DNA
<213> ORGANISM: Homo sapiens

<400> SEQUENCE: 83

| | |
|---|---|
| atgccctctt gggcttggca gatgccagtg gatccataca actgctccgc ctggtggaat | 60 |
| ctgagggccg ggaccagcc cttgaagatc atcagcagtg actccacagg gcagctccac | 120 |
| ctcctgatgg tgaatgagac gaggcccagg ctgcagaaag tggcctcatg gcaggcacat | 180 |
| caattcgagg cctggattgc tgctttcaat tactggcatc cagaaattgt gtattcaggg | 240 |
| ggcgacgatg gccttctgag gggctgggac accagggtac ccggcaaatt tctcttcacc | 300 |
| agcaaaagac acaccatggg tgtgtgcagc atccagagca gccctcatcg ggagcacatc | 360 |

```
ctggccacgg gaagctatga tgaacacatc ctactgtggg acacacgaaa catgaagcag    420
ccgttggcag atacgcctgt gcagggtggg gtatggagaa tcaagtggca cccttttccac   480 caccacctgc tcctggccgc ctgcatgcac agtggcttta agatcctcaa ctgccaaaag    540
gcaatggagg agaggcagga ggcgacggtc ctgacatctc acacattgcc cgactcgctg    600
gtgtatggag ccgactggtc ctggctgctc ttccgttctc tgcagcgggc ccctcgtgg    660 tcctttccta gcaacctagg aaccaagacg gcagacctga agggtgcaag cgagttgcca    720
acaccctgtc atgaatgcag agaggataac gatggggagg ccatgccag acccccagagt    780 ggaatgaagc cactcacaga gggcatgagg aagaatggca cctggctgca ggctacagca    840
gccaccacac gtgactgtgg cgtgaaccca aagaagcag actcagcctt cagcctcctg    900
gccacctgct ccttctatga ccatgcgctc cacctctggg agtgggaggg gaactga      957
```

<210> SEQ ID NO 84
<211> LENGTH: 906
<212> TYPE: DNA
<213> ORGANISM: Homo sapiens

<400> SEQUENCE: 84

```
atgatgggct gtttcgccct gcaaacggtg gacaccgagc tgaccgcgga ctcggtggag    60
tggtgcccgc tgcaaggctg caggcacctg ctggcgtgcg ggacctacca gctgcggcgg   120
ccggaggacc ggcctgccgg cccccagaac aagggtggaa tggaagttaa ggagcctcag   180
gtccgtttag ccgtctcttc cctgtacagt ttcaatgaca caactctat tcaccctctg    240 gtcgaggtcc aaagaaaaga tacttctgca atcctggaca tgaaatggtg tcacatcccg   300
gtggctggac atgcccctctt gggcttggca gatgccagtg gatccatca actgctccgc   360 ctggtggaat ctgagaagag ccacgtgctg gagccattgt ccagccttgc cctggaggag   420
cagtgtctgg ctttgtccct agattggtcc actgggaaaa ctggaagggc cggggaccag   480
cccttgaaga tcatcagcag tgactccaca gggcagctcc acctcctgat ggtgaatgag   540
acgaggccca ggctgcagaa agtggcctca tggcaggcac atcaattcga ggcctggatt   600
gctgctttca attactggca tccagaaatt gtgtattcag ggggcgacga tggccttctg   660
aggggctggg acaccagggt acccggcaaa tttctcttca ccagcaaaag ctatgatgaa   720
cacatcctac tgtgggacac acgaaacatg aagcagccgt tggcagatac gcctgtgcag   780
ggtggggtat ggagaatcaa gtggcaccct ttccaccacc acctgctcct ggccgcctgc   840
atgcacagtg gctttaagat cctcaactgc caaaaggcaa tgggctgtgg ctctctgagg   900
gcttag                                                              906
```

<210> SEQ ID NO 85
<211> LENGTH: 831
<212> TYPE: DNA
<213> ORGANISM: Homo sapiens

<400> SEQUENCE: 85

```
atggtgaatg agacgaggcc caggctgcag aaagtggcct catggcaggc acatcaattc    60
gaggcctgga ttgctgcttt caattactgg catccagaaa ttgtgtattc agggggcgac   120
gatggccttc tgaggggctg ggacaccagg gtacccggca aatttctctt caccagcaaa   180
agacacacca tgggtgtgtg cagcatccag agcagccctc atcggagca catcctggcc   240 acgggaagct atgatgaaca catcctactg tgggacacac gaaacatgaa gcagccgttg   300
```

```
gcagatacgc ctgtgcaggg tggggtatgg agaatcaagt ggcacccttt ccaccaccac    360
ctgctcctgg ccgcctgcat gcacagtggc tttaagatcc tcaactgcca aaaggcaatg    420
gaggagaggc aggaggcgac ggtcctgaca tctcacacat gcccgactc gctggtgtat    480 ggagccgact ggtcctggct gctcttccgt tctctgcagc gggccccctc gtggtccttt    540
cctagcaacc taggaaccaa gacggcagac ctgaagggtg caagcgagtt gccaacaccc    600
tgtcatgaat gcagagagga taacgatggg gagggccatg ccagacccca gagtggaatg    660
aagccactca cagagggcat gaggaagaat ggcacctggc tgcaggctac agcagccacc    720
acacgtgact gtggcgtgaa cccagaagaa gcagactcag ccttcagcct cctggccacc    780
tgctccttct atgaccatgc gctccacctc tgggagtggg aggggaactg a              831
```

<210> SEQ ID NO 86
<211> LENGTH: 831
<212> TYPE: DNA
<213> ORGANISM: Homo sapiens

<400> SEQUENCE: 86

```
atggtgaatg agacgaggcc caggctgcag aaagtggcct catggcaggc acatcaattc     60
gaggcctgga ttgctgcttt caattactgg catccagaaa ttgtgtattc agggggcgac    120
gatggccttc tgaggggctg ggacaccagg gtacccggca aatttctctt caccagcaaa    180
agacacacca tgggtgtgtg cagcatccag agcagccctc atcgggagca catcctggcc    240
acgggaagct atgatgaaca catcctactg tgggacacac gaaacatgaa gcagccgttg    300
gcagatacgc ctgtgcaggg tggggtatgg agaatcaagt ggcacccttt ccaccaccac    360
ctgctcctgg ccgcctgcat gcacagtggc tttaagatcc tcaactgcca aaaggcaatg    420
gaggagaggc aggaggcgac ggtcctgaca tctcacacat gcccgactc gctggtgtat    480 ggagccgact ggtcctggct gctcttccgt tctctgcagc gggccccctc gtggtccttt    540
cctagcaacc taggaaccaa gacggcagac ctgaagggtg caagcgagtt gccaacaccc    600
tgtcatgaat gcagagagga taacgatggg gagggccatg ccagacccca gagtggaatg    660
aagccactca cagagggcat gaggaagaat ggcacctggc tgcaggctac agcagccacc    720
acacgtgact gtggcgtgaa cccagaagaa gcagactcag ccttcagcct cctggccacc    780
tgctccttct atgaccatgc gctccacctc tgggagtggg aggggaactg a              831
```

<210> SEQ ID NO 87
<211> LENGTH: 831
<212> TYPE: DNA
<213> ORGANISM: Homo sapiens

<400> SEQUENCE: 87

```
atggtgaatg agacgaggcc caggctgcag aaagtggcct catggcaggc acatcaattc     60
gaggcctgga ttgctgcttt caattactgg catccagaaa ttgtgtattc agggggcgac    120
gatggccttc tgaggggctg ggacaccagg gtacccggca aatttctctt caccagcaaa    180
agacacacca tgggtgtgtg cagcatccag agcagccctc atcgggagca catcctggcc    240
acgggaagct atgatgaaca catcctactg tgggacacac gaaacatgaa gcagccgttg    300
gcagatacgc ctgtgcaggg tggggtatgg agaatcaagt ggcacccttt ccaccaccac    360
ctgctcctgg ccgcctgcat gcacagtggc tttaagatcc tcaactgcca aaaggcaatg    420
gaggagaggc aggaggcgac ggtcctgaca tctcacacat gcccgactc gctggtgtat    480 ggagccgact ggtcctggct gctcttccgt tctctgcagc gggccccctc gtggtccttt    540
```

| | |
|---|---|
| cctagcaacc taggaaccaa gacggcagac ctgaagggtg caagcgagtt gccaacaccc | 600 |
| tgtcatgaat gcagagagga taacgatggg gagggccatg ccagacccca gagtggaatg | 660 |
| aagccactca cagagggcat gaggaagaat ggcacctggc tgcaggctac agcagccacc | 720 |
| acacgtgact gtggcgtgaa cccagaagaa gcagactcag ccttcagcct cctggccacc | 780 |
| tgctcctttct atgaccatgc gctccacctc tgggagtggg aggggaactg a | 831 |

<210> SEQ ID NO 88
<211> LENGTH: 831
<212> TYPE: DNA
<213> ORGANISM: Homo sapiens

<400> SEQUENCE: 88

| | |
|---|---|
| atggtgaatg agacgaggcc caggctgcag aaagtggcct catggcaggc acatcaattc | 60 |
| gaggcctgga ttgctgcttt caattactgg catccagaaa ttgtgtattc aggggggcgac | 120 |
| gatggccttc tgaggggctg gacaccagg gtacccggca aatttctctt caccagcaaa | 180 |
| agacacacca tgggtgtgtg cagcatccag agcagccctc atcgggagca catcctggcc | 240 |
| acgggaagct atgatgaaca catcctactg tgggacacac gaaacatgaa gcagccgttg | 300 |
| gcagatacgc ctgtgcaggg tggggtatgg agaatcaagt ggcacccttt ccaccaccac | 360 |
| ctgctcctgg ccgcctgcat gcacagtggc tttaagatcc tcaactgcca aaaggcaatg | 420 |
| gaggagaggc aggaggcgac ggtcctgaca tctcacacat gcccgactc gctggtgtat | 480 |
| ggagccgact ggtcctggct gctcttccgt tctctgcagc gggccccctc gtggtccttt | 540 |
| cctagcaacc taggaaccaa gacggcagac ctgaagggtg caagcgagtt gccaacaccc | 600 |
| tgtcatgaat gcagagagga taacgatggg gagggccatg ccagacccca gagtggaatg | 660 |
| aagccactca cagagggcat gaggaagaat ggcacctggc tgcaggctac agcagccacc | 720 |
| acacgtgact gtggcgtgaa cccagaagaa gcagactcag ccttcagcct cctggccacc | 780 |
| tgctcctttct atgaccatgc gctccacctc tgggagtggg aggggaactg a | 831 |

<210> SEQ ID NO 89
<211> LENGTH: 831
<212> TYPE: DNA
<213> ORGANISM: Homo sapiens

<400> SEQUENCE: 89

| | |
|---|---|
| atggtgaatg agacgaggcc caggctgcag aaagtggcct catggcaggc acatcaattc | 60 |
| gaggcctgga ttgctgcttt caattactgg catccagaaa ttgtgtattc aggggggcgac | 120 |
| gatggccttc tgaggggctg gacaccagg gtacccggca aatttctctt caccagcaaa | 180 |
| agacacacca tgggtgtgtg cagcatccag agcagccctc atcgggagca catcctggcc | 240 |
| acgggaagct atgatgaaca catcctactg tgggacacac gaaacatgaa gcagccgttg | 300 |
| gcagatacgc ctgtgcaggg tggggtatgg agaatcaagt ggcacccttt ccaccaccac | 360 |
| ctgctcctgg ccgcctgcat gcacagtggc tttaagatcc tcaactgcca aaaggcaatg | 420 |
| gaggagaggc aggaggcgac ggtcctgaca tctcacacat gcccgactc gctggtgtat | 480 |
| ggagccgact ggtcctggct gctcttccgt tctctgcagc gggccccctc gtggtccttt | 540 |
| cctagcaacc taggaaccaa gacggcagac ctgaagggtg caagcgagtt gccaacaccc | 600 |
| tgtcatgaat gcagagagga taacgatggg gagggccatg ccagacccca gagtggaatg | 660 |
| aagccactca cagagggcat gaggaagaat ggcacctggc tgcaggctac agcagccacc | 720 | acacgtgact gtggcgtgaa cccagaagaa gcagactcag ccttcagcct cctggccacc    780 tgctccttct atgaccatgc gctccacctc tgggagtggg aggggaactg a             831

<210> SEQ ID NO 90
<211> LENGTH: 831
<212> TYPE: DNA
<213> ORGANISM: Homo sapiens

<400> SEQUENCE: 90
atggtgaatg agacgaggcc caggctgcag aaagtggcct catggcaggc acatcaattc     60
gaggcctgga ttgctgcttt caattactgg catccagaaa ttgtgtattc aggggggcgac   120 gatggccttc tgagggggctg ggacaccagg gtacccggca aatttctctt caccagcaaa   180
agacacacca tgggtgtgtg cagcatccag agcagccctc atcgggagca catcctggcc   240
acgggaagct atgatgaaca catcctactg tgggacacac gaaacatgaa gcagccgttg   300
gcagatacgc ctgtgcaggg tggggtatgg agaatcaagt ggcaccctt ccaccaccac   360 ctgctcctgg ccgcctgcat gcacagtggc tttaagatcc tcaactgcca aaaggcaatg   420
gaggagaggc aggaggcgac ggtcctgaca tctcacacat tgcccgactc gctggtgtat   480
ggagccgact ggtcctggct gctcttccgt tctctgcagc gggccccctc gtggtccttt   540
cctagcaacc taggaaccaa gacggcagac ctgaagggtg caagcgagtt gccaacaccc   600
tgtcatgaat gcagagagga taacgatggg gagggccatg ccagacccca gagtggaatg   660
aagccactca cagagggcat gaggaagaat ggcacctggc tgcaggctac agcagccacc   720
acacgtgact gtggcgtgaa cccagaagaa gcagactcag ccttcagcct cctggccacc   780
tgctccttct atgaccatgc gctccacctc tgggagtggg aggggaactg a             831

<210> SEQ ID NO 91
<211> LENGTH: 831
<212> TYPE: DNA
<213> ORGANISM: Homo sapiens

<400> SEQUENCE: 91
atggtgaatg agacgaggcc caggctgcag aaagtggcct catggcaggc acatcaattc     60
gaggcctgga ttgctgcttt caattactgg catccagaaa ttgtgtattc aggggggcgac   120 gatggccttc tgagggggctg ggacaccagg gtacccggca aatttctctt caccagcaaa   180
agacacacca tgggtgtgtg cagcatccag agcagccctc atcgggagca catcctggcc   240
acgggaagct atgatgaaca catcctactg tgggacacac gaaacatgaa gcagccgttg   300
gcagatacgc ctgtgcaggg tggggtatgg agaatcaagt ggcaccctt ccaccaccac   360 ctgctcctgg ccgcctgcat gcacagtggc tttaagatcc tcaactgcca aaaggcaatg   420
gaggagaggc aggaggcgac ggtcctgaca tctcacacat tgcccgactc gctggtgtat   480
ggagccgact ggtcctggct gctcttccgt tctctgcagc gggccccctc gtggtccttt   540
cctagcaacc taggaaccaa gacggcagac ctgaagggtg caagcgagtt gccaacaccc   600
tgtcatgaat gcagagagga taacgatggg gagggccatg ccagacccca gagtggaatg   660
aagccactca cagagggcat gaggaagaat ggcacctggc tgcaggctac agcagccacc   720
acacgtgact gtggcgtgaa cccagaagaa gcagactcag ccttcagcct cctggccacc   780
tgctccttct atgaccatgc gctccacctc tgggagtggg aggggaactg a             831

<210> SEQ ID NO 92
<211> LENGTH: 831

<212> TYPE: DNA
<213> ORGANISM: Homo sapiens

<400> SEQUENCE: 92

```
atggtgaatg agacgaggcc caggctgcag aaagtggcct catggcaggc acatcaattc      60
gaggcctgga ttgctgcttt caattactgg catccagaaa ttgtgtattc aggggcgac      120
gatggccttc tgaggggctg ggacaccagg gtacccggca aatttctctt caccagcaaa    180
agacacacca tgggtgtgtg cagcatccag agcagccctc atcggagca catcctggcc     240
acgggaagct atgatgaaca catcctactg tgggacacac gaaacatgaa gcagccgttg    300
gcagatacgc ctgtgcaggg tggggtatgg agaatcaagt ggcaccctt ccaccaccac     360
ctgctcctgg ccgcctgcat gcacagtggc tttaagatcc tcaactgcca aaaggcaatg   420
gaggagaggc aggaggcgac ggtcctgaca tctcacacat gcccgactc gctggtgtat     480
ggagccgact ggtcctggct gctcttccgt tctctgcagc gggccccctc gtggtccttt    540
cctagcaacc taggaaccaa gacggcagac ctgaagggtg caagcgagtt gccaacaccc    600
tgtcatgaat gcagagagga taacgatggg gagggccatg ccagacccca gagtggaatg   660
aagccactca cagagggcat gaggaagaat ggcacctggc tgcaggctac agcagccacc    720
acacgtgact gtggcgtgaa cccagaagaa gcagactcag ccttcagcct cctggccacc    780
tgctccttct atgaccatgc gctccacctc tgggagtggg aggggaactg a            831
```

<210> SEQ ID NO 93
<211> LENGTH: 831
<212> TYPE: DNA
<213> ORGANISM: Homo sapiens

<400> SEQUENCE: 93

```
atggtgaatg agacgaggcc caggctgcag aaagtggcct catggcaggc acatcaattc      60
gaggcctgga ttgctgcttt caattactgg catccagaaa ttgtgtattc aggggcgac      120
gatggccttc tgaggggctg ggacaccagg gtacccggca aatttctctt caccagcaaa    180
agacacacca tgggtgtgtg cagcatccag agcagccctc atcggagca catcctggcc     240
acgggaagct atgatgaaca catcctactg tgggacacac gaaacatgaa gcagccgttg    300
gcagatacgc ctgtgcaggg tggggtatgg agaatcaagt ggcaccctt ccaccaccac     360
ctgctcctgg ccgcctgcat gcacagtggc tttaagatcc tcaactgcca aaaggcaatg   420
gaggagaggc aggaggcgac ggtcctgaca tctcacacat gcccgactc gctggtgtat     480
ggagccgact ggtcctggct gctcttccgt tctctgcagc gggccccctc gtggtccttt    540
cctagcaacc taggaaccaa gacggcagac ctgaagggtg caagcgagtt gccaacaccc    600
tgtcatgaat gcagagagga taacgatggg gagggccatg ccagacccca gagtggaatg   660
aagccactca cagagggcat gaggaagaat ggcacctggc tgcaggctac agcagccacc    720
acacgtgact gtggcgtgaa cccagaagaa gcagactcag ccttcagcct cctggccacc    780
tgctccttct atgaccatgc gctccacctc tgggagtggg aggggaactg a            831
```

<210> SEQ ID NO 94
<211> LENGTH: 831
<212> TYPE: DNA
<213> ORGANISM: Homo sapiens

<400> SEQUENCE: 94

```
atggtgaatg agacgaggcc caggctgcag aaagtggcct catggcaggc acatcaattc      60
```

| | |
|---|---|
| gaggcctgga ttgctgcttt caattactgg catccagaaa ttgtgtattc agggggcgac | 120 |
| gatggccttc tgaggggctg ggacaccagg gtacccggca aatttctctt caccagcaaa | 180 |
| agacacacca tgggtgtgtg cagcatccag agcagccctc atcgggagca catcctggcc | 240 |
| acgggaagct atgatgaaca catcctactg tgggacacac gaaacatgaa gcagccgttg | 300 |
| gcagatacgc ctgtgcaggg tggggtatgg agaatcaagt ggcacccttt ccaccaccac | 360 |
| ctgctcctgg ccgcctgcat gcacagtggc tttaagatcc tcaactgcca aaaggcaatg | 420 |
| gaggagaggc aggaggcgac ggtcctgaca tctcacacat tgcccgactc gctggtgtat | 480 |
| ggagccgact ggtcctggct gctcttccgt tctctgcagc gggcccctc gtggtccttt | 540 |
| cctagcaacc taggaaccaa gacggcagac ctgaagggtg caagcgagtt gccaacaccc | 600 |
| tgtcatgaat gcagagagga taacgatggg gagggccatg ccagacccca gagtggaatg | 660 |
| aagccactca cagagggcat gaggaagaat ggcacctggc tgcaggctac agcagccacc | 720 |
| acacgtgact gtggcgtgaa cccagaagaa gcagactcag ccttcagcct cctggccacc | 780 |
| tgctccttct atgaccatgc gctccacctc tgggagtggg aggggaactg a | 831 |

<210> SEQ ID NO 95
<211> LENGTH: 831
<212> TYPE: DNA
<213> ORGANISM: Homo sapiens

<400> SEQUENCE: 95

| | |
|---|---|
| atggtgaatg agacgaggcc caggctgcag aaagtggcct catggcaggc acatcaattc | 60 |
| gaggcctgga ttgctgcttt caattactgg catccagaaa ttgtgtattc agggggcgac | 120 |
| gatggccttc tgaggggctg ggacaccagg gtacccggca aatttctctt caccagcaaa | 180 |
| agacacacca tgggtgtgtg cagcatccag agcagccctc atcgggagca catcctggcc | 240 |
| acgggaagct atgatgaaca catcctactg tgggacacac gaaacatgaa gcagccgttg | 300 |
| gcagatacgc ctgtgcaggg tggggtatgg agaatcaagt ggcacccttt ccaccaccac | 360 |
| ctgctcctgg ccgcctgcat gcacagtggc tttaagatcc tcaactgcca aaaggcaatg | 420 |
| gaggagaggc aggaggcgac ggtcctgaca tctcacacat tgcccgactc gctggtgtat | 480 |
| ggagccgact ggtcctggct gctcttccgt tctctgcagc gggcccctc gtggtccttt | 540 |
| cctagcaacc taggaaccaa gacggcagac ctgaagggtg caagcgagtt gccaacaccc | 600 |
| tgtcatgaat gcagagagga taacgatggg gagggccatg ccagacccca gagtggaatg | 660 |
| aagccactca cagagggcat gaggaagaat ggcacctggc tgcaggctac agcagccacc | 720 |
| acacgtgact gtggcgtgaa cccagaagaa gcagactcag ccttcagcct cctggccacc | 780 |
| tgctccttct atgaccatgc gctccacctc tgggagtggg aggggaactg a | 831 |

<210> SEQ ID NO 96
<211> LENGTH: 831
<212> TYPE: DNA
<213> ORGANISM: Homo sapiens

<400> SEQUENCE: 96

| | |
|---|---|
| atggtgaatg agacgaggcc caggctgcag aaagtggcct catggcaggc acatcaattc | 60 |
| gaggcctgga ttgctgcttt caattactgg catccagaaa ttgtgtattc agggggcgac | 120 |
| gatggccttc tgaggggctg ggacaccagg gtacccggca aatttctctt caccagcaaa | 180 |
| agacacacca tgggtgtgtg cagcatccag agcagccctc atcgggagca catcctggcc | 240 |
| acgggaagct atgatgaaca catcctactg tgggacacac gaaacatgaa gcagccgttg | 300 |

```
gcagatacgc ctgtgcaggg tggggtatgg agaatcaagt ggcacccttt ccaccaccac   360
ctgctcctgg ccgcctgcat gcacagtggc tttaagatcc tcaactgcca aaaggcaatg   420
gaggagaggc aggaggcgac ggtcctgaca tctcacacat tgcccgactc gctggtgtat   480
ggagccgact ggtcctggct gctcttccgt tctctgcagc gggcccctc gtggtccttt    540 cctagcaacc taggaaccaa gacggcagac ctgaagggtg caagcgagtt gccaacaccc   600
tgtcatgaat gcagagagga taacgatggg gagggccatg ccagacccca gagtggaatg   660
aagccactca cagagggcat gaggaagaat ggcacctggc tgcaggctac agcagccacc   720
acacgtgact gtggcgtgaa cccagaagaa gcagactcag ccttcagcct cctggccacc   780
tgctcctcct atgaccatgc gctccacctc tgggagtggg aggggaactg a            831
```

```
<210> SEQ ID NO 97
<211> LENGTH: 831
<212> TYPE: DNA
<213> ORGANISM: Homo sapiens

<400> SEQUENCE: 97
atggtgaatg agacgaggcc caggctgcag aaagtggcct catggcaggc acatcaattc    60
gaggcctgga ttgctgcttt caattactgg catccagaaa ttgtgtattc aggggggcgac   120 gatggccttc tgagggggctg ggacaccagg gtacccggca aatttctctt caccagcaaa   180
agacacacca tgggtgtgtg cagcatccag agcagccctc atcgggagca catcctggcc    240
acgggaagct atgatgaaca catcctactg tgggacacac gaaacatgaa gcagccgttg    300
gcagatacgc ctgtgcaggg tggggtatgg agaatcaagt ggcacccttt ccaccaccac    360
ctgctcctgg ccgcctgcat gcacagtggc tttaagatcc tcaactgcca aaaggcaatg    420
gaggagaggc aggaggcgac ggtcctgaca tctcacacat tgcccgactc gctggtgtat    480
ggagccgact ggtcctggct gctcttccgt tctctgcagc gggcccctc gtggtccttt     540 cctagcaacc taggaaccaa gacggcagac ctgaagggtg caagcgagtt gccaacaccc    600
tgtcatgaat gcagagagga taacgatggg gagggccatg ccagacccca gagtggaatg    660
aagccactca cagagggcat gaggaagaat ggcacctggc tgcaggctac agcagccacc    720
acacgtgact gtggcgtgaa cccagaagaa gcagactcag ccttcagcct cctggccacc    780
tgctcctcct atgaccatgc gctccacctc tgggagtggg aggggaactg a             831
```

```
<210> SEQ ID NO 98
<211> LENGTH: 831
<212> TYPE: DNA
<213> ORGANISM: Homo sapiens

<400> SEQUENCE: 98
atggtgaatg agacgaggcc caggctgcag aaagtggcct catggcaggc acatcaattc    60
gaggcctgga ttgctgcttt caattactgg catccagaaa ttgtgtattc aggggggcgac   120 gatggccttc tgagggggctg ggacaccagg gtacccggca aatttctctt caccagcaaa   180
agacacacca tgggtgtgtg cagcatccag agcagccctc atcgggagca catcctggcc    240
acgggaagct atgatgaaca catcctactg tgggacacac gaaacatgaa gcagccgttg    300
gcagatacgc ctgtgcaggg tggggtatgg agaatcaagt ggcacccttt ccaccaccac    360
ctgctcctgg ccgcctgcat gcacagtggc tttaagatcc tcaactgcca aaaggcaatg    420
gaggagaggc aggaggcgac ggtcctgaca tctcacacat tgcccgactc gctggtgtat    480
```

| | |
|---|---|
| ggagccgact ggtcctggct gctcttccgt tctctgcagc gggccccctc gtggtccttt | 540 |
| cctagcaacc taggaaccaa gacggcagac ctgaagggtg caagcgagtt gccaacaccc | 600 |
| tgtcatgaat gcagagagga taacgatggg gagggccatg ccagacccca gagtggaatg | 660 |
| aagccactca cagagggcat gaggaagaat ggcacctggc tgcaggctac agcagccacc | 720 |
| acacgtgact gtggcgtgaa cccagaagaa gcagactcag ccttcagcct cctggccacc | 780 |
| tgctccttct atgaccatgc gctccacctc tgggagtggg aggggaactg a | 831 |

<210> SEQ ID NO 99
<211> LENGTH: 831
<212> TYPE: DNA
<213> ORGANISM: Homo sapiens

<400> SEQUENCE: 99

| | |
|---|---|
| atggtgaatg agacgaggcc caggctgcag aaagtggcct catggcaggc acatcaattc | 60 |
| gaggcctgga ttgctgcttt caattactgg catccagaaa ttgtgtattc aggggggcgac | 120 |
| gatggccttc tgaggggctg ggacaccagg gtacccggca aatttctctt caccagcaaa | 180 |
| agacacacca tgggtgtgtg cagcatccag agcagccctc atcgggagca catcctggcc | 240 |
| acgggaagct atgatgaaca catcctactg tgggacacac gaaacatgaa gcagccgttg | 300 |
| gcagatacgc ctgtgcaggg tggggtatgg agaatcaagt ggcaccccttt ccaccaccac | 360 |
| ctgctcctgg ccgcctgcat gcacagtggc tttaagatcc tcaactgcca aaaggcaatg | 420 |
| gaggagaggc aggaggcgac ggtcctgaca tctcacacat gcccgactc gctggtgtat | 480 |
| ggagccgact ggtcctggct gctcttccgt tctctgcagc gggccccctc gtggtccttt | 540 |
| cctagcaacc taggaaccaa gacggcagac ctgaagggtg caagcgagtt gccaacaccc | 600 |
| tgtcatgaat gcagagagga taacgatggg gagggccatg ccagacccca gagtggaatg | 660 |
| aagccactca cagagggcat gaggaagaat ggcacctggc tgcaggctac agcagccacc | 720 |
| acacgtgact gtggcgtgaa cccagaagaa gcagactcag ccttcagcct cctggccacc | 780 |
| tgctccttct atgaccatgc gctccacctc tgggagtggg aggggaactg a | 831 |

<210> SEQ ID NO 100
<211> LENGTH: 831
<212> TYPE: DNA
<213> ORGANISM: Homo sapiens

<400> SEQUENCE: 100

| | |
|---|---|
| atggtgaatg agacgaggcc caggctgcag aaagtggcct catggcaggc acatcaattc | 60 |
| gaggcctgga ttgctgcttt caattactgg catccagaaa ttgtgtattc aggggggcgac | 120 |
| gatggccttc tgaggggctg ggacaccagg gtacccggca aatttctctt caccagcaaa | 180 |
| agacacacca tgggtgtgtg cagcatccag agcagccctc atcgggagca catcctggcc | 240 |
| acgggaagct atgatgaaca catcctactg tgggacacac gaaacatgaa gcagccgttg | 300 |
| gcagatacgc ctgtgcaggg tggggtatgg agaatcaagt ggcaccccttt ccaccaccac | 360 |
| ctgctcctgg ccgcctgcat gcacagtggc tttaagatcc tcaactgcca aaaggcaatg | 420 |
| gaggagaggc aggaggcgac ggtcctgaca tctcacacat gcccgactc gctggtgtat | 480 |
| ggagccgact ggtcctggct gctcttccgt tctctgcagc gggccccctc gtggtccttt | 540 |
| cctagcaacc taggaaccaa gacggcagac ctgaagggtg caagcgagtt gccaacaccc | 600 |
| tgtcatgaat gcagagagga taacgatggg gagggccatg ccagacccca gagtggaatg | 660 |
| aagccactca cagagggcat gaggaagaat ggcacctggc tgcaggctac agcagccacc | 720 |

| | |
|---|---|
| acacgtgact gtggcgtgaa cccagaagaa gcagactcag ccttcagcct cctggccacc | 780 |
| tgctccttct atgaccatgc gctccacctc tgggagtggg aggggaactg a | 831 |

<210> SEQ ID NO 101
<211> LENGTH: 831
<212> TYPE: DNA
<213> ORGANISM: Homo sapiens

<400> SEQUENCE: 101

| | |
|---|---|
| atggtgaatg agacgaggcc caggctgcag aaagtggcct catggcaggc acatcaattc | 60 |
| gaggcctgga ttgctgcttt caattactgg catccagaaa ttgtgtattc aggggggcgac | 120 |
| gatggccttc tgaggggctg ggacaccagg gtacccggca aatttctctt caccagcaaa | 180 |
| agacacacca tgggtgtgtg cagcatccag agcagccctc atcgggagca catcctggcc | 240 |
| acgggaagct atgatgaaca catcctactg tgggacacac gaaacatgaa gcagccgttg | 300 |
| gcagatacgc ctgtgcaggg tggggtatgg agaatcaagt ggcacccttt ccaccaccac | 360 |
| ctgctcctgg ccgcctgcat gcacagtggc tttaagatcc tcaactgcca aaaggcaatg | 420 |
| gaggagaggc aggaggcgac ggtcctgaca tctcacacat gcccgactc gctggtgtat | 480 |
| ggagccgact ggtcctggct gctcttccgt tctctgcagc gggcccctc gtggtccttt | 540 |
| cctagcaacc taggaaccaa gacggcagac ctgaagggtg caagcgagtt gccaacaccc | 600 |
| tgtcatgaat gcagagagga taacgatggg gagggccatg ccagacccca gagtggaatg | 660 |
| aagccactca cagagggcat gaggaagaat ggcacctggc tgcaggctac agcagccacc | 720 |
| acacgtgact gtggcgtgaa cccagaagaa gcagactcag ccttcagcct cctggccacc | 780 |
| tgctccttct atgaccatgc gctccacctc tgggagtggg aggggaactg a | 831 |

<210> SEQ ID NO 102
<211> LENGTH: 831
<212> TYPE: DNA
<213> ORGANISM: Homo sapiens

<400> SEQUENCE: 102

| | |
|---|---|
| atggtgaatg agacgaggcc caggctgcag aaagtggcct catggcaggc acatcaattc | 60 |
| gaggcctgga ttgctgcttt caattactgg catccagaaa ttgtgtattc aggggggcgac | 120 |
| gatggccttc tgaggggctg ggacaccagg gtacccggca aatttctctt caccagcaaa | 180 |
| agacacacca tgggtgtgtg cagcatccag agcagccctc atcgggagca catcctggcc | 240 |
| acgggaagct atgatgaaca catcctactg tgggacacac gaaacatgaa gcagccgttg | 300 |
| gcagatacgc ctgtgcaggg tggggtatgg agaatcaagt ggcacccttt ccaccaccac | 360 |
| ctgctcctgg ccgcctgcat gcacagtggc tttaagatcc tcaactgcca aaaggcaatg | 420 |
| gaggagaggc aggaggcgac ggtcctgaca tctcacacat gcccgactc gctggtgtat | 480 |
| ggagccgact ggtcctggct gctcttccgt tctctgcagc gggcccctc gtggtccttt | 540 |
| cctagcaacc taggaaccaa gacggcagac ctgaagggtg caagcgagtt gccaacaccc | 600 |
| tgtcatgaat gcagagagga taacgatggg gagggccatg ccagacccca gagtggaatg | 660 |
| aagccactca cagagggcat gaggaagaat ggcacctggc tgcaggctac agcagccacc | 720 |
| acacgtgact gtggcgtgaa cccagaagaa gcagactcag ccttcagcct cctggccacc | 780 |
| tgctccttct atgaccatgc gctccacctc tgggagtggg aggggaactg a | 831 |

<210> SEQ ID NO 103

<211> LENGTH: 765
<212> TYPE: DNA
<213> ORGANISM: Homo sapiens

<400> SEQUENCE: 103

| | | |
|---|---|---|
| atggtgaatg agacgaggcc caggctgcag aaagtggcct catggcaggc acatcaattc | 60 |
| gaggcctgga ttgctgcttt caattactgg catccagaaa ttgtgtattc aggggggcgac | 120 |
| gatggccttc tgaggggctg ggacaccagg gtacccggca aatttctctt caccagcaaa | 180 |
| agctatgatg aacacatcct actgtgggac acacgaaaca tgaagcagcc gttggcagat | 240 |
| acgcctgtgc agggtggggt atggagaatc aagtggcacc ctttccacca ccacctgctc | 300 |
| ctggccgcct gcatgcacag tggctttaag atcctcaact gccaaaaggc aatggaggag | 360 |
| aggcaggagg cgacggtcct gacatctcac acattgcccg actcgctggt gtatggagcc | 420 |
| gactggtcct ggctgctctt ccgttctctg cagcgggccc cctcgtggtc ctttcctagc | 480 |
| aacctaggaa ccaagacggc agacctgaag ggtgcaagcg agttgccaac accctgtcat | 540 |
| gaatgcagag aggataacga tggggagggc catgccagac cccagagtgg aatgaagcca | 600 |
| ctcacagagg gcatgaggaa gaatggcacc tggctgcagg ctacagcagc caccacacgt | 660 |
| gactgtggcg tgaacccaga agaagcagac tcagccttca gcctcctggc cacctgctcc | 720 |
| ttctatgacc atgcgctcca cctctgggag tgggagggga actga | 765 |

<210> SEQ ID NO 104
<211> LENGTH: 765
<212> TYPE: DNA
<213> ORGANISM: Homo sapiens

<400> SEQUENCE: 104

| | | |
|---|---|---|
| atggtgaatg agacgaggcc caggctgcag aaagtggcct catggcaggc acatcaattc | 60 |
| gaggcctgga ttgctgcttt caattactgg catccagaaa ttgtgtattc aggggggcgac | 120 |
| gatggccttc tgaggggctg ggacaccagg gtacccggca aatttctctt caccagcaaa | 180 |
| agctatgatg aacacatcct actgtgggac acacgaaaca tgaagcagcc gttggcagat | 240 |
| acgcctgtgc agggtggggt atggagaatc aagtggcacc ctttccacca ccacctgctc | 300 |
| ctggccgcct gcatgcacag tggctttaag atcctcaact gccaaaaggc aatggaggag | 360 |
| aggcaggagg cgacggtcct gacatctcac acattgcccg actcgctggt gtatggagcc | 420 |
| gactggtcct ggctgctctt ccgttctctg cagcgggccc cctcgtggtc ctttcctagc | 480 |
| aacctaggaa ccaagacggc agacctgaag ggtgcaagcg agttgccaac accctgtcat | 540 |
| gaatgcagag aggataacga tggggagggc catgccagac cccagagtgg aatgaagcca | 600 |
| ctcacagagg gcatgaggaa gaatggcacc tggctgcagg ctacagcagc caccacacgt | 660 |
| gactgtggcg tgaacccaga agaagcagac tcagccttca gcctcctggc cacctgctcc | 720 |
| ttctatgacc atgcgctcca cctctgggag tgggagggga actga | 765 |

<210> SEQ ID NO 105
<211> LENGTH: 765
<212> TYPE: DNA
<213> ORGANISM: Homo sapiens

<400> SEQUENCE: 105

| | | |
|---|---|---|
| atggtgaatg agacgaggcc caggctgcag aaagtggcct catggcaggc acatcaattc | 60 |
| gaggcctgga ttgctgcttt caattactgg catccagaaa ttgtgtattc aggggggcgac | 120 |
| gatggccttc tgaggggctg ggacaccagg gtacccggca aatttctctt caccagcaaa | 180 |

```
agctatgatg aacacatcct actgtgggac acacgaaaca tgaagcagcc gttggcagat    240
acgcctgtgc agggtggggt atggagaatc aagtggcacc ctttccacca ccacctgctc    300
ctggccgcct gcatgcacag tggctttaag atcctcaact gccaaaaggc aatggaggag    360
aggcaggagg cgacggtcct gacatctcac acattgcccg actcgctggt gtatggagcc    420
gactggtcct ggctgctctt ccgttctctg cagcgggccc cctcgtggtc ctttcctagc    480
aacctaggaa ccaagacggc agacctgaag ggtgcaagcg agttgccaac accctgtcat    540
gaatgcagag aggataacga tggggagggc catgccagac ccagagtgg aatgaagcca    600 ctcacagagg gcatgaggaa gaatggcacc tggctgcagg ctacagcagc caccacacgt    660
gactgtggcg tgaacccaga agaagcagac tcagccttca gcctcctggc cacctgctcc    720
ttctatgacc atgcgctcca cctctgggag tgggagggga actga                   765

<210> SEQ ID NO 106
<211> LENGTH: 765
<212> TYPE: DNA
<213> ORGANISM: Homo sapiens

<400> SEQUENCE: 106
atggtgaatg agacgaggcc caggctgcag aaagtggcct catggcaggc acatcaattc    60
gaggcctgga ttgctgcttt caattactgg catccagaaa ttgtgtattc aggggggcgac  120 gatggccttc tgaggggctg ggacaccagg gtacccggca aatttctctt caccagcaaa   180
agctatgatg aacacatcct actgtgggac acacgaaaca tgaagcagcc gttggcagat    240
acgcctgtgc agggtggggt atggagaatc aagtggcacc ctttccacca ccacctgctc    300
ctggccgcct gcatgcacag tggctttaag atcctcaact gccaaaaggc aatggaggag    360
aggcaggagg cgacggtcct gacatctcac acattgcccg actcgctggt gtatggagcc    420
gactggtcct ggctgctctt ccgttctctg cagcgggccc cctcgtggtc ctttcctagc    480
aacctaggaa ccaagacggc agacctgaag ggtgcaagcg agttgccaac accctgtcat    540
gaatgcagag aggataacga tggggagggc catgccagac ccagagtgg aatgaagcca    600 ctcacagagg gcatgaggaa gaatggcacc tggctgcagg ctacagcagc caccacacgt    660
gactgtggcg tgaacccaga agaagcagac tcagccttca gcctcctggc cacctgctcc    720
ttctatgacc atgcgctcca cctctgggag tgggagggga actga                   765

<210> SEQ ID NO 107
<211> LENGTH: 452
<212> TYPE: PRT
<213> ORGANISM: Homo sapiens

<400> SEQUENCE: 107

Met Met Gly Cys Phe Ala Leu Gln Thr Val Asp Thr Glu Leu Thr Ala
1               5                   10                  15

Asp Ser Val Glu Trp Cys Pro Leu Gln Gly Cys Arg His Leu Leu Ala
                20                  25                  30

Cys Gly Thr Tyr Gln Leu Arg Arg Pro Glu Asp Arg Pro Ala Gly Pro
            35                  40                  45

Gln Asn Lys Gly Gly Met Glu Val Lys Glu Pro Gln Val Arg Leu Gly
        50                  55                  60

Arg Leu Phe Leu Tyr Ser Phe Asn Asp Asn Ser Ile His Pro Leu
65                  70                  75                  80

Val Glu Val Gln Arg Lys Asp Thr Ser Ala Ile Leu Asp Met Lys Trp
```

```
                       85                  90                  95
Cys His Ile Pro Val Ala Gly His Ala Leu Leu Gly Leu Ala Asp Ala
                   100                 105                 110

Ser Gly Ser Ile Gln Leu Leu Arg Leu Val Glu Ser Glu Lys Ser His
                   115                 120                 125

Val Leu Glu Pro Leu Ser Ser Leu Ala Leu Glu Glu Gln Cys Leu Ala
130                 135                 140

Leu Ser Leu Asp Trp Ser Thr Gly Lys Thr Gly Arg Ala Gly Asp Gln
145                 150                 155                 160

Pro Leu Lys Ile Ile Ser Ser Asp Ser Thr Gly Gln Leu His Leu Leu
                   165                 170                 175

Met Val Asn Glu Thr Arg Pro Arg Leu Gln Lys Val Ala Ser Trp Gln
                   180                 185                 190

Ala His Gln Phe Glu Ala Trp Ile Ala Ala Phe Asn Tyr Trp His Pro
                   195                 200                 205

Glu Ile Val Tyr Ser Gly Gly Asp Asp Gly Leu Leu Arg Gly Trp Asp
                   210                 215                 220

Thr Arg Val Pro Gly Lys Phe Leu Phe Thr Ser Lys Arg His Thr Met
225                 230                 235                 240

Gly Val Cys Ser Ile Gln Ser Ser Pro His Arg Glu His Ile Leu Ala
                   245                 250                 255

Thr Gly Ser Tyr Asp Glu His Ile Leu Leu Trp Asp Thr Arg Asn Met
                   260                 265                 270

Lys Gln Pro Leu Ala Asp Thr Pro Val Gln Gly Gly Val Trp Arg Ile
                   275                 280                 285

Lys Trp His Pro Phe His His His Leu Leu Leu Ala Ala Cys Met His
                   290                 295                 300

Ser Gly Phe Lys Ile Leu Asn Cys Gln Lys Ala Met Glu Glu Arg Gln
305                 310                 315                 320

Glu Ala Thr Val Leu Thr Ser His Thr Leu Pro Asp Ser Leu Val Tyr
                   325                 330                 335

Gly Ala Asp Trp Ser Trp Leu Leu Phe Arg Ser Leu Gln Arg Ala Pro
                   340                 345                 350

Ser Trp Ser Phe Pro Ser Asn Leu Gly Thr Lys Thr Ala Asp Leu Lys
                   355                 360                 365

Gly Ala Ser Glu Leu Pro Thr Pro Cys His Glu Cys Arg Glu Asp Asn
                   370                 375                 380

Asp Gly Glu Gly His Ala Arg Pro Gln Ser Gly Met Lys Pro Leu Thr
385                 390                 395                 400

Glu Gly Met Arg Lys Asn Gly Thr Trp Leu Gln Ala Thr Ala Ala Thr
                   405                 410                 415

Thr Arg Asp Cys Gly Val Asn Pro Glu Glu Ala Asp Ser Ala Phe Ser
                   420                 425                 430

Leu Leu Ala Thr Cys Ser Phe Tyr Asp His Ala Leu His Leu Trp Glu
                   435                 440                 445

Trp Glu Gly Asn
    450

<210> SEQ ID NO 108
<211> LENGTH: 430
<212> TYPE: PRT
<213> ORGANISM: Homo sapiens

<400> SEQUENCE: 108
```

```
Met Met Gly Cys Phe Ala Leu Gln Thr Val Asp Thr Glu Leu Thr Ala
1               5                   10                  15

Asp Ser Val Glu Trp Cys Pro Leu Gln Gly Cys Arg His Leu Leu Ala
            20                  25                  30

Cys Gly Thr Tyr Gln Leu Arg Arg Pro Glu Asp Arg Pro Ala Gly Pro
                35                  40                  45

Gln Asn Lys Gly Gly Met Glu Val Lys Glu Pro Gln Val Arg Leu Gly
    50                  55                  60

Arg Leu Phe Leu Tyr Ser Phe Asn Asp Asn Ser Ile His Pro Leu
65                  70                  75                  80

Val Glu Val Gln Arg Lys Asp Thr Ser Ala Ile Leu Asp Met Lys Trp
                85                  90                  95

Cys His Ile Pro Val Ala Gly His Ala Leu Leu Gly Leu Ala Asp Ala
                100                 105                 110

Ser Gly Ser Ile Gln Leu Leu Arg Leu Val Glu Ser Glu Lys Ser His
            115                 120                 125

Val Leu Glu Pro Leu Ser Ser Leu Ala Leu Glu Gln Cys Leu Ala
            130                 135                 140

Leu Ser Leu Asp Trp Ser Thr Gly Lys Thr Gly Arg Ala Gly Asp Gln
145                 150                 155                 160

Pro Leu Lys Ile Ile Ser Ser Asp Ser Thr Gly Gln Leu His Leu Leu
                165                 170                 175

Met Val Asn Glu Thr Arg Pro Arg Leu Gln Lys Val Ala Ser Trp Gln
                180                 185                 190

Ala His Gln Phe Glu Ala Trp Ile Ala Ala Phe Asn Tyr Trp His Pro
    195                 200                 205

Glu Ile Val Tyr Ser Gly Gly Asp Asp Gly Leu Leu Arg Gly Trp Asp
    210                 215                 220

Thr Arg Val Pro Gly Lys Phe Leu Phe Thr Ser Lys Ser Tyr Asp Glu
225                 230                 235                 240

His Ile Leu Leu Trp Asp Thr Arg Asn Met Lys Gln Pro Leu Ala Asp
                245                 250                 255

Thr Pro Val Gln Gly Gly Val Trp Arg Ile Lys Trp His Pro Phe His
                260                 265                 270

His His Leu Leu Leu Ala Ala Cys Met His Ser Gly Phe Lys Ile Leu
        275                 280                 285

Asn Cys Gln Lys Ala Met Glu Glu Arg Gln Glu Ala Thr Val Leu Thr
    290                 295                 300

Ser His Thr Leu Pro Asp Ser Leu Val Tyr Gly Ala Asp Trp Ser Trp
305                 310                 315                 320

Leu Leu Phe Arg Ser Leu Gln Arg Ala Pro Ser Trp Ser Phe Pro Ser
            325                 330                 335

Asn Leu Gly Thr Lys Thr Ala Asp Leu Lys Gly Ala Ser Glu Leu Pro
            340                 345                 350

Thr Pro Cys His Glu Cys Arg Glu Asp Asn Asp Gly Glu Gly His Ala
            355                 360                 365

Arg Pro Gln Ser Gly Met Lys Pro Leu Thr Glu Gly Met Arg Lys Asn
    370                 375                 380

Gly Thr Trp Leu Gln Ala Thr Ala Thr Arg Asp Cys Gly Val
385                 390                 395                 400

Asn Pro Glu Glu Ala Asp Ser Ala Phe Ser Leu Leu Ala Thr Cys Ser
            405                 410                 415

Phe Tyr Asp His Ala Leu His Leu Trp Glu Trp Glu Gly Asn
```

420 425 430

<210> SEQ ID NO 109
<211> LENGTH: 336
<212> TYPE: PRT
<213> ORGANISM: Homo sapiens

<400> SEQUENCE: 109

Met Met Gly Cys Phe Ala Leu Gln Thr Val Asp Thr Glu Leu Thr Ala
1               5                   10                  15

Asp Ser Val Glu Trp Cys Pro Leu Gln Gly Cys Arg His Leu Leu Ala
            20                  25                  30

Cys Gly Thr Tyr Gln Leu Arg Arg Pro Glu Asp Arg Pro Ala Gly Pro
        35                  40                  45

Gln Asn Lys Gly Gly Met Glu Val Lys Glu Pro Gln Val Arg Leu Gly
    50                  55                  60

Arg Leu Phe Leu Tyr Ser Phe Asn Asp Asn Ser Ile His Pro Leu
65                  70                  75                  80

Val Glu Val Gln Arg Lys Asp Thr Ser Ala Ile Leu Asp Met Lys Trp
                85                  90                  95

Cys His Ile Pro Val Ala Gly His Ala Leu Leu Gly Leu Ala Asp Ala
            100                 105                 110

Ser Gly Ser Ile Gln Leu Leu Arg Leu Val Glu Ser Glu Lys Ser His
        115                 120                 125

Val Leu Glu Pro Leu Ser Ser Leu Ala Leu Glu Glu Gln Cys Leu Ala
    130                 135                 140

Leu Ser Leu Asp Trp Ser Thr Gly Lys Thr Gly Arg Ala Gly Asp Gln
145                 150                 155                 160

Pro Leu Lys Ile Ile Ser Ser Asp Ser Thr Gly Gln Leu His Leu Leu
                165                 170                 175

Met Val Asn Glu Thr Arg Pro Arg Leu Gln Lys Val Ala Ser Trp Gln
            180                 185                 190

Ala His Gln Phe Glu Ala Trp Ile Ala Ala Phe Asn Tyr Trp His Pro
        195                 200                 205

Glu Ile Val Tyr Ser Gly Gly Asp Asp Gly Leu Leu Arg Gly Trp Asp
    210                 215                 220

Thr Arg Val Pro Gly Lys Phe Leu Phe Thr Ser Lys Arg His Thr Met
225                 230                 235                 240

Gly Val Cys Ser Ile Gln Ser Ser Pro His Arg Glu His Ile Leu Ala
                245                 250                 255

Thr Gly Ser Tyr Asp Glu His Ile Leu Leu Trp Asp Thr Arg Asn Met
            260                 265                 270

Lys Gln Pro Leu Ala Asp Thr Pro Val Gln Gly Gly Val Trp Arg Ile
        275                 280                 285

Lys Trp His Pro Phe His His His Leu Leu Leu Ala Ala Cys Met His
    290                 295                 300

Ser Gly Phe Lys Ile Leu Asn Cys Gln Lys Ala Met Ala Val Glu Glu
305                 310                 315                 320

Val Leu Leu Ala Arg Val Asp Val Leu Ser Asp Cys Trp Met Lys Asp
                325                 330                 335

<210> SEQ ID NO 110
<211> LENGTH: 323
<212> TYPE: PRT
<213> ORGANISM: Homo sapiens -continued

<400> SEQUENCE: 110

Met Met Gly Cys Phe Ala Leu Gln Thr Val Asp Thr Glu Leu Thr Ala
1               5                   10                  15

Asp Ser Val Glu Trp Cys Pro Leu Gln Gly Cys Arg His Leu Leu Ala
            20                  25                  30

Cys Gly Thr Tyr Gln Leu Arg Arg Pro Glu Asp Arg Pro Ala Gly Pro
        35                  40                  45

Gln Asn Lys Gly Gly Met Glu Val Lys Glu Pro Gln Val Arg Leu Gly
    50                  55                  60

Arg Leu Phe Leu Tyr Ser Phe Asn Asp Asn Ser Ile His Pro Leu
65                  70                  75                  80

Val Glu Val Gln Arg Lys Asp Thr Ser Ala Ile Leu Asp Met Lys Trp
            85                  90                  95

Cys His Ile Pro Val Ala Gly His Ala Leu Leu Gly Leu Ala Asp Ala
        100                 105                 110

Ser Gly Ser Ile Gln Leu Leu Arg Leu Val Glu Ser Glu Lys Ser His
    115                 120                 125

Val Leu Glu Pro Leu Ser Ser Leu Ala Leu Glu Glu Gln Cys Leu Ala
130                 135                 140

Leu Ser Leu Asp Trp Ser Thr Gly Lys Thr Gly Arg Ala Gly Asp Gln
145                 150                 155                 160

Pro Leu Lys Ile Ile Ser Ser Asp Ser Thr Gly Gln Leu His Leu Leu
            165                 170                 175

Met Val Asn Glu Thr Arg Pro Arg Leu Gln Lys Val Ala Ser Trp Gln
        180                 185                 190

Ala His Gln Phe Glu Ala Trp Ile Ala Ala Phe Asn Tyr Trp His Pro
    195                 200                 205

Glu Ile Val Tyr Ser Gly Gly Asp Asp Gly Leu Leu Arg Gly Trp Asp
210                 215                 220

Thr Arg Val Pro Gly Lys Phe Leu Phe Thr Ser Lys Arg His Thr Met
225                 230                 235                 240

Gly Val Cys Ser Ile Gln Ser Ser Pro His Arg Glu His Ile Leu Ala
            245                 250                 255

Thr Gly Ser Tyr Asp Glu His Ile Leu Leu Trp Asp Thr Arg Asn Met
        260                 265                 270

Lys Gln Pro Leu Ala Asp Thr Pro Val Gln Gly Gly Val Trp Arg Ile
    275                 280                 285

Lys Trp His Pro Phe His His His Leu Leu Leu Ala Ala Cys Met His
290                 295                 300

Ser Gly Phe Lys Ile Leu Asn Cys Gln Lys Ala Met Gly Cys Gly Ser
305                 310                 315                 320

Leu Arg Ala

<210> SEQ ID NO 111
<211> LENGTH: 318
<212> TYPE: PRT
<213> ORGANISM: Homo sapiens

<400> SEQUENCE: 111

Met Pro Ser Trp Ala Trp Gln Met Pro Val Asp Pro Tyr Asn Cys Ser
1               5                   10                  15

Ala Trp Trp Asn Leu Arg Ala Gly Asp Gln Pro Leu Lys Ile Ile Ser
            20                  25                  30

Ser Asp Ser Thr Gly Gln Leu His Leu Leu Met Val Asn Glu Thr Arg

```
            35                  40                  45
Pro Arg Leu Gln Lys Val Ala Ser Trp Gln Ala His Gln Phe Glu Ala
 50                  55                  60
Trp Ile Ala Ala Phe Asn Tyr Trp His Pro Glu Ile Val Tyr Ser Gly
 65                  70                  75                  80
Gly Asp Asp Gly Leu Arg Gly Trp Asp Thr Arg Val Pro Gly Lys
                 85                  90                  95
Phe Leu Phe Thr Ser Lys Arg His Thr Met Gly Val Cys Ser Ile Gln
                100                 105                 110
Ser Ser Pro His Arg Glu His Ile Leu Ala Thr Gly Ser Tyr Asp Glu
                115                 120                 125
His Ile Leu Leu Trp Asp Thr Arg Asn Met Lys Gln Pro Leu Ala Asp
130                 135                 140
Thr Pro Val Gln Gly Gly Val Trp Arg Ile Lys Trp His Pro Phe His
145                 150                 155                 160
His His Leu Leu Leu Ala Ala Cys Met His Ser Gly Phe Lys Ile Leu
                165                 170                 175
Asn Cys Gln Lys Ala Met Glu Glu Arg Gln Glu Ala Thr Val Leu Thr
                180                 185                 190
Ser His Thr Leu Pro Asp Ser Leu Val Tyr Gly Ala Asp Trp Ser Trp
                195                 200                 205
Leu Leu Phe Arg Ser Leu Gln Arg Ala Pro Ser Trp Ser Phe Pro Ser
210                 215                 220
Asn Leu Gly Thr Lys Thr Ala Asp Leu Lys Gly Ala Ser Glu Leu Pro
225                 230                 235                 240
Thr Pro Cys His Glu Cys Arg Glu Asp Asn Asp Gly Glu Gly His Ala
                245                 250                 255
Arg Pro Gln Ser Gly Met Lys Pro Leu Thr Glu Gly Met Arg Lys Asn
                260                 265                 270
Gly Thr Trp Leu Gln Ala Thr Ala Ala Thr Thr Arg Asp Cys Gly Val
                275                 280                 285
Asn Pro Glu Glu Ala Asp Ser Ala Phe Ser Leu Leu Ala Thr Cys Ser
290                 295                 300
Phe Tyr Asp His Ala Leu His Leu Trp Glu Trp Gly Asn
305                 310                 315

<210> SEQ ID NO 112
<211> LENGTH: 301
<212> TYPE: PRT
<213> ORGANISM: Homo sapiens

<400> SEQUENCE: 112

Met Met Gly Cys Phe Ala Leu Gln Thr Val Asp Thr Glu Leu Thr Ala
1               5                   10                  15
Asp Ser Val Glu Trp Cys Pro Leu Gln Gly Cys Arg His Leu Leu Ala
                20                  25                  30
Cys Gly Thr Tyr Gln Leu Arg Arg Pro Glu Asp Arg Pro Ala Gly Pro
                35                  40                  45
Gln Asn Lys Gly Gly Met Glu Val Lys Glu Pro Gln Val Arg Leu Gly
 50                  55                  60
Arg Leu Phe Leu Tyr Ser Phe Asn Asp Asn Asn Ser Ile His Pro Leu
 65                  70                  75                  80
Val Glu Val Gln Arg Lys Asp Thr Ser Ala Ile Leu Asp Met Lys Trp
                85                  90                  95
```

```
Cys His Ile Pro Val Ala Gly His Ala Leu Leu Gly Leu Ala Asp Ala
                100                 105                 110

Ser Gly Ser Ile Gln Leu Leu Arg Leu Val Glu Ser Glu Lys Ser His
            115                 120                 125

Val Leu Glu Pro Leu Ser Ser Leu Ala Leu Glu Glu Gln Cys Leu Ala
130                 135                 140

Leu Ser Leu Asp Trp Ser Thr Gly Lys Thr Gly Arg Ala Gly Asp Gln
145                 150                 155                 160

Pro Leu Lys Ile Ile Ser Ser Asp Ser Thr Gly Gln Leu His Leu Leu
                165                 170                 175

Met Val Asn Glu Thr Arg Pro Arg Leu Gln Lys Val Ala Ser Trp Gln
            180                 185                 190

Ala His Gln Phe Glu Ala Trp Ile Ala Ala Phe Asn Tyr Trp His Pro
        195                 200                 205

Glu Ile Val Tyr Ser Gly Gly Asp Asp Gly Leu Leu Arg Gly Trp Asp
        210                 215                 220

Thr Arg Val Pro Gly Lys Phe Leu Phe Thr Ser Lys Ser Tyr Asp Glu
225                 230                 235                 240

His Ile Leu Leu Trp Asp Thr Arg Asn Met Lys Gln Pro Leu Ala Asp
                245                 250                 255

Thr Pro Val Gln Gly Gly Val Trp Arg Ile Lys Trp His Pro Phe His
            260                 265                 270

His His Leu Leu Leu Ala Ala Cys Met His Ser Gly Phe Lys Ile Leu
        275                 280                 285

Asn Cys Gln Lys Ala Met Gly Cys Gly Ser Leu Arg Ala
        290                 295                 300

<210> SEQ ID NO 113
<211> LENGTH: 276
<212> TYPE: PRT
<213> ORGANISM: Homo sapiens

<400> SEQUENCE: 113

Met Val Asn Glu Thr Arg Pro Arg Leu Gln Lys Val Ala Ser Trp Gln
1               5                   10                  15

Ala His Gln Phe Glu Ala Trp Ile Ala Ala Phe Asn Tyr Trp His Pro
            20                  25                  30

Glu Ile Val Tyr Ser Gly Gly Asp Asp Gly Leu Leu Arg Gly Trp Asp
        35                  40                  45

Thr Arg Val Pro Gly Lys Phe Leu Phe Thr Ser Lys Arg His Thr Met
    50                  55                  60

Gly Val Cys Ser Ile Gln Ser Ser Pro His Arg Glu His Ile Leu Ala
65                  70                  75                  80

Thr Gly Ser Tyr Asp Glu His Ile Leu Leu Trp Asp Thr Arg Asn Met
                85                  90                  95

Lys Gln Pro Leu Ala Asp Thr Pro Val Gln Gly Gly Val Trp Arg Ile
            100                 105                 110

Lys Trp His Pro Phe His His His Leu Leu Leu Ala Ala Cys Met His
        115                 120                 125

Ser Gly Phe Lys Ile Leu Asn Cys Gln Lys Ala Met Glu Glu Arg Gln
    130                 135                 140

Glu Ala Thr Val Leu Thr Ser His Thr Leu Pro Asp Ser Leu Val Tyr
145                 150                 155                 160

Gly Ala Asp Trp Ser Trp Leu Leu Phe Arg Ser Leu Gln Arg Ala Pro
                165                 170                 175
```

```
Ser Trp Ser Phe Pro Ser Asn Leu Gly Thr Lys Thr Ala Asp Leu Lys
            180                 185                 190

Gly Ala Ser Glu Leu Pro Thr Pro Cys His Glu Cys Arg Glu Asp Asn
        195                 200                 205

Asp Gly Glu Gly His Ala Arg Pro Gln Ser Gly Met Lys Pro Leu Thr
    210                 215                 220

Glu Gly Met Arg Lys Asn Gly Thr Trp Leu Gln Ala Thr Ala Ala Thr
225                 230                 235                 240

Thr Arg Asp Cys Gly Val Asn Pro Glu Glu Ala Asp Ser Ala Phe Ser
                245                 250                 255

Leu Leu Ala Thr Cys Ser Phe Tyr Asp His Ala Leu His Leu Trp Glu
            260                 265                 270

Trp Glu Gly Asn
        275

<210> SEQ ID NO 114
<211> LENGTH: 254
<212> TYPE: PRT
<213> ORGANISM: Homo sapiens

<400> SEQUENCE: 114

Met Val Asn Glu Thr Arg Pro Arg Leu Gln Lys Val Ala Ser Trp Gln
1               5                   10                  15

Ala His Gln Phe Glu Ala Trp Ile Ala Phe Asn Tyr Trp His Pro
            20                  25                  30

Glu Ile Val Tyr Ser Gly Gly Asp Asp Gly Leu Leu Arg Gly Trp Asp
        35                  40                  45

Thr Arg Val Pro Gly Lys Phe Leu Phe Thr Ser Lys Ser Tyr Asp Glu
    50                  55                  60

His Ile Leu Leu Trp Asp Thr Arg Asn Met Lys Gln Pro Leu Ala Asp
65                  70                  75                  80

Thr Pro Val Gln Gly Gly Val Trp Arg Ile Lys Trp His Pro Phe His
                85                  90                  95

His His Leu Leu Leu Ala Ala Cys Met His Ser Gly Phe Lys Ile Leu
            100                 105                 110

Asn Cys Gln Lys Ala Met Glu Glu Arg Gln Glu Ala Thr Val Leu Thr
        115                 120                 125

Ser His Thr Leu Pro Asp Ser Leu Val Tyr Gly Ala Asp Trp Ser Trp
    130                 135                 140

Leu Leu Phe Arg Ser Leu Gln Arg Ala Pro Ser Trp Ser Phe Pro Ser
145                 150                 155                 160

Asn Leu Gly Thr Lys Thr Ala Asp Leu Lys Gly Ala Ser Glu Leu Pro
                165                 170                 175

Thr Pro Cys His Glu Cys Arg Glu Asp Asn Asp Gly Glu Gly His Ala
            180                 185                 190

Arg Pro Gln Ser Gly Met Lys Pro Leu Thr Glu Gly Met Arg Lys Asn
        195                 200                 205

Gly Thr Trp Leu Gln Ala Thr Ala Ala Thr Thr Arg Asp Cys Gly Val
    210                 215                 220

Asn Pro Glu Glu Ala Asp Ser Ala Phe Ser Leu Leu Ala Thr Cys Ser
225                 230                 235                 240

Phe Tyr Asp His Ala Leu His Leu Trp Glu Trp Glu Gly Asn
                245                 250
```

<210> SEQ ID NO 115
<211> LENGTH: 1434
<212> TYPE: DNA
<213> ORGANISM: Mus musculus

<400> SEQUENCE: 115

| | |
|---|---|
| atggcgggta gccacgcagg gacgttgcga gtcctgcagg cagtagacac tgagcttacc | 60 |
| gcggactcgg tggaatggtg cccagtagaa ggttaccagc atctgctggc ctgcggaacc | 120 |
| taccagctgc gagcgcccag ggaccagcct gcactggatg gcagtgagcc tcaagttcgt | 180 |
| ttaggtcgtc tctacctgtt cagcttcagt gagcacaaca cggctaaacc tctgcttgag | 240 |
| gtccaaagaa gggactcttc tgctgtcctg acatgaaat ggtgccacat cccagtctct | 300 |
| ggccatgtgc ttttaggctt ggcaaacgcc agtggatcca tagggctgct ccgcctgatg | 360 |
| gaatgtgaga caacagtta caccctgcag ccaatatcca gcctcgccct ggatgagaat | 420 |
| tgtctgtcct tgtcaatgga ttggtccact gggaaatctg tcagggccag agaacagccc | 480 |
| ttgaagatca ttagcagtga ttctaagggg cagttgcacc tcctgatggt gaatgagggc | 540 |
| acagctgaac tacagctagt agcatcttgg ccagcccatc actttgaggc ctggattgct | 600 |
| gctttcaatt actggcagac agaactcgtg tattcagggg gagatgactg ccttctgaga | 660 |
| ggctgggaca ctaggatgct gggcacacct gtcttcacta gcaaaagaca ttgcatgggt | 720 |
| gtgtgcagca tccagagcag cccccatcag gagcatatac tggcaactgg aagctatgat | 780 |
| gagcatgttc tgctgtggga cactcgaaac ataagacagc cattggcgga tgtaccagtg | 840 |
| caaggaggtg tgtggaggct caagtggcac ccagttcacc accatctact cctggcggcc | 900 |
| tgcatgcaca atggcttcaa gattctcaac tgccagaagg ccattgagga aagcaggac | 960 |
| ataactgttt taacatccca cgaaatgcct aactcattag tatatggggc tgactggtcc | 1020 |
| tggcttttcc attccatgaa gcccactcct acctggttct ttgatcagaa tgacatggga | 1080 |
| gtcaaagcag cagaccactc tagcctaaag gtcacagagg agccaccaat acattctcag | 1140 |
| gaacaaacca tggatcgcca agtggaaggc cccgctaacg ctcataccag agctgaactg | 1200 |
| aaggcttctc tccttccatt aacagaggac atgaaaaaca gcaaagactg ctcctcatcc | 1260 |
| tcagtcaaga ctcgtgatct tagccactgc tctggtgggc agagctttga caatagcctc | 1320 |
| ctggccacct gctccttta tgaccatgtt ctccacctttt ggaagtggga gacgaatcaa | 1380 |
| gctcgcactc tttgcagtgg cactggatgt gatttgggga gtgctgacca ttga | 1434 |

<210> SEQ ID NO 116
<211> LENGTH: 1068
<212> TYPE: DNA
<213> ORGANISM: Mus musculus

<400> SEQUENCE: 116

| | |
|---|---|
| atgaacaaca gttacaccct gcagccaata tccagcctcg ccctggatga gaattgtctg | 60 |
| tccttgtcaa tggattggtc cactgggaaa tctgtcaggg ccagagaaca gcccttgaag | 120 |
| atcattagca gtgattctaa ggggcagttg cacctcctga tggtgaatga gggcacagct | 180 |
| gaactacagc tagtagcatc tttggccagcc catcactttg aggcctggat tgctgctttc | 240 |
| aattactggc agacagaact cgtgtattca ggggagatg actgccttct gagaggctgg | 300 |
| gacactagga tgctgggcac acctgtcttc actagcaaaa gacattgcat gggtgtgtgc | 360 |
| agcatccaga gcagcccca tcaggagcat atactggcaa ctggaagcta tgatgagcat | 420 |
| gttctgctgt gggacactcg aaacataaga cagccattgg cggatgtacc agtgcaagga | 480 |

| | |
|---|---|
| ggtgtgtgga ggctcaagtg cacccagtt caccaccatc tactcctggc ggcctgcatg | 540 |
| cacaatggct tcaagattct caactgccag aaggccattg aggagaagca ggacataact | 600 |
| gttttaacat cccacgaaat gcctaactca ttagtatatg gggctgactg gtcctggctt | 660 |
| ttccattcca tgaagcccac tcctacctgg ttctttgatc agaatgacat gggagtcaaa | 720 |
| gcagcagacc actctagcct aaaggtcaca gaggagccac caatacattc tcaggaacaa | 780 |
| accatggatc gccaagtgga aggccccgct aacgctcata ccagagctga actgaaggct | 840 |
| tctctccttc cattaacaga ggacatgaaa aacagcaaag actgctcctc atcctcagtc | 900 |
| aagactcgtg atcttagcca ctgctctggt gggcagagct ttgacaatag cctcctggcc | 960 |
| acctgctcct tttatgacca tgttctccac ctttggaagt gggagacgaa tcaagctcgc | 1020 |
| actctttgca gtggcactgg atgtgatttg gggagtgctg accattga | 1068 |

<210> SEQ ID NO 117
<211> LENGTH: 999
<212> TYPE: DNA
<213> ORGANISM: Mus musculus

<400> SEQUENCE: 117

| | |
|---|---|
| atggattggt ccactgggaa atctgtcagg gccagagaac agcccttgaa gatcattagc | 60 |
| agtgattcta aggggcagtt gcacctcctg atggtgaatg agggcacagc tgaactacag | 120 |
| ctagtagcat cttggccagc ccatcacttt gaggcctgga ttgctgcttt caattactgg | 180 |
| cagacagaac tcgtgtattc agggggagat gactgccttc tgagaggctg ggacactagg | 240 |
| atgctgggca cacctgtctt cactagcaaa agacattgca tgggtgtgtg cagcatccag | 300 |
| agcagccccc atcaggagca tatactggca actggaagct atgatgagca tgttctgctg | 360 |
| tgggacactc gaaacataag acagccattg gcggatgtac cagtgcaagg aggtgtgtgg | 420 |
| aggctcaagt ggcacccagt tcaccaccat ctactcctgg cggcctgcat gcacaatggc | 480 |
| ttcaagattc tcaactgcca gaaggccatt gaggagaagc aggacataac tgttttaaca | 540 |
| tcccacgaaa tgcctaactc attagtatat ggggctgact ggtcctggct tttccattcc | 600 |
| atgaagccca ctcctacctg gttctttgat cagaatgaca tgggagtcaa agcagcagac | 660 |
| cactctagcc taaaggtcac agaggagcca caatacattc tcaggaaca aaccatggat | 720 |
| cgccaagtgg aaggccccgc taacgctcat accagagctg aactgaaggc ttctctcctt | 780 |
| ccattaacag aggacatgaa aaacagcaaa gactgctcct catcctcagt caagactcgt | 840 |
| gatcttagcc actgctctgg tgggcagagc tttgacaata gcctcctggc cacctgctcc | 900 |
| ttttatgacc atgttctcca cctttggaag tgggagacga atcaagctcg cactctttgc | 960 |
| agtggcactg gatgtgattt ggggagtgct gaccattga | 999 |

<210> SEQ ID NO 118
<211> LENGTH: 999
<212> TYPE: DNA
<213> ORGANISM: Mus musculus

<400> SEQUENCE: 118

| | |
|---|---|
| atggattggt ccactgggaa atctgtcagg gccagagaac agcccttgaa gatcattagc | 60 |
| agtgattcta aggggcagtt gcacctcctg atggtgaatg agggcacagc tgaactacag | 120 |
| ctagtagcat cttggccagc ccatcacttt gaggcctgga ttgctgcttt caattactgg | 180 |
| cagacagaac tcgtgtattc agggggagat gactgccttc tgagaggctg ggacactagg | 240 |
| atgctgggca cacctgtctt cactagcaaa agacattgca tgggtgtgtg cagcatccag | 300 |

```
agcagccccc atcaggagca tatactggca actggaagct atgatgagca tgttctgctg    360
tgggacactc gaaacataag acagccattg gcggatgtac cagtgcaagg aggtgtgtgg    420
aggctcaagt ggcacccagt tcaccaccat ctactcctgg cggcctgcat gcacaatggc    480
ttcaagattc tcaactgcca gaaggccatt gaggagaagc aggacataac tgttttaaca    540
tcccacgaaa tgcctaactc attagtatat ggggctgact ggtcctggct tttccattcc    600
atgaagccca ctcctacctg gttctttgat cagaatgaca tgggagtcaa agcagcagac    660
cactctagcc taaaggtcac agaggagcca ccaatacatt ctcaggaaca aaccatggat    720
cgccaagtgg aaggccccgc taacgctcat accagagctg aactgaaggc ttctctcctt    780
ccattaacag aggacatgaa aaacagcaaa gactgctcct catcctcagt caagactcgt    840
gatcttagcc actgctctgg tgggcagagc tttgacaata gcctcctggc cacctgctcc    900
ttttatgacc atgttctcca cctttggaag tgggagacga atcaagctcg cactctttgc    960
agtggcactg gatgtgattt ggggagtgct gaccattga                           999

<210> SEQ ID NO 119
<211> LENGTH: 999
<212> TYPE: DNA
<213> ORGANISM: Mus musculus

<400> SEQUENCE: 119
atggattggt ccactgggaa atctgtcagg gccagagaac agcccttgaa gatcattagc     60
agtgattcta aggggcagtt gcacctcctg atggtgaatg agggcacagc tgaactacag    120
ctagtagcat cttggccagc ccatcacttt gaggcctgga ttgctgcttt caattactgg    180
cagacagaac tcgtgtattc agggggagat gactgccttc tgagaggctg ggacactagg    240
atgctgggca cacctgtctt cactagcaaa agacattgca tgggtgtgtg cagcatccag    300
agcagccccc atcaggagca tatactggca actggaagct atgatgagca tgttctgctg    360
tgggacactc gaaacataag acagccattg gcggatgtac cagtgcaagg aggtgtgtgg    420
aggctcaagt ggcacccagt tcaccaccat ctactcctgg cggcctgcat gcacaatggc    480
ttcaagattc tcaactgcca gaaggccatt gaggagaagc aggacataac tgttttaaca    540
tcccacgaaa tgcctaactc attagtatat ggggctgact ggtcctggct tttccattcc    600
atgaagccca ctcctacctg gttctttgat cagaatgaca tgggagtcaa agcagcagac    660
cactctagcc taaaggtcac agaggagcca ccaatacatt ctcaggaaca aaccatggat    720
cgccaagtgg aaggccccgc taacgctcat accagagctg aactgaaggc ttctctcctt    780
ccattaacag aggacatgaa aaacagcaaa gactgctcct catcctcagt caagactcgt    840
gatcttagcc actgctctgg tgggcagagc tttgacaata gcctcctggc cacctgctcc    900
ttttatgacc atgttctcca cctttggaag tgggagacga atcaagctcg cactctttgc    960
agtggcactg gatgtgattt ggggagtgct gaccattga                           999

<210> SEQ ID NO 120
<211> LENGTH: 999
<212> TYPE: DNA
<213> ORGANISM: Mus musculus

<400> SEQUENCE: 120
atggattggt ccactgggaa atctgtcagg gccagagaac agcccttgaa gatcattagc     60
agtgattcta aggggcagtt gcacctcctg atggtgaatg agggcacagc tgaactacag    120
```

| | |
|---|---|
| ctagtagcat cttggccagc ccatcacttt gaggcctgga ttgctgcttt caattactgg | 180 |
| cagacagaac tcgtgtattc aggggagat gactgccttc tgagaggctg ggacactagg | 240 |
| atgctgggca cacctgtctt cactagcaaa agacattgca tgggtgtgtg cagcatccag | 300 |
| agcagccccc atcaggagca tatactggca actggaagct atgatgagca tgttctgctg | 360 |
| tgggacactc gaaacataag acagccattg gcggatgtac cagtgcaagg aggtgtgtgg | 420 |
| aggctcaagt ggcacccagt tcaccaccat ctactcctgg cggcctgcat gcacaatggc | 480 |
| ttcaagattc tcaactgcca gaaggccatt gaggagaagc aggacataac tgttttaaca | 540 |
| tcccacgaaa tgcctaactc attagtatat gggctgact ggtcctggct tttccattcc | 600 |
| atgaagccca ctcctacctg gttctttgat cagaatgaca tgggagtcaa agcagcagac | 660 |
| cactctagcc taaaggtcac agaggagcca ccaatacatt ctcaggaaca aaccatggat | 720 |
| cgccaagtgg aaggcccgc taacgctcat accagagctg aactgaaggc ttctctcctt | 780 |
| ccattaacag aggacatgaa aaacagcaaa gactgctcct catcctcagt caagactcgt | 840 |
| gatcttagcc actgctctgg tgggcagagc tttgacaata gcctcctggc cacctgctcc | 900 |
| ttttatgacc atgttctcca cctttggaag tgggagacga atcaagctcg cactctttgc | 960 |
| agtggcactg gatgtgattt ggggagtgct gaccattga | 999 |

<210> SEQ ID NO 121
<211> LENGTH: 849
<212> TYPE: DNA
<213> ORGANISM: Mus musculus

<400> SEQUENCE: 121

| | |
|---|---|
| atgagaattg tctgtccttg tcaatggatt ggtccactgg gaaatctgtc aggggagat | 60 |
| gactgccttc tgagaggctg ggacactagg atgctgggca cacctgtctt cactagcaaa | 120 |
| agacattgca tgggtgtgtg cagcatccag agcagccccc atcaggagca tatactggca | 180 |
| actggaagct atgatgagca tgttctgctg tgggacactc gaaacataag acagccattg | 240 |
| gcggatgtac cagtgcaagg aggtgtgtgg aggctcaagt ggcacccagt tcaccaccat | 300 |
| ctactcctgg cggcctgcat gcacaatggc ttcaagattc tcaactgcca gaaggccatt | 360 |
| gaggagaagc aggacataac tgttttaaca tcccacgaaa tgcctaactc attagtatat | 420 |
| gggctgact ggtcctggct tttccattcc atgaagccca ctcctacctg gttctttgat | 480 |
| cagaatgaca tgggagtcaa agcagcagac cactctagcc taaaggtcac agaggagcca | 540 |
| ccaatacatt ctcaggaaca aaccatggat cgccaagtgg aaggcccgc taacgctcat | 600 |
| accagagctg aactgaaggc ttctctcctt ccattaacag aggacatgaa aaacagcaaa | 660 |
| gactgctcct catcctcagt caagactcgt gatcttagcc actgctctgg tgggcagagc | 720 |
| tttgacaata gcctcctggc cacctgctcc ttttatgacc atgttctcca cctttggaag | 780 |
| tgggagacga atcaagctcg cactctttgc agtggcactg gatgtgattt ggggagtgct | 840 |
| gaccattga | 849 |

<210> SEQ ID NO 122
<211> LENGTH: 524
<212> TYPE: PRT
<213> ORGANISM: Artificial sequence
<220> FEATURE:
<223> OTHER INFORMATION: /note="Description of Artificial Sequence:
    SL-401 DRT88-IL3 conjugate amino acid sequence"

<400> SEQUENCE: 122

-continued

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Arg Pro His Met Ala Pro Met Thr Gln Thr Thr Ser Leu
385                 390                 395                 400

Lys Thr Ser Trp Val Asn Cys Ser Asn Met Ile Asp Glu Ile Ile Thr
                405                 410                 415

His Leu Lys Gln Pro Pro Leu Pro Leu Leu Asp Phe Asn Asn Leu Asn
```

```
                420             425             430
Gly Glu Asp Gln Asp Ile Leu Met Glu Asn Asn Leu Arg Arg Pro Asn
            435                 440                 445

Leu Glu Ala Phe Asn Arg Ala Val Lys Ser Leu Gln Asn Ala Ser Ala
        450                 455                 460

Ile Glu Ser Ile Leu Lys Asn Leu Leu Pro Cys Leu Pro Leu Ala Thr
465                 470                 475                 480

Ala Ala Pro Thr Arg His Pro Ile His Ile Lys Asp Gly Asp Trp Asn
                485                 490                 495

Glu Phe Arg Arg Lys Leu Thr Phe Tyr Leu Lys Thr Leu Glu Asn Ala
            500                 505                 510

Gln Ala Gln Gln Thr Thr Leu Ser Leu Ala Ile Phe
            515                 520

<210> SEQ ID NO 123
<211> LENGTH: 819
<212> TYPE: DNA
<213> ORGANISM: Mus musculus

<400> SEQUENCE: 123
atggacttct gtcttcccac aggggagat gactgccttc tgagaggctg ggacactagg      60
atgctgggca cacctgtctt cactagcaaa agacattgca tgggtgtgtg cagcatccag    120
agcagccccc atcaggagca tatactggca actggaagct atgatgagca tgttctgctg    180
tgggacactc gaaacataag acagccattg gcggatgtac cagtgcaagg aggtgtgtgg    240
aggctcaagt ggcacccagt tcaccaccat ctactcctgg cggcctgcat gcacaatggc    300
ttcaagattc tcaactgcca gaaggccatt gaggagaagc aggacataac tgttttaaca    360
tcccacgaaa tgcctaactc attagtatat ggggctgact ggtcctggct tttccattcc    420
atgaagccca ctcctacctg gttctttgat cagaatgaca tgggagtcaa agcagcagac    480
cactctagcc taaaggtcac agaggagcca ccaatacatt ctcaggaaca aaccatggat    540
cgccaagtgg aaggccccgc taacgctcat accagagctg aactgaaggc ttctctcctt    600
ccattaacag aggacatgaa aaacagcaaa gactgctcct catcctcagt caagactcgt    660
gatcttagcc actgctctgg tgggcagagc tttgacaata gcctcctggc cacctgctcc    720 tttatgacc atgttctcca cctttggaag tgggagacga atcaagctcg cactctttgc    780
agtggcactg gatgtgattt ggggagtgct gaccattga                           819

<210> SEQ ID NO 124
<211> LENGTH: 477
<212> TYPE: PRT
<213> ORGANISM: Mus musculus

<400> SEQUENCE: 124

Met Ala Gly Ser His Ala Gly Thr Leu Arg Val Leu Gln Ala Val Asp
1               5                   10                  15

Thr Glu Leu Thr Ala Asp Ser Val Glu Trp Cys Pro Val Glu Gly Tyr
            20                  25                  30

Gln His Leu Leu Ala Cys Gly Thr Tyr Gln Leu Arg Ala Pro Arg Asp
        35                  40                  45

Gln Pro Ala Leu Asp Gly Ser Glu Pro Gln Val Arg Leu Gly Arg Leu
    50                  55                  60

Tyr Leu Phe Ser Phe Ser Glu His Asn Thr Ala Lys Pro Leu Leu Glu
65                  70                  75                  80
```

```
Val Gln Arg Arg Asp Ser Ser Ala Val Leu Asp Met Lys Trp Cys His
             85                  90                  95

Ile Pro Val Ser Gly His Val Leu Leu Gly Leu Ala Asn Ala Ser Gly
        100                 105                 110

Ser Ile Gly Leu Leu Arg Leu Met Glu Cys Glu Asn Asn Ser Tyr Thr
        115                 120                 125

Leu Gln Pro Ile Ser Ser Leu Ala Leu Asp Glu Asn Cys Leu Ser Leu
    130                 135                 140

Ser Met Asp Trp Ser Thr Gly Lys Ser Val Arg Ala Arg Glu Gln Pro
145                 150                 155                 160

Leu Lys Ile Ile Ser Ser Asp Ser Lys Gly Gln Leu His Leu Leu Met
                165                 170                 175

Val Asn Glu Gly Thr Ala Glu Leu Gln Leu Val Ala Ser Trp Pro Ala
            180                 185                 190

His His Phe Glu Ala Trp Ile Ala Ala Phe Asn Tyr Trp Gln Thr Glu
        195                 200                 205

Leu Val Tyr Ser Gly Gly Asp Asp Cys Leu Leu Arg Gly Trp Asp Thr
    210                 215                 220

Arg Met Leu Gly Thr Pro Val Phe Thr Ser Lys Arg His Cys Met Gly
225                 230                 235                 240

Val Cys Ser Ile Gln Ser Ser Pro His Gln Glu His Ile Leu Ala Thr
                245                 250                 255

Gly Ser Tyr Asp Glu His Val Leu Leu Trp Asp Thr Arg Asn Ile Arg
            260                 265                 270

Gln Pro Leu Ala Asp Val Pro Val Gln Gly Gly Val Trp Arg Leu Lys
        275                 280                 285

Trp His Pro Val His His Leu Leu Leu Ala Ala Cys Met His Asn
    290                 295                 300

Gly Phe Lys Ile Leu Asn Cys Gln Lys Ala Ile Glu Glu Lys Gln Asp
305                 310                 315                 320

Ile Thr Val Leu Thr Ser His Glu Met Pro Asn Ser Leu Val Tyr Gly
                325                 330                 335

Ala Asp Trp Ser Trp Leu Phe His Ser Met Lys Pro Thr Pro Thr Trp
            340                 345                 350

Phe Phe Asp Gln Asn Asp Met Gly Val Lys Ala Ala Asp His Ser Ser
        355                 360                 365

Leu Lys Val Thr Glu Glu Pro Pro Ile His Ser Gln Glu Gln Thr Met
    370                 375                 380

Asp Arg Gln Val Glu Gly Pro Ala Asn Ala His Thr Arg Ala Glu Leu
385                 390                 395                 400

Lys Ala Ser Leu Leu Pro Leu Thr Glu Asp Met Lys Asn Ser Lys Asp
                405                 410                 415

Cys Ser Ser Ser Val Lys Thr Arg Asp Leu Ser His Cys Ser Gly
            420                 425                 430

Gly Gln Ser Phe Asp Asn Ser Leu Leu Ala Thr Cys Ser Phe Tyr Asp
        435                 440                 445

His Val Leu His Leu Trp Lys Trp Glu Thr Asn Gln Ala Arg Thr Leu
    450                 455                 460

Cys Ser Gly Thr Gly Cys Asp Leu Gly Ser Ala Asp His
465                 470                 475

<210> SEQ ID NO 125
<211> LENGTH: 355
<212> TYPE: PRT
```

<213> ORGANISM: Mus musculus

<400> SEQUENCE: 125

Met Asn Asn Ser Tyr Thr Leu Gln Pro Ile Ser Ser Leu Ala Leu Asp
1               5                   10                  15

Glu Asn Cys Leu Ser Leu Ser Met Asp Trp Ser Thr Gly Lys Ser Val
            20                  25                  30

Arg Ala Arg Glu Gln Pro Leu Lys Ile Ile Ser Ser Asp Ser Lys Gly
        35                  40                  45

Gln Leu His Leu Leu Met Val Asn Glu Gly Thr Ala Glu Leu Gln Leu
    50                  55                  60

Val Ala Ser Trp Pro Ala His His Phe Glu Ala Trp Ile Ala Ala Phe
65                  70                  75                  80

Asn Tyr Trp Gln Thr Glu Leu Val Tyr Ser Gly Gly Asp Asp Cys Leu
                85                  90                  95

Leu Arg Gly Trp Asp Thr Arg Met Leu Gly Thr Pro Val Phe Thr Ser
            100                 105                 110

Lys Arg His Cys Met Gly Val Cys Ser Ile Gln Ser Ser Pro His Gln
        115                 120                 125

Glu His Ile Leu Ala Thr Gly Ser Tyr Asp Glu His Val Leu Leu Trp
    130                 135                 140

Asp Thr Arg Asn Ile Arg Gln Pro Leu Ala Asp Val Pro Val Gln Gly
145                 150                 155                 160

Gly Val Trp Arg Leu Lys Trp His Pro Val His His Leu Leu Leu
                165                 170                 175

Ala Ala Cys Met His Asn Gly Phe Lys Ile Leu Asn Cys Gln Lys Ala
            180                 185                 190

Ile Glu Glu Lys Gln Asp Ile Thr Val Leu Thr Ser His Glu Met Pro
        195                 200                 205

Asn Ser Leu Val Tyr Gly Ala Asp Trp Ser Trp Leu Phe His Ser Met
    210                 215                 220

Lys Pro Thr Pro Thr Trp Phe Phe Asp Gln Asn Asp Met Gly Val Lys
225                 230                 235                 240

Ala Ala Asp His Ser Ser Leu Lys Val Thr Glu Glu Pro Pro Ile His
                245                 250                 255

Ser Gln Glu Gln Thr Met Asp Arg Gln Val Glu Gly Pro Ala Asn Ala
            260                 265                 270

His Thr Arg Ala Glu Leu Lys Ala Ser Leu Leu Pro Leu Thr Glu Asp
        275                 280                 285

Met Lys Asn Ser Lys Asp Cys Ser Ser Ser Val Lys Thr Arg Asp
    290                 295                 300

Leu Ser His Cys Ser Gly Gly Gln Ser Phe Asp Asn Ser Leu Leu Ala
305                 310                 315                 320

Thr Cys Ser Phe Tyr Asp His Val Leu His Leu Trp Lys Trp Glu Thr
                325                 330                 335

Asn Gln Ala Arg Thr Leu Cys Ser Gly Thr Gly Cys Asp Leu Gly Ser
            340                 345                 350

Ala Asp His
        355

<210> SEQ ID NO 126
<211> LENGTH: 332
<212> TYPE: PRT
<213> ORGANISM: Mus musculus

<400> SEQUENCE: 126

Met Asp Trp Ser Thr Gly Lys Ser Val Arg Ala Arg Glu Gln Pro Leu
1               5                   10                  15

Lys Ile Ile Ser Ser Asp Ser Lys Gly Gln Leu His Leu Leu Met Val
            20                  25                  30

Asn Glu Gly Thr Ala Glu Leu Gln Leu Val Ala Ser Trp Pro Ala His
        35                  40                  45

His Phe Glu Ala Trp Ile Ala Ala Phe Asn Tyr Trp Gln Thr Glu Leu
    50                  55                  60

Val Tyr Ser Gly Gly Asp Asp Cys Leu Leu Arg Gly Trp Asp Thr Arg
65              70                  75                  80

Met Leu Gly Thr Pro Val Phe Thr Ser Lys Arg His Cys Met Gly Val
                85                  90                  95

Cys Ser Ile Gln Ser Ser Pro His Gln Glu His Ile Leu Ala Thr Gly
            100                 105                 110

Ser Tyr Asp Glu His Val Leu Leu Trp Asp Thr Arg Asn Ile Arg Gln
        115                 120                 125

Pro Leu Ala Asp Val Pro Val Gln Gly Gly Val Trp Arg Leu Lys Trp
    130                 135                 140

His Pro Val His His Leu Leu Leu Ala Ala Cys Met His Asn Gly
145                 150                 155                 160

Phe Lys Ile Leu Asn Cys Gln Lys Ala Ile Glu Glu Lys Gln Asp Ile
                165                 170                 175

Thr Val Leu Thr Ser His Glu Met Pro Asn Ser Leu Val Tyr Gly Ala
            180                 185                 190

Asp Trp Ser Trp Leu Phe His Ser Met Lys Pro Thr Pro Thr Trp Phe
        195                 200                 205

Phe Asp Gln Asn Asp Met Gly Val Lys Ala Ala Asp His Ser Ser Leu
    210                 215                 220

Lys Val Thr Glu Glu Pro Pro Ile His Ser Gln Glu Gln Thr Met Asp
225                 230                 235                 240

Arg Gln Val Glu Gly Pro Ala Asn Ala His Thr Arg Ala Glu Leu Lys
                245                 250                 255

Ala Ser Leu Leu Pro Leu Thr Glu Asp Met Lys Asn Ser Lys Asp Cys
            260                 265                 270

Ser Ser Ser Val Lys Thr Arg Asp Leu Ser His Cys Ser Gly Gly
        275                 280                 285

Gln Ser Phe Asp Asn Ser Leu Leu Ala Thr Cys Ser Phe Tyr Asp His
    290                 295                 300

Val Leu His Leu Trp Lys Trp Glu Thr Asn Gln Ala Arg Thr Leu Cys
305                 310                 315                 320

Ser Gly Thr Gly Cys Asp Leu Gly Ser Ala Asp His
                325                 330

<210> SEQ ID NO 127
<211> LENGTH: 282
<212> TYPE: PRT
<213> ORGANISM: Mus musculus

<400> SEQUENCE: 127

Met Arg Ile Val Cys Pro Cys Gln Trp Ile Gly Pro Leu Gly Asn Leu
1               5                   10                  15

Ser Gly Gly Asp Asp Cys Leu Leu Arg Gly Trp Asp Thr Arg Met Leu
            20                  25                  30

Gly Thr Pro Val Phe Thr Ser Lys Arg His Cys Met Gly Val Cys Ser
                35                  40                  45

Ile Gln Ser Ser Pro His Gln Glu His Ile Leu Ala Thr Gly Ser Tyr
 50                  55                  60

Asp Glu His Val Leu Leu Trp Asp Thr Arg Asn Ile Arg Gln Pro Leu
 65                  70                  75                  80

Ala Asp Val Pro Val Gln Gly Val Trp Arg Leu Lys Trp His Pro
                 85                  90                  95

Val His His His Leu Leu Leu Ala Ala Cys Met His Asn Gly Phe Lys
                100                 105                 110

Ile Leu Asn Cys Gln Lys Ala Ile Glu Glu Lys Gln Asp Ile Thr Val
                115                 120                 125

Leu Thr Ser His Glu Met Pro Asn Ser Leu Val Tyr Gly Ala Asp Trp
130                 135                 140

Ser Trp Leu Phe His Ser Met Lys Pro Thr Pro Thr Trp Phe Phe Asp
145                 150                 155                 160

Gln Asn Asp Met Gly Val Lys Ala Ala Asp His Ser Ser Leu Lys Val
                165                 170                 175

Thr Glu Glu Pro Pro Ile His Ser Gln Glu Gln Thr Met Asp Arg Gln
                180                 185                 190

Val Glu Gly Pro Ala Asn Ala His Thr Arg Ala Glu Leu Lys Ala Ser
                195                 200                 205

Leu Leu Pro Leu Thr Glu Asp Met Lys Asn Ser Lys Asp Cys Ser Ser
                210                 215                 220

Ser Ser Val Lys Thr Arg Asp Leu Ser His Cys Ser Gly Gly Gln Ser
225                 230                 235                 240

Phe Asp Asn Ser Leu Leu Ala Thr Cys Ser Phe Tyr Asp His Val Leu
                245                 250                 255

His Leu Trp Lys Trp Glu Thr Asn Gln Ala Arg Thr Leu Cys Ser Gly
                260                 265                 270

Thr Gly Cys Asp Leu Gly Ser Ala Asp His
                275                 280

<210> SEQ ID NO 128
<211> LENGTH: 272
<212> TYPE: PRT
<213> ORGANISM: Mus musculus

<400> SEQUENCE: 128

Met Asp Phe Cys Leu Pro Thr Gly Gly Asp Cys Leu Leu Arg Gly
 1                   5                  10                  15

Trp Asp Thr Arg Met Leu Gly Thr Pro Val Phe Thr Ser Lys Arg His
                 20                  25                  30

Cys Met Gly Val Cys Ser Ile Gln Ser Ser Pro His Gln Glu His Ile
                 35                  40                  45

Leu Ala Thr Gly Ser Tyr Asp Glu His Val Leu Leu Trp Asp Thr Arg
 50                  55                  60

Asn Ile Arg Gln Pro Leu Ala Asp Val Pro Val Gln Gly Gly Val Trp
 65                  70                  75                  80

Arg Leu Lys Trp His Pro Val His His Leu Leu Leu Ala Ala Cys
                 85                  90                  95

Met His Asn Gly Phe Lys Ile Leu Asn Cys Gln Lys Ala Ile Glu Glu
                100                 105                 110

Lys Gln Asp Ile Thr Val Leu Thr Ser His Glu Met Pro Asn Ser Leu
                115                 120                 125

```
Val Tyr Gly Ala Asp Trp Ser Trp Leu Phe His Ser Met Lys Pro Thr
            130                 135                 140

Pro Thr Trp Phe Phe Asp Gln Asn Asp Met Gly Val Lys Ala Ala Asp
145                 150                 155                 160

His Ser Ser Leu Lys Val Thr Glu Glu Pro Pro Ile His Ser Gln Glu
                165                 170                 175

Gln Thr Met Asp Arg Gln Val Glu Gly Pro Ala Asn Ala His Thr Arg
            180                 185                 190

Ala Glu Leu Lys Ala Ser Leu Leu Pro Leu Thr Glu Asp Met Lys Asn
        195                 200                 205

Ser Lys Asp Cys Ser Ser Ser Val Lys Thr Arg Asp Leu Ser His
    210                 215                 220

Cys Ser Gly Gly Gln Ser Phe Asp Asn Ser Leu Leu Ala Thr Cys Ser
225                 230                 235                 240

Phe Tyr Asp His Val Leu His Leu Trp Lys Trp Glu Thr Asn Gln Ala
                245                 250                 255

Arg Thr Leu Cys Ser Gly Thr Gly Cys Asp Leu Gly Ser Ala Asp His
            260                 265                 270

<210> SEQ ID NO 129
<211> LENGTH: 20
<212> TYPE: DNA
<213> ORGANISM: Artificial sequence
<220> FEATURE:
<223> OTHER INFORMATION: /note="Description of Artificial Sequence:
      Synthetic sgRNA targeting sequence"

<400> SEQUENCE: 129
acggaggcta agcgtcgcaa                                              20

<210> SEQ ID NO 130
<211> LENGTH: 20
<212> TYPE: DNA
<213> ORGANISM: Artificial sequence
<220> FEATURE:
<223> OTHER INFORMATION: /note="Description of Artificial Sequence:
      Synthetic sgRNA targeting sequence"

<400> SEQUENCE: 130
cgcttccgcg gcccgttcaa                                              20

<210> SEQ ID NO 131
<211> LENGTH: 20
<212> TYPE: DNA
<213> ORGANISM: Artificial sequence
<220> FEATURE:
<223> OTHER INFORMATION: /note="Description of Artificial Sequence:
      Synthetic sgRNA targeting sequence"

<400> SEQUENCE: 131
gtcttgaacg gaggtgtcca                                              20

<210> SEQ ID NO 132
<211> LENGTH: 20
<212> TYPE: DNA
<213> ORGANISM: Artificial sequence
<220> FEATURE:
<223> OTHER INFORMATION: /note="Description of Artificial Sequence:
      Synthetic sgRNA targeting sequence"

<400> SEQUENCE: 132
agctgtgacc atagtgcacc                                              20
```

```
<210> SEQ ID NO 133
<211> LENGTH: 20
<212> TYPE: DNA
<213> ORGANISM: Artificial sequence
<220> FEATURE:
<223> OTHER INFORMATION: /note="Description of Artificial Sequence:
      Synthetic sgRNA targeting sequence"

<400> SEQUENCE: 133
gttgacttcc tggtgcacta                                              20

<210> SEQ ID NO 134
<211> LENGTH: 20
<212> TYPE: DNA
<213> ORGANISM: Artificial sequence
<220> FEATURE:
<223> OTHER INFORMATION: /note="Description of Artificial Sequence:
      Synthetic sgRNA targeting sequence"

<400> SEQUENCE: 134
gggttgttca ggacctcagg                                              20
```